US011466269B2

(12) United States Patent
Lippmeier et al.

(10) Patent No.: US 11,466,269 B2
(45) Date of Patent: Oct. 11, 2022

(54) CRISPR-CAS SYSTEM FOR AN ALGAL HOST CELL

(71) Applicant: DSM IP Assets B.V., TE Heerlen (NL)

(72) Inventors: James Casey Lippmeier, Columbia, MD (US); Yelena Betz, Columbia, MD (US); Johannes Andries Roubos, Pijnacker (NL); René Verwaal, Nootdorp (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/309,304

(22) PCT Filed: Jul. 13, 2017

(86) PCT No.: PCT/US2017/041949
§ 371 (c)(1),
(2) Date: Dec. 12, 2018

(87) PCT Pub. No.: WO2018/013821
PCT Pub. Date: Jan. 18, 2018

(65) Prior Publication Data
US 2020/0131511 A1    Apr. 30, 2020

Related U.S. Application Data

(60) Provisional application No. 62/361,741, filed on Jul. 13, 2016.

(51) Int. Cl.
| C12N 15/11 | (2006.01) |
| C12N 9/22 | (2006.01) |
| C12N 15/86 | (2006.01) |
| C12P 21/00 | (2006.01) |

(52) U.S. Cl.
CPC ............ *C12N 15/11* (2013.01); *C12N 9/22* (2013.01); *C12N 15/86* (2013.01); *C12P 21/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 7,001,772 | B2 | 2/2006 | Roessler et al. |
| 8,003,772 | B2 | 8/2011 | Weaver et al. |
| 8,637,651 | B2 | 1/2014 | Apt et al. |
| 8,940,884 | B2 | 1/2015 | Apt et al. |
| 2010/0233760 | A1 | 9/2010 | Apt |
| 2011/0059502 | A1 | 3/2011 | Chalasani |
| 2014/0186842 | A1 | 7/2014 | Seshadri et al. |
| 2016/0177255 | A1* | 6/2016 | Radakovits ............ C07C 57/03 435/243 |
| 2016/0298096 | A1* | 10/2016 | Charpentier ......... C12N 15/907 |

FOREIGN PATENT DOCUMENTS

| CN | 102648207 A | 8/2012 |
| CN | 104988078 A | 10/2015 |
| CN | 105238806 A | 1/2016 |
| EP | 3412765 A4 | 5/2019 |
| WO | WO1998046772 | 10/1998 |
| WO | WO2006077258 A1 | 7/2006 |
| WO | WO2008000632 A1 | 1/2008 |
| WO | 2010102982 A1 | 9/2010 |
| WO | 2010107709 A1 | 9/2010 |
| WO | WO2010121933 A1 | 10/2010 |
| WO | WO2014065596 A1 | 5/2014 |
| WO | 2014191521 A2 | 12/2014 |
| WO | 2015004241 A2 | 1/2015 |
| WO | 2015086798 A2 | 6/2015 |
| WO | WO2015086795 | 6/2015 |
| WO | WO2016109840 | 7/2016 |
| WO | WO2016197136 | 12/2016 |
| WO | WO2017019867 A1 | 2/2017 |

OTHER PUBLICATIONS

Sidik et al Efficient Genome Engineereing of Toxoplasma gondii Using CRISPR/Cas9 PLOS ONE 9:1-8 (Year: 2014).*
Aggarwal et al, Structure of the multimodular endonuclease FokI bound to DNA, letters to nature, 1997, 97-100, 388.
Altschul et al., Basic Local Alignment Search Tool, J. Mol. Biol., 1990, 403-410, 215.
Ausubel et al, Current Protocols in Molecular Biology, John Wiley & Sons, Current Protocols in Molecular Biology, John Wiley & Sons, 1995, (BOOK), Abstract.
Carillo et al., The Multiple Sequence Alignment Problem in Biology, SIAM J. Appl. Math, 1988, 1073-1082, 48(5).
Cheng et al, Agrobacterium tumefaciens mediated transformation of marine microoalgae Schizochytrium, Microbiolgical Research, 2012, 179-186, 167.
Devereux et al, A comprehensive set of sequence analysis programs for the VAX, Nucleic Acids Research, 1984, 387-395, 12(1).
Durai et al, Zinc finger nucleases: custom-designed molecular scissors for genome engineering of plant and mammalian cells, Nucleic Acids Research, 2005, 5978-5990, 33(18).
Egholm et al, PNA hybridizes ro complementary oligonucleotides, letters to nature, 1993, 566-568, 365.
Gaj et al, ZFN, TALEN, and CRISPR/Cas-based methods for genome engineering, Trends Biotechnol, Jul. 31, 2013, 397-405, 7, Cell Press.
Govindaraju et al., Backbone-extended pyrrolidine peptide nucleic acids (bepPNA): design, synthesis and DNA/RNA binding studies, Chem Communication, 2005, 495-497.
Griffin et al, MolecularB iology:C urrent Innovationsa nd Future Trends (Part 1), Horizon Scientific, 1995, 461, 11.
Guilinger et al, Fusion of catalytically inactive Cas9 to FokI nuclease, nature biotechnology, 2014, 577-583, 32.
Gupta et al, Studies on Polynucleotides, LXXXVIII* Enzymatic, Institute for Enzyme Research, University of Wisconsin, Madison, 1968, 1338-1344.

(Continued)

*Primary Examiner* — Brent T Page
(74) *Attorney, Agent, or Firm* — McBee Moore & Vanik IP, LLC; Susan McBee; Chester Moore

(57) ABSTRACT

The present invention relates to the field of molecular biology and cell biology. More specifically, the present invention relates to a CRISPR-Cas system for a Labyrinthulomycetes host cell.

20 Claims, 22 Drawing Sheets

Specification includes a Sequence Listing.

(56) References Cited

OTHER PUBLICATIONS

Henikoff et al, Amino acid substitution matrices from protein blocks, Proc Natl Acad Sci, 1992, 10915-10919, 89.
Herbert et al, The Biosynthesis of Secondary Metabolites, The Biosynthesis of Secondary Metabolites, 1981, (BOOK), Abstract, Chapman and Hall, New York.
Ho et al, Site-directed mutagenesis by overlap extension using the polymerase chain reaction, Gene, 1989, 51-59, 77, Elsevier.
J.Z.Jacobs, Implementation of the CRISPR-Cas9 system in fission yeast, Nature communications, 2014, DOI: 10.1038 ncommso34i4.
Jinek et al, A Programmable Dual-RNA-Guided DNA endonuclease in adaptive bacterial immunity, science, 2012, 816-822, 337.
Jinek et al, RNA-programmed genome editing in human cells, eLIFE, 2013, 1-9, 2(e00471).
Kornberg, Roger D., Eukaryotic transcriptional control, Millennium issue, 1999, M46-M48.
Larson et al., CRISPR interference (CRISPRi) for sequence-specific control of gene expression, Protocol, 2013, 2180-2196, 8(11).
Lian et al, Increase of Docosahexaenoic Acid Production, Appl Biochem Biotechnol, 2010, 935-941, 162.
Mali et al, Cas9 as a versatile tool for engineering biology, Nature, 2013, 957-963, 10.
Marck et al., The RNA polymerase III-dependent family of genes in hemiascomycetes: comparative RNomics, decoding strategies, transcription and evolutionary implications, Nucleic Acids Research, 2006, 1816-1835, 34(6).
Morita et al, 2'-O, 4'-C-Ethylene-bridged nucleic acids (ENA) with nuclease-resistance and high affnity for RNA, Oxford University Press, 2001, 241-242, Suppl 1.
Nakamura et al, Codon usage tabulated from international DNA, Nucleid Acids Research, 2000, 292-, 28.
Needleman et al., A General Method Applicable to the Search for Similarities in the Amino Acid Sequence of Two Proteins, J. Mol. Biol., 1970, 443-453, 48.
Nielsen et al, Sequence specific inhibition of DNA restriction enzyme, Nucleic Acids Research, 1991, 197-200, 21.
Ran et al, Double Nicking by RNA-Guided, Cell, 2013, 1380-1389, 154.
Ren et al, Effect of biotin and cerulenin addition on DHA production by *Schizochytrium* sp., Chinese Journal of Bioprocess Engineering, 2012, 42-45, 10(1).
Ryan et al, Multiplex Engineering of Industrial Yeast Genomes Using CRISPRm, Methods in Enzymology, Jan. 1, 2014, 473-489, 546.
Sambrook et al., Molecular Cloning: A Laboratory Manual, BOOK, 2001.
Sander et al, CriSPr-Cas systems for editing, regulating, Nature Biotechnology, Apr. 2014, 347-355, 32-4, NPG.
Scarpulla et al, Use of a New Retrieving Adaptor in the Cloning of a Synthetic Human, Analytical Biochemistry, 1982, 356-365, 121.
Stemmer et al, Single-step assembly of a gene and entire plasmid from large numbers of, Gene, 1995, 49-53, 164.
Tour et al, Geneticaaly targeted chromophore-assisted light inactivation, Nature Biotechnology, 2003, 1505-1508, 21.
Tsai et al, Dimeric CRISPR RNA-guided FokI nucleases for highly, Nature Biotechnology, 2014, 569-577, 32.
Wah et al, FokI dimerization is required for DNA cleavage, Proc. Natl. Acad. Sci. USA, 1998, 10570-10575, 95.
Wah et al., Structure of the multimodular endonuclease FokI bound to DNA, Letters to Nature, 1997, 97-100.
Y.Gao et al, Self-processing of ribozyme-flanked RNAs into guide RNAs in vitro and in vivo for CRISPR-mediated genome editing, JIPB, 2014, 343-349, 56-4.
Young et al, Two-step total gene synthesis method, Nucleic Acids Research, 2004, e59, 32(7).
Nodvig et al, A CRISPR-Cas9 System for Genetic Engineering of Filamentous Fungi, PLOS ONE, Jul. 15, 2015, p. e8133885, vol. 10, No. 7.
Guo et al., "CRISPR/Cas9 Systems: The Next Generation Gene Targeted Editing Tool," Proc. Natl. Acad. Sci., India, Sect. B Biol. Sci. (Apr.-Jun. 2015) 85(2):377-387.
Li et al., "CRISPR/Cas: a novel way of RNA-guided genome editing," Hereditas, China, 2013, vol. 35, Issue (11) 1265-1273, doi: 10.3724/SP.J.1005.2013.01265, with abstract.

* cited by examiner

SEQUENCE LISTING

<160> NUMBER OF SEQ ID NOS: 47

<210> SEQ ID NO 1
<211> LENGTH: 9920
<212> TYPE: DNA
<213> ORGANISM: Artificial Sequence
<220> FEATURE:
<223> OTHER INFORMATION: pCL122-Cas9 vector
<220> FEATURE:
<221> NAME/KEY: misc_feature
<222> LOCATION: (1)..(1064)
<223> OTHER INFORMATION: EF-1 alpha promoter
<220> FEATURE:
<221> NAME/KEY: misc_feature
<222> LOCATION: (1070)..(5209)
<223> OTHER INFORMATION: Cas9
<220> FEATURE:
<221> NAME/KEY: misc_feature
<222> LOCATION: (5229)..(5868)
<223> OTHER INFORMATION: OrfC_terminator
<220> FEATURE:
<221> NAME/KEY: misc_feature
<222> LOCATION: (7153)..(8013)
<223> OTHER INFORMATION: AmpR_gene
<220> FEATURE:
<221> NAME/KEY: misc_feature
<222> LOCATION: (8403)..(8851)
<223> OTHER INFORMATION: alpha_tubulin_promoter
<220> FEATURE:
<221> NAME/KEY: misc_feature
<222> LOCATION: (8852)..(9646)
<223> OTHER INFORMATION: paromomycin_resistance_gene
<220> FEATURE:
<221> NAME/KEY: misc_feature
<222> LOCATION: (9647)..(9920)
<223> OTHER INFORMATION: SV40_terminator

<400> SEQUENCE: 1

```
ctcttatctg cctcgcgccg ttgaccgccg cttgactctt ggcgcttgcc gctcgcatcc      60
tgcctcgctc gcgcaggcgg gcgggcgagt gggtgggtcc gcagccttcc gcgctcgccc     120
gctagctcgc tcgcgccgtg ctgcagccag cagggcagca ccgcacggca ggcaggtccc     180
ggcgcggatc gatcgatcca tcgatccatc gatccatcga tcgtgcggtc aaaaagaaag     240
gaagaagaaa ggaaaaagaa aggcgtgcgc acccgagtgc gcgctgagcg cccgctcgcg     300
gtcccgcgga gcctccgcgt tagtccccgc cccgcgccgc gcagtccccc gggaggcatc     360
gcgcacctct cgccgccccc tcgcgcctcg ccgattcccc gcctcccctt ttccgcttct     420
tcgccgcctc cgctcgcggc cgcgtcgccc gcgccccgct ccctatctgc tccccagggg     480
ggcactccgc accttttgcg cccgctgccg ccgccgcggc cgccccgccg ccctggtttc     540
ccccgcgagc gcggccgcgt cgccgcgcaa agactcgccg cgtgccgccc cgagcaacgg     600
gtggcggcgg cgcggcggcg ggcggggcgc ggcggcgcgt aggcggggct aggcgccggc     660
taggcgaaac gccgcccccg ggcgccgccg ccgcccgctc cagagcagtc gccgcgccag     720
accgccaacg cagagaccga gaccgaggta cgtcgcgccc gagcacgccg cgacgcgcgg     780
cagggacgag gagcacgacg ccgcgccgcg ccgcgcgggg ggggggaggg agaggcagga     840
cgcgggagcg agcgtgcatg tttccgcgcg agacgacgcc gcgcgcgctg gagaggagat     900
aaggcgcttg gatcgcgaga gggccagcca ggctggaggc gaaaatgggt ggagaggata     960
gtatcttgcg tgcttggacg aggagactga cgaggaggac ggatacgtcg atgatgatgt    1020
gcacagagaa gaagcagttc gaaagcgact actagcaagc aagggatcca tggataagaa    1080
gtactcgatc ggcctcgaca ttggcaccaa cagcgtcggc tgggccgtca ttactgatga    1140
gtacaaggtc ccgtcgaaga agtttaaggt cctcggcaac actgaccgcc actccatcaa    1200
```

```
gaagaacctc atcggtgccc tccttttga ctccggcgag accgctgagg ccactcgcct    1260
caagcgcact gcccgccgcc gttacacccg ccgcaagaac cgcatctgct acctccagga    1320
gattttctcg aacgaaatgg ccaaggtcga tgactccttt ttccaccgtc tcgaagaatc    1380
gttcctcgtc gaggaggaca agaagcacga gcgccacccc atcttcggta acattgtcga    1440
tgaggttgcc taccacgaga agtacccgac catctaccac ctccgcaaga agctcgtcga    1500
ctccaccgac aaggccgatc tccgccttat ctacctcgcc ctcgcccaca tgatcaagtt    1560
ccgcggccac tttcttatcg agggtgatct caaccctgat aactctgacg tcgacaagct    1620
tttcatccag ctcgtccaga cttacaacca gctcttcgag gagaacccca tcaacgcttc    1680
cggcgtcgac gcgaaggcca ttctcagcgc ccgcctcagc aagtcccgcc gcctcgaaaa    1740
cctcattgcc cagcttcccg gcgagaagaa gaacggcctc ttcggcaacc tcattgccct    1800
cagccttggc ctcaccccta acttcaagtc gaactttgac ctcgccgagg acgccaagct    1860
ccagcttttcc aaggacactt acgacgacga tctcgacaac ctcctcgctc agattggcga    1920
ccagtacgct gacctcttcc tcgccgccaa gaaccttagc gatgccatcc tcctctccga    1980
catccttcgt gttaacacgg aaatcacgaa ggctccgctc tccgcctcca tgatcaagcg    2040
ttacgacgag caccatcagg acctcaccct cctcaaggcc ctcgtccgcc agcagctccc    2100
cgagaagtac aaggagatct tcttcgacca gagcaagaac ggctacgccg gctacattga    2160
cggcggcgcg tcgcaggagg agttttacaa gtttatcaag cccattcttg agaagatgga    2220
cggcaccgag gagctcctcg tcaagctcaa ccgtgaggac cttctccgca agcagcgcac    2280
gttcgacaac ggctctattc cccatcagat ccacctcggt gagcttcacg cgattcttcg    2340
ccgccaggaa gacttttacc cgttcctcaa ggacaaccgc gagaagattg agaagatcct    2400
caccttttcgc attccctact acgtcggccc cctcgcccgc ggcaactcgc gctttgcttg    2460
gatgacccgc aagtccgagg agaccatcac cccgtggaac ttcgaagagg tcgtcgacaa    2520
gggcgcctcc gcgcagtctt tcatcgagcg catgactaac tttgacaaga acctcccgaa    2580
cgagaaggtc ctccccaagc acagcctcct ttacgaatac tttacggtgt acaacgagct    2640
cacgaaggtc aagtacgtca ctgagggcat gcgcaagccg gcgttccttt cgggcgagca    2700
gaagaaggct atcgtcgacc tccttttcaa gaccaaccgc aaggttaccg tcaagcagct    2760
caaggaggac tacttcaaga agatcgagtg ctttgactcg gtcgagattt cgggcgtgga    2820
ggaccgtttc aacgcctccc tcggcactta ccacgacctt ctcaagatca tcaaggacaa    2880
ggactttctc gacaacgagg agaacgagga cattctcgag gacatcgtcc tcacgctcac    2940
cctctttgag gaccgtgaga tgatcgagga gcgcctcaag acctacgccc atctctttga    3000
cgacaaggtc atgaagcagc tcaagcgccg ccgctacacc ggctggggcc gccttttcccg    3060
caagctcatc aacggcatcc gcgacaagca gtctggcaag accatccttg actttcttaa    3120
gtctgatggt ttcgccaacc gcaacttcat gcagctcatc cacgacgaca gcctcacttt    3180
caaggaggac attcagaagg cccaggtctc cggccagggt gactctctcc acgaacacat    3240
cgccaacctt gctggcagcc cggctattaa gaagggcatc ctccagaccg tcaaggtcgt    3300
cgacgagctc gtcaaggtta tgggccgcca caagcccgag aacatcgtca ttgagatggc    3360
tcgcgaaaac cagaccaccc agaagggtca gaagaactcc cgcgagcgca tgaagcgtat    3420
cgaggagggc atcaaggagc tcggcagcca gatcctcaag gagcacccgg tcgagaacac    3480
ccagctccag aacgaaaagc tctacctcta ctacctccag aacggccgtg acatgtacgt    3540
```

```
tgaccaggag ctcgacatta accgcctctc cgattacgac gtcgaccata ttgtccccca   3600
gagctttctc aaggacgaca gcatcgacaa caaggtcctc acccgctcgg acaagaaccg   3660
cggcaagtcc gacaacgtcc cttccgagga ggtcgtgaag aagatgaaga actactggcg   3720
ccagcttctc aacgctaagc ttattactca gcgcaagttc gataacctca ccaaggccga   3780
acgcggcggc ctctccgagc tcgacaaggc cggttttatc aagcgccagc tcgttgagac   3840
tcgccagatc accaagcacg tggcgcagat cctcgactcg cgcatgaaca cgaagtacga   3900
cgagaacgac aagctcatcc gcgaggtcaa ggtcatcacc cttaagtcga agctcgtgtc   3960
cgactttcgc aaggacttcc agttctacaa ggtccgtgaa attaacaact accaccacgc   4020
tcacgacgct acctcaacg cggtcgtggg taccgcgctc atcaagaagt acccgaagct   4080
cgagtcggag tttgtctacg cgactacaa ggtctacgac gtgcgcaaga tgatcgccaa   4140
gtccgagcag gagatcggca aggccacggc caagtacttt ttctactcca acattatgaa   4200
cttctttaag actgagatca cccttgccaa cggcgagatc cgcaagcgcc cccttatcga   4260
gaccaacggc gagaccggcg aaattgtgtg ggataagggt cgcgactttg ccaccgtccg   4320
caaggtcctc agcatgcccc aggtcaacat tgttaagaag accgaggtcc agacgggcgg   4380 cttttagcaag gagtctatcc tccccaagcg taacagcgac aagctcatcg cccgcaagaa   4440
ggactgggac cctaagaagt acggcggctt cgattcgcct acggtcgcct acagcgtcct   4500
cgtcgtcgcc aaggtcgaga agggcaagtc caagaagctc aagtccgtca aggagctcct   4560
cggcatcacg atcatggagc gctccagctt tgagaagaac cccattgact cctcgaggc   4620 taagggttac aaggaggtca agaaggacct tatcatcaag ctccccaagt actccctctt   4680
tgagctcgaa aacggccgca agcgtatgct cgctagcgct ggcgaactcc agaagggcaa   4740
cgagctcgcc ctccccagca gtacgtcaa ctttctctac ctcgcctccc actacgagaa   4800
gctcaagggt agcccggagg ataacgagca gaagcagctt tttgtggagc agcacaagca   4860
ctaccttgac gagatcattg aacagatctc cgagttctcc aagcgtgtta ttcttgctga   4920
cgccaacctc gataaggtgc tctccgcgta caacaagcac cgcgacaagc ctatccgcga   4980
gcaggccgag aacatcatcc acctctttac cctcaccaac ctcggcgccc cggccgcctt   5040
taagtacttt gatacgacta tcgaccgcaa gcgctacact tcgactaagg aggtcctcga   5100 cgctacccte attcaccagt ccattaccgg cctctacgag acccgcattg acctttcgca   5160
gctcggtggc gactcgcgtg cggaccctaa gaagaagcgc aaggtctaac atatgagtta   5220
tgagatccga aagtgaacct tgtcctaacc cgacagcgaa tggcgggagg gggcgggcta   5280
aaagatcgta ttacatagta ttttttcccct actctttgtg tttgtctttt ttttttttt   5340 gaacgcattc aagccacttg tctgggttta cttgtttgtt tgcttgcttg cttgcttgct   5400
tgcctgcttc ttggtcagac ggcccaaaaa agggaaaaaa ttcattcatg gcacagataa   5460
gaaaaagaaa aagtttgtcg accaccgtca tcagaaagca agagaagaga aacactcgcg   5520
ctcacattct cgctcgcgta agaatcttag ccacgcatac gaagtaattt gtccatctgg   5580
cgaatcttta catgagcgtt ttcaagctgg agcgtgagat catacctttc ttgatcgtaa   5640
tgttccaacc ttgcataggc ctcgttgcga tccgctagca atgcgtcgta ctcccgttgc   5700
aactgcgcca tcgcctcatt gtgacgtgag ttcagattct tctcgagacc ttcgagcgct   5760
gctaatttcg cctgacgctc cttcttttgt gcttccatga cacgccgctt caccgtgcgt   5820
tccacttctt cctcagacat gcccttggct gcctcgacct gctcggtaaa acgggcccca   5880
gcacgtgcta cgagatttcg attccaccgc cgccttctat gaaaggttgg gcttcggaat   5940
```

```
cgttttccgg gacgccggct ggatgatcct ccagcgcggg gatctcatgc tggagttctt    6000
cgcccacccc aacttgttta ttgcagctta taatggttac aaataaagca atagcatcac    6060
aaatttcaca aataaagcat ttttttcact gcattctagt tgtggtttgt ccaaactcat    6120
caatgtatct tatcatacat ggtcgacctg caggaacctg cattaatgaa tcggccaacg    6180
cgcggggaga ggcggtttgc gtattgggcg ctcttccgct tcctcgctca ctgactcgct    6240
gcgctcggtc gttcggctgc ggcgagcggt atcagctcac tcaaaggcgg taatacggtt    6300
atccacagaa tcaggggata acgcaggaaa gaacatgtga gcaaaaggcc agcaaaaggc    6360
caggaaccgt aaaaaggccg cgttgctggc gtttttccat aggctccgcc ccctgacga    6420 gcatcacaaa aatcgacgct caagtcagag gtggcgaaac ccgacaggac tataaagata    6480
ccaggcgttt cccctggaa gctccctcgt gcgctctcct gttccgaccc tgccgcttac    6540
cggatacctg tccgccttc tcccttcggg aagcgtggcg ctttctcata gctcacgctg    6600
taggtatctc agttcggtgt aggtcgttcg ctccaagctg ggctgtgtgc acgaaccccc    6660
cgttcagccc gaccgctgcg ccttatccgg taactatcgt cttgagtcca acccggtaag    6720
acacgactta tcgccactgg cagcagccac tggtaacagg attagcagag cgaggtatgt    6780
aggcggtgct acagagttct tgaagtggtg cctaactac ggctacacta agaacagt     6840 atttggtatc tgcgctctgc tgaagccagt taccttcgga aaagagttg gtagctcttg    6900 atccggcaaa caaaccaccg ctggtagcgg tggtttttt gtttgcaagc agcagattac    6960
gcgcagaaaa aaggatctc aagaagatcc tttgatcttt tctacggggt ctgacgctca    7020
gtggaacgaa aactcacgtt aagggatttt ggtcatgaga ttatcaaaaa ggatcttcac    7080
ctagatcctt ttaaattaaa aatgaagttt taaatcaatc taaagtatat atgagtaaac    7140
ttggtctgac agttaccaat gcttaatcag tgaggcacct atctcagcga tctgtctatt    7200
tcgttcatcc atagttgcct gactccccgt cgtgtagata actacgatac gggagggctt    7260
accatctggc cccagtgctg caatgatacc gcgagaccca cgctcaccgg ctccagattt    7320
atcagcaata accagccag ccggaagggc cgagcgcaga agtggtcctg caactttatc    7380
cgcctccatc cagtctatta attgttgccg ggaagctaga gtaagtagtt cgccagttaa    7440 tagtttcgc aacgttgttg ccattgctac aggcatcgtg gtgtcacgct cgtcgtttgg    7500
tatggcttca ttcagctccg gttcccaacg atcaaggcga gttacatgat cccccatgtt    7560
gtgcaaaaaa gcggttagct ccttcggtcc tccgatcgtt gtcagaagta agttggccgc    7620
agtgttatca ctcatggtta tggcagcact gcataattct cttactgtca tgccatccgt    7680
aagatgcttt tctgtgactg gtgagtactc aaccaagtca ttctgagaat agtgtatgcg    7740
gcgaccgagt tgctcttgcc cggcgtcaat acgggataat accgcgccac atagcagaac    7800
tttaaaagtg ctcatcattg gaaaacgttc ttcgggcga aaactctcaa ggatcttacc    7860
gctgttgaga tccagttcga tgtaacccac tcgtgcaccc aactgatctt cagcatcttt    7920
tactttcacc agcgtttctg ggtgagcaaa acaggaagg caaatgccg caaaaaggg    7980 aataagggcg acacggaaat gttgaatact catactcttc cttttcaat attattgaag    8040 catttatcag ggttattgtc tcatgagcgg atacatattt gaatgtattt agaaaaataa    8100
acaaataggg gttccgcgca catttccccg aaagtgcca cctgacgtct aagaaaccat    8160
tattatcatg acattaacct ataaaaatag gcgtatcacg aggccctttc gtctcgcgcg    8220
tttcggtgat gacggtgaaa acctctgaca catgcagctc ccggagacgg tcacagcttg    8280
```

| | |
|---|---:|
| tctgtaagcg gatgccggga gcagacaagc ccgtcagggc gcgtcagcgg gtgttggcgg | 8340 |
| gtgtcgggc tggcttaact atgcggcatc agagcagatt gtactgagag tgcaccaagc | 8400 |
| ttccaatttt aggcccccca ctgaccgagg tctgtcgata atccactttt ccattgattt | 8460 |
| tccaggtttc gttaactcat gccactgagc aaaacttcgg tctttcctaa caaaagctct | 8520 |
| cctcacaaag catggcgcgg caacggacgt gtcctcatac tccactgcca cacaaggtcg | 8580 |
| ataaactaag ctcctcacaa atagaggaga attccactga caactgaaaa caatgtatga | 8640 |
| gagacgatca ccactggagc ggcgcggcgg ttgggcgcgg aggtcggcag caaaaacaag | 8700 |
| cgactcgccg agcaaacccg aatcagcctt cagacggtcg tgcctaacaa cacgccgttc | 8760 |
| taccccgcct tcttcgcgcc ccttcgcgtc caagcatcct tcaagtttat ctctctagtt | 8820 |
| caacttcaag aagaacaaca ccaccaacac catgattgaa caagatggat tgcacgcagg | 8880 |
| ttctccggcc gcttgggtgg agaggctatt cggctatgac tgggcacaac agacaatcgg | 8940 |
| ctgctctgat gccgccgtgt tccggctgtc agcgcagggg cgcccggttc ttttgtcaa | 9000 |
| gaccgacctg tccggtgccc tgaatgaact gcaggacgag gcagcgcggc tatcgtggct | 9060 |
| ggccacgacg ggcgttcctt gcgcagctgt gctcgacgtt gtcactgaag cgggaaggga | 9120 |
| ctggctgcta ttgggcgaag tgccggggca ggatctcctg tcatctcacc ttgctcctgc | 9180 |
| cgagaaagta tccatcatgg ctgatgcaat gcggcggctg catacgcttg atccggctac | 9240 |
| ctgcccattc gaccaccaag cgaaacatcg catcgagcga gcacgtactc ggatggaagc | 9300 |
| cggtcttgtc gatcaggatg atctggacga agagcatcag gggctcgcgc cagccgaact | 9360 |
| gttcgccagg ctcaaggcgc gcatgcccga cggcgatgat ctcgtcgtga cccatggcga | 9420 |
| tgcctgcttg ccgaatatca tggtggaaaa tggccgcttt tctggattca tcgactgtgg | 9480 |
| ccggctgggt gtggcggacc gctatcagga catagcgttg gctacccgtg atattgctga | 9540 |
| agagcttggc ggcgaatggg ctgaccgctt cctcgtgctt tacggtatcg ccgctcccga | 9600 |
| ttcgcagcgc atcgccttct atcgccttct tgacgagttc ttctgacacg tgctacgaga | 9660 |
| tttcgattcc accgccgcct tctatgaaag gttgggcttc ggaatcgttt tccgggacgc | 9720 |
| cggctggatg atcctccagc gcggggatct catgctggag ttcttcgccc acccccaactt | 9780 |
| gtttattgca gcttataatg gttacaaata aagcaatagc atcacaaatt tcacaaataa | 9840 |
| agcattttt tcactgcatt ctagttgtgg tttgtccaaa ctcatcaatg tatcttatca | 9900 |
| tgtctgaatt cccggggtac | 9920 |

```
<210> SEQ ID NO 2
<211> LENGTH: 7393
<212> TYPE: DNA
<213> ORGANISM: Artificial Sequence
<220> FEATURE:
<223> OTHER INFORMATION: pYB31 vector
<220> FEATURE:
<221> NAME/KEY: misc_feature
<222> LOCATION: (2)..(450)
<223> OTHER INFORMATION: alpha_tubulin_promoter
<220> FEATURE:
<221> NAME/KEY: misc_feature
<222> LOCATION: (457)..(549)
<223> OTHER INFORMATION: Sec1_signal_for_eGFP
<220> FEATURE:
<221> NAME/KEY: misc_feature
<222> LOCATION: (550)..(1266)
<223> OTHER INFORMATION: eGFP
<220> FEATURE:
<221> NAME/KEY: misc_feature
<222> LOCATION: (1294)..(2293)
<223> OTHER INFORMATION: OrfA_terminator
```

```
<220> FEATURE:
<221> NAME/KEY: misc_feature
<222> LOCATION: (4971)..(5970)
<223> OTHER INFORMATION: OrfA_UP_homology
<220> FEATURE:
<221> NAME/KEY: misc_feature
<222> LOCATION: (5974)..(6289)
<223> OTHER INFORMATION: OrfC_terminator
<220> FEATURE:
<221> NAME/KEY: misc_feature
<222> LOCATION: (6296)..(6744)
<223> OTHER INFORMATION: alpha_tubulin_promoter
<220> FEATURE:
<221> NAME/KEY: misc_feature
<222> LOCATION: (6745)..(7119)
<223> OTHER INFORMATION: Sh_ble_gene
<220> FEATURE:
<221> NAME/KEY: misc_feature
<222> LOCATION: (7120)..(7393)
<223> OTHER INFORMATION: SV40_terminator

<400> SEQUENCE: 2 cccaattttta ggcccccccac tgaccgaggt ctgtcgataa tccacttttc cattgatttt      60
ccaggtttcg ttaactcatg ccactgagca aaacttcggt cttcctaac aaaagctctc      120 ctcacaaagc atggcgcggc aacggacgtg tcctcatact ccactgccac acaaggtcga      180
taaactaagc tcctcacaaa tagaggagaa ttccactgac aactgaaaac aatgtatgag      240
agacgatcac cactggagcg gcgcggcggt tgggcgcgga ggtcggcagc aaaaacaagc      300
gactcgccga gcaaacccga atcagccttc agacggtcgt gcctaacaac acgccgttct      360
accccgcctt cttcgcgccc cttcgcgtcc aagcatcctt caagtttatc tctctagttc      420
aacttcaaga agaacaacac caccaacacc ggatccatga agttcgcgac ctcggtcgca      480
attttgcttg tggccaacat agccaccgcc ctcgcgcaga gcgatggctg caccccccacc      540 gaccagacga tggtgagcaa gggcgaggag ctgttcaccg gggtggtgcc catcctggtc      600
gagctggacg gcgacgtaaa cggccacaag ttcagcgtgt ccggcgaggg cgagggcgat      660
gccacctacg gcaagctgac cctgaagttc atctgcacca ccggcaagct gcccgtgccc      720
tggcccaccc tcgtgaccac cctgacctac ggcgtgcagt gcttcagccg ctaccccgac      780
cacatgaagc agcacgactt cttcaagtcc gccatgcccg aaggctacgt ccaggagcgc      840
accatcttct tcaaggacga cggcaactac aagacccgcg ccgaggtgaa gttcgagggc      900
gacaccctgg tgaaccgcat cgagctgaag ggcatcgact tcaaggagga cggcaacatc      960
ctggggcaca gctggagta caactacaac agccacaacg tctatatcat ggccgacaag      1020
cagaagaacg gcatcaaggt gaacttcaag atccgccaca acatcgagga cggcagcgtg      1080
cagctcgccg accactacca gcagaacacc cccatcggcg acggccccgt gctgctgccc      1140
gacaaccact acctgagcac ccagtccgcc ctgagcaaag accccaacga gaagcgcgat      1200
cacatggtcc tgctggagtt cgtgaccgcc gccgggatca ctctcggcat ggacgagctg      1260
tacaagcacc accatcacca ccactaacat atgatctaaa ctagtgaatc gcgacaagtt      1320 gtcttttttgt tactctacgt actgctcttt ctaattttac gacgtatgct tctgctcttg      1380
acgacgacaa ccatggcaat aaaagtaagg caagaagtga gtgcgtgctc gctcacaagg      1440
tctaggccga aacgaggcgc cttaggattg gttgtctccg tcgtaagtca tgacggagcg      1500
taggacaccg acggcctgcc gcgcaaatat acgaaccgct gcacaattct tttcgttgag      1560
aacaacctcg aacggcctgc cttgctgagc tgccgacacg gtggaaggaa gcatagcggc      1620
caatcgaggg gatgctatta attaggcttg gcgctgctgc cgccgtgcct gaagatgtgc      1680
```

```
gcaagcgtgg caacaccgtc caccttgcca ttaaagtcat gcactccaaa tacctcgaac   1740
agagcctctc gcatgtttgg ccaagcacct tcgagagagt ctggactctc actccttcct   1800
caccgttgtc gccattctca gcgagctcat gcaatcacca ggacggagag acggccagct   1860
gcttttctgc tttccattgt tattagagaa acgcttctcg ctctcatcgt cttagtagac   1920
attccgatgg cttcgttcgc caatttgtca cctaagtaag ctagagtgtt aagtctaaat   1980
gcctttgacc cgcgtacggc gtcacgtaga tgcctgtcct tgccagcaaa cgctagttcg   2040
cggtgtgcgt aatttggccc gcattatgct ggctctcaaa atcaaccgcc accactcgcg   2100
gctgcacgat gattttcgtg cactcatgac atgagaaatg tgatactcaa actagtatag   2160
acctcctact cctactgctg cttttctcgt cagagctgtc tccggaaaag ttgacaagtt   2220
gttggccttc ttcttctctg ctagtaagta gatcatcatg gatgagacga tgatgataat   2280
gatgatgatg ataatttaaa tctcgagacc ttcgagcgct gctaatttcg cctgacgctc   2340
cttcttttgt gcttccatga cacgccgctt caccgtgcgt tccacttctt cctcagacat   2400
gcccttggct gcctcgacct gctcggtaaa acgggcccca gcacgtgcta cgagatttcg   2460
attccaccgc cgccttctat gaaaggttgg gcttcggaat cgttttccgg gacgccggct   2520
ggatgatcct ccagcgcggg gatctcatgc tggagttctt cgcccacccc aacttgttta   2580
ttgcagctta taatggttac aaataaagca atagcatcac aaatttcaca aataaagcat   2640
ttttttcact gcattctagt tgtggttttgt ccaaactcat caatgtatct tatcatacat   2700
ggtcgacctg caggaacctg cattaatgaa tcggccaacg cgcggggaga ggcggtttgc   2760
gtattgggcg ctcttccgct tcctcgctca ctgactcgct gcgctcggtc gttcggctgc   2820
ggcgagcggt atcagctcac tcaaaggcgg taatacggtt atccacagaa tcaggggata   2880
acgcaggaaa gaacatgtga gcaaaaggcc agcaaaaggc caggaaccgt aaaaaggccg   2940
cgttgctggc gttttttccat aggctccgcc ccctgacga gcatcacaaa aatcgacgct   3000
caagtcagag gtggcgaaac ccgacaggac tataaagata ccaggcgttt ccccctggaa   3060
gctccctcgt gcgctctcct gttccgaccc tgccgcttac cggatacctg tccgcctttc   3120
tcccttcggg aagcgtggcg ctttctcata gctcacgctg taggtatctc agttcggtgt   3180
aggtcgttcg ctccaagctg ggctgtgtgc acgaacccccc cgttcagccc gaccgctgcg   3240
ccttatccgg taactatcgt cttgagtcca acccggtaag acacgactta tcgccactgg   3300
cagcagccac tggtaacagg attagcagag cgaggtatgt aggcggtgct acagagttct   3360
tgaagtggtg gcctaactac ggctacacta gaagaacagt atttggtatc tgcgctctgc   3420
tgaagccagt taccttcgga aaaagagttg gtagctcttg atccggcaaa caaaccaccg   3480
ctggtagcgg tggttttttt gtttgcaagc agcagattac gcgcagaaaa aaaggatctc   3540
aagaagatcc tttgatcttt tctacggggt ctgacgctca gtggaacgaa aactcacgtt   3600
aagggatttt ggtcatgaga ttatcaaaaa ggatcttcac ctagatcctt ttaaattaaa   3660
aatgaagttt taaatcaatc taaagtatat atgagtaaac ttggtctgac agttaccaat   3720
gcttaatcag tgaggcacct atctcagcga tctgtctatt tcgttcatcc atagttgcct   3780
gactccccgt cgtgtagata actacgatac gggagggctt accatctggc cccagtgctg   3840
caatgatacc gcgagaccca cgctcaccgg ctccagattt atcagcaata aaccagccag   3900
ccggaagggc cgagcgcaga agtggtcctg caactttatc cgcctccatc cagtctatta   3960
attgttgccg ggaagctaga gtaagtagtt cgccagttaa tagtttgcgc aacgttgttg   4020
ccattgctac aggcatcgtg gtgtcacgct cgtcgtttgg tatggcttca ttcagctccg   4080
```

```
gttcccaacg atcaaggcga gttacatgat cccccatgtt gtgcaaaaaa gcggttagct    4140
ccttcggtcc tccgatcgtt gtcagaagta agttggccgc agtgttatca ctcatggtta    4200
tggcagcact gcataattct cttactgtca tgccatccgt aagatgcttt tctgtgactg    4260
gtgagtactc aaccaagtca ttctgagaat agtgtatgcg cgaccgagt tgctcttgcc     4320 cggcgtcaat acgggataat accgcgccac atagcagaac tttaaaagtg ctcatcattg    4380
gaaaacgttc ttcggggcga aaactctcaa ggatcttacc gctgttgaga tccagttcga    4440
tgtaacccac tcgtgcaccc aactgatctt cagcatcttt tactttcacc agcgtttctg    4500
ggtgagcaaa acaggaagg caaaatgccg caaaaaggg aataagggcg acacggaaat      4560
gttgaatact catactcttc cttttcaat attattgaag catttatcag ggttattgtc     4620
tcatgagcgg atacatattt gaatgtattt agaaaaataa acaaataggg gttccgcgca    4680
catttccccg aaaagtgcca cctgacgtct aagaaaccat tattatcatg acattaacct    4740
ataaaaatag gcgtatacg aggcccttc gtctcgcgcg tttcggtgat gacggtgaaa      4800
acctctgaca catgcagctc ccggagacgg tcacagcttg tctgtaagcg gatgccggga    4860
gcagacaagc ccgtcagggc gcgtcagcgg gtgttggcgg gtgtcgggc tggcttaact     4920 atgcggcatc agagcagatt gtactgagag tgcaccaagc ttatttaaat ctttatcggt    4980
gtggcgcgcc ttgacggccg cctcggattc acttcgcagg gcacttctga cgcgctcaag    5040
cgtgcccagc gtggtgccat cttggcctc tgcaagacca tcggcctcga gtggtccgag     5100
tctgacgtct ttcccgcgg cgtggacatt gctcagggca tgcacccga ggatgccgcc      5160 gtggcgattg tgcgcgagat ggcgtgcgct gacattcgca ttcgcgaggt cggcattggc    5220
gcaaaccagc agcgctgcac gatccgtgcc gccaagctcg agaccggcaa cccgcagcgc    5280
cagatcgcca aggacgacgt gctgctcgtt tctggcggcg ctcgcggcat cacgcctctt    5340
tgcatccggg agatcacgcg ccagatcgcg ggcggcaagt acattctgct tggccgcagc    5400
aaggtctctg cgagcgaacc ggcatggtgc gctggcatca ctgacgagaa ggctgtgcaa    5460
aaggctgcta cccaggagct caagcgcgcc tttagcgctg gcagggccc caagcccacg     5520 ccccgcgctg tcactaagct tgtgggctct gttcttggcg ctcgcgaggt gcgcagctct    5580
attgctgcga ttgaagcgct cggcggcaag gccatctact cgtcgtgcga cgtgaactct    5640
gccgccgacg tggccaaggc cgtgcgcgat gccgagtccc agctcggtgc ccgcgtctcg    5700
ggcatcgttc atgcctcggg cgtgctccgc gaccgtctca tcgagaagaa gctccccgac    5760
gagttcgacg ccgtctttgg caccaaggtc accggtctcg agaacctcct cgccgccgtc    5820
gaccgcgcca acctcaagca catggtcctc ttcagctcgc tcgccggctt ccacggcaac    5880
gtcggccagt ctgactacgc catggccaac gaggcccta acaagatggg cctcgagctc     5940
gccaaggacg tctcggtcaa gtcgatctgc taagaaagtg aaccttgtcc taacccgaca    6000
gcgaatggcg ggaggggcg ggctaaaaga tcgtattaca tagtattttc ccctactctt     6060
tgtgtttgtc tttttttttt ttgaacgcat tcaagccact tgtcttggtt tacttgtttg    6120
tttgcttgct tgcttgcttg cttgcctgct tcttggtcag acggaccaa aaaagggaaa     6180 aaattcattc atggcacaga taagaaaaag aaaaagtttg tcgaccaccg tcatcagaaa    6240
gcaagagaag agaaacactc gcgctcacat tctcgctcgc gtaagaatca agcttccaat    6300
tttaggcccc ccactgaccg aggtctgtcg ataatccact tttccattga ttttccaggt    6360
ttcgttaact catgccactg agcaaaactt cggtctttcc taacaaaagc tctcctcaca    6420
```

```
aagcatggcg cggcaacgga cgtgtcctca tactccactg ccacacaagg tcgataaact    6480
aagctcctca caaatagagg agaattccac tgacaactga aaacaatgta tgagagacga    6540
tcaccactgg agcggcgcgg cggttgggcg cggaggtcgg cagcaaaaac aagcgactcg    6600
ccgagcaaac ccgaatcagc cttcagacgg tcgtgcctaa caacacgccg ttctaccccg    6660
ccttcttcgc gccccttcgc gtccaagcat ccttcaagtt tatctctcta gttcaacttc    6720
aagaagaaca acaccaccaa caccatggcc aagttgacca gtgccgttcc ggtgctcacc    6780
gcgcgcgacg tcgccggagc ggtcgagttc tggaccgacc ggctcgggtt ctcccgggac    6840
ttcgtggagg acgacttcgc cggtgtggtc cgggacgacg tgaccctgtt catcagcgcg    6900
gtccaggacc aggtggtgcc ggacaacacc ctggcctggg tgtgggtgcg cggcctggac    6960
gagctgtacg ccgagtggtc ggaggtcgtg tccacgaact ccggacgcg ctccgggccg    7020 gccatgaccg agatcggcga gcagccgtgg gggcgggagt tcgccctgcg cgacccggcc    7080
ggcaactgcg tgcacttcgt ggccgaggag caggactgac acgtgctacg agatttcgat    7140
tccaccgccg ccttctatga aaggttgggc ttcggaatcg ttttccggga cgccggctgg    7200
atgatcctcc agcgcgggga tctcatgctg gagttcttcg cccacccccaa cttgtttatt    7260 gcagcttata atggttacaa ataaagcaat agcatcacaa atttcacaaa taaagcattt    7320
ttttcactgc attctagttg tggtttgtcc aaactcatca atgtatctta tcatgtctga    7380
attcccgggg tac                                                       7393
```

<210> SEQ ID NO 3
<211> LENGTH: 10702
<212> TYPE: DNA
<213> ORGANISM: Artificial Sequence
<220> FEATURE:
<223> OTHER INFORMATION: pYB32 vector
<220> FEATURE:
<221> NAME/KEY: misc_feature
<222> LOCATION: (2)..(450)
<223> OTHER INFORMATION: alpha tubulin promoter
<220> FEATURE:
<221> NAME/KEY: misc_feature
<222> LOCATION: (457)..(4596)
<223> OTHER INFORMATION: Cas9
<220> FEATURE:
<221> NAME/KEY: misc_feature
<222> LOCATION: (4603)..(5602)
<223> OTHER INFORMATION: OrfA terminator
<220> FEATURE:
<221> NAME/KEY: misc_feature
<222> LOCATION: (8280)..(9279)
<223> OTHER INFORMATION: OrfA UP homology
<220> FEATURE:
<221> NAME/KEY: misc_feature
<222> LOCATION: (9283)..(9598)
<223> OTHER INFORMATION: OrfC terminator
<220> FEATURE:
<221> NAME/KEY: misc_feature
<222> LOCATION: (9605)..(10053)
<223> OTHER INFORMATION: alpha tubulin promoter
<220> FEATURE:
<221> NAME/KEY: misc_feature
<222> LOCATION: (10054)..(10428)
<223> OTHER INFORMATION: Sh ble gene
<220> FEATURE:
<221> NAME/KEY: misc_feature
<222> LOCATION: (10429)..(10702)
<223> OTHER INFORMATION: SV40_terminator

<400> SEQUENCE: 3

```
cccaattttta ggcccccccac tgaccgaggt ctgtcgataa tccactttc cattgatttt     60 ccaggtttcg ttaactcatg ccactgagca aaacttcggt cttttcctaac aaaagctctc    120
```

```
ctcacaaagc atggcgcggc aacggacgtg tcctcatact ccactgccac acaaggtcga    180
taaactaagc tcctcacaaa tagaggagaa ttccactgac aactgaaaac aatgtatgag    240
agacgatcac cactggagcg gcgcggcggt tgggcgcgga ggtcggcagc aaaaacaagc    300
gactcgccga gcaaacccga atcagccttc agacggtcgt gcctaacaac acgccgttct    360
accccgcctt cttcgcgccc cttcgcgtcc aagcatcctt caagtttatc tctctagttc    420
aacttcaaga agaacaacac caccaacacc ggatccatgg ataagaagta ctcgatcggc    480
ctcgacattg gcaccaacag cgtcggctgg gccgtcatta ctgatgagta caaggtcccg    540
tcgaagaagt ttaaggtcct cggcaacact gaccgccact ccatcaagaa gaacctcatc    600
ggtgccctcc tttttgactc cggcgagacc gctgaggcca ctcgcctcaa gcgcactgcc    660
cgccgccgtt acacccgccg caagaaccgc atctgctacc tccaggagat tttctcgaac    720
gaaatggcca aggtcgatga ctccttttc caccgtctcg aagaatcgtt cctcgtcgag    780
gaggacaaga agcacgagcg ccaccccatc ttcggtaaca ttgtcgatga ggttgcctac    840
cacgagaagt acccgaccat ctaccacctc cgcaagaagc tcgtcgactc caccgacaag    900
gccgatctcc gccttatcta cctcgccctc gcccacatga tcaagttccg cggccacttt    960
cttatcgagg gtgatctcaa ccctgataac tctgacgtcg acaagctttt catccagctc   1020
gtccagactt acaaccagct cttcgaggag aacccccatca acgcttccgg cgtcgacgcg   1080
aaggccattc tcagcgcccg cctcagcaag tcccgccgcc tcgaaaacct cattgcccag   1140
cttcccggcg agaagaagaa cggcctcttc ggcaacctca ttgccctcag ccttggcctc   1200
acccctaact tcaagtcgaa cttgacctc gccgaggacg ccaagctcca gctttccaag   1260
gacacttacg acgacgatct cgacaacctc ctcgctcaga ttggcgacca gtacgctgac   1320
ctcttcctcg ccgccaagaa cctagcgat gccatcctcc tctccgacat ccttcgtgtt   1380
aacacggaaa tcacgaaggc tccgctctcc gcctccatga tcaagcgtta cgacgagcac   1440
catcaggacc tcacctcct caaggccctc gtccgccagc agctccccga agtacaag     1500 gagatcttct tcgaccagag caagaacggc tacgccggct acattgacgg cggcgcgtcg   1560
caggaggagt tttacaagtt tatcaagccc attcttgaga gatggacgg caccgaggag   1620 ctcctcgtca agctcaaccg tgaggacctt ctccgcaagc agcgcacgtt cgacaacggc   1680
tctattcccc atcagatcca cctcggtgag cttcacgcga ttcttcgccg ccaggaagac   1740
ttttacccgt tcctcaagga caaccgcgag aagattgaga agatcctcac ctttcgcatt   1800
ccctactacg tcggcccccct cgcccgcggc aactcgcgct ttgcttggat gacccgcaag   1860
tccgaggaga ccatcacccc gtggaacttc gaagaggtcg tcgacaaggg cgcctccgcg   1920
cagtctttca tcgagcgcat gactaacttt gacaagaacc tccgaacga gaaggtcctc   1980 cccaagcaca gcctcctta cgaatacttt acggtgtaca acgagctcac gaaggtcaag   2040
tacgtcactg agggcatgcg caagccggcg ttcctttcgg gcgagcagaa gaaggctatc   2100
gtcgacctcc ttttcaagac caaccgcaag gttaccgtca agcagctcaa ggaggactac   2160
ttcaagaaga tcgagtgctt tgactcggtc gagatttcgg gcgtggagga ccgtttcaac   2220
gcctccctcg gcacttacca cgaccttctc aagatcatca aggacaagga ctttctcgac   2280
aacgaggaga acgaggacat tctcgaggac atcgtcctca cgctcaccct ctttgaggac   2340
cgtgagatga tcgaggagcg cctcaagacc tacgcccatc tctttgacga caaggtcatg   2400
aagcagctca agcgccgccg ctacaccggc tggggccgcc tttcccgcaa gctcatcaac   2460
```

```
ggcatccgcg acaagcagtc tggcaagacc atccttgact ttcttaagtc tgatggtttc    2520
gccaaccgca acttcatgca gctcatccac gacgacagcc tcactttcaa ggaggacatt    2580
cagaaggccc aggtctccgg ccagggtgac tctctccacg aacacatcgc caaccttgct    2640
ggcagcccgg ctattaagaa gggcatcctc cagaccgtca aggtcgtcga cgagctcgtc    2700
aaggttatgg gccgccacaa gcccgagaac atcgtcattg agatggctcg cgaaaaccag    2760
accacccaga agggtcagaa gaactcccgc gagcgcatga agcgtatcga ggagggcatc    2820
aaggagctcg gcagccagat cctcaaggag cacccggtcg agaacaccca gctccagaac    2880
gaaaagctct acctctacta cctccagaac ggccgtgaca tgtacgttga ccaggagctc    2940
gacattaacc gcctctccga ttacgacgtc gaccatattg tcccccagag ctttctcaag    3000
gacgacagca tcgacaacaa ggtcctcacc cgctcggaca agaaccgcgg caagtccgac    3060
aacgtcccct tccgaggagg tcgtgaagaag atgaagaact actggcgcca gcttctcaac    3120
gctaagctta ttactcagcg caagttcgat aacctcacca aggccgaacg cggcggcctc    3180
tccgagctcg acaaggccgg ttttatcaag cgccagctcg ttgagactcg ccagatcacc    3240
aagcacgtgg cgcagatcct cgactcgcgc atgaacacga agtacgacga aacgacaag    3300 ctcatccgcg aggtcaaggt catcacccct aagtcgaagc tcgtgtccga cttccgcaag    3360
gacttccagt tctacaaggt ccgtgaaatt aacaactacc accacgctca cgacgcttac    3420
ctcaacgcgg tcgtgggtac cgcgctcatc aagaagtacc cgaagctcga gtcggagttt    3480
gtctacggcg actacaaggt ctacgacgtg cgcaagatga tcgccaagtc cgagcaggag    3540
atcggcaagg ccacgccaa gtacttttc tactccaaca ttatgaactt ctttaagact    3600
gagatcaccc ttgccaacgg cgagatccgc aagcgccccc ttatcgagac caacggcgag    3660
accggcgaaa ttgtgtggga taagggtcgc gactttgcca ccgtccgcaa ggtcctcagc    3720
atgccccagg tcaacattgt taagaagacc gaggtccaga cgggcggctt tagcaaggag    3780
tctatcctcc ccaagcgtaa cagcgacaag ctcatcgccc gcaagaagga ctgggaccct    3840
aagaagtacg gcggcttcga ttcgcctacg gtcgcctaca gcgtcctcgt cgtcgccaag    3900
gtcgagaagg gcaagtccaa gaagctcaag tccgtcaagg agctcctcgg catcacgatc    3960
atggagcgct ccagctttga gaagaacccc attgacttcc tcgaggctaa gggttacaag    4020
gaggtcaaga gaggaccttat catcaagctc cccaagtact ccctctttga gctcgaaaac    4080
ggccgcaagc gtatgctcgc tagcgctggc gaactccaga gggcaacga gctcgccctc    4140 cccagcaagt acgtcaactt tctctacctc gcctcccact acgagaagct caagggtagc    4200
ccggaggata acgagcagaa gcagctttttt gtggagcagc acaagcacta ccttgacgag    4260
atcattgaac agatctccga gttctccaag cgtgttattc ttgctgacgc caacctcgat    4320
aaggtgctct ccgcgtacaa caagcaccgc gacaagccta tccgcgagca ggccgagaac    4380
atcatccacc tctttaccct caccaacctc ggcgccccgg ccgcctttaa gtactttgat    4440
acgactatcg accgcaagcg ctacacttcg actaaggagg tcctcgacgc taccctcatt    4500
caccagtcca ttaccggcct ctacgagacc cgcattgacc tttcgcagct cggtggcgac    4560
tcgcgtgcgg accctaagaa gaagcgcaag gtctaacata tgatctaaac tagtgaatcg    4620
cgacaagttg tctttttgtt actctacgta ctgctctttc taattttacg acgtatgctt    4680
ctgctcttga cgacgacaac catggcaata aaagtaaggc aagaagtgag tgcgtgctcg    4740
ctcacaaggt ctaggccgaa acgaggcgcc ttaggattgg ttgtctccgt cgtaagtcat    4800
gacggagcgt aggacaccga cggcctgccg cgcaaatata cgaaccgctg cacaattctt    4860
```

| | | | | |
|---|---|---|---|---|
| ttcgttgaga | acaacctcga | acggcctgcc | ttgctgagct | gccgacacgg | tggaaggaag | 4920 |
| catagcggcc | aatcgagggg | atgctattaa | ttaggcttgg | cgctgctgcc | gccgtgcctg | 4980 |
| aagatgtgcg | caagcgtggc | aacaccgtcc | accttgccat | taaagtcatg | cactccaaat | 5040 |
| acctcgaaca | gagcctctcg | catgtttggc | caagcacctt | cgagagagtc | tggactctca | 5100 |
| ctccttcctc | accgttgtcg | ccattctcag | cgagctcatg | caatcaccag | gacggagaga | 5160 |
| cggccagctg | cttttctgct | ttccattgtt | attagagaaa | cgcttctcgc | tctcatcgtc | 5220 |
| ttagtagaca | ttccgatggc | ttcgttcgcc | aatttgtcac | ctaagtaagc | tagagtgtta | 5280 |
| agtctaaatg | cctttgaccc | gcgtacggcg | tcacgtagat | gcctgtcctt | gccagcaaac | 5340 |
| gctagttcgc | ggtgtgcgta | atttggcccg | cattatgctg | gctctcaaaa | tcaaccgcca | 5400 |
| ccactcgcgc | ctgcacgatg | attttcgtgc | actcatgaca | tgagaaatgt | gatactcaaa | 5460 |
| ctagtataga | cctcctactc | ctactgctgc | ttttctcgtc | agagctgtct | ccggaaaagt | 5520 |
| tgacaagttg | ttggccttct | tcttctctgc | tagtaagtag | atcatcatgg | atgagacgat | 5580 |
| gatgataatg | atgatgatga | taatttaaat | ctcgagacct | cgagcgctg | ctaatttcgc | 5640 |
| ctgacgctcc | ttcttttgtg | cttccatgac | acgccgcttc | accgtgcgtt | ccacttcttc | 5700 |
| ctcagacatg | cccttggctg | cctcgacctg | ctcggtaaaa | cgggccccag | cacgtgctac | 5760 |
| gagatttcga | ttccaccgcc | gccttctatg | aaaggttggg | cttcggaatc | gttttccggg | 5820 |
| acgccggctg | gatgatcctc | cagcgcgggg | atctcatgct | ggagttcttc | gcccaccca | 5880 |
| acttgtttat | tgcagcttat | aatggttaca | aataaagcaa | tagcatcaca | aatttcacaa | 5940 |
| ataaagcatt | ttttcactg | cattctagtt | gtggtttgtc | caaactcatc | aatgtatctt | 6000 |
| atcatacatg | gtcgacctgc | aggaacctgc | attaatgaat | cggccaacgc | gcggggagag | 6060 |
| gcggtttgcg | tattgggcgc | tcttccgctt | cctcgctcac | tgactcgctg | cgctcggtcg | 6120 |
| ttcggctgcg | gcgagcggta | tcagctcact | caaaggcggt | aatacggtta | tccacagaat | 6180 |
| caggggataa | cgcaggaaag | aacatgtgag | caaaaggcca | gcaaaaggcc | aggaaccgta | 6240 |
| aaaaggccgc | gttgctggcg | ttttccata | ggctccgccc | ccctgacgag | catcacaaaa | 6300 |
| atcgacgctc | aagtcagagg | tggcgaaacc | cgacaggact | ataaagatac | caggcgtttc | 6360 |
| cccctggaag | ctccctcgtg | cgctctcctg | ttccgaccct | gccgcttacc | ggatacctgt | 6420 |
| ccgcctttct | cccttcggga | agcgtggcgc | tttctcatag | ctcacgctgt | aggtatctca | 6480 |
| gttcggtgta | ggtcgttcgc | tccaagctgg | gctgtgtgca | cgaaccccc | gttcagcccg | 6540 |
| accgctgcgc | cttatccggt | aactatcgtc | ttgagtccaa | cccggtaaga | cacgacttat | 6600 |
| cgccactggc | agcagccact | ggtaacagga | ttagcagagc | gaggtatgta | ggcggtgcta | 6660 |
| cagagttctt | gaagtggtgg | cctaactacg | gctacactag | aagaacagta | tttggtatct | 6720 |
| gcgctctgct | gaagccagtt | accttcggaa | aaagagttgg | tagctcttga | tccggcaaac | 6780 |
| aaaccaccgc | tggtagcggt | ggttttttg | tttgcaagca | gcagattacg | cgcagaaaaa | 6840 |
| aaggatctca | agaagatcct | ttgatctttt | ctacgggtc | tgacgctcag | tggaacgaaa | 6900 |
| actcacgtta | agggattttg | gtcatgagat | tatcaaaaag | gatcttcacc | tagatccttt | 6960 |
| taaattaaaa | atgaagtttt | aaatcaatct | aaagtatata | tgagtaaact | tggtctgaca | 7020 |
| gttaccaatg | cttaatcagt | gaggcaccta | tctcagcgat | ctgtctattt | cgttcatcca | 7080 |
| tagttgcctg | actccccgtc | gtgtagataa | ctacgatacg | ggagggctta | ccatctggcc | 7140 |
| ccagtgctgc | aatgataccg | cgagacccac | gctcaccggc | tccagattta | tcagcaataa | 7200 |

```
accagccagc cggaagggcc gagcgcagaa gtggtcctgc aactttatcc gcctccatcc    7260
agtctattaa ttgttgccgg gaagctagag taagtagttc gccagttaat agtttgcgca    7320
acgttgttgc cattgctaca ggcatcgtgg tgtcacgctc gtcgtttggt atggcttcat    7380
tcagctccgg ttcccaacga tcaaggcgag ttacatgatc ccccatgttg tgcaaaaaag    7440
cggttagctc cttcggtcct ccgatcgttg tcagaagtaa gttggccgca gtgttatcac    7500
tcatggttat ggcagcactg cataattctc ttactgtcat gccatccgta agatgctttt    7560
ctgtgactgg tgagtactca accaagtcat tctgagaata gtgtatgcgg cgaccgagtt    7620
gctcttgccc ggcgtcaata cgggataata ccgcgccaca tagcagaact ttaaaagtgc    7680
tcatcattgg aaaacgttct cggggcgaaa actctcaag gatcttaccg ctgttgagat     7740
ccagttcgat gtaacccact cgtgcaccca actgatcttc agcatctttt actttcacca    7800
gcgtttctgg gtgagcaaaa acaggaaggc aaaatgccgc aaaaaaggga ataagggcga    7860
cacggaaatg ttgaatactc atactcttcc tttttcaata ttattgaagc atttatcagg    7920
gttattgtct catgagcgga tacatatttg aatgtatttta gaaaaataaa caaataggggg   7980 ttccgcgcac atttccccga aaagtgccac ctgacgtcta agaaaccatt attatcatga    8040
cattaaccta taaaaatagg cgtatcacga ggccctttcg tctcgcgcgt ttcggtgatg    8100
acggtgaaaa cctctgacac atgcagctcc cggagacggt cacagcttgt ctgtaagcgg    8160
atgccgggag cagacaagcc cgtcagggcg cgtcagcggg tgttggcggg tgtcggggct    8220
ggcttaacta tgcggcatca gagcagattg tactgagagt gcaccaagct tatttaaatc    8280
tttatcggtg tggcgcgcct tgacggccgc ctcggattca cttcgcaggg cacttctgac    8340
gcgctcaagc gtgcccagcg tggtgccatc tttggcctct gcaagaccat cggcctcgag    8400
tggtccgagt ctgacgtctt ttcccgcggc gtggacattg ctcagggcat gcaccccgag    8460
gatgccgccg tggcgattgt gcgcgagatg gcgtgcgctg acattcgcat tcgcgaggtc    8520
ggcattggcg caaaccagca gcgctgcacg atccgtgccg ccaagctcga gaccggcaac    8580
ccgcagcgcc agatcgccaa ggacgacgtg ctgctcgttt ctggcggcgc tcgcggcatc    8640 acgcctctt gcatccggga gatcacgcgc cagatcgcgg gcggcaagta cattctgctt     8700
ggccgcagca aggtctctgc gagcgaaccg gcatggtgcg ctggcatcac tgacgagaag    8760
gctgtgcaaa aggctgctac ccaggagctc aagcgcgcct ttagcgctgg cgagggcccc    8820
aagcccacgc cccgcgctgt cactaagctt gtgggctctg ttcttggcgc tcgcgaggtg    8880
cgcagctcta ttgctgcgat tgaagcgctc ggcggcaagg ccatctactc gtcgtgcgac    8940
gtgaactctg ccgccgacgt ggccaaggcc gtgcgcgatg ccgagtccca gctcggtgcc    9000
cgcgtctcgg gcatcgttca tgcctcgggc gtgctccgcg accgtctcat cgagaagaag    9060
ctccccgacg agttcgacgc cgtctttggc accaaggtca ccggtctcga gaacctcctc    9120
gccgccgtcg accgcgccaa cctcaagcac atggtcctct tcagctcgct cgccggcttc    9180
cacggcaacg tcgccagtc tgactacgcc atggccaacg aggcccttaa caagatgggc    9240
ctcgagctcg ccaaggacgt ctcggtcaag tcgatctgct aagaaagtga accttgtcct    9300
aacccgacag cgaatggcgg gaggggggcgg gctaaaagat cgtattacat agtattttcc    9360
cctactcttt gtgtttgtct tttttttttt tgaacgcatt caagccactt gtcttggttt    9420
acttgtttgt ttgcttgctt gcttgcttgc ttgcctgctt cttggtcaga cggacccaaa    9480
aaagggaaaa aattcattca tggcacagat aagaaaaaga aaaagtttgt cgaccaccgt    9540
catcagaaag caagagaaga gaaacactcg cgctcacatt ctcgctcgcg taagaatcaa    9600
```

-continued

```
gcttccaatt ttaggcccccc cactgaccga ggtctgtcga taatccactt ttccattgat    9660
tttccaggtt tcgttaactc atgccactga gcaaaacttc ggtctttcct aacaaaagct    9720
ctcctcacaa agcatggcgc ggcaacggac gtgtcctcat actccactgc cacacaaggt    9780
cgataaacta agctcctcac aaatagagga gaattccact gacaactgaa aacaatgtat    9840
gagagacgat caccactgga gcggcgcggc ggttgggcgc ggaggtcggc agcaaaaaca    9900
agcgactcgc cgagcaaacc cgaatcagcc ttcagacggt cgtgcctaac aacacgccgt    9960
tctaccccgc cttcttcgcg ccccttcgcg tccaagcatc cttcaagttt atctctctag   10020
ttcaacttca agaagaacaa caccaccaac accatggcca agttgaccag tgccgttccg   10080
gtgctcaccg cgcgcgacgt cgccggagcg gtcgagttct ggaccgaccg gctcgggttc   10140
tcccgggact tcgtggagga cgacttcgcc ggtgtggtcc gggacgacgt gaccctgttc   10200
atcagcgcgg tccaggacca ggtggtgccg gacaacaccc tggcctgggt gtgggtgcgc   10260
ggcctggacg agctgtacgc cgagtggtcg gaggtcgtgt ccacgaactt ccgggacgcc   10320
tccgggccgg ccatgaccga gatcggcgag cagccgtggg ggcgggagtt cgccctgcgc   10380
gacccggccg gcaactgcgt gcacttcgtg gccgaggagc aggactgaca cgtgctacga   10440
gatttcgatt ccaccgccgc cttctatgaa aggttgggct tcggaatcgt tttccgggac   10500
gccggctgga tgatcctcca gcgcggggat ctcatgctgg agttcttcgc ccaccccaac   10560
ttgtttattg cagcttataa tggttacaaa taaagcaata gcatcacaaa tttcacaaat   10620
aaagcatttt tttcactgca ttctagttgt ggtttgtcca aactcatcaa tgtatcttat   10680
catgtctgaa ttcccggggt ac                                             10702
```

<210> SEQ ID NO 4
<211> LENGTH: 11332
<212> TYPE: DNA
<213> ORGANISM: Artificial Sequence
<220> FEATURE:
<223> OTHER INFORMATION: pYB33 vector
<220> FEATURE:
<221> NAME/KEY: misc_feature
<222> LOCATION: (2)..(1006)
<223> OTHER INFORMATION: CS_promoter
<220> FEATURE:
<221> NAME/KEY: misc_feature
<222> LOCATION: (1013)..(5152)
<223> OTHER INFORMATION: Cas9
<220> FEATURE:
<221> NAME/KEY: misc_feature
<222> LOCATION: (5159)..(6158)
<223> OTHER INFORMATION: OrfA_terminator
<220> FEATURE:
<221> NAME/KEY: misc_feature
<222> LOCATION: (8836)..(9835)
<223> OTHER INFORMATION: OrfA_UP_homology
<220> FEATURE:
<221> NAME/KEY: misc_feature
<222> LOCATION: (9839)..(10154)
<223> OTHER INFORMATION: OrfC_terminator
<220> FEATURE:
<221> NAME/KEY: misc_feature
<222> LOCATION: (10161)..(10609)
<223> OTHER INFORMATION: alpha_tubulin_promoter
<220> FEATURE:
<221> NAME/KEY: misc_feature
<222> LOCATION: (10610)..(10984)
<223> OTHER INFORMATION: Sh_ble_gene
<220> FEATURE:
<221> NAME/KEY: misc_feature
<222> LOCATION: (10985)..(11258)
<223> OTHER INFORMATION: SV40_terminator

<400> SEQUENCE: 4

```
cgagcgggcg attccaccgt caactggtct tcgcctgtgc cttccagcgc agtgcgcctt      60
gccccgctcg gtcttattat tcttggcgct ctcgtcaatg tgatcatgat ctagtcgaac     120
gtgcaatcta gccaatgaaa aaagagtcca gttctatctg aattttttcac tttctaaatc    180
tcgcatcgac aatctacttt tcaaatctcg caacaaagct gatcttgttt ctccctcacc     240
cagttctatc tgaattttttc cttttctgaa gctcgcgtta caatctact tttcgaatct     300
gtcaacaaag ctgatcttgt ttctccccccc tatccccttc cctcccccct tctttgggat    360
cttgttgtgc gtgtcgcccc ttcaacttct ttgttcgacg atgacctcca cctagcctgt     420
gaagctcatc gtctccgagt atttctggcc tgctccaatt cctctcttcc attctccatc     480
gcatacatgc atgttctttg gtctcactcc gagccatgct tcttcggtca ctacttcatc     540
tatttgacta ggcctctgtt cgagcgacga accctccgtg ttcgcgggtg ttcattctct     600
gcaaagtggt ccgtaaccgt gactaccgga cacctcgcgt acactacatt cgggacggac     660
gcggccgagc gcgacgtctc tgggcccggc ctgccgcccc cggggccgcg gcttcctcgc     720
gccgccagcc gcgtccaagt cgccagcgcg aggtcgcgcg agtcgaagga gacgttgtcg     780
atctcgaccc tcgccatgcg cgtgacgggt gaccgcctca ccggatcccg ccctccgcgc     840
gctgccttca ttccttcatt ccttcattcc ttcactcaat cctgcatcat ccatcgcccg     900
cccgcccgct cgcacgcacc agaggcgcgc attgcgggcc agggcgccgc ctgcagaccg     960
ccatcgcgcc cgccttctgc cgcgcctcgc tcgctcggag accgagggat ccatggataa    1020
gaagtactcg atcggcctcg acattggcac caacagcgtc ggctgggccg tcattactga    1080
tgagtacaag gtcccgtcga agaagtttaa ggtcctcggc aacactgacc gccactccat    1140
caagaagaac ctcatcggtg ccctcctttt tgactccggc gagaccgctg aggccactcg    1200
cctcaagcgc actgcccgcc gccgttacac ccgccgcaag aaccgcatct gctacctcca    1260
ggagattttt tcgaacgaaa tggccaaggt cgatgactcc ttttttccacc gtctcgaaga    1320
atcgttcctc gtcgaggagg acaagaagca cgagcgccac cccatcttcg gtaacattgt    1380
cgatgaggtt gcctaccacg agaagtaccc gaccatctac cacctccgca agaagctcgt    1440
cgactccacc gacaaggccg atctccgcct tatctacctc gccctcgccc acatgatcaa    1500
gttccgcggc cactttctta tcgagggtga tctcaaccct gataactctg acgtcgacaa    1560
gcttttcatc cagctcgtcc agacttacaa ccagctcttc gaggagaacc ccatcaacgc    1620
ttccggcgtc gacgcgaagg ccattctcag cgcccgcctc agcaagtccc gccgcctcga    1680
aaacctcatt gcccagcttc ccggcgagaa gaagaacggc ctcttcggca acctcattgc    1740
cctcagcctt ggcctcaccc ctaacttcaa gtcgaacttt gacctcgccg aggacgccaa    1800
gctccagctt tccaaggaca cttacgacga cgatctcgac aacctcctcg ctcagattgg    1860
cgaccagtac gctgacctct tcctcgccgc caagaacctt agcgatgcca tcctcctctc    1920
cgacatcctt cgtgttaaca cggaaatcac gaaggctccg ctctccgcct ccatgatcaa    1980
gcgttacgac gagcaccatc aggacctcac cctcctcaag gccctcgtcc gccagcagct    2040
ccccgagaag tacaaggaga tcttcttcga ccagagcaag aacggctacg ccggctacat    2100
tgacggcggc gcgtcgcagg aggagtttta caagtttatc aagcccattc ttgagaagat    2160
ggacggcacc gaggagctcc tcgtcaagct caaccgtgag gacctctccc gcaagcagcg    2220
cacgttcgac aacggctcta ttccccatca gatccacctc ggtgagcttc acgcgattct    2280
tcgccgccag gaagactttt acccgttcct caaggacaac cgcgagaaga ttgagaagat    2340
```

```
cctcacctttt cgcattccct actacgtcgg ccccctcgcc cgcggcaact cgcgctttgc    2400
ttggatgacc cgcaagtccg aggagaccat caccccgtgg aacttcgaag aggtcgtcga    2460
caagggcgcc tccgcgcagt ctttcatcga gcgcatgact aactttgaca agaacctccc    2520
gaacgagaag gtcctcccca agcacagcct cctttacgaa tactttacgg tgtacaacga    2580
gctcacgaag gtcaagtacg tcactgaggg catgcgcaag ccggcgttcc tttcgggcga    2640
gcagaagaag gctatcgtcg acctccttttt caagaccaac cgcaaggtta ccgtcaagca    2700
gctcaaggag gactacttca agaagatcga gtgctttgac tcggtcgaga tttcgggcgt    2760
ggaggaccgt ttcaacgcct ccctcggcac ttaccacgac cttctcaaga tcatcaagga    2820
caaggacttt ctcgacaacg aggagaacga ggacattctc gaggacatcg tcctcacgct    2880 cacccctcttt gaggaccgtg agatgatcga ggagcgcctc aagacctacg cccatctctt    2940
tgacgacaag gtcatgaagc agctcaagcg ccgccgctac accggctggg gccgcctttc    3000
ccgcaagctc atcaacggca tccgcgacaa gcagtctggc aagaccatcc ttgactttct    3060
taagtctgat ggtttcgcca accgcaactt catgcagctc atccacgacg acagcctcac    3120
tttcaaggag gacattcaga aggcccaggt ctccggccag ggtgactctc tccacgaaca    3180
catcgccaac cttgctggca gcccggctat taagaagggc atcctccaga ccgtcaaggt    3240
cgtcgacgag ctcgtcaagg ttatgggccg ccacaagccc gagaacatcg tcattgagat    3300
ggctcgcgaa aaccagacca cccagaaggg tcagaagaac tcccgcgagc gcatgaagcg    3360
tatcgaggag ggcatcaagg agctcggcag ccagatcctc aaggagcacc cggtcgagaa    3420
cacccagctc cagaacgaaa agctctacct ctactacctc cagaacggcc gtgacatgta    3480
cgttgaccag gagctcgaca ttaaccgcct ctccgattac gacgtcgacc atattgtccc    3540
ccagagcttt ctcaaggacg acagcatcga caacaaggtc ctcacccgct cggacaagaa    3600
ccgcggcaag tccgacaacg tcccttccga ggaggtcgtg aagaagatga agaactactg    3660
gcgccagctt ctcaacgcta agcttattac tcagcgcaag ttcgataacc tcaccaaggc    3720
cgaacgcggc ggcctctccg agctcgacaa ggccggtttt atcaagcgcc agctcgttga    3780
gactcgccag atcaccaagc acgtggcgca gatcctcgac tcgcgcatga acacgaagta    3840
cgacgagaac gacaagctca tccgcgaggt caaggtcatc acccttaagt cgaagctcgt    3900
gtccgacttt cgcaaggact tccagttcta caaggtccgt gaaattaaca actaccacca    3960
cgctcacgac gcttacctca acgcggtcgt gggtaccgcg ctcatcaaga agtacccgaa    4020
gctcgagtcg gagtttgtct acggcgacta caaggtctac gacgtgcgca agatgatcgc    4080
caagtccgag caggagatcg gcaaggccac ggccaagtac tttttctact ccaacattat    4140
gaacttcttt aagactgaga tcaccccttgc caacggcgga atccgcaagc gccccttat    4200 cgagaccaac ggcgagaccg gcgaaattgt gtgggataag ggtcgcgact ttgccaccgt    4260
ccgcaaggtc ctcagcatgc cccaggtcaa cattgttaag aagaccgagg tccagacggg    4320
cggctttagc aaggagtcta tcctccccca gcgtaacagc gacaagctca tcgcccgcaa    4380
gaaggactgg gaccctaaga agtacggcgg cttcgattcg cctacggtcg cctacagcgt    4440
cctcgtcgtc gccaaggtcg agaagggcaa gtccaagaag ctcaagtccg tcaaggagct    4500
cctcggcatc acgatcatgg agcgctccag ctttgagaag aaccccattg acttcctcga    4560
ggctaagggt acaaggaggg tcaagaagga ccttatcatc aagctcccca gtactccct    4620 ctttgagctc gaaaacggcc gcaagcgtat gctcgctagc gctggcgaac tccagaaggg    4680
```

```
caacgagctc gccctcccca gcaagtacgt caactttctc tacctcgcct cccactacga    4740
gaagctcaag ggtagcccgg aggataacga gcagaagcag cttttttgtgg agcagcacaa    4800
gcactacctt gacgagatca ttgaacagat ctccgagttc tccaagcgtg ttattcttgc    4860
tgacgccaac ctcgataagg tgctctccgc gtacaacaag caccgcgaca agcctatccg    4920
cgagcaggcc gagaacatca tccacctctt taccctcacc aacctcggcg ccccggccgc    4980
ctttaagtac tttgatacga ctatcgaccg caagcgctac acttcgacta aggaggtcct    5040
cgacgctacc ctcattcacc agtccattac cggcctctac gagacccgca ttgacctttc    5100
gcagctcggt ggcgactcgc gtgcggaccc taagaagaag cgcaaggtct aacatatgat    5160
ctaaactagt gaatcgcgac aagttgtctt tttgttactc tacgtactgc tctttctaat    5220
tttacgacgt atgcttctgc tcttgacgac gacaaccatg gcaataaaag taaggcaaga    5280
agtgagtgcg tgctcgctca caaggtctag gccgaaacga ggcgccttag gattggttgt    5340
ctccgtcgta agtcatgacg gagcgtagga caccgacggc ctgccgcgca aatatacgaa    5400
ccgctgcaca attctttcg ttgagaacaa cctcgaacgg cctgccttgc tgagctgccg    5460
acacggtgga aggaagcata gcggccaatc gaggggatgc tattaattag gcttggcgct    5520
gctgccgccg tgcctgaaga tgtgcgcaag cgtggcaaca ccgtccacct tgccattaaa    5580
gtcatgcact ccaaatacct cgaacagagc ctctcgcatg tttggccaag caccttcgag    5640
agagtctgga ctctcactcc ttcctcaccg ttgtcgccat tctcagcgag ctcatgcaat    5700
caccaggacg gagagacggc cagctgcttt tctgctttcc attgttatta gagaaacgct    5760
tctcgctctc atcgtcttag tagacattcc gatggcttcg ttcgccaatt tgtcacctaa    5820
gtaagctaga gtgttaagtc taaatgcctt tgacccgcgt acggcgtcac gtagatgcct    5880
gtccttgcca gcaaacgcta gttcgcggtg tgcgtaattt ggcccgcatt atgctggctc    5940
tcaaaatcaa ccgccaccac tcgcggctgc acgatgattt tcgtgcactc atgacatgag    6000
aaatgtgata ctcaaactag tatagacctc ctactcctac tgctgctttt ctcgtcagag    6060
ctgtctccgg aaaagttgac aagttgttgg ccttcttctt ctctgctagt aagtagatca    6120
tcatggatga gacgatgatg ataatgatga tgatgataat ttaaatctcg agaccttcga    6180
gcgctgctaa tttcgcctga cgctccttct tttgtgcttc catgacacgc cgcttcaccg    6240
tgcgttccac ttcttcctca gacatgccct ggctgcctc gacctgctcg gtaaaacggg    6300
ccccagcacg tgctacgaga tttcgattcc accgccgcct tctatgaaag gttgggcttc    6360
ggaatcgttt tccgggacgc cggctggatg atcctccagc gcgggatct catgctggag    6420
ttcttcgccc accccaactt gtttattgca gcttataatg gttacaaata aagcaatagc    6480
atcacaaatt tcacaaataa agcatttttt tcactgcatt ctagttgtgg tttgtccaaa    6540
ctcatcaatg tatcttatca tacatggtcg acctgcagga acctgcatta atgaatcggc    6600
caacgcgcgg ggagaggcgg tttgcgtatt gggcgctctt ccgcttcctc gctcactgac    6660
tcgctgcgct cggtcgttcg gctgcggcga gcggtatcag ctcactcaaa ggcggtaata    6720
cggttatcca cagaatcagg ggataacgca ggaaagaaca tgtgagcaaa aggccagcaa    6780
aaggccagga accgtaaaaa ggccgcgttg ctggcgtttt tccataggct ccgcccccct    6840
gacgagcatc acaaaaatcg acgctcaagt cagaggtggc gaaacccgac aggactataa    6900
agataccagg cgtttccccc tggaagctcc ctcgtgcgct ctcctgttcc gaccctgccg    6960
cttaccggat acctgtccgc ctttctccct tcggaagcg tggcgctttc tcatagctca    7020
cgctgtaggt atctcagttc ggtgtaggtc gttcgctcca agctgggctg tgtgcacgaa    7080
```

```
cccccccgttc agcccgaccg ctgcgcctta tccggtaact atcgtcttga gtccaacccg    7140
gtaagacacg acttatcgcc actggcagca gccactggta acaggattag cagagcgagg    7200
tatgtaggcg gtgctacaga gttcttgaag tggtggccta actacggcta cactagaaga    7260
acagtatttg gtatctgcgc tctgctgaag ccagttacct tcggaaaaag agttggtagc    7320
tcttgatccg gcaaacaaac caccgctggt agcggtggtt ttttttgtttg caagcagcag    7380 attacgcgca gaaaaaaagg atctcaagaa gatcctttga tcttttctac ggggtctgac    7440
gctcagtgga acgaaaactc acgttaaggg attttggtca tgagattatc aaaaaggatc    7500
ttcacctaga tccttttaaa ttaaaaatga agttttaaat caatctaaag tatatatgag    7560
taaacttggt ctgacagtta ccaatgctta atcagtgagg cacctatctc agcgatctgt    7620
ctatttcgtt catccatagt tgcctgactc cccgtcgtgt agataactac gatacgggag    7680
ggcttaccat ctggccccag tgctgcaatg ataccgcgag acccacgctc accggctcca    7740
gatttatcag caataaacca gccagccgga agggccgagc gcagaagtgg tcctgcaact    7800
ttatccgcct ccatccagtc tattaattgt tgccgggaag ctagagtaag tagttcgcca    7860
gttaatagtt tgcgcaacgt tgttgccatt gctacaggca tcgtggtgtc acgctcgtcg    7920
tttggtatgg cttcattcag ctccggttcc caacgatcaa ggcgagttac atgatccccc    7980
atgttgtgca aaaaagcggt tagctccttc ggtcctccga tcgttgtcag aagtaagttg    8040
gccgcagtgt tatcactcat ggttatggca gcactgcata attctcttac tgtcatgcca    8100
tccgtaagat gcttttctgt gactggtgag tactcaacca agtcattctg agaatagtgt    8160
atgcggcgac cgagttgctc ttgcccggcg tcaatacggg ataataccgc gccacatagc    8220
agaactttaa aagtgctcat cattggaaaa cgttcttcgg ggcgaaaact ctcaaggatc    8280
ttaccgctgt tgagatccag ttcgatgtaa cccactcgtg cacccaactg atcttcagca    8340
tcttttactt tcaccagcgt ttctgggtga gcaaaaacag gaaggcaaaa tgccgcaaaa    8400
aagggaataa gggcgacacg gaaatgttga atactcatac tcttcctttt tcaatattat    8460
tgaagcattt atcagggtta ttgtctcatg agcggataca tatttgaatg tatttagaaa    8520
aataaacaaa tagggggttcc gcgcacattt ccccgaaaag tgccacctga cgtctaagaa    8580
accattatta tcatgacatt aacctataaa aataggcgta tcacgaggcc ctttcgtctc    8640
gcgcgtttcg gtgatgacgg tgaaaacctc tgacacatgc agctcccgga gacggtcaca    8700
gcttgtctgt aagcggatgc cgggagcaga caagcccgtc agggcgcgtc agcgggtgtt    8760
ggcgggtgtc ggggctggct taactatgcg gcatcagagc agattgtact gagagtgcac    8820
caagcttatt taaatctta tcggtgtggc gcgccttgac ggccgcctcg gattcacttc    8880
gcagggcact tctgacgcgc tcaagcgtgc ccagcgtggt gccatctttg gcctctgcaa    8940
gaccatcggc ctcgagtggt ccgagtctga cgtcttttcc cgcggcgtgg acattgctca    9000
gggcatgcac cccgaggatg ccgccgtggc gattgtgcgc gagatggcgt gcgctgacat    9060
tcgcattcgc gaggtcggca ttggcgcaaa ccagcagcgc tgcacgatcc gtgccgccaa    9120
gctcgagacc ggcaacccgc agcgccagat cgccaaggac gacgtgctgc tcgtttctgg    9180
cggcgctcgc ggcatcacgc ctctttgcat ccggagatc acgcgccaga tcgcgggcgg    9240
caagtacatt ctgcttggcc gcagcaaggt ctctgcgagc gaaccggcat ggtgcgctgg    9300
catcactgac gagaaggctg tgcaaaaggc tgctacccag gagctcaagc gcgccttttag    9360 cgctggcgag ggccccaagc ccacgccccg cgctgtcact aagcttgtgg gctctgttct    9420
```

```
tggcgctcgc gaggtgcgca gctctattgc tgcgattgaa gcgctcggcg gcaaggccat   9480
ctactcgtcg tgcgacgtga actctgccgc cgacgtggcc aaggccgtgc gcgatgccga   9540
gtcccagctc ggtgcccgcg tctcgggcat cgttcatgcc tcgggcgtgc tccgcgaccg   9600
tctcatcgag aagaagctcc ccgacgagtt cgacgccgtc tttggcacca aggtcaccgg   9660
tctcgagaac ctcctcgccg ccgtcgaccg cgccaacctc aagcacatgg tcctcttcag   9720
ctcgctcgcc ggcttccacg gcaacgtcgg ccagtctgac tacgccatgg ccaacgaggc   9780
ccttaacaag atgggcctcg agctcgccaa ggacgtctcg gtcaagtcga tctgctaaga   9840
aagtgaacct tgtcctaacc cgacagcgaa tggcgggagg gggcgggcta aaagatcgta   9900
ttacatagta ttttccccta ctctttgtgt ttgtcttttt ttttttgaa cgcattcaag    9960 ccacttgtct tggtttactt gtttgtttgc ttgcttgctt gcttgcttgc ctgcttcttg   10020
gtcagacgga cccaaaaaag ggaaaaaatt cattcatggc acagataaga aaagaaaaa   10080 gtttgtcgac caccgtcatc agaaagcaag agaagagaaa cactcgcgct cacattctcg   10140
ctcgcgtaag aatcaagctt ccaattttag gccccccact gaccgaggtc tgtcgataat   10200 ccactttttcc attgattttc caggtttcgt taactcatgc cactgagcaa aacttcggtc   10260
tttcctaaca aaagctctcc tcacaaagca tggcgcggca acgacgtgt cctcatactc    10320 cactgccaca caaggtcgat aaactaagct cctcacaaat agaggagaat tccactgaca   10380
actgaaaaca atgtatgaga gacgatcacc actggagcgg cgcggcggtt gggcgcggag   10440
gtcggcagca aaaacaagcg actcgccgag caaacccgaa tcagccttca gacggtcgtg   10500
cctaacaaca cgccgttcta ccccgccttc ttcgcgcccc ttcgcgtcca gcatccttc    10560 aagtttatct ctctagttca acttcaagaa gaacaacacc accaacaccc caatttagg    10620 ccccccactg accgaggtct gtcgataatc cactttttcca ttgattttcc aggtttcgtt   10680
aactcatgcc actgagcaaa acttcggtct ttcctaacaa aagctctcct cacaaagcat   10740
ggcgcggcaa cggacgtgtc ctcatactcc actgccacac aaggtcgata aactaagctc   10800
ctcacaaata gaggagaatt ccactgacaa ctgaaaacaa tgtatgagag acgatcacca   10860
ctggagcggc gcggcggttg gcgcggagg tcggcagcaa aaacaagcga ctcgccgagc    10920
aaacccgaat cagccttcag acggtcgtgc ctaacaacac gccgttctac cccgccttct    10980
tcgcgcccct tcgcgtccaa gcatccttca agtttatctc tctagttcaa cttcaagaag   11040
aacaacacca ccaacaccca cgtgctacga gatttcgatt ccaccgccgc cttctatgaa   11100
aggttgggct tcggaatcgt tttccgggac gccggctgga tgatcctcca gcgcggggat   11160
ctcatgctgg agttcttcgc ccaccccaac ttgtttattg cagcttataa tggttacaaa   11220
taaagcaata gcatcacaaa tttcacaaat aaagcatttt tttcactgca ttctagttgt   11280
ggtttgtcca aactcatcaa tgtatcttat catgtctgaa ttcccggggt ac           11332
```

<210> SEQ ID NO 5
<211> LENGTH: 4777
<212> TYPE: DNA
<213> ORGANISM: Artificial Sequence
<220> FEATURE:
<223> OTHER INFORMATION: pCL399 vector
<220> FEATURE:
<221> NAME/KEY: misc_feature
<222> LOCATION: (1)..(2523)
<223> OTHER INFORMATION: FAS_fragment
<220> FEATURE:
<221> NAME/KEY: misc_feature
<222> LOCATION: (2528)..(4777)
<223> OTHER INFORMATION: pSP73_fragment

<400> SEQUENCE: 5

| | | | | | |
|---|---|---|---|---|---|
| gtttaaactc | gcggcgtctt | cgccgtcgag | gcgcgtcttt | cgaggcgggc | gaggtgtttt | 60 |
| tcttttcttt | tcttctcgct | gcagctgcgc | cgcggcgaac | gcagttcgcc | gcggcggctg | 120 |
| cgacgcgcct | gcgatgtcta | tgcgcaggca | aggcacgacg | tcttgcggcg | ccgcttcctg | 180 |
| cgccgccttg | cgtcttggcc | ccgccgacga | cgcaagcagc | ggcggcgccc | ccccgccctc | 240 |
| ctccactgtg | ggccgcagcc | ctccttttcg | cgcgcccgca | gccgcgcggc | gcgccccgcg | 300 |
| aacaaagagc | cgccgcgccg | gtccgcactg | cgcgggccgc | cccgcaagtg | ccgcaaacgc | 360 |
| cggcccgaac | cgccgcaaac | gcgcccgcag | ccgcgcccgc | agccgcgcgc | gacccgcggt | 420 |
| ggggacgcgc | gccaagcgtc | cccttccgcg | ggatgacgta | ggcggcggcc | ccgcctatgc | 480 |
| aatacgggag | gaaccaggaa | ccgggagggg | ggggggggcgg | cgcgcgcgcc | gtccagtgcg | 540 |
| ggaccgatcg | gcgccgggat | gcccgggcgg | gagggacaca | gccaggcagt | cagtcagtca | 600 |
| gccgcacaga | gagagcgcgc | ctgcgagtcc | cgtctggtct | cggaattgta | tcccgcgcag | 660 |
| agctcagaat | cgcaggtcga | tcgatcgagc | gatggatcca | tcgctctatc | cgtccatcga | 720 |
| tccatcgcat | ccatcgcatc | catcgcatcc | atcgttgcat | cgcttgcacc | gcccgcttgc | 780 |
| atcgcgtgcg | tgcgcaggcg | ggcggcggcc | acgacgcgac | cgagagcggc | ggcgagtgca | 840 |
| gacgccgccg | gcgcccgcgg | ctgcgtcgcc | gcaggaagaa | ggagggggc | gcgtgtttcc | 900 |
| cgcgggaggg | aggagggagg | gagggaggtg | gttgggccaa | aaagggcggc | ctggacaggc | 960 |
| aggcaggccg | gaagcgacgc | cagcgagcga | aggaagagga | gagagccgcg | cgggcggcca | 1020 |
| gcgcggggcg | ggcggcagca | aacccgctac | tcagggtaaa | agacagacag | ctcttcgagc | 1080 |
| gagcttgttc | acttcgcgga | agcacgcgcg | caggcacgca | ggcacgcagg | cagcatagcg | 1140 |
| agcagcagca | gcatcgcgag | cagcattgcg | agaggaggcg | ctgaccgccg | gcctcgagca | 1200 |
| acaaaagaag | cagcagcagc | agcagcacga | gcagcagcag | cagcagcacg | agcagcagca | 1260 |
| gcacgagcag | cagcagcagc | agcagcaaga | tggcgcagcc | cgagtcgacg | acgccgacca | 1320 |
| tgacgcccga | ggaaggccag | atggaggggg | cgccgcagca | ggataatgcc | caggtgaaga | 1380 |
| agcactgctt | cgccgacgcc | gatgtggcaa | cctgcatcgc | cgcctttggc | ggtcagggaa | 1440 |
| gcgactggct | cagtgagctg | cgctccctcc | aggaaaaggg | ccagaccaac | gtgcgagaaa | 1500 |
| ccatcgaact | cgcactcgac | aaactcgagg | atcttgtcaa | ggccgagccc | tggtacgagg | 1560 |
| agcacggagg | atgcgatatc | cgcgcctggc | tcgagagcga | cgacaatgtc | cccaacttcg | 1620 |
| acctcctccg | ctacgcgccc | gtctccttcc | ccctcatctt | cctcacccaa | atgtgcaatt | 1680 |
| acatgcgtgt | cctcgagaaa | ctcggcacct | gccatgaaga | cgccctccaa | aagggctggg | 1740 |
| tcaaggcctc | gctcggacac | agccaggcg | tcgtctccgc | cgccgtcgtt | gccgcagcca | 1800 |
| acaccgaccg | cgagctgcgc | aacctcgtgg | tctccggcct | cgaatacatg | tcaaaagtcg | 1860 |
| gcatcgccgc | ccagcgcacg | ctcgactacg | agctcggacg | ccgcaacgcc | ggcccggaga | 1920 |
| ccccgatgct | cgctgtacag | ggaatggacg | aaaaagtcct | taccaaggcc | ttcaaggccg | 1980 |
| ccgtctcgct | ctccaacgag | aagcaggcca | tgatggccaa | aatctccca | cggccgccgc | 2040 |
| cgccaccgcc | gccccggccg | ccgttagcga | cgaagatcgc | ttctccatcg | ccctccgcaa | 2100 |
| cggccacgac | gactttgtcg | tctgcggcga | gcccaaggac | ctgcgcgtcc | tccgcaaggt | 2160 |
| catcgagaaa | cagagcgccg | agcccggcaa | ggaggcacag | gcgcgcacgc | cttttccaa | 2220 |
| gcgcaagccc | gtcacccaga | ccaccttcct | ccgcatgacg | gccgtcttcc | acagcgctct | 2280 |

```
caacaaggac gccctcgccc agatcaacac atgggcccg gagtccgcct ttagcaaggc    2340
cttcgcccag gcctcgctcc gtgttcccgt ctttgacacc aagtctggcg ctaatctgca    2400
agatgttccc gccgccgatg ttgtcgccca tcttaccacc aacatgctca ctgagcgcgc    2460
cgacgttctc gtctccctcc gtgccgccga gaccaagacc gacgccagcc acctcctctg    2520
tttaaacgtt aacctgcatt aatgaatcgg ccaacgcgcg gggagaggcg gtttgcgtat    2580
tgggcgctct ccgcttcct cgctcactga ctcgctgcgc tcggtcgttc ggctgcggcg    2640
agcggtatca gctcactcaa aggcggtaat acggttatcc acagaatcag gggataacgc    2700
aggaaagaac atgtgagcaa aaggccagca aaaggccagg aaccgtaaaa aggccgcgtt    2760
gctggcgttt ttccataggc tccgcccccc tgacgagcat cacaaaaatc gacgctcaag    2820
tcagaggtgg cgaaacccga caggactata aagataccag gcgtttcccc ctggaagctc    2880
cctcgtgcgc tctcctgttc cgaccctgcc gcttaccgga tacctgtccg cctttctccc    2940
ttcgggaagc gtggcgcttt ctcaatgctc acgctgtagg tatctcagtt cggtgtaggt    3000
cgttcgctcc aagctgggct gtgtgcacga accccccgtt cagcccgacc gctgcgcctt    3060
atccggtaac tatcgtcttg agtccaaccc ggtaagacac gacttatcgc cactggcagc    3120
agccactggt aacaggatta gcagagcgag gtatgtaggc ggtgctacag agttcttgaa    3180
gtggtggcct aactacggct acactagaag gacagtattt ggtatctgcg ctctgctgaa    3240
gccagttacc ttcggaaaaa gagttggtag ctcttgatcc ggcaaacaaa ccaccgctgg    3300
tagcggtggt ttttttgttt gcaagcagca gattacgcgc agaaaaaaag gatctcaaga    3360
agatcctttg atcttttcta cggggtctga cgctcagtgg aacgaaaact cacgttaagg    3420
gattttggtc atgagattat caaaaaggat cttcacctag atccttttaa attaaaaatg    3480
aagttttaaa tcaatctaaa gtatatatga gtaaacttgg tctgacagtt accaatgctt    3540
aatcagtgag gcacctatct cagcgatctg tctatttcgt tcatccatag ttgcctgact    3600
ccccgtcgtg tagataacta cgatacggga gggcttacca tctggcccca gtgctgcaat    3660
gataccgcga gacccacgct caccggctcc agatttatca gcaataaacc agccagccgg    3720
aagggccgag cgcagaagtg gtcctgcaac tttatccgcc tccatccagt ctattaattg    3780
ttgccgggaa gctagagtaa gtagttcgcc agttaatagt ttgcgcaacg ttgttgccat    3840
tgctacaggc atcgtggtgt cacgctcgtc gtttggtatg gcttcattca gctccgttc    3900 ccaacgatca aggcgagtta catgatcccc catgttgtgc aaaaaagcgg ttagctcctt    3960
cggtcctccg atcgttgtca gaagtaagtt ggccgcagtg ttatcactca tggttatggc    4020
agcactgcat aattctctta ctgtcatgcc atccgtaaga tgcttttctg tgactggtga    4080
gtactcaacc aagtcattct gagaatagtg tatgcggcga ccgagttgct cttgcccggc    4140
gtcaatacgg gataataccg cgccacatag cagaacttta aaagtgctca tcattggaaa    4200
acgttcttcg gggcgaaaac tctcaaggat cttaccgctg ttgagatcca gttcgatgta    4260
acccactcgt gcacccaact gatcttcagc atcttttact ttcaccagcg tttctgggtg    4320
agcaaaaaca ggaaggcaaa atgccgcaaa aagggaata agggcgacac ggaaatgttg    4380
aatactcata ctcttccttt ttcaatatta ttgaagcatt tatcagggtt attgtctcat    4440
gagcggatac atatttgaat gtatttagaa aaataaacaa ataggggttc cgcgcacatt    4500
tccccgaaaa gtgccacctg acgtctaaga aaccattatt atcatgacat aacctataa    4560 aaataggcgt atcacgaggc cctttcgtct cgcgcgtttc ggtgatgacg gtgaaaacct    4620
ctgacacatg cagctcccgg agacggtcac agcttgtctg taagcggatg ccgggagcag    4680
```

-continued

```
acaagcccgt cagggcgcgt cagcgggtgt tggcgggtgt cggggctggc ttaactatgc   4740
ggcatcagag cagattgtac tgagagtgca ccatatg                            4777
```

<210> SEQ ID NO 6
<211> LENGTH: 4775
<212> TYPE: DNA
<213> ORGANISM: Artificial Sequence
<220> FEATURE:
<223> OTHER INFORMATION: pCL400 vector
<220> FEATURE:
<221> NAME/KEY: misc_feature
<222> LOCATION: (1)..(2528)
<223> OTHER INFORMATION: Fas_fragment
<220> FEATURE:
<221> NAME/KEY: misc_feature
<222> LOCATION: (2533)..(4775)
<223> OTHER INFORMATION: pSP73_fragment

<400> SEQUENCE: 6

```
ccatggttta aactcgcggc gtcttcgccg tcgaggcgcg tctttcgagg cgggcgaggt     60
gttttctttt tcttttcttc tcgctgcagc tgcgccgcgg cgaacgcagt tcgccgcggc    120
ggctgcgacg cgcctgcgat gtctatgcgc aggcaaggca cgacgtcttg cggcgccgct    180
tcctgcgccg ccttgcgtct tggccccgcc gacgacgcaa gcagcggcgg cgcccccccg    240
ccctcctcca ctgtgggccg cagccctcct tttcgcgcgc ccgcagccgc gcggcgcgcc    300
ccgcgaacaa agagccgccg cgccggtccg cactgcgcgg gccgccccgc aagtgccgca    360
aacgccggcc cgaaccgccg caaacgcgcc cgcagccgcg cccgcagccg cgcgcgaccc    420
gcggtgggga cgcgcgccaa gcgtcccctt ccgcgggatg acgtaggcgg cggccccgcc    480
tatgcaatac gggaggaacc aggaaccggg aggggggggg ggcggcgcgc gcgccgtcca    540
gtgcgggacc gatcggcgcc gggatgcccg gcgggaggg acacagccag gcagtcagtc     600
agtcagccgc acagagagag cgcgcctgcg agtcccgtct ggtctcggaa ttgtatcccg    660
cgcagagctc agaatcgcag gtcgatcgat cgagcgatgg atccatcgct ctatccgtcc    720
atcgatccat cgcatccatc gcatccatcg catccatcgt tgcatcgctt gcaccgcccg    780
cttgcatcgc gtgcgtgcgc aggcgggcgg cggccacgac gcgaccgaga gcggcggcga    840
gtgcagacgc cgccggcgcc cgcggctgcg tcgccgcagg aagaaggagg ggggcgcgtg    900
tttcccgcgg gagggaggag ggagggaggg aggtggttgg gccaaaaagg gcggcctgga    960
caggcaggca ggccggaagc gacgccagcg agcgaaggaa gaggagagag ccgcgcgggc   1020
ggccagcgcg gggcgggcgg cagcaaaccc gctactcagg gtaaaagaca gacagctctt   1080
cgagcgagct tgttcacttc gcggaagcac gcgcgcaggc acgcaggcac gcaggcagca   1140
tagcgagcag cagcagcatc gcgagcagca ttgcgagagg aggcgctgac cgccggcctc   1200
gagcaacaaa agaagcagca gcagcagcag cacgagcagc agcagcagca gcacgagcag   1260
cagcagcacg agcagcagca gcagcagcag caagatggcg cagcccgagt cgacgacgcc   1320
gaccatgacg cccgaggaag gccagatgga gggggcgccg cagcaggata atgcccaggt   1380
gaagaagcac tgcttcgccg acgccgatgt ggcaacctgc atcgccgcct ttggcggtca   1440
gggaagcgac tggctcagtg agctgcgctc cctccaggaa aagggccaga ccaacgtgcg   1500
agaaaccatc gaactcgcac tcgacaaact cgaggatctt gtcaaggccg agccctggta   1560
cgaggagcac ggaggatgcg atatccgcgc ctggctcgag agcgacgaca atgtccccaa   1620
cttcgacctc ctccgctacg cgcccgtctc cttcccccctc atcttcctca cccaaatgtg   1680
```

```
caattacatg cgtgtcctcg agaaactcgg cacctgccat gaagacgccc tccaaaaggg   1740
ctgggtcaag gcctcgctcg gacacagcca gggcgtcgtc tccgccgccg tcgttgccgc   1800
agccaacacc gaccgcgagc tgcgcaacct cgtggtctcc ggcctcgaat acatgtcaaa   1860
agtcggcatc gccgcccagc gcacgctcga ctacgagctc ggacgccgca acgccggccc   1920 ggagacccg atgctcgctg tacagggaat ggacgaaaaa gtccttacca aggccttcaa   1980
ggccgccgtc tcgctctcca cgagaagca ggccatgatg ccaaaatct ccccacggcc   2040 gccgccgcca ccgccgcccc ggccgccgtt agcgacgaag atcgcttctc catcgccctc   2100
cgcaacggcc acgacgactt tgtcgtctgc ggcgagccca aggacctgcg cgtcctccgc   2160
aaggtcatcg agaaacagag cgccgagccc ggcaaggagg cacaggcgcg cacgcccttt   2220
tccaagcgca agcccgtcac ccagaccacc ttcctccgca tgacggccgt cttccacagc   2280
gctctcaaca aggacgccct cgcccagatc aacacatggg ccccggagtc cgcctttagc   2340
aaggccttcg cccaggcctc gctccgtgtt cccgtctttg acaccaagtc tggcgctaat   2400
ctgcaagatg ttcccgccgc cgatgttgtc gcccatctta ccaccaacat gctcactgag   2460
cgcgccgacg ttctcgtctc cctccgtgcc gccgagacca agaccgacgc cagccacctc   2520
ctctgtttaa acgttaacct gcattaatga atcggccaac gcgcggggag aggcggtttg   2580
cgtattgggc gctcttccgc ttcctcgctc actgactcgc tgcgctcggt cgttcggctg   2640
cggcgagcgg tatcagctca ctcaaaggcg gtaatacggt tatccacaga atcaggggat   2700
aacgcaggaa agaacatgtg agcaaaaggc cagcaaaagg ccaggaaccg taaaaaggcc   2760
gcgttgctgg cgttttttcca taggctccgc ccccctgacg agcatcacaa aaatcgacgc   2820
tcaagtcaga ggtggcgaaa cccgacagga ctataaagat accaggcgtt ccccctgga   2880 agctccctcg tgcgctctcc tgttccgacc ctgccgctta ccggatacct gtccgccttt   2940
ctcccttcgg gaagcgtggc gctttctcaa tgctcacgct gtaggtatct cagttcggtg   3000
taggtcgttc gctccaagct gggctgtgtg cacgaacccc ccgttcagcc cgaccgctgc   3060
gccttatccg gtaactatcg tcttgagtcc aacccggtaa gacacgactt atcgccactg   3120
gcagcagcca ctggtaacag gattagcaga gcgaggtatg taggcggtgc tacagagttc   3180
ttgaagtggt ggcctaacta cggctacact agaaggacag tatttggtat ctgcgctctg   3240
ctgaagccag ttaccttcgg aaaaagagtt ggtagctctt gatccggcaa acaaaccacc   3300
gctggtagcg gtggtttttt tgtttgcaag cagcagatta cgcgcagaaa aaaggatct   3360 caagaagatc ctttgatctt ttctacgggg tctgacgctc agtggaacga aaactcacgt   3420
taagggattt tggtcatgag attatcaaaa aggatcttca cctagatcct tttaaattaa   3480
aaatgaagtt ttaaatcaat ctaaagtata tatgagtaaa cttggtctga cagttaccaa   3540
tgcttaatca gtgaggcacc tatctcagcg atctgtctat ttcgttcatc catagttgcc   3600 tgactcccg tcgtgtagat aactacgata cgggagggct taccatctgg ccccagtgct   3660
gcaatgatac cgcgagaccc acgctcaccg gctccagatt tatcagcaat aaaccagcca   3720
gccggaaggg ccgagcgcag aagtggtcct gcaactttat ccgcctccat ccagtctatt   3780
aattgttgcc gggaagctag agtaagtagt tcgccagtta atagtttgcg caacgttgtt   3840
gccattgcta caggcatcgt ggtgtcacgc tcgtcgtttg gtatggcttc attcagctcc   3900
ggttcccaac gatcaaggcg agttacatga tcccccatgt tgtgcaaaaa agcggttagc   3960
tccttcggtc ctccgatcgt tgtcagaagt aagttggccg cagtgttatc actcatggtt   4020
atggcagcac tgcataattc tcttactgtc atgccatccg taagatgctt ttctgtgact   4080
```

```
ggtgagtact caaccaagtc attctgagaa tagtgtatgc ggcgaccgag ttgctcttgc    4140
ccggcgtcaa tacgggataa taccgcgcca catagcagaa ctttaaaagt gctcatcatt    4200
ggaaaacgtt cttcggggcg aaaactctca aggatcttac cgctgttgag atccagttcg    4260
atgtaaccca ctcgtgcacc caactgatct tcagcatctt ttactttcac cagcgtttct    4320
gggtgagcaa aaacaggaag gcaaaatgcc gcaaaaaagg gaataagggc gacacggaaa    4380
tgttgaatac tcatactctt ccttttcaa tattattgaa gcatttatca gggttattgt     4440
ctcatgagcg gatacatatt tgaatgtatt tagaaaaata acaaataggg gttccgcgc     4500 acatttcccc gaaaagtgcc acctgacgtc taagaaacca ttattatcat gacattaacc    4560
tataaaaata ggcgtatcac gaggccctt cgtctcgcgc gtttcggtga tgacggtgaa     4620
aacctctgac acatgcagct cccggagacg gtcacagctt gtctgtaagc ggatgccggg    4680
agcagacaag cccgtcaggg cgcgtcagcg ggtgttggcg ggtgtcgggg ctggcttaac    4740
tatgcggcat cagagcagat tgtactgaga gtgca                               4775
```

<210> SEQ ID NO 7
<211> LENGTH: 5991
<212> TYPE: DNA
<213> ORGANISM: Artificial Sequence
<220> FEATURE:
<223> OTHER INFORMATION: pCL401 vector
<220> FEATURE:
<221> NAME/KEY: misc_feature
<222> LOCATION: (1)..(1063)
<223> OTHER INFORMATION: EF-1_alpha_promoter
<220> FEATURE:
<221> NAME/KEY: misc_feature
<222> LOCATION: (1076)..(1112)
<223> OTHER INFORMATION: Hammerhead_ribozyme
<220> FEATURE:
<221> NAME/KEY: misc_feature
<222> LOCATION: (1113)..(1132)
<223> OTHER INFORMATION: carotene_synthase_target_1
<220> FEATURE:
<221> NAME/KEY: misc_feature
<222> LOCATION: (1133)..(1212)
<223> OTHER INFORMATION: gRNA
<220> FEATURE:
<221> NAME/KEY: misc_feature
<222> LOCATION: (1213)..(1280)
<223> OTHER INFORMATION: HDV_ribozyme
<220> FEATURE:
<221> NAME/KEY: misc_feature
<222> LOCATION: (1300)..(1939)
<223> OTHER INFORMATION: OrfC_terminator
<220> FEATURE:
<221> NAME/KEY: misc_feature
<222> LOCATION: (4474)..(4922)
<223> OTHER INFORMATION: alpha_tubulin_promoter
<220> FEATURE:
<221> NAME/KEY: misc_feature
<222> LOCATION: (4923)..(5717)
<223> OTHER INFORMATION: paromomycin_resistance_gene
<220> FEATURE:
<221> NAME/KEY: misc_feature
<222> LOCATION: (5718)..(5991)
<223> OTHER INFORMATION: SV40_terminator

<400> SEQUENCE: 7

```
ctcttatctg cctcgcgccg ttgaccgccg cttgactctt ggcgcttgcc gctcgcatcc      60
tgcctcgctc gcgcaggcgg gcgggcgagt gggtgggtcc gcagccttcc gcgctcgccc     120
gctagctcgc tcgcgccgtg ctgcagccag cagggcagca ccgcacggca ggcaggtccc     180
ggcgcggatc gatcgatcca tcgatccatc gatccatcga tcgtgcggtc aaaaagaaag     240
```

| | | |
|---|---|---|
| gaagaagaaa ggaaaaagaa aggcgtgcgc acccgagtgc gcgctgagcg cccgctcgcg | 300 | |
| gtcccgcgga gcctccgcgt tagtcccccgc cccgcgccgc gcagtccccc gggaggcatc | 360 | |
| gcgcacctct cgccgccccc tcgcgcctcg ccgattcccc gcctcccctt ttccgcttct | 420 | |
| tcgccgcctc cgctcgcggc cgcgtcgccc gcgccccgct ccctatctgc tccccagggg | 480 | |
| ggcactccgc acctttttgcg cccgctgccg ccgccgcggc cgccccgccg ccctggtttc | 540 | |
| ccccgcgagc gcggccgcgt cgccgcgcaa agactcgccg cgtgccgccc cgagcaacgg | 600 | |
| gtggcggcgg cgcggcggcg ggcggggcgc ggcggcgcgt aggcggggct aggcgccggc | 660 | |
| taggcgaaac gccgccccg ggcgccgccg ccgcccgctc cagagcagtc gccgcgccag | 720 | |
| accgccaacg cagagaccga gaccgaggta cgtcgcgccc gagcacgccg cgacgcgcgg | 780 | |
| cagggacgag gagcacgacg ccgcgccgcg ccgcgcgggg gggggagggg agaggcagga | 840 | |
| cgcgggagcg agcgtgcatg tttccgcgcg agacgacgcc gcgcgcgctg gagaggagat | 900 | |
| aaggcgcttg gatcgcgaga gggccagcca ggctggaggc gaaaatgggt ggagaggata | 960 | |
| gtatcttgcg tgcttggacg aggagactga cgaggaggac ggatacgtcg atgatgatgt | 1020 | |
| gcacagagaa gaagcagttc gaaagcgact actagcaagc aagagatcta gcacgctgat | 1080 | |
| gagtccgtga ggacgaaacg agtaagctcg tctgcggacg tcgtggacgc gcgttttaga | 1140 | |
| gctagaaata gcaagttaaa ataaggctag tccgttatca acttgaaaaa gtggcaccga | 1200 | |
| gtcggtgctt ttggccggca tggtcccagc ctcctcgctg gcgccggctg ggcaacatgc | 1260 | |
| ttcggcatgg cgaatgggac catatgagtt atgagatccg aaagtgaacc ttgtcctaac | 1320 | |
| ccgacagcga atggcgggag ggggcgggct aaaagatcgt attacatagt attttttccc | 1380 | |
| tactctttgt gtttgtcttt tttttttttt tgaacgcatt caagccactt gtctgggttt | 1440 | |
| acttgttttgt ttgcttgctt gcttgcttgc ttgcctgctt cttggtcaga cggcccaaaa | 1500 | |
| aagggaaaaa attcattcat ggcacagata agaaaaagaa aaagtttgtc gaccaccgtc | 1560 | |
| atcagaaagc aagagaagag aaacactcgc gctcacattc tcgctcgcgt aagaatctta | 1620 | |
| gccacgcata cgaagtaatt tgtccatctg gcgaatcttt acatgagcgt tttcaagctg | 1680 | |
| gagcgtgaga tcatacccttt cttgatcgta atgttccaac cttgcatagg cctcgttgcg | 1740 | |
| atccgctagc aatgcgtcgt actcccgttg caactgcgcc atcgcctcat tgtgacgtga | 1800 | |
| gttcagattc ttctcgagac cttcgagcgc tgctaatttc gcctgacgct ccttcttttg | 1860 | |
| tgcttccatg acacgccgct tcaccgtgcg ttccacttct tcctcagaca tgcccttggc | 1920 | |
| tgcctcgacc tgctcggtaa aacgggcccc agcacgtgct acgagatttc gattccaccg | 1980 | |
| ccgccttcta tgaaaggttg ggcttcggaa tcgttttccg ggacgccggc tggatgatcc | 2040 | |
| tccagcgcgg ggatctcatg ctggagttct tcgcccaccc caacttgttt attgcagctt | 2100 | |
| ataatggtta caaataaagc aatagcatca caaattttcac aaataaagca ttttttttcac | 2160 | |
| tgcattctag ttgtggtttg tccaaactca tcaatgtatc ttatcataca tggtcgacct | 2220 | |
| gcaggaacct gcattaatga atcggccaac gcgcggggag aggcggtttg cgtattgggc | 2280 | |
| gctcttccgc ttcctcgctc actgactcgc tgcgctcggt cgttcggctg cggcgagcgg | 2340 | |
| tatcagctca ctcaaaggcg gtaatacggt tatccacaga atcaggggat aacgcaggaa | 2400 | |
| agaacatgtg agcaaaaggc cagcaaaagg ccaggaaccg taaaaaggcc gcgttgctgg | 2460 | |
| cgttttttcca taggctccgc cccccctgacg agcatcacaa aaatcgacgc tcaagtcaga | 2520 | |
| ggtggcgaaa cccgacagga ctataaagat accaggcgtt tccccctgga agctccctcg | 2580 | |
| tgcgctctcc tgttccgacc ctgccgctta ccggatacct gtccgccttt ctcccttcgg | 2640 | |

```
gaagcgtggc gctttctcat agctcacgct gtaggtatct cagttcggtg taggtcgttc    2700
gctccaagct gggctgtgtg cacgaacccc ccgttcagcc cgaccgctgc gccttatccg    2760
gtaactatcg tcttgagtcc aacccggtaa gacacgactt atcgccactg gcagcagcca    2820
ctggtaacag gattagcaga gcgaggtatg taggcggtgc tacagagttc ttgaagtggt    2880
ggcctaacta cggctacact agaagaacag tatttggtat ctgcgctctg ctgaagccag    2940
ttaccttcgg aaaaagagtt ggtagctctt gatccggcaa acaaaccacc gctggtagcg    3000
gtggtttttt tgtttgcaag cagcagatta cgcgcagaaa aaaggatctc aagaagatc     3060
ctttgatctt ttctacgggg tctgacgctc agtggaacga aaactcacgt taagggattt    3120
tggtcatgag attatcaaaa aggatcttca cctagatcct tttaaattaa aaatgaagtt    3180
ttaaatcaat ctaaagtata tatgagtaaa cttggtctga cagttaccaa tgcttaatca    3240
gtgaggcacc tatctcagcg atctgtctat ttcgttcatc catagttgcc tgactccccg    3300
tcgtgtagat aactacgata cgggagggct taccatctgg ccccagtgct gcaatgatac    3360
cgcgagaccc acgctcaccg gctccagatt tatcagcaat aaaccagcca gccggaaggg    3420
ccgagcgcag aagtggtcct gcaactttat ccgcctccat ccagtctatt aattgttgcc    3480
gggaagctag agtaagtagt tcgccagtta atagtttgcg caacgttgtt gccattgcta    3540
caggcatcgt ggtgtcacgc tcgtcgtttg gtatggcttc attcagctcc ggttcccaac    3600
gatcaaggcg agttacatga tcccccatgt tgtgcaaaaa agcggttagc tccttcggtc    3660
ctccgatcgt tgtcagaagt aagttggccg cagtgttatc actcatggtt atggcagcac    3720
tgcataattc tcttactgtc atgccatccg taagatgctt ttctgtgact ggtgagtact    3780
caaccaagtc attctgagaa tagtgtatgc ggcgaccgag ttgctcttgc ccggcgtcaa    3840
tacgggataa taccgcgcca catagcagaa ctttaaaagt gctcatcatt ggaaaacgtt    3900
cttcggggcg aaaactctca aggatcttac cgctgttgag atccagttcg atgtaaccca    3960
ctcgtgcacc caactgatct tcagcatctt ttactttcac cagcgtttct gggtgagcaa    4020
aaacaggaag gcaaaatgcc gcaaaaaagg gaataagggc gacacggaaa tgttgaatac    4080
tcatactctt ccttttcaa tattattgaa gcatttatca gggttattgt ctcatgagcg    4140
gatacatatt tgaatgtatt tagaaaaata aacaaatagg ggttccgcgc acatttcccc    4200
gaaaagtgcc acctgacgtc taagaaacca ttattatcat gacattaacc tataaaaata    4260
ggcgtatcac gaggcccttt cgtctcgcgc gtttcggtga tgacggtgaa aacctctgac    4320
acatgcagct cccggagacg tcacagcttg tctgtaagc ggatgccggg agcagacaag    4380
cccgtcaggg cgcgtcagcg ggtgttggcg ggtgtcgggg ctggcttaac tatgcggcat    4440
cagagcagat tgtactgaga gtgcaccaag cttccaattt taggcccccc actgaccgag    4500
gtctgtcgat aatccacttt tccattgatt ttccaggttt cgttaactca tgccactgag    4560
caaaacttcg gtcttttccta acaaaagctc tcctcacaaa gcatggcgcg caacggacg    4620
tgtcctcata ctccactgcc acacaaggtc gataaactaa gctcctcaca aatagaggag    4680
aattccactg acaactgaaa acaatgtatg agagacgatc accactggag cggcgcggcg    4740
gttgggcgcg gaggtcggca gcaaaaacaa gcgactcgcc gagcaaaccc gaatcagcct    4800
tcagacggtc gtgcctaaca acacgccgtt ctaccccgcc ttcttcgcgc cccttcgcgt    4860
ccaagcatcc ttcaagttta tctctctagt tcaacttcaa gaagaacaac accaccaaca    4920
ccatgattga acaagatgga ttgcacgcag gttctccggc cgcttgggtg gagaggctat    4980
```

-continued

```
tcggctatga ctgggcacaa cagacaatcg gctgctctga tgccgccgtg ttccggctgt    5040
cagcgcaggg gcgcccggtt cttttttgtca agaccgacct gtccggtgcc ctgaatgaac    5100
tgcaggacga ggcagcgcgg ctatcgtggc tggccacgac gggcgttcct tgcgcagctg    5160
tgctcgacgt tgtcactgaa gcgggaaggg actggctgct attgggcgaa gtgccggggc    5220
aggatctcct gtcatctcac cttgctcctg ccgagaaagt atccatcatg gctgatgcaa    5280
tgcggcggct gcatacgctt gatccggcta cctgcccatt cgaccaccaa gcgaaacatc    5340
gcatcgagcg agcacgtact cggatggaag ccggtcttgt cgatcaggat gatctggacg    5400
aagagcatca ggggctcgcg ccagccgaac tgttcgccag gctcaaggcg cgcatgcccg    5460
acggcgatga tctcgtcgtg acccatggcg atgcctgctt gccgaatatc atggtggaaa    5520
atggccgctt ttctggattc atcgactgtg gccggctggg tgtggcggac cgctatcagg    5580
acatagcgtt ggctacccgt gatattgctg aagagcttgg cggcgaatgg gctgaccgct    5640
tcctcgtgct ttacggtatc gccgctcccg attcgcagcg catcgccttc tatcgccttc    5700
ttgacgagtt cttctgacac gtgctacgag atttcgattc caccgccgcc ttctatgaaa    5760
ggttgggctt cggaatcgtt ttccgggacg ccggctggat gatcctccag cgcggggatc    5820
tcatgctgga gttcttcgcc cacccccaact tgtttattgc agcttataat ggttacaaat    5880
aaagcaatag catcacaaat ttcacaaata aagcattttt ttcactgcat tctagttgtg    5940
gtttgtccaa actcatcaat gtatcttatc atgtctgaat tccgggggta c    5991
```

```
<210> SEQ ID NO 8
<211> LENGTH: 7612
<212> TYPE: DNA
<213> ORGANISM: Artificial Sequence
<220> FEATURE:
<223> OTHER INFORMATION: pCL402 vector
<220> FEATURE:
<221> NAME/KEY: misc_feature
<222> LOCATION: (5)..(1198)
<223> OTHER INFORMATION: FAS_upstream_fragment
<220> FEATURE:
<221> NAME/KEY: misc_feature
<222> LOCATION: (1199)..(1647)
<223> OTHER INFORMATION: alpha_tubulin_promoter
<220> FEATURE:
<221> NAME/KEY: misc_feature
<222> LOCATION: (1648)..(2442)
<223> OTHER INFORMATION: paromomycin_resistance_gene
<220> FEATURE:
<221> NAME/KEY: misc_feature
<222> LOCATION: (2443)..(2716)
<223> OTHER INFORMATION: SV40_terminator
<220> FEATURE:
<221> NAME/KEY: misc_feature
<222> LOCATION: (2717)..(3779)
<223> OTHER INFORMATION: EF-1_alpha_promoter
<220> FEATURE:
<221> NAME/KEY: misc_feature
<222> LOCATION: (3792)..(3828)
<223> OTHER INFORMATION: Hammerhead_ribozyme
<220> FEATURE:
<221> NAME/KEY: misc_feature
<222> LOCATION: (3829)..(3848)
<223> OTHER INFORMATION: carotene_synthase_target_1
<220> FEATURE:
<221> NAME/KEY: misc_feature
<222> LOCATION: (3849)..(3928)
<223> OTHER INFORMATION: gRNA
<220> FEATURE:
<221> NAME/KEY: misc_feature
<222> LOCATION: (3929)..(3996)
<223> OTHER INFORMATION: HDV_ribozyme
<220> FEATURE:
<221> NAME/KEY: misc_feature
```

```
<222> LOCATION: (4016)..(4534)
<223> OTHER INFORMATION: OrfC_terminator
<220> FEATURE:
<221> NAME/KEY: misc_feature
<222> LOCATION: (4535)..(5360)
<223> OTHER INFORMATION: FAS_downstream_fragment
<220> FEATURE:
<221> NAME/KEY: misc_feature
<222> LOCATION: (5365)..(7612)
<223> OTHER INFORMATION: pSP73

<400> SEQUENCE: 8
gtttaaactc gcggcgtctt cgccgtcgag gcgcgtcttt cgaggcgggc gaggtgtttt      60
tcttttcttt tcttctcgct gcagctgcgc cgcggcgaac gcagttcgcc gcggcggctg     120
cgacgcgcct gcgatgtcta tgcgcaggca aggcacgacg tcttgcggcg ccgcttcctg     180
cgccgccttg cgtcttggcc ccgccgacga cgcaagcagc ggcggcgccc cccgccctc      240 ctccactgtg ggccgcagcc ctccttttcg cgcgcccgca gccgcgcggc gcgccccgcg     300
aacaaagagc cgccgcgccg gtccgcactg cgcgggccgc cccgcaagtg ccgcaaacgc     360
cggcccgaac cgccgcaaac gcgcccgcag ccgcgcccgc agccgcgcgc gacccgcggt     420
ggggacgcgc gccaagcgtc cccttccgcg ggatgacgta ggcggcggcc ccgcctatgc     480
aatacgggag gaaccaggaa ccgggagggg ggggggcgg cgcgcgcgcc gtccagtgcg      540
ggaccgatcg gcgccgggat gcccgggcgg gagggacaca gccaggcagt cagtcagtca     600
gccgcacaga gagagcgcgc ctgcgagtcc cgtctggtct cggaattgta tcccgcgcag     660
agctcagaat cgcaggtcga tcgatcgagc gatggatcca tcgctctatc cgtccatcga     720
tccatcgcat ccatcgcatc catcgcatcc atcgttgcat cgcttgcacc gccgcttgc      780 atcgcgtgcg tgcgcaggcg ggcggcggcc acgacgcgac cgagagcggc ggcgagtgca     840
gacgccgccg gcgcccgcgg ctgcgtcgcc gcaggaagaa ggaggggggc gcgtgtttcc     900
cgcgggaggg aggagggagg gagggaggtg gttgggccaa aaaggggcgg ctggacaggc     960
aggcaggccg gaagcgacgc cagcgagcga aggaagagga gagagccgcg cgggcggcca    1020
gcgcggggcg ggcggcagca aacccgctac tcagggtaaa agacagacag ctcttcgagc    1080
gagcttgttc acttcgcgga agcacgcgcg caggcacgca ggcacgcagg cagcatagcg    1140
agcagcagca gcatcgcgag cagcattgcg agaggaggcg ctgaccgccg gcctcgagcc    1200
aattttaggc cccccactga ccgaggtctg tcgataatcc acttttccat tgattttcca    1260
ggtttcgtta actcatgcca ctgagcaaaa cttcggtctt tcctaacaaa agctctcctc    1320
acaaagcatg gcgcggcaac ggacgtgtcc tcatactcca ctgccacaca aggtcgataa    1380
actaagctcc tcacaaatag aggagaattc cactgacaac tgaaaacaat gtatgagaga    1440
cgatcaccac tggagcggcg cggcggttgg gcgcggaggt cggcagcaaa acaagcgac     1500 tcgccgagca aacccgaatc agccttcaga cggtcgtgcc taacaacacg ccgttctacc    1560
ccgccttctt cgcgcccctt cgcgtccaag catccttcaa gtttatctct ctagttcaac    1620
ttcaagaaga acaacaccac caacaccatg attgaacaag atggattgca cgcaggttct    1680
ccggccgctt gggtggagag gctattcggc tatgactggg cacaacagac aatcggctgc    1740
tctgatgccg ccgtgttccg gctgtcagcg caggggcgcc cggttctttt tgtcaagacc    1800
gacctgtccg gtgccctgaa tgaactgcag gacgaggcag cgcggctatc gtggctggcc    1860
acgacgggcg ttccttgcgc agctgtgctc gacgttgtca ctgaagcggg aagggactgg    1920
ctgctattgg gcgaagtgcc ggggcaggat ctcctgtcat ctcaccttgc tcctgccgag    1980
```

```
aaagtatcca tcatggctga tgcaatgcgg cggctgcata cgcttgatcc ggctacctgc    2040
ccattcgacc accaagcgaa acatcgcatc gagcgagcac gtactcggat ggaagccggt    2100
cttgtcgatc aggatgatct ggacgaagag catcaggggc tcgcgccagc cgaactgttc    2160
gccaggctca aggcgcgcat gcccgacggc gatgatctcg tcgtgaccca tggcgatgcc    2220
tgcttgccga atatcatggt ggaaaatggc cgcttttctg gattcatcga ctgtggccgg    2280
ctgggtgtgg cggaccgcta tcaggacata gcgttggcta cccgtgatat tgctgaagag    2340
cttggcggcg aatgggctga ccgcttcctc gtgctttacg gtatcgccgc tcccgattcg    2400
cagcgcatcg ccttctatcg ccttcttgac gagttcttct gacacgtgct acgagatttc    2460
gattccaccg ccgccttcta tgaaaggttg ggcttcggaa tcgttttccg ggacgccggc    2520
tggatgatcc tccagcgcgg ggatctcatg ctggagttct tcgcccaccc caacttgttt    2580
attgcagctt ataatggtta caaataaagc aatagcatca caaatttcac aaataaagca    2640
tttttttcac tgcattctag ttgtggtttg tccaaactca tcaatgtatc ttatcatgtc    2700
tgaattcccg gggtacctct tatctgcctc gcgccgttga ccgccgcttg actcttggcg    2760
cttgccgctc gcatcctgcc tcgctcgcgc aggcgggcgg gcgagtgggt gggtccgcag    2820
ccttccgcgc tcgcccgcta gctcgctcgc gccgtgctgc agccagcagg gcagcaccgc    2880
acggcaggca ggtcccggcg cggatcgatc gatccatcga tccatcgatc catcgatcgt    2940
gcggtcaaaa agaaaggaag aagaaaggaa aagaaaggc gtgcgcaccc gagtgcgcgc    3000
tgagcgcccg ctcgcggtcc cgcggagcct ccgcgttagt ccccgccccg cgccgcgcag    3060
tcccccggga ggcatcgcgc acctctcgcc gccccctcgc gcctcgccga ttccccgcct    3120
ccccttttcc gcttcttcgc cgcctccgct cgcggccgcg tcgcccgcgc ccgctccct    3180
atctgctccc cagggggggca ctccgcacct tttgcgcccg ctgccgccgc cgcggccgcc    3240
ccgccgccct ggtttccccc gcgagcgcgg ccgcgtcgcc gcgcaaagac tcgccgcgtg    3300
ccgccccgag caacgggtgg cggcggcgcg cggcgggcg gggcgcggcg gcgcgtaggc    3360
ggggctaggc gccggctagg cgaaacgccg ccccccgggcg ccgccgccgc ccgctccaga    3420
gcagtcgccg cgccagaccg ccaacgcaga gaccgagacc gaggtacgtc gcgcccgagc    3480
acgccgcgac gcgcggcagg gacgaggagc acgacgccgc gccgcgccgc gcggggggg    3540
ggagggagag gcaggacgcg ggagcgagcg tgcatgtttc gcgcgagac gacgccgcgc    3600
gcgctggaga ggagataagg cgcttggatc gcgagagggc cagccaggct ggaggcgaaa    3660
atgggtggag aggatagtat cttgcgtgct tggacgagga gactgacgag gaggacggat    3720
acgtcgatga tgatgtgcac agagaagaag cagttcgaaa gcgactacta gcaagcaaga    3780
gatctagcac gctgatgagt ccgtgaggac gaaacgagta agctcgtctg cggacgtcgt    3840
ggacgcgcgt tttagagcta gaaatagcaa gttaaaataa ggctagtccg ttatcaactt    3900
gaaaaagtgg caccgagtcg gtgcttttgg ccggcatggt cccagcctcc tcgctggcgc    3960
cggctgggca acatgcttcg gcatggcgaa tgggaccata tgagttatga gatccgaaag    4020
tgaaccttgt cctaacccga cagcgaatgg cgggagggggg cgggctaaaa gatcgtatta    4080
catagtattt ttcccctact ctttgtgttt gtctttttt tttttttgaa cgcattcaag    4140
ccacttgtct gggtttactt gtttgtttgc ttgcttgctt gcttgcttgc ctgcttcttg    4200
gtcagacggc caaaaaagg gaaaaaattc attcatggca cagataagaa aaagaaaaag    4260
tttgtcgacc accgtcatca gaaagcaaga gaagagaaac actcgcgctc acattctcgc    4320
tcgcgtaaga atcttagcca cgcatacgaa gtaatttgtc catctggcga atctttacat    4380
```

```
gagcgttttc aagctggagc gtgagatcat acctttcttg atcgtaatgt tccaaccttg   4440
cataggcctc gttgcgatcc gctagcaatg cgtcgtactc ccgttgcaac tgcgccatcg   4500
cctcattgtg acgtgagttc agattcttct cgagaaactc ggcacctgcc atgaagacgc   4560
cctccaaaag ggctgggtca aggcctcgct cggacacagc cagggcgtcg tctccgccgc   4620
cgtcgttgcc gcagccaaca ccgaccgcga gctgcgcaac ctcgtggtct ccggcctcga   4680
atacatgtca aaagtcggca tcgccgccca gcgcacgctc gactacgagc tcggacgccg   4740
caacgccggc ccggagaccc cgatgctcgc tgtacaggga atggacgaaa aagtccttac   4800
caaggccttc aaggccgccg tctcgctctc caacgagaag caggccatga tggccaaaat   4860
ctccccacgg ccgccgccgc caccgccgcc ccggccgccg ttagcgacga agatcgcttc   4920
tccatcgccc tccgcaacgg ccacgacgac tttgtcgtct gcggcgagcc caaggacctg   4980
cgcgtcctcc gcaaggtcat cgagaaacag agcgccgagc ccggcaagga ggcacaggcg   5040
cgcacgcccc tttccaagcg caagcccgtc acccagacca ccttcctccg catgacggcc   5100
gtcttccaca gcgctctcaa caaggacgcc ctcgcccaga tcaacacatg gccccggag   5160 tccgccttta gcaaggcctt cgcccaggcc tcgctccgtg ttcccgtctt tgacaccaag   5220
tctggcgcta atctgcaaga tgttcccgcc gccgatgttg tcgcccatct taccaccaac   5280
atgctcactg agcgcgccga cgttctcgtc tccctccgtg ccgccgagac caagaccgac   5340
gccagccacc tcctctgttt aaacgttaac ctgcattaat gaatcggcca acgcgcgggg   5400
agaggcggtt tgcgtattgg gcgctcttcc gcttcctcgc tcactgactc gctgcgctcg   5460
gtcgttcggc tgcggcgagc ggtatcagct cactcaaagg cggtaatacg gttatccaca   5520
gaatcagggg ataacgcagg aaagaacatg tgagcaaaag gccagcaaaa ggccaggaac   5580
cgtaaaaagg ccgcgttgct ggcgttttc cataggctcc gccccctga cgagcatcac   5640 aaaaatcgac gctcaagtca gaggtggcga acccgacag gactataaag ataccaggcg   5700
tttccccctg gaagctccct cgtgcgctct cctgttccga ccctgccgct taccggatac   5760
ctgtccgcct ttctcccttc gggaagcgtg gcgctttctc aatgctcacg ctgtaggtat   5820
ctcagttcgg tgtaggtcgt tcgctccaag ctgggctgtg tgcacgaacc ccccgttcag   5880
cccgaccgct gcgccttatc cggtaactat cgtcttgagt ccaacccggt aagacgac   5940 ttatcgccac tggcagcagc cactggtaac aggattagca gagcgaggta tgtaggcggt   6000
gctacagagt tcttgaagtg gtggcctaac tacggctaca ctagaaggac agtatttggt   6060
atctgcgctc tgctgaagcc agttaccttc ggaaaaagag ttggtagctc ttgatccggc   6120
aaacaaacca ccgctggtag cggtggtttt tttgtttgca agcagcagat tacgcgcaga   6180
aaaaaaggat ctcaagaaga tcctttgatc ttttctacgg ggtctgacgc tcagtggaac   6240
gaaaactcac gttaagggat tttggtcatg agattatcaa aaaggatctt cacctagatc   6300
cttttaaatt aaaaatgaag ttttaaatca atctaaagta tatatgagta aacttggtct   6360
gacagttacc aatgcttaat cagtgaggca cctatctcag cgatctgtct atttcgttca   6420
tccatagttg cctgactccc cgtcgtgtag ataactacga tacgggaggg cttaccatct   6480
ggccccagtg ctgcaatgat accgcgagac ccacgctcac cggctccaga tttatcagca   6540 ataaccagc cagccggaag ggccgagcgc agaagtggtc ctgcaacttt atccgcctcc   6600
atccagtcta ttaattgttg ccgggaagct agagtaagta gttcgccagt taatagtttg   6660
cgcaacgttg ttgccattgc tacaggcatc gtggtgtcac gctcgtcgtt tggtatggct   6720
```

-continued

```
tcattcagct ccggttccca acgatcaagg cgagttacat gatcccccat gttgtgcaaa      6780
aaagcggtta gctccttcgg tcctccgatc gttgtcagaa gtaagttggc cgcagtgtta      6840
tcactcatgg ttatggcagc actgcataat tctcttactg tcatgccatc cgtaagatgc      6900
ttttctgtga ctggtgagta ctcaaccaag tcattctgag aatagtgtat gcggcgaccg      6960
agttgctctt gcccggcgtc aatacgggat aataccgcgc cacatagcag aactttaaaa      7020
gtgctcatca ttggaaaacg ttcttcgggg cgaaaactct caaggatctt accgctgttg      7080
agatccagtt cgatgtaacc cactcgtgca cccaactgat cttcagcatc ttttactttc      7140
accagcgttt ctgggtgagc aaaaacagga aggcaaaatg ccgcaaaaaa gggaataagg      7200
gcgacacgga aatgttgaat actcatactc ttcctttttc aatattattg aagcatttat      7260
cagggttatt gtctcatgag cggatacata tttgaatgta tttagaaaaa taaacaaata      7320
ggggttccgc gcacatttcc ccgaaaagtg ccacctgacg tctaagaaac cattattatc      7380
atgacattaa cctataaaaa taggcgtatc acgaggccct ttcgtctcgc gcgtttcggt      7440
gatgacggtg aaaacctctg acacatgcag ctcccggaga cggtcacagc ttgtctgtaa      7500
gcggatgccg ggagcagaca gcccgtcag gcgcgtcag cgggtgttgg cgggtgtcgg       7560
ggctggctta actatgcggc atcagagcag attgtactga gagtgcacca tg             7612
```

<210> SEQ ID NO 9
<211> LENGTH: 7609
<212> TYPE: DNA
<213> ORGANISM: Artificial Sequence
<220> FEATURE:
<223> OTHER INFORMATION: pYB36 vector
<220> FEATURE:
<221> NAME/KEY: misc_feature
<222> LOCATION: (2)..(1192)
<223> OTHER INFORMATION: FAS_upstream_fragment
<220> FEATURE:
<221> NAME/KEY: misc_feature
<222> LOCATION: (1200)..(1648)
<223> OTHER INFORMATION: alpha_tubulin_promoter
<220> FEATURE:
<221> NAME/KEY: misc_feature
<222> LOCATION: (1679)..(2443)
<223> OTHER INFORMATION: paromomycin_resistance_gene
<220> FEATURE:
<221> NAME/KEY: misc_feature
<222> LOCATION: (2444)..(2717)
<223> OTHER INFORMATION: SV40_terminator
<220> FEATURE:
<221> NAME/KEY: misc_feature
<222> LOCATION: (2718)..(3780)
<223> OTHER INFORMATION: EF-1_alpha_promoter
<220> FEATURE:
<221> NAME/KEY: misc_feature
<222> LOCATION: (3797)..(3829)
<223> OTHER INFORMATION: Hammerhead_ribozyme
<220> FEATURE:
<221> NAME/KEY: misc_feature
<222> LOCATION: (3830)..(3849)
<223> OTHER INFORMATION: carotene_synthase_target_1
<220> FEATURE:
<221> NAME/KEY: misc_feature
<222> LOCATION: (3850)..(3929)
<223> OTHER INFORMATION: gRNA
<220> FEATURE:
<221> NAME/KEY: misc_feature
<222> LOCATION: (3930)..(3997)
<223> OTHER INFORMATION: HDV_ribozyme
<220> FEATURE:
<221> NAME/KEY: misc_feature
<222> LOCATION: (4017)..(4535)
<223> OTHER INFORMATION: OrfC_terminator
<220> FEATURE:
<221> NAME/KEY: misc_feature

```
<222> LOCATION: (4536)..(5368)
<223> OTHER INFORMATION: FAS_downstream_fragment
<220> FEATURE:
<221> NAME/KEY: misc_feature
<222> LOCATION: (6367)..(7227)
<223> OTHER INFORMATION: AmpR_gene

<400> SEQUENCE: 9
gtttaaactc gcggcgtctt cgccgtcgag gcgcgtcttt cgaggcgggc gaggtgtttt      60
tcttttcttt tcttctcgct gcagctgcgc gcggcgaac gcagttcgcc gcggcggctg      120
cgacgcgcct gcgatgtcta tgcgcaggca aggcacgacg tcttgcggcg ccgcttcctg      180
cgccgccttg cgtcttggcc ccgccgacga cgcaagcagc ggcggcgccc cccgccctc       240
ctccactgtg ggccgcagcc ctccttttcg cgcgcccgca gccgcgcggc gcgcccgcg       300
aacaaagagc cgccgcgccg gtccgcactg cgcgggccgc cccgcaagtg ccgcaaacgc      360
cggcccgaac cgccgcaaac gcgcccgcag ccgcgcccgc agccgcgcgc gacccgcggt      420
ggggacgcgc gccaagcgtc cccttccgcg ggatgacgta ggcggcggcc ccgcctatgc      480
aatacgggag gaaccaggaa ccgggagggg ggggggcgg cgcgcgcgcc gtccagtgcg       540
ggaccgatcg gcgccgggat gcccgggcgg gaggacaca gccaggcagt cagtcagtca      600
gccgcacaga gagagcgcgc ctgcgagtcc cgtctggtct cggaattgta tcccgcgcag      660
agctcagaat cgcaggtcga tcgatcgagc gatggatcca tcgctctatc cgtccatcga      720
tccatcgcat ccatcgcatc catcgcatcc atcgttgcat cgcttgcacc gcccgcttgc      780
atcgcgtgcg tgcgcaggcg ggcggcggcc acgacgcgac cgagagcggc ggcgagtgca      840
gacgccgccg gcgcccgcgg ctgcgtcgcc gcaggaagaa ggagggggc gcgtgtttcc       900
cgcgggaggg aggagggagg gagggaggtg gttgggccaa aaaggcggc ctggacaggc       960
aggcaggccg gaagcgacgc cagcgagcga aggaagagga gagagccgcg cgggcggcca     1020
gcgcggggcg ggcggcagca aacccgctac tcagggtaaa agacagacag ctcttcgagc     1080
gagcttgttc acttcgcgga agcacgcgcg caggcacgca ggcacgcagg cagcatagcg     1140
agcagcagca gcatcgcgag cagcattgcg agaggaggcg ctgaccgccg gccaagcttc     1200
caattttagg cccccccactg accgaggtct gtcgataatc cacttttcca ttgattttcc    1260
aggtttcgtt aactcatgcc actgagcaaa acttcggtct ttcctaacaa aagctctcct    1320
cacaaagcat ggcgcggcaa cggacgtgtc ctcatactcc actgccacac aaggtcgata    1380
aactaagctc ctcacaaata gaggagaatt ccactgacaa ctgaaaacaa tgtatgagag    1440
acgatcacca ctggagcggc gcggcggttg ggcgcggagg tcggcagcaa aaacaagcga    1500
ctcgccgagc aaacccgaat cagccttcag acggtcgtgc ctaacaacac gccgttctac    1560
cccgccttct tcgcgcccct tcgcgtccaa gcatccttca agtttatctc tctagttcaa    1620
cttcaagaag aacaacacca ccaacaccat gattgaacaa gatggattgc acgcaggttc    1680
tccggccgct tgggtggaga ggctattcgg ctatgactgg gcacaacaga caatcggctg    1740
ctctgatgcc gccgtgttcc ggctgtcagc gcagggcgc ccggttcttt tgtcaagac      1800
cgacctgtcc ggtgccctga atgaactgca ggacgaggca gcgcggctat cgtggctggc    1860
cacgacgggc gttccttgcg cagctgtgct cgacgttgtc actgaagcgg gaagggactg    1920
gctgctattg ggcgaagtgc cggggcagga tctcctgtca tctcaccttg ctcctgccga    1980
gaaagtatcc atcatggctg atgcaatgcg gcggctgcat acgcttgatc cggctacctg    2040
cccattcgac caccaagcga aacatcgcat cgagcgagca cgtactcgga tggaagccgg    2100
```

| | |
|---|---|
| tcttgtcgat caggatgatc tggacgaaga gcatcagggg ctcgcgccag ccgaactgtt | 2160 |
| cgccaggctc aaggcgcgca tgcccgacgg cgatgatctc gtcgtgaccc atggcgatgc | 2220 |
| ctgcttgccg aatatcatgg tggaaaatgg ccgcttttct ggattcatcg actgtggccg | 2280 |
| gctgggtgtg gcggaccgct atcaggacat agcgttggct acccgtgata ttgctgaaga | 2340 |
| gcttggcggc gaatgggctg accgcttcct cgtgctttac ggtatcgccg ctcccgattc | 2400 |
| gcagcgcatc gccttctatc gccttcttga cgagttcttc tgacacgtgc tacgagattt | 2460 |
| cgattccacc gccgccttct atgaaaggtt gggcttcgga atcgttttcc gggacgccgg | 2520 |
| ctggatgatc ctccagcgcg gggatctcat gctggagttc ttcgcccacc ccaacttgtt | 2580 |
| tattgcagct tataatggtt acaaataaag caatagcatc acaaatttca caaataaagc | 2640 |
| attttttca ctgcattcta gttgtggttt gtccaaactc atcaatgtat cttatcatgt | 2700 |
| ctgaattccc ggggtacctc ttatctgcct cgcgccgttg accgccgctt gactcttggc | 2760 |
| gcttgccgct cgcatcctgc ctcgctcgcg caggcgggcg ggcgagtggg tgggtccgca | 2820 |
| gccttccgcg ctcgcccgct agctcgctcg cgccgtgctg cagccagcag ggcagcaccg | 2880 |
| cacggcaggc aggtcccggc gcggatcgat cgatccatcg atccatcgat ccatcgatcg | 2940 |
| tgcggtcaaa aagaaaggaa gaagaaagga aaaagaaagg cgtgcgcacc cgagtgcgcg | 3000 |
| ctgagcgccc gctcgcggtc ccgcggagcc tccgcgttag tccccgcccc gcgccgcgca | 3060 |
| gtcccccggg aggcatcgcg cacctctcgc cgcccctcg cgcctcgccg attccccgcc | 3120 |
| tccccttttc cgcttcttcg ccgcctccgc tcgcggccgc gtcgcccgcg cccgctccc | 3180 |
| tatctgctcc ccaggggggc actccgcacc ttttgcgccc gctgccgccg ccgcggccgc | 3240 |
| ccgccgcccc tggtttcccc cgcgagcgcg gccgcgtcgc cgcgcaaaga ctcgccgcgt | 3300 |
| gccgccccga gcaacgggtg gcggcggcgc ggcggcgggc ggggcgcggc ggcgcgtagg | 3360 |
| cggggctagg cgccggctag gcgaaacgcc gccccgggc gccgccgccg cccgctccag | 3420 |
| agcagtcgcc gcgccagacc gccaacgcag agaccgagac cgaggtacgt cgcgcccgag | 3480 |
| cacgccgcga cgcgcggcag ggacgaggag cacgacgccg cgccgcgccg cgcgggggg | 3540 |
| gggagggaga ggcaggacgc gggagcgagc gtgcatgttt ccgcgcgaga cgacgccgcg | 3600 |
| cgcgctggag aggagataag gcgcttggat cgcgagaggg ccagccaggc tggaggcgaa | 3660 |
| aatgggtgga gaggatagta tcttgcgtgc ttggacgagg agactgacga ggaggacgga | 3720 |
| tacgtcgatg atgatgtgca cagagaagaa gcagttcgaa agcgactact agcaagcaag | 3780 |
| agatcttccg cactgatgag tccgtgagga cgaaacgagt aagctcgtct gcggacgtcg | 3840 |
| tggacgcgcg tttagagct agaaatagca agttaaaata aggctagtcc gttatcaact | 3900 |
| tgaaaaagtg gcaccgagtc ggtgcttttg gccggcatgg tcccagcctc ctcgctggcg | 3960 |
| ccggctgggc aacatgcttc ggcatggcga atggaccat atgagttatg agatccgaaa | 4020 |
| gtgaaccttg tcctaacccg cacagcgaatg gcgggagggg gcgggctaaa agatcgtatt | 4080 |
| acatagtatt tttccccctac tctttgtgtt tgtctttttt tttttttga acgcattcaa | 4140 |
| gccacttgtc tgggtttact tgtttgtttg cttgcttgct tgcttgcttg cctgcttctt | 4200 |
| ggtcagacgg cccaaaaaag ggaaaaaatt cattcatggc acagataaga aaagaaaaa | 4260 |
| gtttgtcgac caccgtcatc agaaagcaag agaagagaaa cactcgcgct cacattctcg | 4320 |
| ctcgcgtaag aatcttagcc acgcatacga agtaatttgt ccatctggcg aatctttaca | 4380 |
| tgagcgtttt caagctggag cgtgagatca tacctttctt gatcgtaatg ttccaacctt | 4440 |
| gcataggcct cgttgcgatc cgctagcaat gcgtcgtact cccgttgcaa ctgcgccatc | 4500 |

```
gcctcattgt gacgtgagtt cagattcttc tcgagaaact cggcacctgc catgaagacg    4560
ccctccaaaa gggctgggtc aaggcctcgc tcggacacag ccagggcgtc gtctccgccg    4620
ccgtcgttgc cgcagccaac accgaccgcg agctgcgcaa cctcgtggtc tccggcctcg    4680
aatacatgtc aaaagtcggc atcgccgccc agcgcacgct cgactacgag ctcggacgcc    4740
gcaacgccgg cccggagacc ccgatgctcg ctgtacaggg aatggacgaa aaagtcctta    4800
ccaaggcctt caaggccgcc gtctcgctct ccaacgagaa gcaggccatg atggccaaaa    4860 tctcccacg gccgccgccg ccaccgccgc cccggccgcc gttagcgacg aagatcgctt    4920
ctccatcgcc ctccgcaacg gccacgacga ctttgtcgtc tgcggcgagc ccaaggacct    4980
gcgcgtcctc cgcaaggtca tcgagaaaca gagcgccgag cccggcaagg aggcacaggc    5040
gcgcacgccc ttttccaagc gcaagcccgt cacccagacc accttcctcc gcatgacggc    5100
cgtcttccac agcgctctca acaaggacgc cctcgcccag atcaacacat gggccccgga    5160
gtccgccttt agcaaggcct tcgcccaggc ctcgctccgt gttccgtct ttgacaccaa    5220 gtctggcgct aatctgcaag atgttcccgc cgccgatgtt gtcgcccatc ttaccaccaa    5280
catgctcact gagcgcgccg acgttctcgt ctccctccgt gccgccgaga ccaagaccga    5340
cgccagccac ctcctctgtt taaacgttaa cctgcattaa tgaatcggcc aacgcgcggg    5400
gagaggcggt ttgcgtattg gcgctcttc cgcttcctcg ctcactgact cgctgcgctc    5460
ggtcgttcgg ctgcggcgag cggtatcagc tcactcaaag gcggtaatac ggttatccac    5520
agaatcaggg gataacgcag gaaagaacat gtgagcaaaa ggccagcaaa aggccaggaa    5580
ccgtaaaaag gccgcgttgc tggcgttttt ccataggctc cgcccccctg acgagcatca    5640
caaaaatcga cgctcaagtc agaggtggcg aaacccgaca ggactataaa gataccaggc    5700
gtttccccct ggaagctccc tcgtgcgctc tcctgttccg accctgccgc ttaccggata    5760
cctgtccgcc tttctccctt cgggaagcgt ggcgctttct catagctcac gctgtaggta    5820
tctcagttcg gtgtaggtcg ttcgctccaa gctgggctgt gtgcacgaac cccccgttca    5880
gcccgaccgc tgcgccttat ccggtaacta tcgtcttgag tccaacccgg taagacacga    5940
cttatcgcca ctggcagcag ccactggtaa caggattagc agagcgaggt atgtaggcgg    6000
tgctacagag ttcttgaagt ggtggcctaa ctacggctac actagaagaa cagtatttgg    6060
tatctgcgct ctgctgaagc cagttacctt cggaaaaaga gttggtagct cttgatccgg    6120
caaacaaacc accgctggta gcggtggttt ttttgtttgc aagcagcaga ttacgcgcag    6180
aaaaaaagga tctcaagaag atcctttgat cttttctacg gggtctgacg ctcagtggaa    6240
cgaaaactca cgttaaggga ttttggtcat gagattatca aaaaggatct tcacctagat    6300
ccttttaaat taaaaatgaa gttttaaatc aatctaaagt atatatgagt aaacttggtc    6360
tgacagttac caatgcttaa tcagtgaggc acctatctca gcgatctgtc tatttcgttc    6420
atccatagtt gcctgactcc ccgtcgtgta gataactacg atacgggagg cttaccatc    6480 tggccccagt gctgcaatga taccgcgaga cccacgctca ccggctccag atttatcagc    6540
aataaaccag ccagccggaa gggccgagcg cagaagtggt cctgcaactt tatccgcctc    6600
catccagtct attaattgtt gccgggaagc tagagtaagt agttcgccag ttaatagttt    6660
gcgcaacgtt gttgccattg ctacaggcat cgtggtgtca cgctcgtcgt ttggtatggc    6720
ttcattcagc tccggttccc aacgatcaag gcgagttaca tgatccccca tgttgtgcaa    6780
aaaagcggtt agctccttcg gtcctccgat cgttgtcaga agtaagttgg ccgcagtgtt    6840
```

```
atcactcatg gttatggcag cactgcataa ttctcttact gtcatgccat ccgtaagatg    6900
cttttctgtg actggtgagt actcaaccaa gtcattctga gaatagtgta tgcggcgacc    6960
gagttgctct tgcccggcgt caatacggga taataccgcg ccacatagca gaactttaaa    7020
agtgctcatc attggaaaac gttcttcggg gcgaaaactc tcaaggatct taccgctgtt    7080
gagatccagt tcgatgtaac ccactcgtgc acccaactga tcttcagcat cttttacttt    7140
caccagcgtt tctgggtgag caaaaacagg aaggcaaaat gccgcaaaaa agggaataag    7200
ggcgacacgg aaatgttgaa tactcatact cttcctttt  caatattatt gaagcattta    7260
tcagggttat tgtctcatga gcggatacat atttgaatgt atttagaaaa ataaacaaat    7320
aggggttccg cgcacatttc cccgaaaagt gccacctgac gtctaagaaa ccattattat    7380
catgacatta acctataaaa ataggcgtat cacgaggccc tttcgtctcg cgcgtttcgg    7440
tgatgacggt gaaaacctct gacacatgca gctcccggag acggtcacag cttgtctgta    7500
agcggatgcc gggagcagac aagcccgtca gggcgcgtca gcgggtgttg gcgggtgtcg    7560
gggctggctt aactatgcgg catcagagca gattgtactg agagtgcac                7609
```

```
<210> SEQ ID NO 10
<211> LENGTH: 7609
<212> TYPE: DNA
<213> ORGANISM: Artificial Sequence
<220> FEATURE:
<223> OTHER INFORMATION: pYB37 vector
<220> FEATURE:
<221> NAME/KEY: misc_feature
<222> LOCATION: (2)..(1192)
<223> OTHER INFORMATION: FAS_upstream_fragment
<220> FEATURE:
<221> NAME/KEY: misc_feature
<222> LOCATION: (1200)..(1648)
<223> OTHER INFORMATION: alpha_tubulin_promoter
<220> FEATURE:
<221> NAME/KEY: misc_feature
<222> LOCATION: (1679)..(2443)
<223> OTHER INFORMATION: paromomycin_resistance_gene
<220> FEATURE:
<221> NAME/KEY: misc_feature
<222> LOCATION: (2444)..(2717)
<223> OTHER INFORMATION: SV40_terminator
<220> FEATURE:
<221> NAME/KEY: misc_feature
<222> LOCATION: (2718)..(3780)
<223> OTHER INFORMATION: EF-1_alpha_promoter
<220> FEATURE:
<221> NAME/KEY: misc_feature
<222> LOCATION: (3797)..(3829)
<223> OTHER INFORMATION: Hammerhead_ribozyme
<220> FEATURE:
<221> NAME/KEY: misc_feature
<222> LOCATION: (3830)..(3849)
<223> OTHER INFORMATION: carotene_synthase_target_2
<220> FEATURE:
<221> NAME/KEY: misc_feature
<222> LOCATION: (3850)..(3929)
<223> OTHER INFORMATION: gRNA
<220> FEATURE:
<221> NAME/KEY: misc_feature
<222> LOCATION: (3930)..(3997)
<223> OTHER INFORMATION: HDV_ribozyme
<220> FEATURE:
<221> NAME/KEY: misc_feature
<222> LOCATION: (4017)..(4535)
<223> OTHER INFORMATION: OrfC_terminator
<220> FEATURE:
<221> NAME/KEY: misc_feature
<222> LOCATION: (4536)..(5368)
<223> OTHER INFORMATION: FAS_downstream_fragment
<220> FEATURE:
<221> NAME/KEY: misc_feature
```

```
<222> LOCATION: (6367)..(7227)
<223> OTHER INFORMATION: AmpR_gene

<400> SEQUENCE: 10
gtttaaactc gcggcgtctt cgccgtcgag gcgcgtcttt cgaggcgggc gaggtgtttt      60
tcttttcttt tcttctcgct gcagctgcgc cgcggcgaac gcagttcgcc gcggcggctg     120
cgacgcgcct gcgatgtcta tgcgcaggca aggcacgacg tcttgcggcg ccgcttcctg     180
cgccgccttg cgtcttggcc ccgccgacga cgcaagcagc ggcggcgccc cccgccctc      240 ctccactgtg ggccgcagcc ctccttttcg cgcgcccgca gccgcgcggc gcgccccgcg     300
aacaaagagc cgccgcgccg gtccgcactg cgcgggccgc cccgcaagtg ccgcaaacgc     360
cggcccgaac cgccgcaaac gcgcccgcag ccgcccccgc agccgcgcgc gacccgcggt     420
ggggacgcgc gccaagcgtc cccttccgcg ggatgacgta ggcggcggcc ccgcctatgc     480
aatacgggag gaaccaggaa ccgggagggg gggggggcgg cgcgcgcgcc gtccagtgcg     540
ggaccgatcg gcgccgggat gcccgggcgg gagggacaca gccaggcagt cagtcagtca     600
gccgcacaga gagagcgcgc ctgcgagtcc cgtctggtct cggaattgta tcccgcgcag     660
agctcagaat cgcaggtcga tcgatcgagc gatggatcca tcgctctatc cgtccatcga     720
tccatcgcat ccatcgcatc catcgcatcc atcgttgcat cgcttgcacc gcccgcttgc     780
atcgcgtgcg tgcgcaggcg ggcggcggcc acgacgcgac cgagagcggc ggcgagtgca     840
gacgccgccg gcgcccgcgg ctgcgtcgcc gcaggaagaa ggagggggc gcgtgtttcc      900 cgcgggaggg aggagggagg gagggaggtg gttgggccaa aaaggggcggc ctggacaggc    960 aggcaggccg gaagcgacgc cagcgagcga aggaagagga gagagccgcg cgggcggcca   1020
gcgcggggcg ggcggcagca aacccgctac tcagggtaaa agacagacag ctcttcgagc   1080
gagcttgttc acttcgcgga agcacgcgcg caggcacgca ggcacgcagg cagcatagcg   1140
agcagcagca gcatcgcgag cagcattgcg agagaggcg ctgaccgccg gccaagcttc     1200 caatttagg ccccccactg accgaggtct gtcgataatc cacttttcca ttgattttcc     1260
aggtttcgtt aactcatgcc actgagcaaa acttcggtct ttcctaacaa aagctctcct   1320
cacaaagcat ggcgcggcaa cggacgtgtc ctcatactcc actgccacac aaggtcgata   1380
aactaagctc ctcacaaata gaggagaatt ccactgacaa ctgaaaacaa tgtatgagag   1440
acgatcacca ctggagcggc gcggcggttg ggcgcggagg tcggcagcaa aaacaagcga   1500
ctcgccgagc aaacccgaat cagccttcag acggtcgtgc ctaacaacac gccgttctac   1560
cccgccttct tcgcgcccct tcgcgtccaa gcatccttca agtttatctc tctagttcaa   1620
cttcaagaag aacaacacca ccaacaccat gattgaacaa gatggattgc acgcaggttc   1680
tccggccgct tgggtggaga ggctattcgg ctatgactgg gcacaacaga caatcggctg   1740
ctctgatgcc gccgtgttcc ggctgtcagc gcaggggcgc ccggttcttt ttgtcaagac   1800
cgacctgtcc ggtgccctga tgaactgca ggacgaggca gcgcggctat cgtggctggc   1860
cacgacgggc gttccttgcg cagctgtgct cgacgttgtc actgaagcgg gaagggactg   1920
gctgctattg ggcgaagtgc cggggcagga tctcctgtca tctcaccttg ctcctgccga   1980
gaaagtatcc atcatggctg atgcaatgcg gcggctgcat acgcttgatc cggctacctg   2040
cccattcgac caccaagcga aacatcgcat cgagcgagca cgtactcgga tggaagccgg   2100
tcttgtcgat caggatgatc tggacgaaga gcatcagggg ctcgcgccag ccgaactgtt   2160
cgccaggctc aaggcgcgca tgcccgacgg cgatgatctc gtcgtgaccc atggcgatgc   2220
```

-continued

```
ctgcttgccg aatatcatgg tggaaaatgg ccgcttttct ggattcatcg actgtggccg      2280
gctgggtgtg gcggaccgct atcaggacat agcgttggct acccgtgata ttgctgaaga      2340
gcttggcggc gaatgggctg accgcttcct cgtgctttac ggtatcgccg ctcccgattc      2400
gcagcgcatc gccttctatc gccttcttga cgagttcttc tgacacgtgc tacgagattt      2460
cgattccacc gccgccttct atgaaaggtt gggcttcgga atcgttttcc gggacgccgg      2520
ctggatgatc ctccagcgcg gggatctcat gctggagttc ttcgcccacc ccaacttgtt      2580
tattgcagct tataatggtt acaaataaag caatagcatc acaaatttca caaataaagc      2640
atttttttca ctgcattcta gttgtggttt gtccaaactc atcaatgtat cttatcatgt      2700
ctgaattccc ggggtacctc ttatctgcct cgcgccgttg accgccgctt gactcttggc      2760
gcttgccgct cgcatcctgc ctcgctcgcg caggcgggcg ggcgagtggg tgggtccgca      2820
gccttccgcg ctcgcccgct agctcgctcg cgccgtgctg cagccagcag ggcagcaccg      2880
cacggcaggc aggtcccggc gcggatcgat cgatccatcg atccatcgat ccatcgatcg      2940
tgcggtcaaa aagaaaggaa gaagaaagga aaaagaaagg cgtgcgcacc cgagtgcgcg      3000
ctgagcgccc gctcgcggtc cgcggagcc tccgcgttag tccccgcccc gcgccgcgca      3060
gtcccccggg aggcatcgcg cacctctcgc cgcccctcg cgcctcgccg attccccgcc      3120 tcccctttc cgcttcttcg ccgcctccgc tcgcggccgc gtcgcccgcg ccccgctccc      3180
tatctgctcc ccagggggc actccgcacc ttttgcgccc gctgccgccg ccgcggccgc      3240
cccgccgccc tggtttcccc cgcgagcgcg gccgcgtcgc cgcgcaaaga ctcgccgcgt      3300
gccgccccga gcaacgggtg gcggcggcgc ggcggcgggc ggggcgcggc ggcgcgtagg      3360
cggggctagg cgccggctag gcgaaacgcc gccccgggc gccgccgccg cccgctccag      3420
agcagtcgcc gcgccagacc gccaacgcag agaccgagac cgaggtacgt cgcgcccgag      3480
cacgccgcga cgcgcggcag ggacgaggag cacgacgccg cgccgcgccg cgcggggggg      3540
gggagggaga ggcaggacgc gggagcgagc gtgcatgttt ccgcgcgaga cgacgccgcg      3600
cgcgctggag aggagataag gcgcttggat cgcgagaggg ccagccaggc tggaggcgaa      3660
aatgggtgga gaggatagta tcttgcgtgc ttggacgagg agactgacga ggaggacgga      3720
tacgtcgatg atgatgtgca cagagaagaa gcagttcgaa agcgactact agcaagcaag      3780
agatcttccg cactgatgag tccgtgagga cgaaacgagt aagctcgtcg cagaccttaa      3840
gttcgacgcg ttttagagct agaaatagca agttaaaata aggctagtcc gttatcaact      3900
tgaaaaagtg gcaccgagtc ggtgcttttg gccggcatgg tcccagcctc ctcgctggcg      3960
ccggctgggc aacatgcttc ggcatggcga atgggaccat atgagttatg agatccgaaa      4020
gtgaaccttg tcctaacccg acagcgaatg gcgggagggg gcgggctaaa agatcgtatt      4080
acatagtatt tttccccctac tctttgtgtt tgtctttttt ttttttttga acgcattcaa      4140
gccacttgtc tgggtttact tgtttgtttg cttgcttgct tgcttgcttg cctgcttctt      4200
ggtcagacgg cccaaaaaag ggaaaaaatt cattcatggc acagataaga aaagaaaaa      4260 gtttgtcgac caccgtcatc agaaagcaag agaagagaaa cactcgcgct cacattctcg      4320
ctcgcgtaag aatcttagcc acgcatacga agtaatttgt ccatctggcg aatctttaca      4380
tgagcgtttt caagctggag cgtgagatca tacctttctt gatcgtaatg ttccaacctt      4440
gcataggcct cgttgcgatc cgctagcaat gcgtcgtact cccgttgcaa ctgcgccatc      4500
gcctcattgt gacgtgagtt cagattcttc tcgagaaact cggcacctgc catgaagacg      4560
ccctccaaaa gggctgggtc aaggcctcgc tcggacacag ccagggcgtc gtctccgccg      4620
```

```
ccgtcgttgc cgcagccaac accgaccgcg agctgcgcaa cctcgtggtc tccggcctcg   4680
aatacatgtc aaaagtcggc atcgccgccc agcgcacgct cgactacgag ctcggacgcc   4740
gcaacgccgg cccggagacc ccgatgctcg ctgtacaggg aatggacgaa aaagtcctta   4800
ccaaggcctt caaggccgcc gtctcgctct ccaacgagaa gcaggccatg atggccaaaa   4860
tctccccacg gccgccgccg ccaccgccgc cccggccgcc gttagcgacg aagatcgctt   4920
ctccatcgcc ctccgcaacg gccacgacga ctttgtcgtc tgcggcgagc ccaaggacct   4980
gcgcgtcctc cgcaaggtca tcgagaaaca gagcgccgag cccggcaagg aggcacaggc   5040
gcgcacgccc ttttccaagc gcaagcccgt cacccagacc accttcctcc gcatgacggc   5100
cgtcttccac agcgctctca acaaggacgc cctcgcccag atcaacacat gggccccgga   5160
gtccgccttt agcaaggcct tcgcccaggc ctcgctccgt gttccgtct ttgacaccaa   5220 gtctggcgct aatctgcaag atgttcccgc cgccgatgtt gtcgcccatc ttaccaccaa   5280
catgctcact gagcgcgccg acgttctcgt ctccctccgt gccgccgaga ccaagaccga   5340
cgccagccac ctcctctgtt taaacgttaa cctgcattaa tgaatcggcc aacgcgcggg   5400
gagaggcggt ttgcgtattg ggcgctcttc cgcttcctcg ctcactgact cgctgcgctc   5460
ggtcgttcgg ctgcggcgag cggtatcagc tcactcaaag gcggtaatac ggttatccac   5520
agaatcaggg gataacgcag gaaagaacat gtgagcaaaa ggccagcaaa aggccaggaa   5580
ccgtaaaaag gccgcgttgc tggcgttttt ccataggctc cgcccccctg acgagcatca   5640 caaaatcga cgctcaagtc agaggtggcg aaacccgaca ggactataaa gataccaggc   5700
gtttccccct ggaagctccc tcgtgcgctc tcctgttccg accctgccgc ttaccggata   5760
cctgtccgcc tttctccctt cgggaagcgt ggcgctttct catagctcac gctgtaggta   5820
tctcagttcg gtgtaggtcg ttcgctccaa gctgggctgt gtgcacgaac cccccgttca   5880
gcccgaccgc tgcgccttat ccggtaacta tcgtcttgag tccaacccgg taagacacga   5940
cttatcgcca ctggcagcag ccactggtaa caggattagc agagcgaggt atgtaggcgg   6000
tgctacagag ttcttgaagt ggtggcctaa ctacggctac actagaagaa cagtatttgg   6060
tatctgcgct ctgctgaagc cagttacctt cggaaaaaga gttggtagct cttgatccgg   6120
caaacaaacc accgctggta gcggtggttt ttttgtttgc aagcagcaga ttacgcgcag   6180
aaaaaaagga tctcaagaag atcctttgat cttttctacg gggtctgacg ctcagtggaa   6240
cgaaaactca cgttaaggga ttttggtcat gagattatca aaaaggatct tcacctagat   6300
ccttttaaat taaaaatgaa gttttaaatc aatctaaagt atatatgagt aaacttggtc   6360
tgacagttac caatgcttaa tcagtgaggc acctatctca gcgatctgtc tatttcgttc   6420
atccatagtt gcctgactcc ccgtcgtgta gataactacg atacgggagg cttaccatc   6480 tggccccagt gctgcaatga taccgcgaga cccacgctca ccggctccag atttatcagc   6540
aataaaccag ccagccggaa gggccgagcg cagaagtggt cctgcaactt tatccgcctc   6600
catccagtct attaattgtt gccgggaagc tagagtaagt agttcgccag ttaatagttt   6660
gcgcaacgtt gttgccattg ctacaggcat cgtggtgtca cgctcgtcgt ttggtatggc   6720
ttcattcagc tccggttccc aacgatcaag gcgagttaca tgatccccca tgttgtgcaa   6780
aaaagcggtt agctccttcg gtcctccgat cgttgtcaga agtaagttgg ccgcagtgtt   6840
atcactcatg gttatggcag cactgcataa ttctcttact gtcatgccat ccgtaagatg   6900
cttttctgtg actggtgagt actcaaccaa gtcattctga gaatagtgta tgcggcgacc   6960
```

```
gagttgctct tgcccggcgt caatacggga taataccgcg ccacatagca gaactttaaa    7020
agtgctcatc attggaaaac gttcttcggg gcgaaaactc tcaaggatct taccgctgtt    7080
gagatccagt tcgatgtaac ccactcgtgc acccaactga tcttcagcat cttttacttt    7140
caccagcgtt tctgggtgag caaaaacagg aaggcaaaat gccgcaaaaa agggaataag    7200
ggcgacacgg aaatgttgaa tactcatact cttcctttttt caatattatt gaagcattta    7260
tcagggttat tgtctcatga gcggatacat atttgaatgt atttagaaaa ataaacaaat    7320
aggggttccg cgcacatttc cccgaaaagt gccacctgac gtctaagaaa ccattattat    7380
catgacatta acctataaaa ataggcgtat cacgaggccc tttcgtctcg cgcgtttcgg    7440
tgatgacggt gaaaacctct gacacatgca gctcccggag acggtcacag cttgtctgta    7500
agcggatgcc gggagcagac aagcccgtca gggcgcgtca gcgggtgttg gcgggtgtcg    7560
gggctggctt aactatgcgg catcagagca gattgtactg agagtgcac                7609
```

```
<210> SEQ ID NO 11
<211> LENGTH: 7609
<212> TYPE: DNA
<213> ORGANISM: Artificial Sequence
<220> FEATURE:
<223> OTHER INFORMATION: pYB38 vector
<220> FEATURE:
<221> NAME/KEY: misc_feature
<222> LOCATION: (2)..(1192)
<223> OTHER INFORMATION: FAS_upstream_fragment
<220> FEATURE:
<221> NAME/KEY: misc_feature
<222> LOCATION: (1200)..(1648)
<223> OTHER INFORMATION: alpha_tubulin_promoter
<220> FEATURE:
<221> NAME/KEY: misc_feature
<222> LOCATION: (1679)..(2443)
<223> OTHER INFORMATION: paromomycin_resistance_gene
<220> FEATURE:
<221> NAME/KEY: misc_feature
<222> LOCATION: (2444)..(2717)
<223> OTHER INFORMATION: SV40_terminator
<220> FEATURE:
<221> NAME/KEY: misc_feature
<222> LOCATION: (2718)..(3780)
<223> OTHER INFORMATION: EF-1_alpha_promoter
<220> FEATURE:
<221> NAME/KEY: misc_feature
<222> LOCATION: (3797)..(3829)
<223> OTHER INFORMATION: Hammerhead_ribozyme
<220> FEATURE:
<221> NAME/KEY: misc_feature
<222> LOCATION: (3830)..(3849)
<223> OTHER INFORMATION: carotene_synthase_target_3
<220> FEATURE:
<221> NAME/KEY: misc_feature
<222> LOCATION: (3850)..(3929)
<223> OTHER INFORMATION: gRNA
<220> FEATURE:
<221> NAME/KEY: misc_feature
<222> LOCATION: (3930)..(3997)
<223> OTHER INFORMATION: HDV_ribozyme
<220> FEATURE:
<221> NAME/KEY: misc_feature
<222> LOCATION: (4017)..(4535)
<223> OTHER INFORMATION: OrfC_terminator
<220> FEATURE:
<221> NAME/KEY: misc_feature
<222> LOCATION: (4536)..(5368)
<223> OTHER INFORMATION: FAS_downstream_fragment
<220> FEATURE:
<221> NAME/KEY: misc_feature
<222> LOCATION: (6367)..(7227)
<223> OTHER INFORMATION: AmpR_gene

<400> SEQUENCE: 11
```

```
gtttaaactc gcggcgtctt cgccgtcgag gcgcgtcttt cgaggcgggc gaggtgtttt    60
tcttttcttt tcttctcgct gcagctgcgc cgcggcgaac gcagttcgcc gcggcggctg   120
cgacgcgcct gcgatgtcta tgcgcaggca aggcacgacg tcttgcggcg ccgcttcctg   180
cgccgccttg cgtcttggcc ccgccgacga cgcaagcagc ggcggcgccc cccgccctc    240
ctccactgtg ggccgcagcc ctccttttcg cgcgcccgca gccgcgcggc gcgcccgcg    300
aacaaagagc cgccgcgccg gtccgcactg cgcgggccgc cccgcaagtg ccgcaaacgc   360
cggcccgaac cgccgcaaac gcgcccgcag ccgcgcccgc agccgcgcgc gacccgcggt   420
ggggacgcgc gccaagcgtc cccttccgcg ggatgacgta ggcggcggcc ccgcctatgc   480
aatacgggag gaaccaggaa ccgggagggg ggggggggcgg cgcgcgcgcc gtccagtgcg   540
ggaccgatcg gcgccgggat gcccgggcgg gagggacaca gccaggcagt cagtcagtca   600
gccgcacaga gagagcgcgc ctgcgagtcc cgtctggtct cggaattgta tcccgcgcag   660
agctcagaat cgcaggtcga tcgatcgagc gatggatcca tcgctctatc cgtccatcga   720
tccatcgcat ccatcgcatc catcgcatcc atcgttgcat cgcttgcacc gcccgcttgc   780
atcgcgtgcg tgcgcaggcg ggcggcggcc acgacgcgac cgagagcggc ggcgagtgca   840
gacgccgccg gcgcccgcgg ctgcgtcgcc gcaggaagaa ggagggggggc gcgtgtttcc   900
cgcgggaggg aggagggagg gagggaggtg gttgggccaa aaaggcggc ctggacaggc    960
aggcaggccg gaagcgacgc cagcgagcga aggaagagga gagagccgcg cgggcggcca  1020
gcgcggggcg ggcggcagca aacccgctac tcagggtaaa agacagacag ctcttcgagc  1080
gagcttgttc acttcgcgga agcacgcgcg caggcacgca ggcacgcagg cagcatagcg  1140
agcagcagca gcatcgcgag cagcattgcg agaggaggcg ctgaccgccg gccaagcttc  1200
caatttagg cccccccactg accgaggtct gtcgataatc cacttttcca ttgatttttcc  1260
aggtttcgtt aactcatgcc actgagcaaa acttcggtct ttcctaacaa aagctctcct  1320
cacaaagcat ggcgcggcaa cggacgtgtc ctcatactcc actgccacac aaggtcgata  1380
aactaagctc ctcacaaata gaggagaatt ccactgacaa ctgaaaacaa tgtatgagag  1440
acgatcacca ctggagcggc gcggcggttg ggcgcggagg tcggcagcaa aaacaagcga  1500
ctcgccgagc aaacccgaat cagccttcag acggtcgtgc ctaacaacac gccgttctac  1560
cccgccttct tcgcgcccct tcgcgtccaa gcatccttca agtttatctc tctagttcaa  1620
cttcaagaag aacaacacca ccaacaccat gattgaacaa gatggattgc acgcaggttc  1680
tccggccgct tgggtggaga ggctattcgg ctatgactgg gcacaacaga caatcggctg  1740
ctctgatgcc gccgtgttcc ggctgtcagc gcaggggcgc ccggttcttt tgtcaagac   1800
cgacctgtcc ggtgccctga tgaactgca ggacgaggca gcgcggctat cgtggctggc   1860
cacgacgggc gttccttgcg cagctgtgct cgacgttgtc actgaagcgg gaagggactg  1920
gctgctattg ggcgaagtgc cggggcagga tctcctgtca tctcaccttg ctcctgccga  1980
gaaagtatcc atcatggctg atgcaatgcg gcggctgcat acgcttgatc cggctacctg  2040
cccattcgac caccaagcga aacatcgcat cgagcgagca cgtactcgga tggaagccgg  2100
tcttgtcgat caggatgatc tggacgaaga gcatcagggg ctcgcgccag ccgaactgtt  2160
cgccaggctc aaggcgcgca tgcccgacgg cgatgatctc gtcgtgaccc atggcgatgc  2220
ctgcttgccg aatatcatgg tggaaaatgg ccgcttttct ggattcatcg actgtggccg  2280
gctgggtgtg gcggaccgct atcaggacat agcgttggct acccgtgata ttgctgaaga  2340
```

```
gcttggcggc gaatgggctg accgcttcct cgtgctttac ggtatcgccg ctcccgattc    2400
gcagcgcatc gccttctatc gccttcttga cgagttcttc tgacacgtgc tacgagattt    2460
cgattccacc gccgccttct atgaaaggtt gggcttcgga atcgttttcc gggacgccgg    2520
ctggatgatc ctccagcgcg gggatctcat gctggagttc ttcgcccacc ccaacttgtt    2580
tattgcagct tataatggtt acaaataaag caatagcatc acaaatttca caaataaagc    2640 attttttca ctgcattcta gttgtggttt gtccaaactc atcaatgtat cttatcatgt    2700
ctgaattccc ggggtacctc ttatctgcct cgcgccgttg accgccgctt gactcttggc    2760
gcttgccgct cgcatcctgc ctcgctcgcg caggcgggcg ggcgagtggg tgggtccgca    2820
gccttccgcg ctcgcccgct agctcgctcg cgccgtgctg cagccagcag ggcagcaccg    2880
cacggcaggc aggtcccggc gcggatcgat cgatccatcg atccatcgat ccatcgatcg    2940
tgcggtcaaa aagaaaggaa gaagaaagga aaaagaaagg cgtgcgcacc cgagtgcgcg    3000
ctgagcgccc gctcgcggtc ccgcggagcc tccgcgttag tccccgcccc gcgccgcgca    3060
gtcccccggg aggcatcgcg cacctctcgc cgcccctcg cgcctcgccg attccccgcc    3120
tccccttttc cgcttcttcg ccgcctccgc tcgcggccgc gtcgcccgcg ccccgctccc    3180
tatctgctcc ccagggggc actccgcacc ttttgcgccc gctgccgccg ccgcggccgc    3240
cccgccgccc tggtttcccc cgcgagcgcg gccgcgtcgc cgcgcaaaga ctcgccgcgt    3300
gccgccccga gcaacgggtg gcggcggcgc ggcggcgggg ggggcgcggc ggcgcgtagg    3360
cggggctagg cgccggctag gcgaaacgcc gccccgggc gccgccgccg cccgctccag    3420
agcagtcgcc gcgccagacc gccaacgcag agaccgagac cgaggtacgt cgcgcccgag    3480
cacgccgcga cgcgcggcag ggacgaggag cacgacgccg cgccgcgccg cgcgggggg    3540 gggagggaga ggcaggacgc gggagcgagc gtgcatgttt ccgcgcgaga cgacgccgcg    3600
cgcgctggag aggagataag gcgcttggat cgcgagaggg ccagccaggc tggaggcgaa    3660
aatgggtgga gaggatagta tcttgcgtgc ttggacgagg agactgacga ggaggacgga    3720
tacgtcgatg atgatgtgca cagagaagaa gcagttcgaa agcgactact agcaagcaag    3780
agatcttccg cactgatgag tccgtgagga cgaaacgagt aagctcgtcc cgactcgtcg    3840
accgtctcag tttagagct agaaatagca agttaaaata aggctagtcc gttatcaact    3900
tgaaaaagtg gcaccgagtc ggtgcttttg gccggcatgg tcccagcctc ctcgctggcg    3960
ccggctgggc aacatgcttc ggcatggcga atgggaccat atgagttatg agatccgaaa    4020
gtgaaccttg tcctaacccg acagcgaatg gcgggagggg gcgggctaaa agatcgtatt    4080
acatagtatt tttcccctac tctttgtgtt tgtcttttt ttttttga acgcattcaa    4140 gccacttgtc tgggtttact tgtttgtttg cttgcttgct tgcttgcttg cctgcttctt    4200
ggtcagacgg cccaaaaaag ggaaaaaatt cattcatggc acagataaga aaagaaaaa    4260 gtttgtcgac caccgtcatc agaaagcaag agaagagaaa cactcgcgct cacattctcg    4320
ctcgcgtaag aatcttagcc acgcatacga agtaatttgt ccatctggcg aatctttaca    4380
tgagcgtttt caagctggag cgtgagatca tacctttctt gatcgtaatg ttccaacctt    4440
gcataggcct cgttgcgatc cgctagcaat gcgtcgtact cccgttgcaa ctgcgccatc    4500
gcctcattgt gacgtgagtt cagattcttc tcgagaaact cggcacctgc catgaagacg    4560
ccctccaaaa gggctgggtc aaggcctcgc tcggacacag ccaggcgtc gtctccgccg    4620 ccgtcgttgc cgcagccaac accgaccgcg agctcgcaa cctcgtggtc tccgcctcg    4680 aatacatgtc aaaagtcggc atcgccgccc agcgcacgct cgactacgag ctcggacgcc    4740
```

```
gcaacgccgg cccggagacc ccgatgctcg ctgtacaggg aatggacgaa aaagtcctta   4800
ccaaggcctt caaggccgcc gtctcgctct ccaacgagaa gcaggccatg atggccaaaa   4860
tctccccacg gccgccgccg ccaccgccgc cccggccgcc gttagcgacg aagatcgctt   4920
ctccatcgcc ctccgcaacg gccacgacga ctttgtcgtc tgcggcgagc ccaaggacct   4980
gcgcgtcctc cgcaaggtca tcgagaaaca gagcgccgag cccggcaagg aggcacaggc   5040
gcgcacgccc ttttccaagc gcaagcccgt cacccagacc accttcctcc gcatgacggc   5100
cgtcttccac agcgctctca acaaggacgc cctcgcccag atcaacacat gggccccgga   5160
gtccgccttt agcaaggcct tcgcccaggc ctcgctccgt gttcccgtct ttgacaccaa   5220
gtctggcgct aatctgcaag atgttcccgc cgccgatgtt gtcgcccatc ttaccaccaa   5280
catgctcact gagcgcgccg acgttctcgt ctccctccgt gccgccgaga ccaagaccga   5340
cgccagccac ctcctctgtt taaacgttaa cctgcattaa tgaatcggcc aacgcgcggg   5400
gagaggcggt ttgcgtattg ggcgctcttc cgcttcctcg ctcactgact cgctgcgctc   5460
ggtcgttcgg ctgcggcgag cggtatcagc tcactcaaag gcggtaatac ggttatccac   5520
agaatcaggg gataacgcag gaaagaacat gtgagcaaaa ggccagcaaa aggccaggaa   5580
ccgtaaaaag gccgcgttgc tggcgttttt ccataggctc cgcccccctg acgagcatca   5640
caaaatcga cgctcaagtc agaggtggcg aaacccgaca ggactataaa gataccaggc   5700
gtttccccct ggaagctccc tcgtgcgctc tcctgttccg accctgccgc ttaccggata   5760
cctgtccgcc tttctccctt cgggaagcgt ggcgctttct catagctcac gctgtaggta   5820
tctcagttcg gtgtaggtcg ttcgctccaa gctgggctgt gtgcacgaac cccccgttca   5880
gcccgaccgc tgcgccttat ccggtaacta tcgtcttgag tccaacccgg taagacacga   5940
cttatcgcca ctggcagcag ccactggtaa caggattagc agagcgaggt atgtaggcgg   6000
tgctacagag ttcttgaagt ggtggcctaa ctacggctac actagaagaa cagtatttgg   6060
tatctgcgct ctgctgaagc cagttacctt cggaaaaaga gttggtagct cttgatccgg   6120
caaacaaacc accgctggta gcggtggttt ttttgtttgc aagcagcaga ttacgcgcag   6180
aaaaaaagga tctcaagaag atcctttgat cttttctacg gggtctgacg ctcagtggaa   6240
cgaaaactca cgttaaggga ttttggtcat gagattatca aaaaggatct cacctagat   6300
ccttttaaat taaaaatgaa gttttaaatc aatctaaagt atatatgagt aaacttggtc   6360
tgacagttac caatgcttaa tcagtgaggc acctatctca gcgatctgtc tatttcgttc   6420
atccatagtt gcctgactcc ccgtcgtgta gataactacg atacgggagg cttaccatc   6480
tggccccagt gctgcaatga taccgcgaga cccacgctca ccggctccag atttatcagc   6540
aataaaccag ccagccggaa gggccgagcg cagaagtggg cctgcaactt tatccgcctc   6600
catccagtct attaattgtt gccgggaagc tagagtaagt agttcgccag ttaatagttt   6660
gcgcaacgtt gttgccattg ctacaggcat cgtggtgtca cgctcgtcgt ttggtatggc   6720
ttcattcagc tccggttccc aacgatcaag gcgagttaca tgatccccca tgttgtgcaa   6780
aaaagcggtt agctccttcg gtcctccgat cgttgtcaga agtaagttgg ccgcagtgtt   6840
atcactcatg gttatggcag cactgcataa ttctcttact gtcatgccat ccgtaagatg   6900
cttttctgtg actggtgagt actcaaccaa gtcattctga gaatagtgta tgcggcgacc   6960
gagttgctct tgcccggcgt caatacggga taataccgcg ccacatagca gaactttaaa   7020
agtgctcatc attggaaaac gttcttcggg gcgaaaactc tcaaggatct taccgctgtt   7080
```

-continued

```
gagatccagt tcgatgtaac ccactcgtgc acccaactga tcttcagcat cttttacttt    7140
caccagcgtt tctgggtgag caaaaacagg aaggcaaaat gccgcaaaaa agggaataag    7200
ggcgacacgg aaatgttgaa tactcatact cttccttttt caatattatt gaagcattta    7260
tcagggttat tgtctcatga gcggatacat atttgaatgt atttagaaaa ataaacaaat    7320
aggggttccg cgcacatttc cccgaaaagt gccacctgac gtctaagaaa ccattattat    7380
catgacatta acctataaaa ataggcgtat cacgaggccc tttcgtctcg cgcgtttcgg    7440
tgatgacggt gaaaacctct gacacatgca gctcccggag acggtcacag cttgtctgta    7500
agcggatgcc gggagcagac aagcccgtca gggcgcgtca gcgggtgttg gcgggtgtcg    7560
gggctggctt aactatgcgg catcagagca gattgtactg agagtgcac               7609
```

```
<210> SEQ ID NO 12
<211> LENGTH: 7608
<212> TYPE: DNA
<213> ORGANISM: Artificial Sequence
<220> FEATURE:
<223> OTHER INFORMATION: pYB39 vector
<220> FEATURE:
<221> NAME/KEY: misc_feature
<222> LOCATION: (2)..(1192)
<223> OTHER INFORMATION: FAS_upstream_fragment
<220> FEATURE:
<221> NAME/KEY: misc_feature
<222> LOCATION: (1200)..(1648)
<223> OTHER INFORMATION: alpha_tubulin_promoter
<220> FEATURE:
<221> NAME/KEY: misc_feature
<222> LOCATION: (1679)..(2443)
<223> OTHER INFORMATION: paromomycin_resistance_gene
<220> FEATURE:
<221> NAME/KEY: misc_feature
<222> LOCATION: (2444)..(2717)
<223> OTHER INFORMATION: SV40_terminator
<220> FEATURE:
<221> NAME/KEY: misc_feature
<222> LOCATION: (2718)..(3780)
<223> OTHER INFORMATION: EF-1_alpha_promoter
<220> FEATURE:
<221> NAME/KEY: misc_feature
<222> LOCATION: (3792)..(3828)
<223> OTHER INFORMATION: Hammerhead_ribozyme
<220> FEATURE:
<221> NAME/KEY: misc_feature
<222> LOCATION: (3829)..(3848)
<223> OTHER INFORMATION: carotene_synthase_target_4
<220> FEATURE:
<221> NAME/KEY: misc_feature
<222> LOCATION: (3848)..(3928)
<223> OTHER INFORMATION: gRNA
<220> FEATURE:
<221> NAME/KEY: misc_feature
<222> LOCATION: (3929)..(3996)
<223> OTHER INFORMATION: HDV_ribozyme
<220> FEATURE:
<221> NAME/KEY: misc_feature
<222> LOCATION: (4016)..(4534)
<223> OTHER INFORMATION: OrfC_terminator
<220> FEATURE:
<221> NAME/KEY: misc_feature
<222> LOCATION: (4535)..(5367)
<223> OTHER INFORMATION: FAS_downstream_fragment
<220> FEATURE:
<221> NAME/KEY: misc_feature
<222> LOCATION: (6366)..(7226)
<223> OTHER INFORMATION: AmpR_gene

<400> SEQUENCE: 12
gtttaaactc gcggcgtctt cgccgtcgag gcgcgtcttt cgaggcgggc gaggtgtttt     60
tcttttcttt tcttctcgct gcagctgcgc cgcggcgaac gcagttcgcc gcggcggctg    120
```

```
cgacgcgcct gcgatgtcta tgcgcaggca aggcacgacg tcttgcggcg ccgcttcctg     180
cgccgccttg cgtcttggcc ccgccgacga cgcaagcagc ggcggcgccc cccgcccctc     240
ctccactgtg ggccgcagcc ctccttttcg cgcgcccgca gccgcgcggc gcgccccgcg     300
aacaaagagc cgccgcgccg gtccgcactg cgcgggccgc cccgcaagtg ccgcaaacgc     360
cggcccgaac cgccgcaaac gcgcccgcag ccgcgcccgc agccgcgcgc gacccgcggt     420
ggggacgcgc gccaagcgtc cccttccgcg ggatgacgta ggcggcggcc ccgcctatgc     480
aatacgggag gaaccaggaa ccgggagggg gggggggcgg cgcgcgcgcc gtccagtgcg     540
ggaccgatcg gcgccgggat gcccgggcgg gagggacaca gccaggcagt cagtcagtca     600
gccgcacaga gagagcgcgc ctgcgagtcc cgtctggtct cggaattgta tcccgcgcag     660
agctcagaat cgcaggtcga tcgatcgagc gatggatcca tcgctctatc cgtccatcga     720
tccatcgcat ccatcgcatc catcgcatcc atcgttgcat cgcttgcacc gccgcttgc     780 atcgcgtgcg tgcgcaggcg ggcggcgccc acgacgcgac cgagagcggc ggcgagtgca     840
gacgccgccg gcgccgcgg ctgcgtcgcc gcaggaagaa ggaggggggc gcgtgtttcc     900
cgcgggaggg aggagggagg gagggaggtg gttgggccaa aaaggcggc ctggacaggc     960 aggcaggccg gaagcgacgc cagcgagcga aggaagagga gagagccgcg cgggcggcca    1020
gcgcggggcg ggcggcagca aacccgctac tcagggtaaa agacagacag ctcttcgagc    1080
gagcttgttc acttcgcgga agcacgcgcg caggcacgca ggcacgcagg cagcatagcg    1140
agcagcagca gcatcgcgag cagcattgcg agaggaggcg ctgaccgccg gccaagcttc    1200 caatttagg cccccactg accgaggtct gtcgataatc cacttttcca ttgattttcc     1260
aggtttcgtt aactcatgcc actgagcaaa acttcggtct ttcctaacaa aagctctcct    1320
cacaaagcat ggcgcggcaa cggacgtgtc ctcatactcc actgccacac aaggtcgata    1380
aactaagctc ctcacaaata gaggagaatt ccactgacaa ctgaaaacaa tgtatgagag    1440
acgatcacca ctggagcggc gcggcggttg ggcgcggagg tcggcagcaa aaacaagcga    1500
ctcgccgagc aaacccgaat cagccttcag acggtcgtgc ctaacaacac gccgttctac    1560
cccgccttct tcgcgcccct tcgcgtccaa gcatccttca agtttatctc tctagttcaa    1620
cttcaagaag aacaacacca ccaacaccat gattgaacaa gatggattgc acgcaggttc    1680
tccggccgct tgggtggaga ggctattcgg ctatgactgg gcacaacaga caatcggctg    1740
ctctgatgcc gccgtgttcc ggctgtcagc gcaggggcgc ccggttcttt ttgtcaagac    1800
cgacctgtcc ggtgccctga atgaactgca ggacgaggca gcgcggctat cgtggctggc    1860
cacgacgggc gttccttgcg cagctgtgct cgacgttgtc actgaagcgg aagggactg     1920 gctgctattg ggcgaagtgc cggggcagga tctcctgtca tctcaccttg ctcctgccga    1980
gaaagtatcc atcatggctg atgcaatgcg gcggctgcat acgcttgatc cggctacctg    2040
cccattcgac caccaagcga aacatcgcat cgagcgagca cgtactcgga tggaagccgg    2100
tcttgtcgat caggatgatc tggacgaaga gcatcagggg ctcgcgccag ccgaactgtt    2160
cgccaggctc aaggcgcgca tgcccgacgg cgatgatctc gtcgtgaccc atggcgatgc    2220
ctgcttgccg aatatcatgg tggaaaatgg ccgcttttct ggattcatcg actgtggccg    2280
gctgggtgtg gcggaccgct atcaggacat agcgttggct acccgtgata ttgctgaaga    2340
gcttggcggc gaatgggctg accgcttcct cgtgctttac ggtatcgccg ctcccgattc    2400
gcagcgcatc gccttctatc gccttcttga cgagttcttc tgacacgtgc tacgagattt    2460
```

```
cgattccacc gccgccttct atgaaaggtt gggcttcgga atcgttttcc gggacgccgg    2520
ctggatgatc ctccagcgcg gggatctcat gctggagttc ttcgcccacc ccaacttgtt    2580
tattgcagct tataatggtt acaaataaag caatagcatc acaaatttca caaataaagc    2640
atttttttca ctgcattcta gttgtggttt gtccaaactc atcaatgtat cttatcatgt    2700
ctgaattccc ggggtaccct ttatctgcct cgcgccgttg accgccgctt gactcttggc    2760
gcttgccgct cgcatcctgc ctcgctcgcg caggcgggcg ggcgagtggg tgggtccgca    2820
gccttccgcg ctcgcccgct agctcgctcg cgccgtgctg cagccagcag ggcagcaccg    2880
cacggcaggc aggtcccggc gcggatcgat cgatccatcg atccatcgat ccatcgatcg    2940
tgcggtcaaa aagaaaggaa gaagaaagga aaaagaaagg cgtgcgcacc cgagtgcgcg    3000
ctgagcgccc gctcgcggtc ccgcggagcc tccgcgttag tccccgcccc gcgccgcgca    3060
gtccccgggg aggcatcgcg cacctctcgc cgccccctcg cgcctcgccg attcccgcc    3120 tccccttttc cgcttcttcg ccgcctccgc tcgcggccgc gtcgcccgcg ccccgctccc    3180
tatctgctcc caggggggc actccgcacc ttttgcgccc gctgccgccg ccgcggccgc    3240
cccgccgccc tggtttcccc cgcgagcgcg gccgcgtcgc cgcgcaaaga ctcgccgcgt    3300
gccgccccga gcaacgggtg gcggcggcgc ggcggcgggc ggggcgcggc ggcgcgtagg    3360
cggggctagg cgccggctag gcgaaacgcc gcccccgggc gccgccgccg cccgctccag    3420
agcagtcgcc gcgccagacc gccaacgcag agaccgagac cgaggtacgt cgcgcccgag    3480
cacgccgcga cgcgcggcag ggacgaggag cacgacgccg cgccgcgccg cgcgggggg    3540 gggagggaga ggcaggacgc gggagcgagc gtgcatgttt ccgcgcgaga cgacgccgcg    3600
cgcgctggag aggagataag gcgcttggat cgcgagaggg ccagccaggc tggaggcgaa    3660
aatgggtgga gaggatagta tcttgcgtgc ttggacgagg agactgacga ggaggacgga    3720
tacgtcgatg atgatgtgca cagagaagaa gcagttcgaa agcgactact agcaagcaag    3780
agatcttctt cctgatgagt ccgtgaggac gaaacgagta agctcgtcga agaacatgta    3840
ctcttcaagt tttagagcta gaaatagcaa gttaaaataa ggctagtccg ttatcaactt    3900
gaaaaagtgg caccgagtcg gtgcttttgg ccggcatggt cccagcctcc tcgctggcgc    3960
cggctgggca acatgcttcg gcatggcgaa tgggaccata tgagttatga gatccgaaag    4020
tgaaccttgt cctaacccga cagcgaatgg cgggagggg cgggctaaaa gatcgtatta    4080
catagtattt ttcccctact ctttgtgttt gtctttttt tttttttgaa cgcattcaag    4140
ccacttgtct gggtttactt gtttgtttgc ttgcttgctt gcttgcttgc ctgcttcttg    4200
gtcagacggc ccaaaaaagg gaaaaaattc attcatggca cagataagaa aaagaaaaag    4260
tttgtcgacc accgtcatca gaaagcaaga gaagagaaac actcgcgctc acattctcgc    4320
tcgcgtaaga atcttagcca cgcatacgaa gtaatttgtc catctggcga atctttacat    4380
gagcgttttc aagctggagc gtgagatcat acctttcttg atcgtaatgt tccaaccttg    4440
cataggcctc gttgcgatcc gctagcaatg cgtcgtactc ccgttgcaac tgcgccatcg    4500
cctcattgtg acgtgagttc agattcttct cgagaaactc ggcacctgcc atgaagacgc    4560
cctccaaaag ggctgggtca aggcctgct cggacacagc cagggcgtcg tctccgccgc    4620
cgtcgttgcc gcagccaaca ccgaccgcga gctgcgcaac ctcgtggtct ccggcctcga    4680
atacatgtca aaagtcggca tcgccgccca gcgcacgctc gactacgagc tcggacgccg    4740
caacgccggc ccggagaccc cgatgctcgc tgtacaggga atggacgaaa aagtccttac    4800
caaggccttc aaggccgccg tctcgctctc caacgagaag caggccatga tggccaaaat    4860
```

```
ctccccacgg ccgccgccgc caccgccgcc ccggccgccg ttagcgacga agatcgcttc      4920
tccatcgccc tccgcaacgg ccacgacgac tttgtcgtct gcggcgagcc caaggacctg      4980
cgcgtcctcc gcaaggtcat cgagaaacag agcgccgagc ccggcaagga ggcacaggcg      5040
cgcacgccct tttccaagcg caagcccgtc acccagacca ccttcctccg catgacggcc      5100
gtcttccaca gcgctctcaa caaggacgcc ctcgcccaga tcaacacatg gccccggag       5160 tccgcccttta gcaaggcctt cgcccaggcc tcgctccgtg ttcccgtctt tgacaccaag     5220
tctggcgcta atctgcaaga tgttcccgcc gccgatgttg tcgcccatct taccaccaac      5280
atgctcactg agcgcgccga cgttctcgtc tccctccgtg ccgccgagac caagaccgac     5340
gccagccacc tcctctgttt aaacgttaac ctgcattaat gaatcggcca acgcgcgggg     5400
agaggcggtt tgcgtattgg gcgctcttcc gcttcctcgc tcactgactc gctgcgctcg     5460
gtcgttcggc tgcggcgagc ggtatcagct cactcaaagg cggtaatacg ttatccaca      5520 gaatcagggg ataacgcagg aaagaacatg tgagcaaaag gccagcaaaa ggccaggaac     5580
cgtaaaaagg ccgcgttgct ggcgtttttc cataggctcc gcccccctga cgagcatcac     5640
aaaaatcgac gctcaagtca gaggtggcga acccgacag gactataaag ataccaggcg      5700
tttccccctg gaagctccct cgtgcgctct cctgttccga ccctgccgct taccggatac     5760
ctgtccgcct ttctcccttc gggaagcgtg gcgctttctc atagctcacg ctgtaggtat     5820
ctcagttcgg tgtaggtcgt tcgctccaag ctgggctgtg tgcacgaacc ccccgttcag    5880
cccgaccgct gcgccttatc cggtaactat cgtcttgagt ccaacccggt aagacacgac    5940
ttatcgccac tggcagcagc cactggtaac aggattagca gagcgaggta tgtaggcggt     6000
gctacagagt tcttgaagtg gtggcctaac tacggctaca ctagaagaac agtatttggt    6060
atctgcgctc tgctgaagcc agttaccttc ggaaaaagag ttggtagctc ttgatccggc    6120
aaacaaacca ccgctggtag cggtggtttt tttgtttgca agcagcagat tacgcgcaga    6180 aaaaaggat ctcaagaaga tcctttgatc ttttctacgg ggtctgacgc tcagtggaac     6240
gaaaactcac gttaagggat tttggtcatg agattatcaa aaaggatctt cacctagatc    6300
cttttaaatt aaaaatgaag ttttaaatca atctaaagta tatatgagta aacttggtct    6360
gacagttacc aatgcttaat cagtgaggca cctatctcag cgatctgtct atttcgttca    6420
tccatagttg cctgactccc cgtcgtgtag ataactacga tacgggaggg cttaccatct    6480
ggccccagtg ctgcaatgat accgcgagac ccacgctcac cggctccaga tttatcagca    6540
ataaaccagc cagccggaag ggccgagcgc agaagtggtc ctgcaacttt atccgcctcc    6600
atccagtcta ttaattgttg ccgggaagct agagtaagta gttcgccagt taatagtttg    6660
cgcaacgttg ttgccattgc tacaggcatc gtggtgtcac gctcgtcgtt tggtatggct    6720
tcattcagct ccggttccca acgatcaagg cgagttacat gatcccccat gttgtgcaaa    6780
aaagcggtta gctccttcgg tcctccgatc gttgtcagaa gtaagttggc cgcagtgtta    6840
tcactcatgg ttatggcagc actgcataat tctcttactg tcatgccatc cgtaagatgc    6900
ttttctgtga ctggtgagta ctcaaccaag tcattctgag aatagtgtat gcggcgaccg    6960
agttgctctt gcccggcgtc aatacgggat aataccgcgc cacatagcag aactttaaaa    7020
gtgctcatca ttggaaaacg ttcttcgggg cgaaaactct caaggatctt accgctgttg    7080
agatccagtt cgatgtaacc cactcgtgca cccaactgat cttcagcatc ttttactttc    7140
accagcgttt ctgggtgagc aaaaacagga aggcaaaatg ccgcaaaaaa gggaataagg    7200
```

-continued

```
gcgacacgga aatgttgaat actcatactc ttccttttc aatattattg aagcatttat    7260
cagggttatt gtctcatgag cggatacata tttgaatgta tttagaaaaa taaacaaata    7320
ggggttccgc gcacatttcc ccgaaaagtg ccacctgacg tctaagaaac cattattatc    7380
atgacattaa cctataaaaa taggcgtatc acgaggccct ttcgtctcgc gcgtttcggt    7440
gatgacggtg aaaacctctg acacatgcag ctcccggaga cggtcacagc ttgtctgtaa    7500
gcggatgccg ggagcagaca agcccgtcag ggcgcgtcag cgggtgttgg cgggtgtcgg    7560
ggctggctta actatgcggc atcagagcag attgtactga gagtgcac                7608
```

<210> SEQ ID NO 13
<211> LENGTH: 22
<212> TYPE: DNA
<213> ORGANISM: Artificial Sequence
<220> FEATURE:
<223> OTHER INFORMATION: 12 Tub seq F primer

<400> SEQUENCE: 13

```
ggatctcatg ctggagttct tc                                               22
```

<210> SEQ ID NO 14
<211> LENGTH: 22
<212> TYPE: DNA
<213> ORGANISM: Artificial Sequence
<220> FEATURE:
<223> OTHER INFORMATION: pYB32/3C R1 primer

<400> SEQUENCE: 14

```
gtacttctcg tggtaggcaa cc                                               22
```

<210> SEQ ID NO 15
<211> LENGTH: 40
<212> TYPE: DNA
<213> ORGANISM: Artificial Sequence
<220> FEATURE:
<223> OTHER INFORMATION: CS pro Kpn IF F1 primer

<400> SEQUENCE: 15

```
gtctgaattc ccggggtacc gagcgggcga ttccaccgtc                            40
```

<210> SEQ ID NO 16
<211> LENGTH: 42
<212> TYPE: DNA
<213> ORGANISM: Artificial Sequence
<220> FEATURE:
<223> OTHER INFORMATION: CS pro BamH IF R1 primer

<400> SEQUENCE: 16

```
gtacttctta tccatggatc cctcggtctc cgagcgagcg ag                         42
```

<210> SEQ ID NO 17
<211> LENGTH: 41
<212> TYPE: DNA
<213> ORGANISM: Artificial Sequence
<220> FEATURE:
<223> OTHER INFORMATION: CS pro BamH IF F2 primer

<400> SEQUENCE: 17

```
tcgctcgctc ggagaccgag ggatccatgg ataagaagta c                          41
```

<210> SEQ ID NO 18
<211> LENGTH: 51
<212> TYPE: DNA
<213> ORGANISM: Artificial Sequence

```
<220> FEATURE:
<223> OTHER INFORMATION: CS pro Nde IF R2 primer

<400> SEQUENCE: 18
gattcactag tttagatcat atgttagacc ttgcgcttct tcttagggtc c          51

<210> SEQ ID NO 19
<211> LENGTH: 19
<212> TYPE: DNA
<213> ORGANISM: Artificial Sequence
<220> FEATURE:
<223> OTHER INFORMATION: O A1-KO F primer

<400> SEQUENCE: 19
ccaagttcgc caaggcttc                                              19

<210> SEQ ID NO 20
<211> LENGTH: 23
<212> TYPE: DNA
<213> ORGANISM: Artificial Sequence
<220> FEATURE:
<223> OTHER INFORMATION: pYB32/3 SV40 R1 primer

<400> SEQUENCE: 20
gtggaatcga atctcgtag cac                                          23

<210> SEQ ID NO 21
<211> LENGTH: 21
<212> TYPE: DNA
<213> ORGANISM: Artificial Sequence
<220> FEATURE:
<223> OTHER INFORMATION: O A1-KO R primer

<400> SEQUENCE: 21
gctgttgcaa ctttgctcca c                                           21

<210> SEQ ID NO 22
<211> LENGTH: 23
<212> TYPE: DNA
<213> ORGANISM: Artificial Sequence
<220> FEATURE:
<223> OTHER INFORMATION: pYB32/3C F1 primer

<400> SEQUENCE: 22
gttaagaaga ccgaggtcca gac                                         23

<210> SEQ ID NO 23
<211> LENGTH: 32
<212> TYPE: DNA
<213> ORGANISM: Artificial Sequence
<220> FEATURE:
<223> OTHER INFORMATION: 5' FAS PmeNde primer

<400> SEQUENCE: 23
tagcatatgt ttaaactcgc ggcgtctttc gc                               32

<210> SEQ ID NO 24
<211> LENGTH: 31
<212> TYPE: DNA
<213> ORGANISM: Artificial Sequence
<220> FEATURE:
<223> OTHER INFORMATION: 3' FAS PmeHpa primer

<400> SEQUENCE: 24
agttaacgtt taaacagagg aggtggctgg c                                31
```

<210> SEQ ID NO 25
<211> LENGTH: 38
<212> TYPE: DNA
<213> ORGANISM: Artificial Sequence
<220> FEATURE:
<223> OTHER INFORMATION: pCL402 IF F primer

<400> SEQUENCE: 25
gaggcgctga ccgccggcca agcttccaat tttaggcc                    38

<210> SEQ ID NO 26
<211> LENGTH: 40
<212> TYPE: DNA
<213> ORGANISM: Artificial Sequence
<220> FEATURE:
<223> OTHER INFORMATION: pCL402 IF R primer

<400> SEQUENCE: 26
gcaggtgccg agtttctcga gaagaatctg aactcacgtc                  40

<210> SEQ ID NO 27
<211> LENGTH: 21
<212> TYPE: DNA
<213> ORGANISM: Artificial Sequence
<220> FEATURE:
<223> OTHER INFORMATION: pYB36 CS1 F primer

<400> SEQUENCE: 27
gagtcgaagg agacgttgtc g                                      21

<210> SEQ ID NO 28
<211> LENGTH: 23
<212> TYPE: DNA
<213> ORGANISM: Artificial Sequence
<220> FEATURE:
<223> OTHER INFORMATION: pYB36 CS1 R primer

<400> SEQUENCE: 28
gtcattgcga atgatgcgat atg                                    23

<210> SEQ ID NO 29
<211> LENGTH: 23
<212> TYPE: DNA
<213> ORGANISM: Artificial Sequence
<220> FEATURE:
<223> OTHER INFORMATION: pYB36 CS3 R primer

<400> SEQUENCE: 29
ggtcatcatg gaatacaacg cag                                    23

<210> SEQ ID NO 30
<211> LENGTH: 26
<212> TYPE: DNA
<213> ORGANISM: Artificial Sequence
<220> FEATURE:
<223> OTHER INFORMATION: pYB36 CS4 F primer

<400> SEQUENCE: 30
cgagctcatt tgtgctacac tctatg                                 26

<210> SEQ ID NO 31
<211> LENGTH: 23
<212> TYPE: DNA
<213> ORGANISM: Artificial Sequence
<220> FEATURE:
<223> OTHER INFORMATION: pYB36 CS4 R primer

<400> SEQUENCE: 31
cacaagattt gcaggattga tgc                                                    23

<210> SEQ ID NO 32
<211> LENGTH: 5562
<212> TYPE: DNA
<213> ORGANISM: Artificial Sequence
<220> FEATURE:
<223> OTHER INFORMATION: pYB30 vector (5562 bp)
<220> FEATURE:
<221> NAME/KEY: misc_feature
<222> LOCATION: (2)..(450)
<223> OTHER INFORMATION: Alpha_Tubulin_promoter
<220> FEATURE:
<221> NAME/KEY: misc_feature
<222> LOCATION: (457)..(549)
<223> OTHER INFORMATION: Sec1_secretion_sequence
<220> FEATURE:
<221> NAME/KEY: misc_feature
<222> LOCATION: (550)..(1287)
<223> OTHER INFORMATION: eGFP
<220> FEATURE:
<221> NAME/KEY: misc_feature
<222> LOCATION: (1307)..(1946)
<223> OTHER INFORMATION: OrfC_terminator
<220> FEATURE:
<221> NAME/KEY: misc_feature
<222> LOCATION: (4481)..(4929)
<223> OTHER INFORMATION: Alpha_tubulin_promoter
<220> FEATURE:
<221> NAME/KEY: misc_feature
<222> LOCATION: (4930)..(5304)
<223> OTHER INFORMATION: Sh_ble_gene
<220> FEATURE:
<221> NAME/KEY: misc_feature
<222> LOCATION: (5305)..(5562)
<223> OTHER INFORMATION: SV40_terminator

<400> SEQUENCE: 32
cccaatttta ggcccccccac tgaccgaggt ctgtcgataa tccacttttc cattgatttt     60
ccaggtttcg ttaactcatg ccactgagca aaacttcggt ctttcctaac aaaagctctc    120
ctcacaaagc atggcgcggc aacggacgtg tcctcatact ccactgccac acaaggtcga    180
taaactaagc tcctcacaaa tagaggagaa ttccactgac aactgaaaac aatgtatgag    240
agacgatcac cactggagcg gcgcggcggt tgggcgcgga ggtcggcagc aaaaacaagc    300
gactcgccga gcaaacccga atcagccttc agacggtcgt gcctaacaac acgccgttct    360
accccgcctt cttcgcgccc cttcgcgtcc aagcatcctt caagtttatc tctctagttc    420
aacttcaaga agaacaacac caccaacacc ggatccatga agttcgcgac ctcggtcgca    480
attttgcttg tggccaacat agccaccgcc ctcgcgcaga gcgatggctg cacccccacc    540
gaccagacga tggtgagcaa gggcgaggag ctgttcaccg gggtggtgcc catcctggtc    600
gagctggacg gcgacgtaaa cggccacaag ttcagcgtgt ccggcgaggg cgagggcgat    660
gccacctacg gcaagctgac cctgaagttc atctgcacca ccggcaagct gcccgtgccc    720
tggcccaccc tcgtgaccac cctgacctac ggcgtgcagt gcttcagccg ctaccccgac    780
cacatgaagc agcacgactt cttcaagtcc gccatgcccg aaggctacgt ccaggagcgc    840
accatcttct tcaaggacga cggcaactac aagacccgcg ccgaggtgaa gttcgagggc    900
gacaccctgg tgaaccgcat cgagctgaag ggcatcgact tcaaggagga cggcaacatc    960
ctggggcaca agctggagta caactacaac agccacaacg tctatatcat ggccgacaag   1020
cagaagaacg gcatcaaggt gaacttcaag atccgccaca acatcgagga cggcagcgtg   1080

```
cagctcgccg accactacca gcagaacacc cccatcggcg acggcccgt gctgctgccc    1140
gacaaccact acctgagcac ccagtccgcc ctgagcaaag accccaacga aagcgcgat    1200
cacatggtcc tgctggagtt cgtgaccgcc gccgggatca ctctcggcat ggacgagctg    1260
tacaagcacc accatcacca ccactaacat atgagttatg agatccgaaa gtgaaccttg    1320
tcctaacccg acagcgaatg gcgggagggg gcgggctaaa agatcgtatt acatagtatt    1380
tttcccctac tctttgtgtt tgtcttttttt ttttttttga acgcattcaa gccacttgtc    1440
tgggtttact tgtttgtttg cttgcttgct tgcttgcttg cctgcttctt ggtcagacgg    1500
cccaaaaaag ggaaaaaatt cattcatggc acagataaga aaagaaaaa gtttgtcgac    1560
caccgtcatc agaaagcaag agaagagaaa cactcgcgct cacattctcg ctcgcgtaag    1620
aatcttagcc acgcatacga agtaatttgt ccatctggcg aatctttaca tgagcgtttt    1680
caagctggag cgtgagatca tacctttctt gatcgtaatg ttccaacctt gcataggcct    1740
cgttgcgatc cgctagcaat gcgtcgtact cccgttgcaa ctgcgccatc gcctcattgt    1800
gacgtgagtt cagattcttc tcgagacctt cgagcgctgc taatttcgcc tgacgctcct    1860
tcttttgtgc ttccatgaca cgccgcttca ccgtgcgttc cacttcttcc tcagacatgc    1920
ccttggctgc ctcgacctgc tcggtaaaac gggcccagc acgtgctacg agatttcgat    1980
tccaccgccg ccttctatga aaggttgggc ttcggaatcg ttttccggga cgccggctgg    2040
atgatcctcc agcgcgggga tctcatgctg gagttcttcg cccacccaa cttgtttatt    2100
gcagcttata atggttacaa ataaagcaat agcatcacaa atttcacaaa taaagcattt    2160
ttttcactgc attctagttg tggttttgtcc aaactcatca atgtatctta tcatacatgg    2220
tcgacctgca ggaacctgca ttaatgaatc ggccaacgcg cggggagagg cggtttgcgt    2280
attgggcgct cttccgcttc ctcgctcact gactcgctgc gctcggtcgt tcggctgcgg    2340
cgagcggtat cagctcactc aaaggcggta atacggttat ccacagaatc aggggataac    2400
gcaggaaaga acatgtgagc aaaaggccag caaaaggcca ggaaccgtaa aaaggccgcg    2460
ttgctggcgt ttttccatag gctccgcccc cctgacgagc atcacaaaaa tcgacgctca    2520
agtcagaggt ggcgaaaccc gacaggacta taaagatacc aggcgtttcc ccctggaagc    2580
tccctcgtgc gctctcctgt tccgaccctg ccgcttaccg gatacctgtc cgcctttctc    2640
ccttcgggaa gcgtggcgct ttctcatagc tcacgctgta ggtatctcag ttcggtgtag    2700
gtcgttcgct ccaagctggg ctgtgtgcac gaaccccccg ttcagcccga ccgctgcgcc    2760
ttatccggta actatcgtct tgagtccaac ccggtaagac acgacttatc gccactggca    2820
gcagccactg gtaacaggat tagcagagcg aggtatgtag gcggtgctac agagttcttg    2880
aagtggtggc ctaactacgg ctacactaga agaacagtat ttggtatctg cgctctgctg    2940
aagccagtta ccttcggaaa aagagttggt agctcttgat ccggcaaaca aaccaccgct    3000
ggtagcggtg gtttttttgt ttgcaagcag cagattacgc gcagaaaaaa aggatctcaa    3060
gaagatcctt tgatcttttc tacggggtct gacgctcagt ggaacgaaaa ctcacgttaa    3120
gggattttgg tcatgagatt atcaaaaagg atcttcacct agatcctttt aaattaaaaa    3180
tgaagtttta atcaatcta aagtatatat gagtaaactt ggtctgacag ttaccaatgc    3240
ttaatcagtg aggcacctat ctcagcgatc tgtctatttc gttcatccat agttgcctga    3300
ctccccgtcg tgtagataac tacgatacgg gagggcttac catctggccc cagtgctgca    3360
atgataccgc gagacccacg ctcaccggct ccagatttat cagcaataaa ccagccagcc    3420
ggaagggccg agcgcagaag tggtcctgca actttatccg cctccatcca gtctattaat    3480
```

```
tgttgccggg aagctagagt aagtagttcg ccagttaata gtttgcgcaa cgttgttgcc    3540
attgctacag gcatcgtggt gtcacgctcg tcgtttggta tggcttcatt cagctccggt    3600
tcccaacgat caaggcgagt tacatgatcc cccatgttgt gcaaaaaagc ggttagctcc    3660
ttcggtcctc cgatcgttgt cagaagtaag ttggccgcag tgttatcact catggttatg    3720
gcagcactgc ataattctct tactgtcatg ccatccgtaa gatgcttttc tgtgactggt    3780
gagtactcaa ccaagtcatt ctgagaatag tgtatgcggc gaccgagttg ctcttgcccg    3840
gcgtcaatac gggataatac cgcgccacat agcagaactt taaaagtgct catcattgga    3900
aaacgttctt cggggcgaaa actctcaagg atcttaccgc tgttgagatc cagttcgatg    3960
taacccactc gtgcacccaa ctgatcttca gcatctttta ctttcaccag cgtttctggg    4020
tgagcaaaaa caggaaggca aaatgccgca aaaaagggaa taaggcgac acggaaatgt    4080 tgaatactca tactcttcct ttttcaatat tattgaagca tttatcaggg ttattgtctc    4140
atgagcggat acatatttga atgtatttag aaaaataaac aaataggggt tccgcgcaca    4200
tttccccgaa aagtgccacc tgacgtctaa gaaaccatta ttatcatgac attaacctat    4260 aaaaatagqc gtatcacqaq qccctttcqt ctcgcgcgtt tcggtgatga cggtgaaaac    4320
ctctgacaca tgcagctccc ggagacggtc acagcttgtc tgtaagcgga tgccgggagc    4380
agacaagccc gtcagggcgc gtcagcgggt gttggcgggt gtcggggctg gcttaactat    4440
gcggcatcag agcagattgt actgagagtg caccaagctt ccaattttag gccccccact    4500
gaccgaggtc tgtcgataat ccacttttcc attgattttc caggtttcgt taactcatgc    4560
cactgagcaa aacttcggtc tttcctaaca aaagctctcc tcacaaagca tggcgcggca    4620
acggacgtgt cctcatactc cactgccaca caaggtcgat aaactaagct cctcacaaat    4680
agaggagaat tccactgaca actgaaaaca atgtatgaga gacgatcacc actggagcgg    4740
cgcggcggtt gggcgcggag gtcggcagca aaaacaagcg actcgccgag caaacccgaa    4800
tcagccttca gacggtcgtg cctaacaaca cgccgttcta ccccgccttc ttcgcgcccc    4860
ttcgcgtcca agcatccttc aagtttatct ctctagttca acttcaagaa gaacaacacc    4920
accaacacca tggccaagtt gaccagtgcc gttccggtgc tcaccgcgcg cgacgtcgcc    4980
ggagcggtcg agttctggac cgaccggctc gggttctccc gggacttcgt ggaggacgac    5040
ttcgccggtg tggtccggga cgacgtgacc ctgttcatca gcgcggtcca ggaccaggtg    5100
gtgccggaca cacccctggc ctgggtgtgg gtgcgcggcc tggacgagct gtacgccgag    5160
tggtcggagg tcgtgtccac gaacttccgg gacgcctccg gccggccat gaccgagatc    5220 ggcgagcagc cgtggggcg ggagttcgcc ctgcgcgacc cggccggcaa ctgcgtgcac    5280
ttcgtggccg aggagcagga ctgacacgtg ctacgagatt cgattccac cgccgccttc    5340 tatgaaaggt tgggcttcgg aatcgttttc cgggacgccg gctggatgat cctccagcgc    5400
ggggatctca tgctggagtt cttcgcccac cccaacttgt ttattgcagc ttataatggt    5460
tacaaataaa gcaatagcat cacaaatttc acaaataaag cattttttc actgcattct    5520 agttgtggtt tgtccaaact catcaatgta tcttatcggt ac                      5562
```

<210> SEQ ID NO 33
<211> LENGTH: 8887
<212> TYPE: DNA
<213> ORGANISM: Artificial Sequence
<220> FEATURE:
<223> OTHER INFORMATION: pYB61 vector (8887 bp)
<220> FEATURE:

```
<221> NAME/KEY: misc_feature
<222> LOCATION: (2)..(450)
<223> OTHER INFORMATION: Alpha_tubulin_promoter
<220> FEATURE:
<221> NAME/KEY: misc_feature
<222> LOCATION: (457)..(4596)
<223> OTHER INFORMATION: Cas9
<220> FEATURE:
<221> NAME/KEY: misc_feature
<222> LOCATION: (4616)..(5255)
<223> OTHER INFORMATION: OrfC_terminator
<220> FEATURE:
<221> NAME/KEY: misc_feature
<222> LOCATION: (6540)..(7400)
<223> OTHER INFORMATION: Ampicillin_resistance_gene
<220> FEATURE:
<221> NAME/KEY: misc_feature
<222> LOCATION: (7790)..(8238)
<223> OTHER INFORMATION: Alpha_tubulin_promoter
<220> FEATURE:
<221> NAME/KEY: misc_feature
<222> LOCATION: (8239)..(8613)
<223> OTHER INFORMATION: Sh_ble_gene
<220> FEATURE:
<221> NAME/KEY: misc_feature
<222> LOCATION: (8614)..(8887)
<223> OTHER INFORMATION: SV40_terminator

<400> SEQUENCE: 33
```

| | | | | |
|---|---|---|---|---|
| cccaattttta | ggccccccac | tgaccgaggt | ctgtcgataa | tccacttttc | cattgatttt | 60 |
| ccaggtttcg | ttaactcatg | ccactgagca | aaacttcggt | ctttcctaac | aaaagctctc | 120 |
| ctcacaaagc | atggcgcggc | aacggacgtg | tcctcatact | ccactgccac | acaaggtcga | 180 |
| taaactaagc | tcctcacaaa | tagaggagaa | ttccactgac | aactgaaaac | aatgtatgag | 240 |
| agacgatcac | cactggagcg | gcgcggcggt | tgggcgcgga | ggtcggcagc | aaaaacaagc | 300 |
| gactcgccga | gcaaacccga | atcagccttc | agacggtcgt | gcctaacaac | acgccgttct | 360 |
| accccgcctt | cttcgcgccc | cttcgcgtcc | aagcatcctt | caagtttatc | tctctagttc | 420 |
| aacttcaaga | agaacaacac | caccaacacc | ggatccatgg | ataagaagta | ctcgatcggc | 480 |
| ctcgacattg | gcaccaacag | cgtcggctgg | gccgtcatta | ctgatgagta | caaggtcccg | 540 |
| tcgaagaagt | ttaaggtcct | cggcaacact | gaccgccact | ccatcaagaa | gaacctcatc | 600 |
| ggtgccctcc | tttttgactc | cggcgagacc | gctgaggcca | ctcgcctcaa | gcgcactgcc | 660 |
| cgccgccgtt | acacccgccg | caagaaccgc | atctgctacc | tccaggagat | tttctcgaac | 720 |
| gaaatggcca | aggtcgatga | ctccttttc | caccgtctcg | aagaatcgtt | cctcgtcgag | 780 |
| gaggacaaga | agcacgagcg | ccaccccatc | ttcggtaaca | ttgtcgatga | ggttgcctac | 840 |
| cacgagaagt | acccgaccat | ctaccacctc | cgcaagaagc | tcgtcgactc | caccgacaag | 900 |
| gccgatctcc | gccttatcta | cctcgccctc | gcccacatga | tcaagttccg | cggccacttt | 960 |
| cttatcgagg | gtgatctcaa | ccctgataac | tctgacgtcg | acaagctttt | catccagctc | 1020 |
| gtccagactt | acaaccagct | cttcgaggag | aaccccatca | acgcttccgg | cgtcgacgcg | 1080 |
| aaggccattc | tcagcgcccg | cctcagcaag | tcccgccgcc | tcgaaaacct | cattgcccag | 1140 |
| cttcccggcg | agaagaagaa | cggcctcttc | ggcaacctca | ttgccctcag | ccttggcctc | 1200 |
| accctaact | tcaagtcgaa | ctttgacctc | gccgaggacg | ccaagctcca | gctttccaag | 1260 |
| gacacttacg | acgacgatct | cgacaacctc | ctcgctcaga | ttggcgacca | gtacgctgac | 1320 |
| ctcttcctcg | ccgccaagaa | ccttagcgat | gccatcctcc | tctccgacat | ccttcgtgtt | 1380 |
| aacacgaaa | tcacgaaggc | tccgctctcc | gcctccatga | tcaagcgtta | cgacgagcac | 1440 |
| catcaggacc | tcaccctcct | caaggccctc | gtccgccagc | agctccccga | gaagtacaag | 1500 |

```
gagatcttct tcgaccagag caagaacggc tacgccggct acattgacgg cggcgcgtcg      1560
caggaggagt tttacaagtt tatcaagccc attcttgaga agatggacgg caccgaggag      1620
ctcctcgtca agctcaaccg tgaggacctt ctccgcaagc agcgcacgtt cgacaacggc      1680
tctattcccc atcagatcca cctcggtgag cttcacgcga ttcttcgccg ccaggaagac      1740
ttttacccgt tcctcaagga caaccgcgag aagattgaga agatcctcac ctttcgcatt      1800
ccctactacg tcggccccct cgcccgcggc aactcgcgct tgcttggat gacccgcaag       1860 tccgaggaga ccatcacccc gtggaacttc aagaggtcg tcgacaaggg cgcctccgcg       1920
cagtctttca tcgagcgcat gactaacttt gacaagaacc tcccgaacga gaaggtcctc     1980
cccaagcaca gcctccttta cgaatacttt acggtgtaca acgagctcac gaaggtcaag     2040
tacgtcactg agggcatgcg caagccggcg ttcctttcgg gcgagcagaa gaaggctatc     2100
gtcgacctcc tttcaagac caaccgcaag gttaccgtca agcagctcaa ggaggactac      2160
ttcaagaaga tcgagtgctt tgactcggtc gagatttcgg gcgtggagga ccgtttcaac    2220
gcctccctcg gcacttacca cgaccttctc aagatcatca aggacaagga ctttctcgac    2280
aacgaggaga acgaggacat tctcgaggac atcgtcctca cgctcaccct ctttgaggac    2340
cgtgagatga tcgaggagcg cctcaagacc tacgcccatc tctttgacga caaggtcatg    2400
aagcagctca agcgccgccg ctacaccggc tggggccgcc tttcccgcaa gctcatcaac    2460
ggcatccgcg acaagcagtc tggcaagacc atccttgact ttcttaagtc tgatggtttc    2520
gccaaccgca acttcatgca gctcatccac gacgacagcc tcactttcaa ggaggacatt    2580
cagaaggccc aggtctccgg ccagggtgac tctctccacg aacacatcgc caaccttgct    2640
ggcagcccgg ctattaagaa gggcatcctc cagaccgtca aggtcgtcga cgagctcgtc    2700
aaggttatgg gccgccacaa gcccgagaac atcgtcattg agatggctcg cgaaaaccag    2760
accacccaga agggtcagaa gaactcccgc gagcgcatga agcgtatcga ggagggcatc    2820
aaggagctcg gcagccagat cctcaaggag cacccggtcg agaacaccca gctccagaac    2880
gaaaagctct acctctacta cctccagaac ggccgtgaca tgtacgttga ccaggagctc    2940
gacattaacc gcctctccga ttacgacgtc gaccatattg tcccccagag ctttctcaag    3000
gacgacagca tcgacaacaa ggtcctcacc cgctcggaca agaaccgcgg caagtccgac    3060
aacgtccctt tcgaggaggt cgtgaagaag atgaagaact actggcgcca gcttctcaac    3120
gctaagctta ttactcagcg caagttcgat aacctcacca aggccgaacg cggcggcctc    3180
tccgagctcg acaaggccgg ttttatcaag cgccagctcg ttgagactcg ccagatcacc    3240
aagcacgtgg cgcagatcct cgactcgcgc atgaacacga agtacgacga gaacgacaag    3300
ctcatccgcg aggtcaaggt catcacccct taagtcgaag tcgtgtccga ctttcgcaag    3360
gacttccagt tctacaaggt ccgtgaaatt aacaactacc accacgctca cgacgcttac    3420
ctcaacgcgc tcgtgggtac cgcgctcatc aagaagtacc cgaagctcga gtcggagttt    3480
gtctacggcg actacaaggt ctacgacgtg cgcaagatga tcgccaagtc cgagcaggag    3540
atcggcaagg ccacggccaa gtacttttc tactccaaca ttatgaactt ctttaagact    3600
gagatcaccc ttgccaacgg cgagatccgc aagcgccccc ttatcgagac caacggcgag    3660
accggcgaaa ttgtgtggga agggtcgc gactttgcca ccgtccgcaa ggtcctcagc      3720
atgccccagg tcaacattgt taagaagacc gaggtccaga cgggcggctt tagcaaggag    3780
tctatcctcc ccaagcgtaa cagcgacaag ctcatcgccc gcaagaagga ctgggaccct    3840
```

```
aagaagtacg gcggcttcga ttcgcctacg gtcgcctaca gcgtcctcgt cgtcgccaag    3900
gtcgagaagg gcaagtccaa gaagctcaag tccgtcaagg agctcctcgg catcacgatc    3960
atggagcgct ccagctttga gaagaacccc attgacttcc tcgaggctaa gggttacaag    4020
gaggtcaaga aggaccttat catcaagctc cccaagtact ccctctttga gctcgaaaac    4080
ggccgcaagc gtatgctcgc tagcgctggc gaactccaga agggcaacga gctcgccctc    4140
cccagcaagt acgtcaactt tctctacctc gcctcccact acgagaagct caagggtagc    4200
ccggaggata acgagcagaa gcagcttttt gtggagcagc acaagcacta ccttgacgag    4260
atcattgaac agatctccga gttctccaag cgtgttattc ttgctgacgc caacctcgat    4320
aaggtgctct ccgcgtacaa caagcaccgc gacaagccta tccgcgagca ggccgagaac    4380
atcatccacc tctttaccct caccaacctc ggcgccccgg ccgcctttaa gtactttgat    4440
acgactatcg accgcaagcg ctacacttcg actaaggagg tcctcgacgc taccctcatt    4500
caccagtcca ttaccggcct ctacgagacc cgcattgacc tttcgcagct cggtggcgac    4560
tcgcgtgcgg accctaagaa gaagcgcaag gtctaacata tgagttatga gatccgaaag    4620
tgaaccttgt cctaacccga cagcgaatgg cgggaggggg cgggctaaaa gatcgtatta    4680
catagtattt ttccctact ctttgtgttt gtcttttttt tttttttgaa cgcattcaag    4740
ccacttgtct gggtttactt gtttgtttgc ttgcttgctt gcttgcttgc ctgcttcttg    4800
gtcagacggc ccaaaaaagg gaaaaaattc attcatggca cagataagaa aaagaaaaag    4860
tttgtcgacc accgtcatca gaaagcaaga gaagagaaac actcgcgctc acattctcgc    4920
tcgcgtaaga atcttagcca cgcatacgaa gtaatttgtc catctggcga atctttacat    4980
gagcgttttc aagctggagc gtgagatcat acctttcttg atcgtaatgt tccaaccttg    5040
cataggcctc gttgcgatcc gctagcaatg cgtcgtactc ccgttgcaac tgcgccatcg    5100
cctcattgtg acgtgagttc agattcttct cgagaccttc gagcgctgct aatttcgcct    5160
gacgctcctt cttttgtgct tccatgacac gccgcttcac cgtgcgttcc acttcttcct    5220
cagacatgcc cttggctgcc tcgacctgct cggtaaaacg ggccccagca cgtgctacga    5280
gatttcgatt ccaccgccgc cttctatgaa aggttgggct tcggaatcgt tttccgggac    5340
gccggctgga tgatcctcca gcgcggggat ctcatgctgg agttcttcgc ccaccccaac    5400
ttgtttattg cagcttataa tggttacaaa taaagcaata gcatcacaaa tttcacaaat    5460
aaagcatttt tttcactgca ttctagttgt ggtttgtcca aactcatcaa tgtatcttat    5520
catacatggt cgacctgcag gaacctgcat taatgaatcg gccaacgcgc ggggagaggc    5580
ggtttgcgta ttgggcgctc ttccgcttcc tcgctcactg actcgctgcg ctcggtcgtt    5640
cggctgcggc gagcggtatc agctcactca aaggcggtaa tacggttatc cacagaatca    5700
ggggataacg caggaaagaa catgtgagca aaaggccagc aaaaggccag gaaccgtaaa    5760
aaggccgcgt tgctggcgtt tttccatagg ctccgccccc ctgacgagca tcacaaaaat    5820
cgacgctcaa gtcagaggtg gcgaaacccg acaggactat aaagatacca ggcgtttccc    5880
cctggaagct ccctcgtgcg ctctcctgtt ccgaccctgc cgcttaccgg atacctgtcc    5940
gcctttctcc cttcgggaag cgtggcgctt tctcatagct cacgctgtag gtatctcagt    6000
tcggtgtagg tcgttcgctc caagctgggc tgtgtgcacg aaccccccgt tcagcccgac    6060
cgctgcgcct tatccggtaa ctatcgtctt gagtccaacc cggtaagaca cgacttatcg    6120
ccactggcag cagccactgg taacaggatt agcagagcga ggtatgtagg cggtgctaca    6180
gagttcttga agtggtggcc taactacggc tacactagaa gaacagtatt tggtatctgc    6240
```

-continued

```
gctctgctga agccagttac cttcggaaaa agagttggta gctcttgatc cggcaaacaa    6300
accaccgctg gtagcggtgg ttttttttgtt tgcaagcagc agattacgcg cagaaaaaaa    6360
ggatctcaag aagatccttt gatcttttct acggggtctg acgctcagtg gaacgaaaac    6420
tcacgttaag ggattttggt catgagatta tcaaaaagga tcttcaccta gatccttta    6480
aattaaaaat gaagttttaa atcaatctaa agtatatatg agtaaacttg gtctgacagt    6540
taccaatgct taatcagtga ggcacctatc tcagcgatct gtctatttcg ttcatccata    6600
gttgcctgac tccccgtcgt gtagataact acgatacggg agggcttacc atctggcccc    6660
agtgctgcaa tgataccgcg agacccacgc tcaccggctc cagatttatc agcaataaac    6720
cagccagccg gaagggccga gcgcagaagt ggtcctgcaa ctttatccgc ctccatccag    6780
tctattaatt gttgccggga agctagagta agtagttcgc cagttaatag tttgcgcaac    6840
gttgttgcca ttgctacagg catcgtggtg tcacgctcgt cgtttggtat ggcttcattc    6900
agctccggtt cccaacgatc aaggcgagtt acatgatccc ccatgttgtg caaaaaagcg    6960
gttagctcct tcggtcctcc gatcgttgtc agaagtaagt tggccgcagt gttatcactc    7020
atggttatgg cagcactgca taattctctt actgtcatgc catccgtaag atgcttttct    7080
gtgactggtg agtactcaac caagtcattc tgagaatagt gtatgcggcg accgagttgc    7140
tcttgcccgg cgtcaatacg ggataatacc gcgccacata gcagaacttt aaaagtgctc    7200
atcattggaa aacgttcttc ggggcgaaaa ctctcaagga tcttaccgct gttgagatcc    7260
agttcgatgt aacccactcg tgcacccaac tgatcttcag catcttttac tttcaccagc    7320
gtttctgggt gagcaaaaac aggaaggcaa aatgccgcaa aaaagggaat aagggcgaca    7380
cggaaatgtt gaatactcat actcttcctt tttcaatatt attgaagcat ttatcagggt    7440
tattgtctca tgagcggata catatttgaa tgtatttaga aaaataaaca aataggggtt    7500
ccgcgcacat ttccccgaaa agtgccacct gacgtctaag aaaccattat tatcatgaca    7560
ttaacctata aaaataggcg tatcacgagg cccttcgtc tcgcgcgttt cggtgatgac    7620
ggtgaaaacc tctgacacat gcagctcccg gagacggtca cagcttgtct gtaagcggat    7680
gccgggagca gacaagcccg tcagggcgcg tcagcgggtg ttggcgggtg tcggggctgg    7740
cttaactatg cggcatcaga gcagattgta ctgagagtgc accaagcttc aatttagg    7800
cccccactg accgaggtct gtcgataatc cacttttcca ttgattttcc aggtttcgtt    7860
aactcatgcc actgagcaaa acttcggtct ttcctaacaa aagctctcct cacaaagcat    7920
ggcgcggcaa cggacgtgtc ctcatactcc actgccacac aaggtcgata aactaagctc    7980
ctcacaaata gaggagaatt ccactgacaa ctgaaaacaa tgtatgagag acgatcacca    8040
ctggagcggc gcgcggttg ggcgcggagg tcggcagcaa aaacaagcga ctcgccgagc    8100
aaacccgaat cagccttcag acggtcgtgc ctaacaacac gccgttctac cccgccttct    8160
tcgcgcccct tcgcgtccaa gcatccttca agtttatctc tctagttcaa cttcaagaag    8220
aacaacacca ccaacaccat ggccaagttg accagtgccg ttccggtgct caccgcgcgc    8280
gacgtcgccg gagcggtcga gttctggacc gaccggctcg ggttctcccg ggacttcgtg    8340
gaggacgact tcgccggtgt ggtccgggac gacgtgaccc tgttcatcag cgcggtccag    8400
gaccaggtgg tgccggacaa cacccctggcc tgggtgtggg tgcgcggcct ggacgagctg    8460
tacgccgagt ggtcggaggt cgtgtccacg aacttccggg acgcctccgg gccggccatg    8520
accgagatcg gcgagcagcc gtgggggcgg gagttcgccc tgcgcgaccc ggccggcaac    8580
```

-continued

```
tgcgtgcact tcgtggccga ggagcaggac tgacacgtgc tacgagattt cgattccacc    8640
gccgccttct atgaaaggtt gggcttcgga atcgttttcc gggacgccgg ctggatgatc    8700
ctccagcgcg gggatctcat gctggagttc ttcgcccacc ccaacttgtt tattgcagct    8760
tataatggtt acaaataaag caatagcatc acaaatttca caaataaagc atttttttca    8820
ctgcattcta gttgtggttt gtccaaactc atcaatgtat cttatcatgt ctgaattccc    8880
ggggtac                                                               8887
```

<210> SEQ ID NO 34
<211> LENGTH: 5997
<212> TYPE: DNA
<213> ORGANISM: Artificial Sequence
<220> FEATURE:
<223> OTHER INFORMATION: pYB66 vector (5997 bp)
<220> FEATURE:
<221> NAME/KEY: misc_feature
<222> LOCATION: (1)..(1064)
<223> OTHER INFORMATION: EF-1alpha_promoter
<220> FEATURE:
<221> NAME/KEY: misc_feature
<222> LOCATION: (1082)..(1118)
<223> OTHER INFORMATION: Hammerhead_ribozyme
<220> FEATURE:
<221> NAME/KEY: misc_feature
<222> LOCATION: (1119)..(1138)
<223> OTHER INFORMATION: gRNA3_CS1_target_sequence
<220> FEATURE:
<221> NAME/KEY: misc_feature
<222> LOCATION: (1139)..(1218)
<223> OTHER INFORMATION: gRNA_scaffold
<220> FEATURE:
<221> NAME/KEY: misc_feature
<222> LOCATION: (1219)..(1286)
<223> OTHER INFORMATION: HDV_ribozyme
<220> FEATURE:
<221> NAME/KEY: misc_feature
<222> LOCATION: (1306)..(1945)
<223> OTHER INFORMATION: OrfC_terminator
<220> FEATURE:
<221> NAME/KEY: misc_feature
<222> LOCATION: (4480)..(4928)
<223> OTHER INFORMATION: Alpha_tubulin_promoter
<220> FEATURE:
<221> NAME/KEY: misc_feature
<222> LOCATION: (4929)..(5723)
<223> OTHER INFORMATION: Neomycin_phosphotransferase_gene
<220> FEATURE:
<221> NAME/KEY: misc_feature
<222> LOCATION: (5724)..(5997)
<223> OTHER INFORMATION: SV40_terminator

<400> SEQUENCE: 34

```
ctcttatctg cctcgcgccg ttgaccgccg cttgactctt ggcgcttgcc gctcgcatcc      60
tgcctcgctc gcgcaggcgg gcgggcgagt gggtgggtcc gcagccttcc gcgctcgccc     120
gctagctcgc tcgcgccgtg ctgcagccag cagggcagca ccgcacggca ggcaggtccc     180
ggcgcggatc gatcgatcca tcgatccatc gatccatcga tcgtgcggtc aaaaagaaag     240
gaagaagaaa ggaaaaagaa aggcgtgcgc acccgagtgc gcgctgagcg cccgctcgcg     300
gtcccgcgga gcctccgcgt tagtccccgc cccgcgccgc gcagtccccc gggaggcatc     360
gcgcacctct cgccgccccc tcgcgcctcg ccgattcccc gcctcccctt ttccgcttct     420
tcgccgcctc cgctcgcggc gcgtcgcccc gcgcccgct ccctatctgc tcccagggg      480 ggcactccgc acctttttgcg cccgctgccg ccgccgcggc gccccgcg ccctggtttc     540 ccccgcgagc gcggccgcgt cgccgcgcaa agactcgccg cgtgccgccc cgagcaacgg    600
gtggcggcgg cgcggcggcg ggcggggcgc ggcggcgcgt aggcggggct aggcgccggc    660
```

```
taggcgaaac gccgccccg ggcgccgccg ccgcccgctc cagagcagtc gccgcgccag      720
accgccaacg cagagaccga gaccgaggta cgtcgcgccc gagcacgccg cgacgcgcgg      780
cagggacgag gagcacgacg ccgcgccgcg ccgcgcgggg gggggagggg agaggcagga      840
cgcgggagcg agcgtgcatg tttccgcgcg agacgacgcc gcgcgcgctg gagaggagat      900
aaggcgcttg gatcgcgaga gggccagcca ggctggaggc gaaaatgggt ggagaggata      960
gtatcttgcg tgcttggacg aggagactga cgaggaggac ggatacgtcg atgatgatgt     1020
gcacagagaa gaagcagttc gaaagcgact actagcaagc aagggatcca gatcttccgc     1080
actgatgagt ccgtgaggac gaaacgagta agctcgtctg cggacgtcgt ggacgcgcgt     1140
tttagagcta gaaatagcaa gttaaaataa ggctagtccg ttatcaactt gaaaaagtgg     1200
caccgagtcg gtgcttttgg ccggcatggt cccagcctcc tcgctggcgc cggctgggca     1260
acatgcttcg gcatggcgaa tgggaccata tgagttatga gatccgaaag tgaaccttgt     1320
cctaacccga cagcgaatgg cgggaggggg cgggctaaaa gatcgtatta catagtattt     1380
ttcccctact ctttgtgttt gtcttttttt ttttttgaa cgcattcaag ccacttgtct     1440
gggtttactt gtttgtttgc ttgcttgctt gcttgcttgc ctgcttcttg gtcagacggc     1500
ccaaaaaagg gaaaaaattc attcatggca cagataagaa aaagaaaaag tttgtcgacc     1560
accgtcatca gaaagcaaga gaagagaaac actcgcgctc acattctcgc tgcgtaaga     1620 atcttagcca cgcatacgaa gtaatttgtc catctggcga atctttacat gagcgttttc     1680
aagctggagc gtgagatcat acctttcttg atcgtaatgt tccaaccttg cataggcctc     1740
gttgcgatcc gctagcaatg cgtcgtactc ccgttgcaac tgcgccatcg cctcattgtg     1800
acgtgagttc agattcttct cgagaccttc gagcgctgct aatttcgcct gacgctcctt     1860
cttttgtgct tccatgacac gccgcttcac cgtgcgttcc acttcttcct cagacatgcc     1920
cttggctgcc tcgacctgct cggtaaaacg ggccccagca cgtgctacga gatttcgatt     1980
ccaccgccgc cttctatgaa aggttgggct tcggaatcgt tttccgggac gccggctgga     2040
tgatcctcca gcgcggggat ctcatgctgg agttcttcgc ccaccccaac ttgtttattg     2100
cagcttataa tggttacaaa taaagcaata gcatcacaaa tttcacaaat aaagcatttt     2160
tttcactgca ttctagttgt ggtttgtcca aactcatcaa tgtatcttat catacatggt     2220
cgacctgcag gaacctgcat taatgaatcg gccaacgcgc ggggagaggc ggtttgcgta     2280
ttgggcgctc ttccgcttcc tcgctcactg actcgctgcg ctcggtcgtt cggctgcggc     2340
gagcggtatc agctcactca aaggcggtaa tacggttatc cacagaatca ggggataacg     2400
caggaaagaa catgtgagca aaaggccagc aaaaggccag gaaccgtaaa aaggccgcgt     2460
tgctggcgtt tttccatagg ctccgccccc ctgacgagca tcacaaaaat cgacgctcaa     2520
gtcagaggtg gcgaaacccg acaggactat aaagatacca ggcgtttccc cctggaagct     2580
ccctcgtgcg ctctcctgtt ccgaccctgc cgcttaccgg atacctgtcc gcctttctcc     2640
cttcgggaag cgtggcgctt tctcatagct cacgctgtag gtatctcagt tcggtgtagg     2700
tcgttcgctc caagctgggc tgtgtgcacg aaccccccgt tcagcccgac cgctgcgcct     2760
tatccggtaa ctatcgtctt gagtccaacc cggtaagaca cgacttatcg ccactggcag     2820
cagccactgg taacaggatt agcagagcga ggtatgtagg cggtgctaca gagttcttga     2880
agtggtggcc taactacggc tacactagaa gaacagtatt tggtatctgc gctctgctga     2940
agccagttac cttcggaaaa agagttggta gctcttgatc cggcaaacaa accaccgctg     3000
```

```
gtagcggtgg ttttttttgtt tgcaagcagc agattacgcg cagaaaaaaa ggatctcaag    3060
aagatccttt gatcttttct acggggtctg acgctcagtg gaacgaaaac tcacgttaag    3120
ggattttggt catgagatta tcaaaaagga tcttcaccta gatccttta aattaaaaat     3180
gaagttttaa atcaatctaa agtatatatg agtaaacttg gtctgacagt taccaatgct    3240
taatcagtga ggcacctatc tcagcgatct gtctatttcg ttcatccata gttgcctgac    3300
tccccgtcgt gtagataact acgatacggg agggcttacc atctggcccc agtgctgcaa    3360
tgataccgcg agacccacgc tcaccggctc cagatttatc agcaataaac cagccagccg    3420
gaagggccga gcgcagaagt ggtcctgcaa ctttatccgc ctccatccag tctattaatt    3480
gttgccggga agctagagta agtagttcgc cagttaatag tttgcgcaac gttgttgcca    3540
ttgctacagg catcgtggtg tcacgctcgt cgtttggtat ggcttcattc agctccggtt    3600
cccaacgatc aaggcgagtt acatgatccc ccatgttgtg caaaaaagcg gttagctcct    3660
tcggtcctcc gatcgttgtc agaagtaagt tggccgcagt gttatcactc atggttatgg    3720
cagcactgca taattctctt actgtcatgc catccgtaag atgcttttct gtgactggtg    3780
agtactcaac caagtcattc tgagaatagt gtatgcggcg accgagttgc tcttgcccgg    3840
cgtcaatacg ggataatacc gcgccacata gcagaacttt aaaagtgctc atcattggaa    3900
aacgttcttc ggggcgaaaa ctctcaagga tcttaccgct gttgagatcc agttcgatgt    3960
aacccactcg tgcacccaac tgatcttcag catcttttac tttcaccagc gtttctgggt    4020
gagcaaaaac aggaaggcaa aatgccgcaa aaagggaat aagggcgaca cggaaatgtt    4080
gaatactcat actcttcctt tttcaatatt attgaagcat ttatcagggt tattgtctca    4140
tgagcggata catatttgaa tgtatttaga aaaataaaca aatagggt tccgcgcacat    4200
ttccccgaaa agtgccacct gacgtctaag aaaccattat tatcatgaca ttaacctata    4260
aaaataggcg tatcacgagg ccctttcgtc tcgcgcgttt cggtgatgac ggtgaaaacc    4320
tctgacacat gcagctcccg gagacggtca gcttgtct gtaagcggat gccgggagca    4380
gacaagcccg tcagggcgcg tcagcgggtg ttggcgggtg tcggggctgg cttaactatg    4440
cggcatcaga gcagattgta ctgagagtgc accagcttc caattttagg ccccccactg    4500
accgaggtct gtcgataatc cacttttcca ttgattttcc aggtttcgtt aactcatgcc    4560
actgagcaaa acttcggtct ttcctaacaa aagctctcct cacaaagcat ggcgcggcaa    4620
cggacgtgtc ctcatactcc actgccacac aaggtcgata aactaagctc ctcacaaata    4680
gaggagaatt ccactgacaa ctgaaaacaa tgtatgagag acgatcacca ctggagcggc    4740
gcggcggttg ggcgcggagg tcggcagcaa aaacaagcga ctcgccgagc aaacccgaat    4800
cagccttcag acggtcgtgc ctaacaacac gccgttctac cccgccttct tcgccccct    4860
tcgcgtccaa gcatccttca agtttatctc tctagttcaa cttcaagaag aacaacacca    4920
ccaacaccat gattgaacaa gatggattgc acgcaggttc tccggccgct tgggtggaga    4980
ggctattcgg ctatgactgg gcacaacaga caatcggctg ctctgatgcc gccgtgttcc    5040
ggctgtcagc gcaggggcgc ccggttcttt ttgtcaagac cgacctgtcc ggtgccctga    5100
atgaactgca ggacgaggca gcgcggctat cgtggctggc cacgacgggc gttccttgcg    5160
cagctgtgct cgacgttgtc actgaagcgg gaagggactg gctgctattg ggcgaagtgc    5220
cggggcagga tctcctgtca tctcaccttg ctcctgccga gaaagtatcc atcatggctg    5280
atgcaatgcg gcggctgcat acgcttgatc cggctacctg cccattcgac caccaagcga    5340
aacatcgcat cgagcgagca cgtactcgga tggaagccgg tcttgtcgat caggatgatc    5400
```

```
tggacgaaga gcatcagggg ctcgcgccag ccgaactgtt cgccaggctc aaggcgcgca      5460
tgcccgacgg cgatgatctc gtcgtgaccc atggcgatgc ctgcttgccg aatatcatgg      5520
tggaaaatgg ccgctttcct ggattcatcg actgtggccg gctgggtgtg gcggaccgct      5580
atcaggacat agcgttggct acccgtgata ttgctgaaga gcttggcggc gaatgggctg      5640
accgcttcct cgtgctttac ggtatcgccg ctcccgattc gcagcgcatc gccttctatc      5700
gccttcttga cgagttcttc tgacacgtgc tacgagattt cgattccacc gccgccttct      5760
atgaaaggtt gggcttcgga atcgtttttc gggacgccgg ctggatgatc ctccagcgcg      5820
gggatctcat gctggagttc ttcgcccacc ccaacttgtt tattgcagct tataatggtt      5880
acaaataaag caatagcatc acaaatttca caaataaagc atttttttca ctgcattcta      5940
gttgtggttt gtccaaactc atcaatgtat cttatcatgt ctgaattccc ggggtac        5997
```

```
<210> SEQ ID NO 35
<211> LENGTH: 10700
<212> TYPE: DNA
<213> ORGANISM: Artificial Sequence
<220> FEATURE:
<223> OTHER INFORMATION: pYB73 vector (10700 bp)
<220> FEATURE:
<221> NAME/KEY: misc_feature
<222> LOCATION: (2)..(450)
<223> OTHER INFORMATION: Alpha_tubulin_promoter
<220> FEATURE:
<221> NAME/KEY: misc_feature
<222> LOCATION: (457)..(4596)
<223> OTHER INFORMATION: Cas9
<220> FEATURE:
<221> NAME/KEY: misc_feature
<222> LOCATION: (4616)..(5255)
<223> OTHER INFORMATION: OrfC_terminator
<220> FEATURE:
<221> NAME/KEY: misc_feature
<222> LOCATION: (5546)..(6608)
<223> OTHER INFORMATION: EF_1alpha_promoter
<220> FEATURE:
<221> NAME/KEY: misc_feature
<222> LOCATION: (6621)..(6657)
<223> OTHER INFORMATION: Hammerhead_ribozyme
<220> FEATURE:
<221> NAME/KEY: misc_feature
<222> LOCATION: (6658)..(6677)
<223> OTHER INFORMATION: gRNA3_CS1_target_sequence
<220> FEATURE:
<221> NAME/KEY: misc_feature
<222> LOCATION: (6678)..(6757)
<223> OTHER INFORMATION: gRNA_scaffold
<220> FEATURE:
<221> NAME/KEY: misc_feature
<222> LOCATION: (6758)..(6825)
<223> OTHER INFORMATION: HDV_ribozyme
<220> FEATURE:
<221> NAME/KEY: misc_feature
<222> LOCATION: (6845)..(7363)
<223> OTHER INFORMATION: OrfC_terminator
<220> FEATURE:
<221> NAME/KEY: misc_feature
<222> LOCATION: (8369)..(9229)
<223> OTHER INFORMATION: Ampicillin_resistance_gene
<220> FEATURE:
<221> NAME/KEY: misc_feature
<222> LOCATION: (9619)..(10067)
<223> OTHER INFORMATION: Alpha_tubulin_promoter
<220> FEATURE:
<221> NAME/KEY: misc_feature
<222> LOCATION: (10068)..(10442)
<223> OTHER INFORMATION: Sh_ble_gene
<220> FEATURE:
<221> NAME/KEY: misc_feature
<222> LOCATION: (10443)..(10700)
```

<223> OTHER INFORMATION: SV40_terminator

<400> SEQUENCE: 35

| | | | | | |
|---|---|---|---|---|---|
| cccaatttta | ggccccccac | tgaccgaggt | ctgtcgataa | tccactttc | cattgattt | 60 |
| ccaggtttcg | ttaactcatg | ccactgagca | aaacttcggt | cttcctaac | aaaagctctc | 120 |
| ctcacaaagc | atggcgcggc | aacggacgtg | tcctcatact | ccactgccac | acaaggtcga | 180 |
| taaactaagc | tcctcacaaa | tagaggagaa | ttccactgac | aactgaaaac | aatgtatgag | 240 |
| agacgatcac | cactggagcg | gcgcggcggt | tgggcgcgga | ggtcggcagc | aaaaacaagc | 300 |
| gactcgccga | gcaaacccga | atcagccttc | agacggtcgt | gcctaacaac | acgccgttct | 360 |
| accccgcctt | cttcgcgccc | cttcgcgtcc | aagcatcctt | caagtttatc | tctctagttc | 420 |
| aacttcaaga | agaacaacac | caccaacacc | ggatccatgg | ataagaagta | ctcgatcggc | 480 |
| ctcgacattg | gcaccaacag | cgtcggctgg | gccgtcatta | ctgatgagta | caaggtcccg | 540 |
| tcgaagaagt | ttaaggtcct | cggcaacact | gaccgccact | ccatcaagaa | gaacctcatc | 600 |
| ggtgccctcc | ttttgactc | cggcgagacc | gctgaggcca | ctcgcctcaa | gcgcactgcc | 660 |
| cgccgccgtt | acacccgccg | caagaaccgc | atctgctacc | tccaggagat | tttctcgaac | 720 |
| gaaatggcca | aggtcgatga | ctccttttc | caccgtctcg | aagaatcgtt | cctcgtcgag | 780 |
| gaggacaaga | agcacgagcg | ccaccccatc | ttcggtaaca | ttgtcgatga | ggttgcctac | 840 |
| cacgagaagt | acccgaccat | ctaccacctc | cgcaagaagc | tcgtcgactc | caccgacaag | 900 |
| gccgatctcc | gccttatcta | cctcgccctc | gcccacatga | tcaagttccg | cggccacttt | 960 |
| cttatcgagg | tgatctcaa | ccctgataac | tctgacgtcg | acaagctttt | catccagctc | 1020 |
| gtccagactt | acaaccagct | cttcgaggag | aaccccatca | acgcttccgg | cgtcgacgcg | 1080 |
| aaggccattc | tcagcgcccg | cctcagcaag | tcccgccgcc | tcgaaaacct | cattgcccag | 1140 |
| cttcccggcg | agaagaagaa | cggcctcttc | ggcaacctca | ttgccctcag | ccttggcctc | 1200 |
| acccctaact | tcaagtcgaa | cttgacctc | gccgaggacg | ccaagctcca | gctttccaag | 1260 |
| gacacttacg | acgacgatct | cgacaacctc | ctcgctcaga | ttggcgacca | gtacgctgac | 1320 |
| ctcttcctcg | ccgccaagaa | ccttagcgat | gccatcctcc | tctccgacat | ccttcgtgtt | 1380 |
| aacacggaaa | tcacgaaggc | tccgctctcc | gcctccatga | tcaagcgtta | cgacgagcac | 1440 |
| catcaggacc | tcacccctcct | caaggcctc | gtccgccagc | agctccccga | agtacaag | 1500 |
| gagatcttct | tcgaccagag | caagaacggc | tacgccggct | acattgacgg | cggcgcgtcg | 1560 |
| caggaggagt | tttacaagtt | tatcaagccc | attcttgaga | agatggacgg | caccgaggag | 1620 |
| ctcctcgtca | agctcaaccg | tgaggacctt | ctccgcaagc | agcgcacgtt | cgacaacggc | 1680 |
| tctattcccc | atcagatcca | cctcggtgag | cttcacgcga | ttcttcgccg | ccaggaagac | 1740 |
| ttttacccgt | tcctcaagga | caaccgcgag | aagattgaga | agatcctcac | ctttcgcatt | 1800 |
| ccctactacg | tcggcccct | cgccgcggc | aactcgcgct | ttgcttggat | gacccgcaag | 1860 |
| tccgaggaga | ccatcacccc | gtggaacttc | gaagaggtcg | tcgacaaggg | cgcctccgcg | 1920 |
| cagtctttca | tcgagcgcat | gactaacttt | gacaagaacc | tcccgaacga | aaggtcctc | 1980 |
| cccaagcaca | gctccttta | cgaatacttt | acggtgtaca | acgagctcac | gaaggtcaag | 2040 |
| tacgtcactg | agggcatgcg | caagccggcg | ttcctttcgg | gcgagcagaa | gaaggctatc | 2100 |
| gtcgacctcc | tttcaagac | caaccgcaag | gttaccgtca | gcagctcaa | ggaggactac | 2160 |
| ttcaagaaga | tcgagtgctt | tgactcggtc | gagatttcgg | gcgtggagga | ccgtttcaac | 2220 |
| gcctccctcg | gcacttacca | cgaccttctc | aagatcatca | aggacaagga | ctttctcgac | 2280 |

```
aacgaggaga acgaggacat tctcgaggac atcgtcctca cgctcaccct ctttgaggac   2340
cgtgagatga tcgaggagcg cctcaagacc tacgcccatc tctttgacga caaggtcatg   2400
aagcagctca agcgccgccg ctacaccggc tggggccgcc tttcccgcaa gctcatcaac   2460
ggcatccgcg acaagcagtc tggcaagacc atccttgact tcttaagtc tgatggtttc    2520
gccaaccgca acttcatgca gctcatccac gacgacagcc tcactttcaa ggaggacatt   2580
cagaaggccc aggtctccgg ccagggtgac tctctccacg aacacatcgc caaccttgct   2640
ggcagcccgg ctattaagaa gggcatcctc cagaccgtca aggtcgtcga cgagctcgtc   2700
aaggttatgg gccgccacaa gcccgagaac atcgtcattg agatggctcg cgaaaaccag   2760
accacccaga agggtcagaa gaactcccgc gagcgcatga agcgtatcga ggagggcatc   2820
aaggagctcg gcagccagat cctcaaggag cacccggtcg agaacaccca gctccagaac   2880
gaaaagctct acctctacta cctccagaac ggccgtgaca tgtacgttga ccaggagctc   2940
gacattaacc gcctctccga ttacgacgtc gaccatattg tcccccagag ctttctcaag   3000
gacgacagca tcgacaacaa ggtcctcacc cgctcggaca agaaccgcgg caagtccgac   3060
aacgtccctt ccgaggaggt cgtgaagaag atgaagaact actggcgcca gcttctcaac   3120
gctaagctta ttactcagcg caagttcgat aacctcacca aggccgaacg cggcggcctc   3180
tccgagctcg acaaggccgg ttttatcaag cgccagctcg ttgagactcg ccagatcacc   3240
aagcacgtgg cgcagatcct cgactcgcgc atgaacacga agtacgacga gaacgacaag   3300
ctcatccgcg aggtcaaggt catcacccct aagtcgaagc tcgtgtccga ctttcgcaag   3360
gacttccagt tctacaaggt ccgtgaaatt aacaactacc accacgctca cgacgcttac   3420
ctcaacgcgg tcgtgggtac cgcgctcatc aagaagtacc cgaagctcga gtcggagttt   3480
gtctacggcg actacaaggt ctacgacgtg cgcaagatga tcgccaagtc cgagcaggag   3540
atcggcaagg ccacggccaa gtactttttc tactccaaca ttatgaactt ctttaagact   3600
gagatcaccc ttgccaacgg cgagatccgc aagcgccccc ttatcgagac caacggcgag   3660
accggcgaaa ttgtgtggga taagggtcgc gactttgcca ccgtccgcaa ggtcctcagc   3720
atgccccagg tcaacattgt taagaagacc gaggtccaga cgggcggctt tagcaaggag   3780
tctatcctcc ccaagcgtaa cagcgacaag ctcatcgccc gcaagaagga ctgggaccct   3840
aagaagtacg gcggcttcga ttcgcctacg gtcgcctaca gcgtcctcgt cgtcgccaag   3900
gtcgagaagg gcaagtccaa gaagctcaag tccgtcaagg agctcctcgg catcacgatc   3960
atggagcgct ccagctttga gaagaacccc attgacttcc tcgaggctaa gggttacaag   4020
gaggtcaaga aggaccttat catcaagctc cccaagtact ccctctttga gctcgaaaac   4080
ggccgcaagc gtatgctcgc tagcgctggc gaactccaga agggcaacga gctcgccctc   4140
cccagcaagt acgtcaactt tctctacctc gcctcccact acgagaagct caagggtagc   4200
ccggaggata cgagcagaa gcagcttttt gtggagcagc acaagcacta ccttgacgag   4260
atcattgaac agatctccga gttctccaag cgtgttattc ttgctgacgc caacctcgat   4320
aaggtgctct ccgcgtacaa caagcaccgc gacaagccta tccgcgagca ggccgagaac   4380
atcatccacc tctttaccct caccaacctc ggcgcccccgg ccgcctttaa gtactttgat   4440
acgactatcg accgcaagcg ctacacttcg actaaggagg tcctcgacgc taccctcatt   4500
caccagtcca ttaccggcct ctacgagacc cgcattgacc tttcgcagct cggtggcgac   4560
tcgcgtgcgg accctaagaa gaagcgcaag gtctaacata tgagttatga gatccgaaag   4620
```

```
tgaaccttgt cctaacccga cagcgaatgg cgggaggggg cgggctaaaa gatcgtatta      4680
catagtattt ttcccctact ctttgtgttt gtctttttt tttttttgaa cgcattcaag       4740
ccacttgtct gggtttactt gtttgtttgc ttgcttgctt gcttgcttgc ctgcttcttg      4800
gtcagacggc ccaaaaaagg gaaaaaattc attcatggca cagataagaa aaagaaaaag     4860
tttgtcgacc accgtcatca gaaagcaaga gaagagaaac actcgcgctc acattctcgc     4920
tcgcgtaaga atcttagcca cgcatacgaa gtaatttgtc catctggcga atctttacat     4980
gagcgttttc aagctggagc gtgagatcat acctttcttg atcgtaatgt ccaaccttg      5040
cataggcctc gttgcgatcc gctagcaatg cgtcgtactc ccgttgcaac tgcgccatcg     5100
cctcattgtg acgtgagttc agattcttct cgagaccttc gagcgctgct aatttcgcct    5160
gacgctcctt cttttgtgct tccatgacac gccgcttcac cgtgcgttcc acttcttcct    5220
cagacatgcc cttggctgcc tcgacctgct cggtaaaacg ggccccagca cgtgctacga    5280
gatttcgatt ccaccgccgc cttctatgaa aggttgggct tcggaatcgt tttccgggac   5340
gccggctgga tgatcctcca gcgcgggat ctcatgctgg agttcttcgc ccaccccaac    5400
ttgtttattg cagcttataa tggttacaaa taaagcaata gcatcacaaa tttcacaaat    5460
aaagcatttt tttcactgca ttctagttgt ggtttgtcca aactcatcaa tgtatcttat   5520
catacatggt cgacctgcag ggtacctctt atctgcctcg cgccgttgac cgccgcttga  5580
ctcttggcgc ttgccgctcg catcctgcct cgctcgcgca ggcgggcggg cgagtgggtg   5640
ggtccgcagc cttccgcgct cgcccgctag ctcgctcgcg ccgtgctgca gccagcaggg  5700
cagcaccgca cggcaggcag gtcccggcgc ggatcgatcg atccatcgat ccatcgatcc  5760
atcgatcgtg cggtcaaaaa gaaggaaga agaaaggaaa aagaaaggcg tgcgcacccg   5820
agtgcgcgct gagcgcccgc tcgcggtccc gcggagcctc cgcgttagtc cccgccccgc  5880
gccgcgcagt ccccgggag gcatcgcgca cctctcgccg cccctcgcg cctcgccgat   5940
tccccgcctc cccttttccg cttcttcgcc gcctccgctc gcggccgcgt cgcccgcgcc 6000
ccgctcccta tctgctcccc aggggggcac tccgcacctt ttgcgcccgc tgccgccgcc 6060
gcggccgccc cgccgccctg gtttcccccg cgagcgcggc cgcgtcgccg cgcaaagact 6120
cgccgcgtgc cgccccgagc aacgggtggc ggcggcgcgg cggcgggcgg ggcgcggcgg 6180
cgcgtaggcg gggctaggcg ccggctaggc gaaacgccgc ccccgggcgc cgccgccgcc 6240
cgctccagag cagtcgccgc gccagaccgc caacgcagag accgagaccg aggtacgtcg 6300
cgcccgagca cgccgcgacg cgcggcaggg acgaggagca cgacgccgcg ccgcgccgcg 6360
cggggggggg gagggagagg caggacgcgg gagcgagcgt gcatgtttcc gcgcgagacg 6420
acgccgcgcg cgctggagag gagataaggc gcttggatcg cgagagggcc agccaggctg 6480
gaggcgaaaa tgggtggaga ggatagtatc ttgcgtgctt ggacgaggag actgacgagg 6540
aggacggata cgtcgatgat gatgtgcaca gagaagaagc agttcgaaag cgactactag 6600
caagcaagag atcttccgca ctgatgagtc cgtgaggacg aaacgagtaa gctcgtctgc 6660
ggacgtcgtg gacgcgcgtt ttagagctag aaatagcaag ttaaaataag gctagtccgt 6720
tatcaacttg aaaaagtggc accgagtcgg tgcttttggc cggcatggtc ccagcctcct 6780
cgctggcgcc ggctgggcaa catgcttcgg catggcgaat gggaccatat gagttatgag 6840
atccgaaagt gaaccttgtc ctaacccgac agcgaatggc gggaggggc gggctaaaag  6900
atcgtattac atagtatttt tcccctactc tttgtgtttg tctttttttt ttttttgaac   6960
gcattcaagc cacttgtctg ggtttacttg tttgtttgct tgcttgcttg cttgcttgcc  7020
```

```
tgcttcttgg tcagacggcc caaaaaaggg aaaaaattca ttcatggcac agataagaaa   7080
aagaaaaagt ttgtcgacca ccgtcatcag aaagcaagag aagagaaaca ctcgcgctca   7140
cattctcgct cgcgtaagaa tcttagccac gcatacgaag taatttgtcc atctggcgaa   7200
tctttacatg agcgttttca agctggagcg tgagatcata cctttcttga tcgtaatgtt   7260
ccaaccttgc ataggcctcg ttgcgatccg ctagcaatgc gtcgtactcc cgttgcaact   7320
gcgccatcgc ctcattgtga cgtgagttca gattcttctc gagctgcagg aacctgcatt   7380
aatgaatcgg ccaacgcgcg gggagaggcg gtttgcgtat gggcgctct tccgcttcct    7440 cgctcactga ctcgctgcgc tcggtcgttc ggctgcggcg agcggtatca gctcactcaa   7500
aggcggtaat acgttatcc acagaatcag gggataacgc aggaaagaac atgtgagcaa    7560
aaggccagca aaaggccagg aaccgtaaaa aggccgcgtt gctggcgttt ttccataggc   7620
tccgcccccc tgacgagcat cacaaaaatc gacgctcaag tcagaggtgg cgaaacccga   7680
caggactata aagataccag gcgtttcccc ctggaagctc cctcgtgcgc tctcctgttc   7740
cgaccctgcc gcttaccgga tacctgtccg cctttctccc ttcgggaagc gtggcgcttt   7800
ctcatagctc acgctgtagg tatctcagtt cggtgtaggt cgttcgctcc aagctgggct   7860
gtgtgcacga accccccgtt cagcccgacc gctgcgcctt atccggtaac tatcgtcttg   7920
agtccaaccc ggtaagacac gacttatcgc cactggcagc agccactggt aacaggatta   7980
gcagagcgag gtatgtaggc ggtgctacag agttcttgaa gtggtggcct aactacggct   8040
acactagaag aacagtattt ggtatctgcg ctctgctgaa gccagttacc ttcggaaaaa   8100
gagttggtag ctcttgatcc ggcaaacaaa ccaccgctgg tagcggtggt ttttttgttt   8160
gcaagcagca gattacgcgc agaaaaaaag gatctcaaga agatcctttg atcttttcta   8220
cggggtctga cgctcagtgg aacgaaaact cacgttaagg gattttggtc atgagattat   8280
caaaaaggat cttcacctag atccttttaa attaaaaatg aagttttaaa tcaatctaaa   8340
gtatatatga gtaaacttgg tctgacagtt accaatgctt aatcagtgag gcacctatct   8400
cagcgatctg tctatttcgt tcatccatag ttgcctgact ccccgtcgtg tagataacta   8460
cgatacggga gggcttacca tctggcccca gtgctgcaat gataccgcga cccacgct    8520 caccggctcc agatttatca gcaataaacc agccagccgg aagggccgag cgcagaagtg   8580
gtcctgcaac tttatccgcc tccatccagt ctattaattg ttgccgggaa gctagagtaa   8640
gtagttcgcc agttaatagt ttgcgcaacg ttgttgccat tgctacaggc atcgtggtgt   8700
cacgctcgtc gtttggtatg gcttcattca gctccggttc ccaacgatca aggcgagtta   8760
catgatcccc catgttgtgc aaaaaagcgg ttagctcctt cggtcctccg atcgttgtca   8820
gaagtaagtt ggccgcagtg ttatcactca tggttatggc agcactgcat aattctctta   8880
ctgtcatgcc atccgtaaga tgcttttctg tgactggtga gtactcaacc aagtcattct   8940
gagaatagtg tatgcggcga ccgagttgct cttgcccggc gtcaatacgg gataataccg   9000
cgccacatag cagaacttta aaagtgctca tcattggaaa acgttcttcg ggcgaaaac    9060 tctcaaggat cttaccgctg ttgagatcca gttcgatgta acccactcgt gcacccaact   9120
gatcttcagc atcttttact ttcaccagcg tttctgggtg agcaaaaaca ggaaggcaaa   9180
atgccgcaaa aaagggaata agggcgacac ggaaatgttg aatactcata ctcttccttt   9240
ttcaatatta ttgaagcatt tatcagggtt attgtctcat gagcggatac atatttgaat   9300
gtatttagaa aaataaacaa ataggggttc cgcgcacatt tccccgaaaa gtgccacctg   9360
```

```
acgtctaaga aaccattatt atcatgacat taacctataa aaataggcgt atcacgaggc    9420
cctttcgtct cgcgcgtttc ggtgatgacg gtgaaaacct ctgacacatg cagctcccgg    9480
agacggtcac agcttgtctg taagcggatg ccgggagcag acaagcccgt cagggcgcgt    9540
cagcgggtgt tggcgggtgt cggggctggc ttaactatgc ggcatcagag cagattgtac    9600
tgagagtgca ccaagcttcc aattttaggc cccccactga ccgaggtctg tcgataatcc    9660
acttttccat tgattttcca ggtttcgtta actcatgcca ctgagcaaaa cttcggtctt    9720
tcctaacaaa agctctcctc acaaagcatg gcgcggcaac ggacgtgtcc tcatactcca    9780
ctgccacaca aggtcgataa actaagctcc tcacaaatag aggagaattc cactgacaac    9840
tgaaaacaat gtatgagaga cgatcaccac tggagcggcg cggcggttgg gcgcggaggt    9900
cggcagcaaa aacaagcgac tcgccgagca aacccgaatc agccttcaga cggtcgtgcc    9960
taacaacacg ccgttctacc ccgccttctt cgcgcccctt cgcgtccaag catccttcaa   10020
gtttatctct ctagttcaac ttcaagaaga acaacaccac caacaccatg gccaagttga   10080
ccagtgccgt tccggtgctc accgcgcgcg acgtcgccgg agcggtcgag ttctggaccg   10140
accggctcgg gttctcccgg gacttcgtgg aggacgactt cgccggtgtg gtccgggacg   10200
acgtgaccct gttcatcagc gcggtccagg accaggtggt gccggacaac accctggcct   10260
gggtgtgggt gcgcggcctg gacgagctgt acgccgagtg gtcggaggtc gtgtccacga   10320
acttccggga cgcctccggg ccggccatga ccgagatcgg cgagcagccg tgggggcggg   10380
agttcgccct gcgcgacccg gccggcaact gcgtgcactt cgtggccgag gagcaggact   10440
gacacgtgct acgagatttc gattccaccg ccgccttcta tgaaaggttg gcttcggaa    10500 tcgtttttccg ggacgccggc tggatgatcc tccagcgcgg ggatctcatg ctggagttct   10560
tcgcccaccc caacttgttt attgcagctt ataatggtta caaataaagc aatagcatca   10620
caaatttcac aaataaagca ttttttttcac tgcattctag ttgtggtttg tccaaactca   10680
tcaatgtatc ttatcggtac                                                10700
```

<210> SEQ ID NO 36
<211> LENGTH: 6300
<212> TYPE: DNA
<213> ORGANISM: Artificial Sequence
<220> FEATURE:
<223> OTHER INFORMATION: pCL310 vector (6300 bp)
<220> FEATURE:
<221> NAME/KEY: misc_feature
<222> LOCATION: (1)..(1064)
<223> OTHER INFORMATION: EF_1alpha_promoter
<220> FEATURE:
<221> NAME/KEY: misc_feature
<222> LOCATION: (1070)..(1981)
<223> OTHER INFORMATION: CarG_gene
<220> FEATURE:
<221> NAME/KEY: misc_feature
<222> LOCATION: (2001)..(2640)
<223> OTHER INFORMATION: OrfC_terminator
<220> FEATURE:
<221> NAME/KEY: misc_feature
<222> LOCATION: (5175)..(5623)
<223> OTHER INFORMATION: Alpha_tubulin_promoter
<220> FEATURE:
<221> NAME/KEY: misc_feature
<222> LOCATION: (5627)..(6019)
<223> OTHER INFORMATION: Bsd_gene
<220> FEATURE:
<221> NAME/KEY: misc_feature
<222> LOCATION: (6020)..(6300)
<223> OTHER INFORMATION: SV40_terminator

<400> SEQUENCE: 36

```
ctcttatctg cctcgcgccg ttgaccgccg cttgactctt ggcgcttgcc gctcgcatcc      60
tgcctcgctc gcgcaggcgg gcgggcgagt gggtgggtcc gcagccttcc gcgctcgccc     120
gctagctcgc tcgcgccgtg ctgcagccag cagggcagca ccgcacggca ggcaggtccc     180
ggcgcggatc gatcgatcca tcgatccatc gatccatcga tcgtgcggtc aaaaagaaag     240
gaagaagaaa ggaaaaagaa aggcgtgcgc acccgagtgc gcgctgagcg cccgctcgcg     300
gtcccgcgga gcctccgcgt tagtcccgc cccgcgccgc gcagtccccc gggaggcatc     360
gcgcacctct cgccgccccc tcgcgcctcg ccgattcccc gcctcccctt ttccgcttct     420
tcgccgcctc cgctcgcggc cgcgtcgccc gcgccccgct ccctatctgc tccccagggg     480
ggcactccgc acctttgcg cccgctgccg ccgccgcggc cgcccgccg ccctggtttc     540
ccccgcgagc gcggccgcgt cgccgcgcaa agactcgccg cgtgccgccc cgagcaacgg     600
gtggcggcgg cgcggcggcg ggcggggcgc ggcggcgcgt aggcggggct aggcgccggc     660
taggcgaaac gccgccccg ggcgccgccg ccgcccgctc cagagcagtc gccgcgccag     720
accgccaacg cagagaccga gaccgaggta cgtcgcgccc gagcacgccg cgacgcgcgg     780
cagggacgag gagcacgacg ccgcgccgcg ccgcgcgggg gggggaggg agaggcagga     840
cgcgggagcg agcgtgcatg tttccgcgcg agacgacgcc gcgcgcgctg gagaggagat     900
aaggcgcttg gatcgcgaga gggccagcca ggctggaggc gaaatgggt ggagaggata     960
gtatcttgcg tgcttggacg aggagactga cgaggaggac ggatacgtcg atgatgatgt    1020
gcacagagaa gaagcagttc gaaagcgact actagcaagc aagggatcca tgctcaactc    1080
gcacaaccgc actgaggagc gctccactga ggacatcatc cttgagccct acacctacct    1140
catttcccag cccggcaagg acatccgcgc taagcttatt tccgctttcg acctctggct    1200
ccatgtcccc aaggacgtcc tctgcgtcat caacaagatt attggcatgc ttcacaacgc    1260
ctccctcatg atcgacgatg tccaggatga ctccgacctt cgccgtggcg tccccgtcgc    1320
ccaccatatc tacggcgtcc cccagacgat caacaccgct aactacgtca ttttctcgc    1380
tctccaggag gtcatgaagc tcaacatccc ctccatgatg caggtctgca ctgaggagct    1440
catcaacctt caccgcggcc agggtatcga gctctactgg cgcgattcgc ttacttgccc    1500
cactgaggag gagtacattg acatggtcaa caacaagacg tccggccttc tccgtcttgc    1560
cgtccgtctc atgcaggccg cctcggagtc cgacatcgac tacaccccctc tcgtcaacat    1620
catcggtatt cactttcagg tccgcgacga ttacatgaac ctccagtcca ctagctacac    1680
gaacaacaag ggtttctgcg aggacctcac ggagggcaag ttttcgttcc ccatcatcca    1740
cgccattcgc aaggaccca gcaaccgcca gctccttaac attatctccc agaagcctac    1800
gtccattgag gttaagaagt acgcccttga ggttattcgc aaggccggca gctttgagta    1860
cgttcgcgag ttcctgcgcc agaaggaggc cgagtccctt aaggagatca agcgccttgg    1920
aggcaaccct ctcctcgaga agtacattga gaccatccgc gtcgaggcca cgaacgacta    1980
acatatgagt tatgagatcc gaaagtgaac cttgtcctaa cccgacagcg aatggcggga    2040
gggggcgggc taaaagatcg tattacatag tatttttccc ctactctttg tgtttgtctt    2100
tttttttttt ttgaacgcat tcaagccact tgtctgggtt tacttgtttg tttgcttgct    2160
tgcttgcttg cttgcctgct tcttggtcag acggcccaaa aaagggaaaa aattcattca    2220
tggcacagat aagaaaaaga aaagtttgt cgaccaccgt catcagaaag caagagaaga    2280
gaaacactcg cgctcacatt ctcgctcgcg taagaatctt agccacgcat acgaagtaat    2340
```

```
ttgtccatct ggcgaatctt tacatgagcg ttttcaagct ggagcgtgag atcatacctt   2400
tcttgatcgt aatgttccaa ccttgcatag gcctcgttgc gatccgctag caatgcgtcg   2460
tactcccgtt gcaactgcgc catcgcctca ttgtgacgtg agttcagatt cttctcgaga   2520
ccttcgagcg ctgctaattt cgcctgacgc tccttctttt gtgcttccat gacacgccgc   2580
ttcaccgtgc gttccacttc ttcctcagac atgcccttgg ctgcctcgac ctgctcggta   2640
aaacgggccc cagcacgtgc tacgagattt cgattccacc gccgccttct atgaaaggtt   2700
gggcttcgga atcgttttcc gggacgccgg ctggatgatc ctccagcgcg gggatctcat   2760
gctggagttc ttcgcccacc ccaacttgtt tattgcagct tataatggtt acaaataaag   2820
caatagcatc acaaatttca caaataaagc atttttttca ctgcattcta gttgtggttt   2880
gtccaaactc atcaatgtat cttatcatac atggtcgacc tgcaggaacc tgcattaatg   2940
aatcggccaa cgcgcgggga gaggcggttt gcgtattggg cgctcttccg cttcctcgct   3000
cactgactcg ctgcgctcgg tcgttcggct gcggcgagcg gtatcagctc actcaaaggc   3060
ggtaatacgg ttatccacag aatcagggga taacgcagga agaacatgt gagcaaaagg   3120 ccagcaaaag gccaggaacc gtaaaaaggc cgcgttgctg gcgttttttcc ataggctccg   3180 cccccctgac gagcatcaca aaaatcgacg ctcaagtcag aggtggcgaa acccgacagg   3240
actataaaga taccaggcgt ttccccctgg aagctccctc gtgcgctctc ctgttccgac   3300
cctgccgctt accggatacc tgtccgcctt tctcccttcg ggaagcgtgg cgctttctca   3360
tagctcacgc tgtaggtatc tcagttcggt gtaggtcgtt cgctccaagc tgggctgtgt   3420
gcacgaaccc cccgttcagc ccgaccgctg cgccttatcc ggtaactatc gtcttgagtc   3480
caacccggta agacacgact tatcgccact ggcagcagcc actggtaaca ggattagcag   3540
agcgaggtat gtaggcggtg ctacagagtt cttgaagtgg tggcctaact acggctacac   3600
tagaagaaca gtatttggta tctgcgctct gctgaagcca gttaccttcg gaaaaagagt   3660
tggtagctct tgatccggca aacaaaccac cgctggtagc ggtggttttt tgtttgcaa   3720 gcagcagatt acgcgcagaa aaaaaggatc tcaagaagat cctttgatct tttctacggg   3780
gtctgacgct cagtggaacg aaaactcacg ttaagggatt ttggtcatga gattatcaaa   3840
aaggatcttc acctagatcc ttttaaatta aaaatgaagt tttaaatcaa tctaaagtat   3900
atatgagtaa acttggtctg acagttacca atgcttaatc agtgaggcac ctatctcagc   3960
gatctgtcta tttcgttcat ccatagttgc ctgactcccc gtcgtgtaga taactacgat   4020
acgggagggc ttaccatctg gccccagtgc tgcaatgata ccgcgagacc cacgctcacc   4080
ggctccagat ttatcagcaa taaaccagcc agccggaagg gccgagcgca gaagtggtcc   4140
tgcaacttta tccgcctcca tccagtctat taattgttgc cgggaagcta gagtaagtag   4200
ttcgccagtt aatagtttgc gcaacgttgt tgccattgct acaggcatcg tggtgtcacg   4260
ctcgtcgttt ggtatggctt cattcagctc cggttcccaa cgatcaaggc gagttacatg   4320
atcccccatg ttgtgcaaaa aagcggttag ctccttcggt cctccgatcg ttgtcagaag   4380
taagttggcc gcagtgttat cactcatggt tatggcagca ctgcataatt ctcttactgt   4440
catgccatcc gtaagatgct tttctgtgac tggtgagtac tcaaccaagt cattctgaga   4500
atagtgtatg cggcgaccga gttgctcttg cccggcgtca atacgggata ataccgcgcc   4560
acatagcaga actttaaaag tgctcatcat tggaaaacgt tcttcggggc gaaaactctc   4620
aaggatctta ccgctgttga gatccagttc gatgtaaccc actcgtgcac ccaactgatc   4680
ttcagcatct tttactttca ccagcgtttc tgggtgagca aaaacaggaa ggcaaaatgc   4740
```

```
cgcaaaaaag ggaataaggg cgacacggaa atgttgaata ctcatactct tcctttttca    4800
atattattga agcatttatc agggttattg tctcatgagc ggatacatat ttgaatgtat    4860
ttagaaaaat aaacaaatag gggttccgcg cacatttccc cgaaaagtgc cacctgacgt    4920
ctaagaaacc attattatca tgacattaac ctataaaaat aggcgtatca cgaggccctt    4980
tcgtctcgcg cgtttcggtg atgacggtga aaacctctga cacatgcagc tcccggagac    5040
ggtcacagct tgtctgtaag cggatgccgg gagcagacaa gcccgtcagg gcgcgtcagc    5100
gggtgttggc gggtgtcggg gctggcttaa ctatgcggca tcagagcaga ttgtactgag    5160
agtgcaccaa gcttccaatt ttaggccccc cactgaccga ggtctgtcga taatccactt    5220
ttccattgat tttccaggtt tcgttaactc atgccactga gcaaaacttc ggtctttcct    5280
aacaaaagct ctcctcacaa agcatggcgc ggcaacggac gtgtcctcat actccactgc    5340
cacacaaggt cgataaacta agctcctcac aaatagagga gaattccact gacaactgaa    5400
aacaatgtat gagagacgat caccactgga gcggcgcggc ggttgggcgc ggaggtcggc    5460
agcaaaaaca agcgactcgc cgagcaaacc cgaatcagcc ttcagacggt cgtgcctaac    5520
aacacgccgt tctaccccgc cttcttcgcg ccccttcgcg tccaagcatc cttcaagttt    5580
atctctctag ttcaacttca agaagaacaa caccaccaac accatgatgc ctttgtctca    5640
agaagaatcc accctcattg aaagagcaac ggctacaatc aacagcatcc ccatctctga    5700
agactacagc gtcgccagcg cagctctctc tagcgacggc cgcatcttca ctggtgtcaa    5760
tgtatatcat tttactgggg gaccttgtgc agaactcgtg gtgctgggca ctgctgctgc    5820
tgcggcagct ggcaacctga cttgtatcgt cgcgatcgga aatgagaaca ggggcatctt    5880
gagcccctgt ggacggtgcc gacaggtgct tctcgatctg catcctggga tcaaagccat    5940
agtgaaggac agtgatggac agccgacggc agttgggatt cgtgaattgc tgccctctgg    6000
ttatgtgtgg gagggctaac acgtgctccg tgctacgaga tttcgattcc accgccgcct    6060
tctatgaaag gttgggcttc ggaatcgttt tccgggacgc cggctggatg atcctccagc    6120
gcggggatct catgctggag ttcttcgccc accccaactt gtttattgca gcttataatg    6180
gttacaaata aagcaatagc atcacaaatt tcacaaataa agcattttt tcactgcatt    6240 ctagttgtgg tttgtccaaa ctcatcaatg tatcttatca tgtctgaatt cccggggtac    6300
```

```
<210> SEQ ID NO 37
<211> LENGTH: 6611
<212> TYPE: DNA
<213> ORGANISM: Artificial Sequence
<220> FEATURE:
<223> OTHER INFORMATION: pCL122 vector (6611 bp)
<220> FEATURE:
<221> NAME/KEY: misc_feature
<222> LOCATION: (1)..(1064)
<223> OTHER INFORMATION: EF_1alpha_promoter
<220> FEATURE:
<221> NAME/KEY: misc_feature
<222> LOCATION: (1070)..(1162)
<223> OTHER INFORMATION: Sec1_secretion_signal
<220> FEATURE:
<221> NAME/KEY: misc_feature
<222> LOCATION: (1163)..(1900)
<223> OTHER INFORMATION: eGFP_gene
<220> FEATURE:
<221> NAME/KEY: misc_feature
<222> LOCATION: (1920)..(2559)
<223> OTHER INFORMATION: OrfC_terminator
<220> FEATURE:
<221> NAME/KEY: misc_feature
<222> LOCATION: (5094)..(5542)
```

```
<223> OTHER INFORMATION: Alpha_tubulin_promoter
<220> FEATURE:
<221> NAME/KEY: misc_feature
<222> LOCATION: (5543)..(6337)
<223> OTHER INFORMATION: NPT_gene
<220> FEATURE:
<221> NAME/KEY: misc_feature
<222> LOCATION: (6338)..(6611)
<223> OTHER INFORMATION: SV40_terminator

<400> SEQUENCE: 37
ctcttatctg cctcgcgccg ttgaccgccg cttgactctt ggcgcttgcc gctcgcatcc      60
tgcctcgctc gcgcaggcgg gcgggcgagt gggtgggtcc gcagccttcc gcgctcgccc     120
gctagctcgc tcgcgccgtg ctgcagccag cagggcagca ccgcacggca ggcaggtccc     180
ggcgcggatc gatcgatcca tcgatccatc gatccatcga tcgtgcggtc aaaaagaaag     240
gaagaagaaa ggaaaagaa aggcgtgcgc acccgagtgc gcgctgagcg cccgctcgcg     300
gtcccgcgga gcctccgcgt tagtcccgc cccgcgccgc gcagtccccc gggaggcatc     360
gcgcacctct cgccgccccc tcgcgcctcg ccgattcccc gcctcccctt ttccgcttct     420
tcgccgcctc cgctcgcggc gcgtcgccc gcgcccgct ccctatctgc tccccagggg     480
ggcactccgc acctttgcg cccgctgccg ccgccgcgg cgccccgccg ccctggtttc     540
ccccgcgagc gcggccgcgt cgccgcgcaa agactcgccg cgtgccgccc cgagcaacgg     600
gtggcggcgg cgcggcggcg ggcggggcgc ggcggcgcgt aggcggggct aggcgccggc     660
taggcgaaac gccgccccg ggcgccgccg ccgcccgctc cagagcagtc gccgcgccag     720
accgccaacg cagagaccga gaccgaggta cgtcgcgccc gagcacgccg cgacgcgcgg     780
cagggacgag gagcacgacg ccgcgccgcg ccgcgcgggg gggggaggg agaggcagga     840 cgcgggagcg agcgtgcatg tttccgcgcg agacacgcc gcgcgcgctg gagaggagat     900
aaggcgcttg gatcgcgaga gggccagcca ggctggaggc gaaaatgggt ggagaggata     960
gtatcttgcg tgcttggacg aggagactga cgaggaggac ggatacgtcg atgatgatgt    1020
gcacagagaa gaagcagttc gaaagcgact actagcaagc aagggatcca tgaagttcgc    1080
gacctcggtc gcaattttgc ttgtggccaa catagccacc gccctcgcgc agagcgatgg    1140 ctgcacccc accgaccaga cgatggtgag caagggcgag gagctgttca ccggggtggt    1200
gcccatcctg gtcgagctgg acggcgacgt aaacggccac aagttcagcg tgtccggcga    1260
gggcgagggc gatgccacct acggcaagct gaccctgaag ttcatctgca ccaccggcaa    1320
gctgcccgtg ccctggccca ccctcgtgac caccctgacc tacggcgtgc agtgcttcag    1380
ccgctacccc gaccacatga agcagcacga cttcttcaag tccgccatgc ccgaaggcta    1440
cgtccaggag cgcaccatct tcttcaagga cgacggcaac tacaagaccc gcgccgaggt    1500
gaagttcgag ggcgacaccc tggtgaaccg catcgagctg aagggcatcg acttcaagga    1560
ggacggcaac atcctgggac acaagctgga gtacaactac aacagccaca acgtctatat    1620
catggccgac aagcagaaga acggcatcaa ggtgaacttc aagatccgcc acaacatcga    1680
ggacggcagc gtgcagctcg ccgaccacta ccagcagaac accccatcg cgacggccc    1740 cgtgctgctg cccgacaacc actacctgag cacccagtcc gccctgagca agacccccaa    1800
cgagaagcgc gatcacatgg tcctgctgga gttcgtgacc gccgccggga tcactctcgg    1860
catggacgag ctgtacaagc accaccatca ccaccactaa catatgagtt atgagatccg    1920
aaagtgaacc ttgtcctaac ccgacagcga atggcgggag ggggcgggct aaaagatcgt    1980
attacatagt attttccccc tactctttgt gtttgtcttt tttttttttt tgaacgcatt    2040
```

```
caagccactt gtctgggttt acttgtttgt ttgcttgctt gcttgcttgc ttgcctgctt    2100
cttggtcaga cggcccaaaa aagggaaaaa attcattcat ggcacagata agaaaaagaa    2160
aaagtttgtc gaccaccgtc atcagaaagc aagagaagag aaacactcgc gctcacattc    2220
tcgctcgcgt aagaatctta gccacgcata cgaagtaatt tgtccatctg gcgaatcttt    2280
acatgagcgt tttcaagctg gagcgtgaga tcatacccttt cttgatcgta atgttccaac    2340
cttgcatagg cctcgttgcg atccgctagc aatgcgtcgt actcccgttg caactgcgcc    2400
atcgcctcat tgtgacgtga gttcagattc ttctcgagac cttcgagcgc tgctaatttc    2460
gcctgacgct ccttcttttg tgcttccatg acacgccgct tcaccgtgcg ttccacttct    2520
tcctcagaca tgcccttggc tgcctcgacc tgctcggtaa acgggcccc agcacgtgct     2580 acgagatttc gattccaccg ccgccttcta tgaaaggttg ggcttcggaa tcgtttttccg   2640 ggacgccggc tggatgatcc tccagcgcgg ggatctcatg ctggagttct cgcccaccc    2700 caacttgttt attgcagctt ataatggtta caaataaagc aatagcatca caaatttcac    2760
aaataaagca tttttttcac tgcattctag ttgtggtttg tccaaactca tcaatgtatc    2820
ttatcataca tggtcgacct gcaggaacct gcattaatga atcggccaac gcgcggggag    2880
aggcggtttg cgtattgggc gctcttccgc ttcctcgctc actgactcgc tgcgctcggt    2940
cgttcggctg cggcgagcgg tatcagctca ctcaaaggcg gtaatacggt tatccacaga    3000
atcaggggat aacgcaggaa agaacatgtg agcaaaaggc cagcaaaagg ccaggaaccg    3060
taaaaaggcc gcgttgctgg cgtttttcca taggctccgc ccccctgacg agcatcacaa    3120
aaatcgacgc tcaagtcaga ggtggcgaaa cccgacagga ctataaagat accaggcgtt    3180
tccccctgga agctccctcg tgcgctctcc tgttccgacc ctgccgctta ccggatacct    3240
gtccgccttt ctcccttcgg gaagcgtggc gctttctcat agctcacgct gtaggtatct    3300
cagttcggtg taggtcgttc gctccaagct gggctgtgtg cacgaacccc ccgttcagcc    3360
cgaccgctgc gccttatccg gtaactatcg tcttgagtcc aacccggtaa gacacgactt    3420
atcgccactg gcagcagcca ctggtaacag gattagcaga gcgaggtatg taggcggtgc    3480
tacagagttc ttgaagtggt ggcctaacta cggctacact agaagaacag tatttggtat    3540
ctgcgctctg ctgaagccag ttaccttcgg aaaaagagtt ggtagctctt gatccggcaa    3600
acaaaccacc gctggtagcg tggtttttttt tgtttgcaag cagcagatta cgcgcagaaa    3660
aaaaggatct caagaagatc ctttgatctt ttctacgggg tctgacgctc agtggaacga    3720
aaactcacgt taagggattt tggtcatgag attatcaaaa aggatcttca cctagatcct    3780
tttaaattaa aaatgaagtt ttaaatcaat ctaaagtata tatgagtaaa cttggtctga    3840
cagttaccaa tgcttaatca gtgaggcacc tatctcagcg atctgtctat ttcgttcatc    3900
catagttgcc tgactccccg tcgtgtagat aactacgata cgggagggct taccatctgg    3960
ccccagtgct gcaatgatac cgcgagaccc acgctcaccg gctccagatt tatcagcaat    4020
aaaccagcca gccggaaggg ccgagcgcag aagtggtcct gcaactttat ccgcctccat    4080
ccagtctatt aattgttgcc gggaagctag agtaagtagt tcgccagtta atagtttgcg    4140
caacgttgtt gccattgcta caggcatcgt ggtgtcacgc tcgtcgtttg gtatggcttc    4200
attcagctcc ggttcccaac gatcaaggcg agttacatga tcccccatgt tgtgcaaaaa    4260
agcggttagc tccttcggtc ctccgatcgt tgtcagaagt aagttggccg cagtgttatc    4320
actcatggtt atggcagcac tgcataattc tcttactgtc atgccatccg taagatgctt    4380
```

```
ttctgtgact ggtgagtact caaccaagtc attctgagaa tagtgtatgc ggcgaccgag    4440
ttgctcttgc ccggcgtcaa tacgggataa taccgcgcca catagcagaa ctttaaaagt    4500
gctcatcatt ggaaaacgtt cttcggggcg aaaactctca aggatcttac cgctgttgag    4560
atccagttcg atgtaaccca ctcgtgcacc caactgatct tcagcatctt ttactttcac    4620
cagcgtttct gggtgagcaa aaacaggaag gcaaaatgcc gcaaaaaagg gaataagggc    4680
gacacggaaa tgttgaatac tcatactctt cctttttcaa tattattgaa gcatttatca    4740
gggttattgt ctcatgagcg gatacatatt tgaatgtatt tagaaaaata aacaaatagg    4800
ggttccgcgc acatttcccc gaaaagtgcc acctgacgtc taagaaacca ttattatcat    4860
gacattaacc tataaaaata ggcgtatcac gaggccctttt cgtctcgcgc gtttcggtga    4920
tgacggtgaa aacctctgac acatgcagct cccggagacg gtcacagctt gtctgtaagc    4980
ggatgccggg agcagacaag cccgtcaggg cgcgtcagcg ggtgttggcg ggtgtcgggg    5040
ctggcttaac tatgcggcat cagagcagat tgtactgaga gtgcaccaag cttccaattt    5100 taggccccccc actgaccgag gtctgtcgat aatccacttt tccattgatt ttccaggttt    5160
cgttaactca tgccactgag caaaacttcg gtctttccta acaaaagctc tcctcacaaa    5220
gcatggcgcg gcaacggacg tgtcctcata ctccactgcc acacaaggtc gataaactaa    5280
gctcctcaca aatagaggag aattccactg acaactgaaa acaatgtatg agagacgatc    5340
accactggag cggcgcggcg gttgggcgcg gaggtcggca gcaaaaacaa gcgactcgcc    5400
gagcaaaccc gaatcagcct tcagacggtc gtgcctaaca acacgccgtt ctaccccgcc    5460
ttcttcgcgc cccttcgcgt ccaagcatcc ttcaagttta tctctctagt tcaacttcaa    5520
gaagaacaac accaccaaca ccatgattga acaagatgga ttgcacgcag gttctccggc    5580
cgcttgggtg gagaggctat tcggctatga ctgggcacaa cagacaatcg gctgctctga    5640
tgccgccgtg ttccggctgt cagcgcaggg gcgcccggtt cttttttgtca agaccgacct    5700 gtccggtgcc ctgaatgaac tgcaggacga ggcagcgcgg ctatcgtggc tggccacgac    5760
gggcgttcct tgcgcagctg tgctcgacgt tgtcactgaa gcgggaaggg actggctgct    5820
attgggcgaa gtgccggggc aggatctcct gtcatctcac cttgctcctg ccgagaaagt    5880
atccatcatg gctgatgcaa tgcggcggct gcatacgctt gatccggcta cctgcccatt    5940
cgaccaccaa gcgaaacatc gcatcgagcg agcacgtact cggatggaag ccggtcttgt    6000
cgatcaggat gatctggacg aagagcatca ggggctcgcg ccagccgaac tgttcgccag    6060
gctcaaggcg cgcatgcccg acggcgatga tctcgtcgtg acccatggcg atgcctgctt    6120
gccgaatatc atggtggaaa atggccgctt ttctggattc atcgactgtg gccggctggg    6180
tgtggcggac cgctatcagg acatagcgtt ggctacccgt gatattgctg aagagcttgg    6240
cggcgaatgg gctgaccgct tcctcgtgct ttacggtatc gccgctcccg attcgcagcg    6300
catcgccttc tatcgccttc ttgacgagtt cttctgacac gtgctacgag atttcgattc    6360
caccgccgcc ttctatgaaa ggttgggctt cggaatcgtt ttccgggacg ccggctggat    6420
gatcctccag cgcggggatc tcatgctgga gttcttcgcc caccccaact tgtttattgc    6480
agcttataat ggttacaaat aaagcaatag catcacaaat ttcacaaata aagcattttt    6540
ttcactgcat tctagttgtg gtttgtccaa actcatcaat gtatcttatc atgtctgaat    6600
tcccggggta c                                                       6611
```

```
<210> SEQ ID NO 38
<211> LENGTH: 32
<212> TYPE: DNA
<213> ORGANISM: Artificial Sequence
<220> FEATURE:
<223> OTHER INFORMATION: pYB66 Bambgl F primer

<400> SEQUENCE: 38
caagggatcc agatcttccg cactgatgag tc                              32

<210> SEQ ID NO 39
<211> LENGTH: 23
<212> TYPE: DNA
<213> ORGANISM: Artificial Sequence
<220> FEATURE:
<223> OTHER INFORMATION: pYB66 Nde R primer

<400> SEQUENCE: 39
aactcatatg gtcccattcg cca                                        23

<210> SEQ ID NO 40
<211> LENGTH: 25
<212> TYPE: DNA
<213> ORGANISM: Artificial Sequence
<220> FEATURE:
<223> OTHER INFORMATION: pYB66 EF1seq F primer

<400> SEQUENCE: 40
gagaggatag tatcttgcgt gcttg                                      25

<210> SEQ ID NO 41
<211> LENGTH: 25
<212> TYPE: DNA
<213> ORGANISM: Artificial Sequence
<220> FEATURE:
<223> OTHER INFORMATION: pCL122 OrfC R primer

<400> SEQUENCE: 41
gcaaggttgg aacattacga tcaag                                      25

<210> SEQ ID NO 42
<211> LENGTH: 41
<212> TYPE: DNA
<213> ORGANISM: Artificial Sequence
<220> FEATURE:
<223> OTHER INFORMATION: pYB73 gRNA Pst Kpn IF F primer

<400> SEQUENCE: 42
catacatggt cgacctgcag ggtacctctt atctgcctcg c                    41

<210> SEQ ID NO 43
<211> LENGTH: 45
<212> TYPE: DNA
<213> ORGANISM: Artificial Sequence
<220> FEATURE:
<223> OTHER INFORMATION: pYB73 gRNA Xho Pst IF R primer

<400> SEQUENCE: 43
attaatgcag gttcctgcag ctcgagaaga atctgaactc acgtc                45

<210> SEQ ID NO 44
<211> LENGTH: 22
<212> TYPE: DNA
<213> ORGANISM: Artificial Sequence
<220> FEATURE:
<223> OTHER INFORMATION: pYB73 seq F primer
```

```
<400> SEQUENCE: 44
caccccaact tgtttattgc ag                                                    22

<210> SEQ ID NO 45
<211> LENGTH: 19
<212> TYPE: DNA
<213> ORGANISM: Artificial Sequence
<220> FEATURE:
<223> OTHER INFORMATION: pYB73 seq R primer

<400> SEQUENCE: 45
gagcgaggaa gcggaagag                                                        19

<210> SEQ ID NO 46
<211> LENGTH: 26
<212> TYPE: DNA
<213> ORGANISM: Artificial Sequence
<220> FEATURE:
<223> OTHER INFORMATION: pYB13 pYB1 seq F primer

<400> SEQUENCE: 46
gagaggatag tatcttgcgt gcttgg                                                26

<210> SEQ ID NO 47
<211> LENGTH: 18
<212> TYPE: DNA
<213> ORGANISM: Artificial Sequence
<220> FEATURE:
<223> OTHER INFORMATION: TT pYB73 HDV R primer

<400> SEQUENCE: 47
gaagcatgtt gcccagcc                                                         18
```

CRISPR-CAS SYSTEM FOR AN ALGAL HOST CELL

CROSS-REFERENCE TO RELATED APPLICATIONS

This application is a National Stage of International Application No. PCT/US2017/041949 filed Jul. 13, 2017, and which claims the benefit of the filing date of U.S. Provisional Patent Application No. 62/361,741 filed Jul. 13, 2016, the entire contents of each of which are hereby incorporated herein by reference in their entireties.

BACKGROUND

Technical Field

The present disclosure relates to the field of molecular biology and cell biology. More specifically, the present invention relates to a CRISPR-Cas system for an algal Labyrinthulomycetes host cell.

Description of Related Art

Recent advances in genomic techniques and analysis methods have significantly accelerated the ability to catalog and map genetic factors associated with a diverse range of biological functions and diseases. Precise genome engineering technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors nucleases (TALENs), or homing meganucleases are available for producing targeted genome perturbations, a need remains for new genome engineering technologies that are affordable, easy to set up, scalable, and amenable to targeting multiple positions within a genome. The engineering of meganucleases has been challenging for most academic researchers because the DNA recognition and cleavage functions of these enzymes are intertwined in a single domain. Robust construction of engineered zinc finger arrays has also proven to be difficult for many laboratories because of the need to account for context-dependent effects between individual finger domains in an array. There thus exists a pressing need for alternative and robust techniques for targeting of specific sequences within a host cell with a wide array of applications. The solution to this technical problem is provided by the embodiments characterized in the claims.

BRIEF SUMMARY

The present application is based on the CRISPR-Cas system, which does not require the generation of customized proteins to target-specific sequences, but rather a single Cas enzyme that can be programmed by a guide-polynucleotide to recognize a specific polynucleotide target; in other words, the Cas enzyme can be recruited to a specific polynucleotide target using said guide-polynucleotide molecule. Adding the CRISPR-Cas system to the repertoire of genomics techniques and analysis methods may significantly simplify existing methodologies in the field of molecular biology.

The present invention provides a non-naturally occurring or engineered composition comprising a source of a CRISPR-Cas system comprising a guide-polynucleotide and a Cas protein, wherein the guide-polynucleotide comprises a sequence that essentially is the reverse complement of a target-polynucleotide in a host cell and the guide-polynucleotide can direct binding of the Cas protein at the target-polynucleotide in the host cell to form a CRISPR-Cas complex.

The present invention further relates to a method of modulating expression of a polynucleotide in a cell, comprising contacting a host cell with the composition according to the present invention, wherein the guide-polynucleotide directs binding of the Cas protein at the target-polynucleotide in the host cell to form a CRISPR-Cas complex.

The present invention further relates to a host cell comprising a composition according to the present invention.

The present invention further relates to a method of producing a host cell, comprising contacting a host cell with the composition according to the present invention, wherein the guide-polynucleotide directs binding of the Cas protein at the target-polynucleotide in the host cell to form a CRISPR-Cas complex.

The present invention further relates to a method for the production of a compound of interest, comprising culturing under conditions conducive to the compound of interest a host cell according to the present invention and optionally purifying or isolating the compound of interest.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DESCRIPTION OF THE SEQUENCE LISTING

Figure 1:
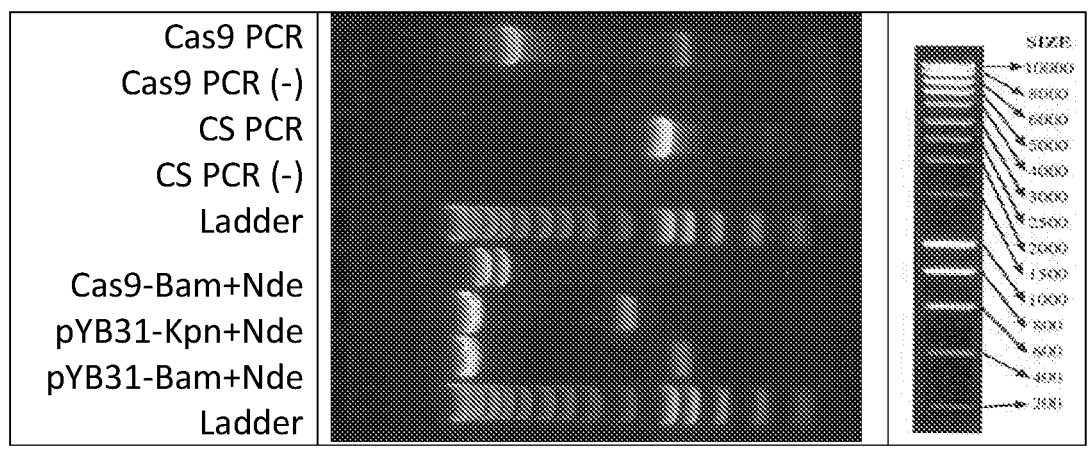
FIG. 1 shows digested plasmids and PCR-amplified fragments run on a 1% agarose gel.

SEQ ID NO:1 sets out the pCL122-Cas9 vector nucleotide sequence.
SEQ ID NO:2 sets out the pYB31 vector nucleotide sequence.
SEQ ID NO:3 sets out the pYB32 vector nucleotide sequence.
SEQ ID NO:4 sets out the pYB33 vector nucleotide sequence.
SEQ ID NO:5 sets out the pCL399 vector nucleotide sequence.
SEQ ID NO:6 sets out the pCL400 vector nucleotide sequence.
SEQ ID NO:7 sets out the pCL401 vector nucleotide sequence.
SEQ ID NO:8 sets out the pCL402 vector nucleotide sequence.
SEQ ID NO:9 sets out the pYB36 vector nucleotide sequence.
SEQ ID NO:10 sets out the pYB37 vector nucleotide sequence.
SEQ ID NO:11 sets out the pYB38 vector nucleotide sequence.
SEQ ID NO:12 sets out the pYB39 vector nucleotide sequence.
SEQ ID NO:13 sets out the 121 Tub seq F primer nucleotide sequence.
SEQ ID NO:14 sets out the pYB32/3 C R1 primer nucleotide sequence.
SEQ ID NO:15 sets out the CS pro Kpn IF F1 primer nucleotide sequence.
SEQ ID NO:16 sets out the CS pro BamH IF R1 primer nucleotide sequence.
SEQ ID NO:17 sets out the CS pro BamH IF F2 primer nucleotide sequence.
SEQ ID NO:18 sets out the CS pro Nde IF R2 primer nucleotide sequence.
SEQ ID NO:19 sets out the O A1-KO F primer nucleotide sequence.
SEQ ID NO:20 sets out the pYB32/3 SV40 R1 primer nucleotide sequence.
SEQ ID NO:21 sets out the O A1-KO R primer nucleotide sequence.
SEQ ID NO:22 sets out the pYB32/3 C F1 primer nucleotide sequence.
SEQ ID NO:23 sets out the 5' FAS PmeNde primer nucleotide sequence.
SEQ ID NO:24 sets out the 3' FAS PmeHpa primer nucleotide sequence.
SEQ ID NO:25 sets out the pCL402 IF F primer nucleotide sequence.
SEQ ID NO:26 sets out the pCL402 IF R primer nucleotide sequence.
SEQ ID NO:27 sets out the pYB36 CS1 F primer nucleotide sequence.
SEQ ID NO:28 sets out the pYB36 CS1 R primer nucleotide sequence.
SEQ ID NO:29 sets out the pYB36 CS3 R primer nucleotide sequence.
SEQ ID NO:30 sets out the pYB36 CS4 F primer nucleotide sequence.
SEQ ID NO:31 sets out the pYB36 CS4 R primer nucleotide sequence.
SEQ ID NO:32 sets out the pYB30 vector nucleotide sequence.
SEQ ID NO:33 sets out the pYB61 vector nucleotide sequence.
SEQ ID NO:34 sets out the pYB66 vector nucleotide sequence.
SEQ ID NO:35 sets out the pYB73 vector nucleotide sequence.
SEQ ID NO:36 sets out the pCL310 vector nucleotide sequence.
SEQ ID NO:37 sets out the pCL122 vector nucleotide sequence.
SEQ ID NO:38 sets out the pYB66 BamBgI F primer nucleotide sequence.
SEQ ID NO:39 sets out the pYB66 Nde R primer nucleotide sequence.
SEQ ID NO:40 sets out the pYB66 EF1seq F primer nucleotide sequence.
SEQ ID NO:41 sets out the pCL122 OrfC R primer nucleotide sequence.
SEQ ID NO:42 sets out the pYB73 gRNA Pst Kpn IF F primer nucleotide sequence.
SEQ ID NO:43 sets out the pYB73 gRNA Xho Pst IF R primer nucleotide sequence.
SEQ ID NO:44 sets out the pYB73 seq F primer nucleotide sequence.
SEQ ID NO:45 sets out the pYB73 seq R primer nucleotide sequence.
SEQ ID NO:46 sets out the pYB13 pYB1 seq F primer nucleotide sequence.
SEQ ID NO:47 sets out the TT pYB73 HDV R primer nucleotide sequence.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In a first aspect, the present invention provides a non-naturally occurring or engineered composition comprising a source of a CRISPR-Cas system comprising a guide-polynucleotide and a Cas protein, wherein the guide-polynucleotide comprises a guide-sequence that essentially is the reverse complement of a target-polynucleotide in a host cell and the guide-polynucleotide can direct binding of the Cas protein at the target-polynucleotide in the host cell to form a CRISPR-Cas complex, wherein the guide-sequence is essentially the reverse complement of the (N)y part of a 5'-(N)yPAM-3' polynucleotide sequence target in the genome of the host cell, wherein y is an integer of 8-30, more preferably 10-30, more preferably 15-30, more preferably 17-27, more preferably 17-20, more preferably 17, 18, 19, 20, 21, 22, 23, 24, 25, 26, or 27, wherein PAM is a protospacer adjacent motif, wherein the host cell is of the Labyrinthulomycete class, preferably of the order Thraustochytriales, more preferably of the family Thraustochytriaceae, more preferably a member of a genus selected from the group consisting of *Aurantiochytrium, Oblongichytrium, Schizochytrium, Thraustochytrium*, and *Ulkenia*, even more preferably *Schizochytrium* sp. ATCC #20888, and wherein PAM is preferably a sequence selected from the group consisting of 5'-XGG-3', 5'-XGGXG-3', 5'-XXAGAAW-3', 5'-XXXXGATT-3', 5'-XXAGAA-3', 5'-XAAAAC-3', wherein X can be any nucleotide or analog thereof, preferably X can be any nucleotide; and W is A or T.

The composition, source, CRISPR-Cas system, guide-polynucleotide, Cas protein, target-polynucleotide, host cell and CRISPR-Cas complex are herein referred to as a composition, source, CRISPR-Cas system, guide-polynucleotide, Cas protein, target-polynucleotide, host cell and CRISPR-Cas complex according to the present invention. For the sake of completeness, since "a" is defined elsewhere herein as "at least one", a composition according to the present invention comprises a source of at least one, i.e. one, two, three or more guide-polynucleotides and/or at least one, i.e. one, two, three or more Cas proteins. Accordingly, the present invention conveniently provides for a multiplex CRISPR-Cas system. Such multiplex CRISPR-Cas system can conveniently be used for introduction of a donor polynucleotide, deletion of a polynucleotide and polynucleotide library insertion into the genome of a host cell. Herein, a multiplex CRISPR-Cas system may refer to the use of one of more Cas proteins, one of more guide-polynucleotides and/or one or more donor polynucleotides.

The terms "CRISPR system", "CRISPR-Cas system" and "CRISPR enzyme system" are used interchangeably herein and refer in the context of all embodiments of the present invention to a collection of elements required to form, together with a target-polynucleotide, a CRISPR-Cas complex; these elements comprise but are not limited to a Cas protein and a guide-polynucleotide.

The term "CRISPR-Cas complex" refers in the context of all embodiments of the present invention to a complex comprising a guide-polynucleotide hybridized to a target-polynucleotide and complexed with a Cas protein. In the most straightforward form, where a non-mutated Cas protein is used such as but not limited to the Cas9 protein of *Streptococcus pyogenes*, the formation of the CRISPR-Cas complex results in cleavage of one or both polynucleotide strands in or near (e.g. within 1, 2, 3, 4, 5, 6, 7, 8, 9, 10, 20, 50, or more base pairs from) the target-polynucleotide. Typically, a target-polynucleotide according to the present invention (defined below herein) is associated with a PAM sequence (defined below herein) and the PAM sequence is preferably immediately downstream (3') of the target-polynucleotide; the formation of the CRISPR-Cas complex typically results in cleavage of one or both polynucleotide strands 3 base pairs upstream (5') of the PAM sequence.

The term "non-naturally occurring composition" refers in the context of all embodiments of the present invention to a composition that in its form used in the present invention does not occur in nature. The individual elements may e.g. occur as such or in combinations with other elements in nature, but the non-naturally occurring composition comprises e.g. at least one element more or less than a naturally composition.

The term "engineered composition" refers in the context of all embodiments of the present invention to a composition wherein at least one of the elements has been engineered, i.e. modified by man, in such a way that resulting element does not occur in nature. It follows that by virtue of comprising at least one engineered element, an engineered composition does not occur in nature.

The terms "polynucleotide", "nucleotide sequence" and "nucleic acid" are used interchangeably herein and refer in the context of all embodiments of the present invention to a polymeric form of nucleotides of any length, either deoxyribonucleotides or ribonucleotides, or mixes or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, oligonucleotides and primers. A polynucleotide may comprise one or more modified nucleotides, such as a methylated nucleotide and a nucleotide analogue or nucleotide equivalent wherein a nucleotide analogue or equivalent is defined as a residue having a modified base, and/or a modified backbone, and/or a non-natural internucleoside linkage, or a combination of these modifications. Preferred nucleotide analogues and equivalents are described in the section "General definitions". As desired, modifications to the nucleotide structure may be introduced before or after assembly of the polynucleotide. A polynucleotide may be further modified after polymerization, such as by conjugation with a labeling compound.

As used herein, a "polynucleotide" can comprise a conventional phosphodiester bond or a non-conventional bond (e.g., an amide bond, such as found in peptide nucleic acids (PNA)). A polynucleotide can contain the nucleotide sequence of the full-length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. Polynucleotides can contain ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters. Polynucleotides can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms. The term nucleic acid molecule refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

The term "isolated" nucleic acid molecule refers to a nucleic acid molecule, DNA or RNA, which has been removed from its native environment. Further examples of isolated nucleic acid molecules include nucleic acid molecules comprising recombinant polynucleotides maintained in heterologous host cells or purified (partially or substantially) polynucleotides in solution. Isolated RNA molecules include in vivo or in vitro RNA transcripts of polynucleotides of the present invention. Isolated nucleic acid molecules according to the present invention further include such molecules produced synthetically. In addition, a nucleic acid molecule or polynucleotide can include a regulatory element such as a promoter, ribosome binding site, or a transcription terminator.

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

In some embodiments, the nucleic acid molecules comprise polynucleotide sequences at least about 80%, 85%, or 90% identical to the polynucleotide sequences reported herein, or at least about 95%, 96%, 97%, 98%, 99%, or 100% identical to the polynucleotide sequences reported herein. The term "percent identity," as known in the art, is a relationship between two or more amino acid sequences or two or more polynucleotide sequences, as determined by comparing the sequences. In the art, "identity" also means the degree of sequence relatedness between amino acid or polynucleotide sequences, as the case may be, as determined by the match between strings of such sequences.

By a nucleic acid molecule having a polynucleotide sequence at least, for example, 95% "identical" to a reference polynucleotide sequence of the present invention, it is intended that the polynucleotide sequence of the nucleic acid molecule is identical to the reference sequence except that the polynucleotide sequence can include up to five nucleotide differences per each 100 nucleotides of the reference polynucleotide sequence. In other words, to obtain a nucleic acid molecule having a polynucleotide sequence at least 95% identical to a reference polynucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular polynucleotide sequence or amino acid sequence is at least 80%, 85%, 90%, 95%, 96%, 97%, 98% or 99% identical to a polynucleotide sequence or amino acid sequence of the present invention can be determined conventionally using known computer programs. A method for determining the best overall match between a query sequence (a sequence of the present invention) and a subject sequence can be determined using the alignment of sequences and calculation of identity scores. The alignments were done using the computer program Geneious (www.geneious.com) with a map to reference algorithm and Geneious reference assembler.

A guide-polynucleotide according to the present invention comprises at least a guide-sequence that is able to hybridize with the target-polynucleotide and is able to direct sequence-specific binding of the CRISPR-Cas system to the target-polynucleotide to form a CRISPR-Cas complex. In order to enable formation of an active CRISPR-Cas complex, the guide-polynucleotide preferably also comprises a sequence that has a specific secondary structure and allows binding of the Cas protein to the guide-polynucleotide. Such sequence is known in the art as tracr RNA, tracr sequence, tracr scaffold or guide-polynucleotide structural component, these terms are used interchangeably herein; wherein the tracr is the abbreviation for transactivating CRISPR; tracrRNA thus means transactivating CRISPR RNA. The tracrRNA in the original CRISPR-Cas system is the endogenous bacterial RNA that links the crRNA (guide-sequence) to the Cas nuclease, being able to bind any crRNA. A guide-polynucleotide structural component may be comprised of a single polynucleotide molecule or may be comprised of two or more molecules hybridized to each other; or two or more molecules which associate with Cas protein or other nucleases of similar function. Such components of a guide-polynucleotide structure may be referred to as a tracr sequence and a tracr-mate sequence.

Accordingly, the guide-polynucleotide preferably also comprises a tracr sequence and/or a tracr-mate sequence. The guide-polynucleotide is a polynucleotide according to the general definition of a polynucleotide set out here above; a preferred guide-polynucleotide comprises ribonucleotides, a more preferred guide-polynucleotide is a RNA (guide-RNA).

In the context of the present invention, a sequence is referred to as essentially the reverse complement of a target-sequence or of a target-polynucleotide if the subject sequence is able to hybridize with the target-sequence or target-polynucleotide, preferably under physiological conditions as in a host cell. The degree of complementarity between a guide-sequence and its corresponding target-sequence, when optimally aligned using a suitable alignment algorithm, is preferably higher than 50%, 60%, 75%, 80%, 85%, 90%, 95%, 97.5%, 99% sequence identity. When the target-polynucleotide is a double stranded polynucleotide, the subject sequence, such as a guide-sequence, may be able to hybridize with either strand of the target-polynucleotide e.g. a coding strand or a non-coding strand.

Preferably, a guide-sequence according to the present invention targets a target-sequence that is unique in the target. Preferably, a guide-sequence according to the present invention has 100% sequence identity with the 8, 9, 10, 11, 12, 13, 14, 15, 16, 17, 18, 19 or 20, more preferably 8, 9, 10, 11 or 12 nucleotides in the target-polynucleotide immediately adjacent to a PAM sequence.

A guide-sequence according to the present invention preferably is 8-30, more preferably 10-30, more preferably 15-30, more preferably 17-27, more preferably 17-20, more preferably 17, 18, 19, 20, 21, 22, 23, 24, 25, 26, or 27 nucleotides in length. The ability of a guide-sequence to direct sequence-specific binding of a CRISPR-Cas system to a target-sequence to form a CRISPR-Cas complex may be assessed by any suitable assay. For example, the components of a CRISPR system sufficient to form a CRISPR-Cas complex, including the guide-sequence to be tested, may be provided to a host cell having the corresponding target-sequence, such, as by transfection with vectors encoding the components of the CRISPR-Cas system, followed by an assessment of preferential cleavage and/or the resulting mutations induced by cellular repair mechanisms within the target-sequence, such as by standard sequence analysis assay. Cleavage of a target-polynucleotide may also be evaluated in a test tube by providing the target-polynucleotide, components of a CRISPR-Cas system, including the guide-sequence to be tested and a control guide-sequence different from the test guide-sequence, and comparing binding or rate of cleavage at the target-sequence between the test and control guide-sequence reactions. Other assays are possible, and are known to a person skilled in the art.

A guide-polynucleotide structural component is believed to be necessary for formation of an active CRISPR-Cas complex. The guide-polynucleotide structural component is believed not necessarily to be operably linked to the guide-sequence; however, a guide-polynucleotide structural component may be operably linked to a guide-sequence within a guide-polynucleotide. A guide-polynucleotide structural component according to the present invention, which may comprise or consist of all or a portion of a wild-type guide-polynucleotide structural component (e.g. about or more than about 20, 26, 32, 45, 48, 54, 63, 67, 85, or more nucleotides of a wild-type tracr-sequence) forms part of a CRISPR-Cas complex; e.g. by hybridization of at least a portion of a tracr-sequence according to the present invention to all or a portion of a tracr-mate sequence according to the present invention and preferably operably linked to a guide-sequence according to the present invention. A tracr-sequence according to the present invention has sufficient complementarity to a tracr-mate sequence according to the present invention to hybridize, preferably under physiological condition as in a host cell, and facilitate formation of a CRISPR-Cas complex. As with the target-sequence according to the present invention, it is believed that complete complementarity is not needed, provided there is sufficient complementarity to be functional. Preferably, the tracr-sequence according to the present invention has at least 50%, 60%, 70%, 80%, 90%, 95% or 99% sequence identity along the length of the tracr-mate sequence according to the present invention when optimally aligned. Optimal alignment may be determined using any suitable algorithm for aligning sequences as discussed above.

In general, a tracr mate sequence according to the present invention includes any sequence that has sufficient complementarity with a tracr sequence according to the present invention to promote formation of a CRISPR-Cas complex at a target-sequence, wherein the CRISPR-Cas complex comprises the tracr mate sequence according to the present invention hybridized to the tracr sequence according to the present invention. The degree of complementarity of the tracr sequence according to the present invention and the tracr mate sequence according to the present invention is preferably defined with respect to optimal alignment of the tracr mate sequence and tracr sequence along the length of the shorter of the two sequences. Optimal alignment may be determined using any suitable algorithm for aligning sequences as discussed above.

Preferably, with respect to a tracr mate sequence according to the present invention and a tracr sequence according to the present invention, secondary structures are taken into account, such as self-complementarity within either the tracr sequence or tracr mate sequence. Preferably, the degree of complementarity between the tracr sequence according to the present invention and tracr mate sequence according to the present invention along the length of the shorter of the two sequences when optimally aligned is higher than 50%, 60%, 75%, 80%, 85%, 90%, 95%, 97.5%, 99% sequence identity. Preferably, the tracr mate sequence according to the present invention is 5, 6, 7, 8, 9, 10, 11, 12, 13, 14, 15, 16, 17, 18, 19, 20, 25, 30, 40, 50, or more nucleotides in length. Preferably, the tracer sequence according to the present invention is 5, 6, 7, 8, 9, 10, 11, 12, 13, 14, 15, 16, 17, 18, 19, 20, 25, 30, 40, 50, or more nucleotides in length. Preferably, the tracr sequence according to the present invention and tracr mate sequence, i.e. the guide-polynucleotide structural component according to the present invention are comprised within a single transcript, such that hybridization between the two produces a hybridization complex comprising a secondary structure, such as a hairpin. Such hybridization complex may also be formed when the tracr sequence and the tracr mate sequence are not comprised in a single transcript. Preferred loop forming sequences in a tracr sequence according to the present invention and/or a tracr mate sequence according to the present invention and/or guide-polynucleotide structural component according to the present invention for formation of hairpin structures are four nucleotides in length, and most preferably have the sequence GAAA; longer or shorter loop sequences may be used, as may alternative sequences. The loop sequences preferably include a nucleotide triplet (for example, AAA), and an additional nucleotide (for example C or G). Examples of loop forming sequences include CAAA and AAAG. Preferably, a tracr sequence according to the present invention and/or tracr mate sequence according to the present invention or hybridization complex thereof and/or guide-polynucleotide structural component according to the present invention comprises or is able to form at least two or more hairpins. More preferably, a tracr sequence according to the present invention and/or tracr mate sequence according to the present invention or hybridization complex thereof and/or guide-polynucleotide structural component according to the present invention comprises or is able to form two, three, four or five hairpins. Preferably, a tracr sequence according to the present invention and/or tracr mate sequence according to the present invention or hybridization complex thereof and/or guide-polynucleotide structural component according to the present invention comprises or is able to form at most five hairpins. Preferably, the single transcript of a tracr sequence according to the present invention and a tracr-mate sequence according to the present invention or hybridization complex of a tracr sequence according to the present invention and a tracr mate sequence according to the present invention and/or guide-polynucleotide structural component according to the present invention further comprises a transcription termination sequence; preferably this is a polyT sequence, for example six T nucleotides. As said, guide-polynucleotide structural components are known to the person skilled in the art; background information can e.g. be found in Gaj et al., 2013.

In the context of all embodiments according to the present invention, the term "target-polynucleotide" refers to a target-sequence according to the present invention to which a guide-sequence according to the present invention is designed to have complementarity, where hybridization between a target-sequence according to the present invention and a guide-sequence according to the present invention promotes the formation of a CRISPR-Cas complex. Full complementarity is not necessarily required, provided there is sufficient complementarity to cause hybridization and promote formation of a CRISPR-Cas complex. Preferably, a guide-sequence according to the present invention targets a target-sequence that is unique in the target. Preferably, a guide-sequence according to the present invention has 100% sequence identity with the 8, 9, 10, 11, 12, 13, 14, 15, 16, 17, 18, 19 or 20, more preferably 8, 9, 10, 11 or 12 nucleotides in the target-polynucleotide immediately adjacent to a PAM sequence. A target-polynucleotide according to the present invention may comprise any polynucleotide, such as DNA or RNA polynucleotides and may be single or double stranded. When the target-polynucleotide is a double strand polynucleotide, a guide-sequence according to the present invention, may be able to hybridize with either strand of the target-polynucleotide e.g. a coding strand or a non-coding strand.

A target-polynucleotide according to the present invention may be located in the nucleus or cytoplasm of a cell. A target-polynucleotide according to the present invention may be located in an organelle of a host cell, for example in a mitochondrion or plastid. A target-polynucleotide according to the present invention may be comprised in a genome, may be comprised in a chromosome or may be extra-chromosomal, may be comprised in an artificial chromosome, may be present in any chromosomal entity or extra-chromosomal entity such as an autosomal replicating entity such as an episomal plasmid or vector. A target-polynucleotide according to the present invention may be native or foreign to the host cell.

A target-polynucleotide according to the present invention is preferably associated with a protospacer adjacent motif (PAM), which is a short polynucleotide recognized by the CRISPR-Cas complex. Preferably, the target-polynucleotide and PAM are linked wherein the PAM is preferably immediately downstream (3') of the target-polynucleotide. The exact sequence and length of the PAM may vary, e.g. different Cas proteins and nucleases of similar function may require different PAM sequences. A preferred PAM according to the present invention is a polynucleotide of 2 to 8 nucleotides in length. A preferred PAM is selected from the group consisting of 5'-XGG-3', 5'-XGGXG-3', 5'-XX-AGAAW-3', 5'-XXXXGATT-3', 5'-XXAGAA-3', 5'-XAAAAC-3', wherein X can be any nucleotide or analog thereof, preferably any nucleotide; and W is A or T. A more preferred PAM is 5'-XGG-3'. The PAM is preferably matched with the Cas protein. The most widely used CAS/CRISPR system is derived from *S. pyogenes* and the matching PAM sequence 5'-XGG-3' is located immediately downstream (3') of the target-sequence. A preferred PAM for a *Neisseria meningitidis* Cas protein is 5'-XXXXGATT-3'; a preferred PAM for a *Streptococcus thermophilus* Cas protein is 5'-XXAGAA-3'; a preferred PAM for a *Treponema denticola* is 5'-XAAAAC-3'. A preferred PAM matches the Cas protein used. A Cas protein according to the present invention may be engineered to match a different PAM than the native PAM matching the wild-type Cas protein. As such, the CRISPR-Cas system according to the present invention may be used for customized specific targeting.

The term "hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence-specific manner. The complex may comprise two strands forming a duplex structure, three or more strands forming a multi stranded complex, a single self-hybridizing strand, or any combination of these. A hybridization reaction may constitute a step in a more extensive process, such as the cleavage of a polynucleotide by an enzyme. Preferred hybridization conditions are physiological conditions as within a host cell according to the present invention.

The term "source" in the context of all embodiments of the present invention refers to any source of a CRISPR-Cas system comprising a guide-polynucleotide and a Cas protein. The guide-polynucleotide and Cas protein may be present in separate sources. In such case, the composition according to the present invention comprises a CRISPR-Cas system comprising a source of a guide-polynucleotide and a source of a Cas-protein. Any source means that the guide-polynucleotide and Cas protein may be present as such in a form that they can function within a CRISPR-Cas system. The guide-polynucleotide and/or the Cas-protein may be provided in its active forms and may e.g. be provided from an inactive form or from another entity. The guide-polynucleotide may e.g. be present on another polynucleotide or may be encoded by a polynucleotide that is transcribed to provide for the actual guide-polynucleotide. The Cas protein may be encoded by a polynucleotide (e.g. DNA or mRNA) that is transcribed and/or translated to provide the actual Cas protein. An encoding polynucleotide may be present in a nucleic acid construct as defined herein and/or in a vector as defined herein. Such nucleic acid construct and vector are herein referred to as a nucleic acid construct according to the present invention and a vector according to the present invention.

Preferably, in the composition according to the present invention, the Cas protein or nuclease of related function is encoded by a polynucleotide and/or the guide-polynucleotide is encoded by or present on a polynucleotide.

Preferably, in the composition according to the present invention, the Cas protein or nuclease of related function is encoded by a polynucleotide and/or the guide-polynucleotide is encoded by or present on another polynucleotide and the polynucleotide or polynucleotides are comprised in a vector.

Preferably, in a composition according to the invention, the guide-polynucleotide is encoded by a polynucleotide that is transcribed to provide for the actual guide-polynucleotide. Accordingly, in an embodiment, in the composition according to the invention, preferably, the guide polynucleotide is present in the form of a polynucleotide encoding for said guide-polynucleotide and the guide-polynucleotide is obtained upon transcription of said polynucleotide in the host cell.

Preferably, in the composition according to the present invention, the Cas protein is encoded by a polynucleotide and the guide-polynucleotide is encoded by or present on another polynucleotide and the polynucleotides are comprised in one vector.

Preferably, in the composition according to the present invention, the Cas protein is encoded by a polynucleotide comprised in a vector and the guide-polynucleotide is encoded by or present on another polynucleotide comprised in another vector. Preferably, the vector encoding the Cas protein is a low copy vector and/or the promoter driving expression of the Cas transcript is a low-strength promoter and the vector encoding the guide-polynucleotide is a high copy vector and/or the promoter driving expression of the gRNA transcript is a high-strength promoter. This allows differential expression of the Cas protein and the guide-polynucleotide; the Cas protein may e.g. be expressed in lower level than the guide-polynucleotide. Promoter strength can be estimated by any means, for example, by RNA sequencing. RNA sequencing (RNAseq) is a highly sensitive and accurate tool for measuring expression across the transcriptome under different conditions. It allows quantitative approximation of gene expression at the transcript level which is reported as RPKM value (Reads Per Kilobase of transcript per Million mapped reads). RPKM values and relative promoter strengths of representative genes from *Schizochytrium* are provided in Table 1.

TABLE 1

| Gene | Ave RPKM value | Relative promoter strength |
| --- | --- | --- |
| Arginase (EC 3.5.3.1) | 3694.34 | Strong |
| Pyruvate kinase (EC 2.7.1.40) | 2127.49 | Strong |
| Heat shock protein 70 | 1857.74 | Strong |
| Glyceraldehyde 3-phosphate dehydrogenase (EC 1.2.1.12) | 1688.00 | Strong |
| Tubulin alpha chain | 696.85 | Medium |
| Protein Translation Elongation Factor 1A (EF-1A) | 682.30 | Medium |
| Isocitrate lyase (EC 4.1.3.1) | 510.45 | Medium |
| Aconitate hydratase 2 (EC 4.2.1.3) | 317.74 | Medium |
| Malate dehydrogenase (EC 1.1.1.37) | 192.47 | Medium |
| Vacuolar ATP synthase subunit D (EC 3.6.3.14) | 163.74 | Medium |
| Acyl-CoA dehydrogenase (EC 1.3.99.3) | 94.43 | Weak |
| Acetylspermidine deacetylase (EC 3.5.1.48) | 90.60 | Weak |
| Acetolactate synthase (EC 2.2.1.6) | 63.21 | Weak |
| Maleylacetoacetate isomerase (EC 5.2.1.2) | 39.46 | Weak |
| Phytoene desaturase (EC 1.14.99.—) (Carotene Synthase) | 31.56 | Weak |
| ATP-dependent RNA helicase | 28.42 | Weak |
| Acetyl-CoA acetyltransferase (EC 2.3.1.9) | 26.74 | Weak |

Examples of low-strength (i.e., weak) *Schizochytrium* promoters include, but are not limited to, those driving expression of carotenoid synthase. Examples of medium-strength (i.e., medium) *Schizochytrium* promoters include, but are not limited to, those driving expression of alpha-tubulin. Examples of high-strength (i.e., strong) *Schizochytrium* promoters include, but are not limited to, those driving expression of elongation factor 1 (EF-1). Although RPKM values are considered generally indicative of relative promoter strength, it is known to those skilled in the art that a promoter in its native genomic context may not have exactly the same strength in the context of an expression vector. Thus, one of skill in the art will understand that the relative promoter strengths provided in Table 1 may vary in the context of the invention.

The invention thus provides for the possibilities that the guide-polynucleotide and the Cas protein are provided as such, or that they are encoded on or present on a vector. In the latter case, the encoding polynucleotides may each be on a separate vector or may both be on a single vector. Accordingly, in an embodiment, the present invention provides for a composition according to the present invention wherein a polynucleotide encoding a Cas protein according to the present invention, a guide-polynucleotide or a polynucleotide encoding a guide-polynucleotide according to the present invention are present on a single vector, which may further comprise any elements necessary for expressing the encoded products such as promoter and terminator elements. Such single (all-in-one) vector has the advantage that all components necessary for a CRISPR-Cas system are present together; in addition, a single transformation event, optionally in combination with a donor polynucleotide, suffices to introduce the components into a host cell.

Vectors

In the context of all embodiments of the present invention, a vector may be any vector (e.g., a plasmid or virus), which can conveniently be subjected to recombinant DNA procedures and can mediate expression of a polynucleotide according to the invention. The choice of the vector will typically depend on the compatibility of the vector with the host cell into which the vector is to be introduced. Preferred vectors are the vectors used in the examples herein. A vector may be a linear polynucleotide or a linear or closed circular plasmid. A vector may be an integrating or autonomously replicating vector, i.e., a vector, which exists as a chromosomal or an extra-chromosomal entity, the replication of which is dependent on or independent of chromosomal replication, e.g., a plasmid, an extra-chromosomal element, a mini-chromosome, or an artificial chromosome.

Preferably a vector may be one which, when introduced into the host cell, becomes integrated into the genome and replicated together with the chromosome(s) into which it has been integrated. An integrative vector may integrate at random or at a predetermined target locus in a chromosome of the host cell. A preferred integrative vector comprises a DNA fragment, which is homologous to a DNA sequence in a predetermined target locus in the genome of the host cell for targeting the integration of the vector to this predetermined locus. In order to promote targeted integration, a vector is preferably linearized prior to transformation of the cell. Linearization is preferably performed such that at least one but preferably either end of the vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell.

The homologous flanking DNA sequences in the vector (which are homologous to the target locus) may be derived from an expressed locus, meaning that they are derived from a gene, which is capable of expression in the host cell. Flanking DNA sequences may be linked with a selectable marker gene, such that transformed cells will grow when culture medium is supplemented with an appropriate selectable agent. The flanking DNA sequences can be designed by any means known to a person skilled in art; one preferred design directs homologous recombination to genes encoding saturated and/or polyunsaturated fatty acid synthases (PUFA synthases), such that mutation or disruption of these synthases creates auxotrophy for saturated and/or polyunsaturated fatty acids. Cells that are auxotrophic for saturated and/or polyunsaturated fatty acids, require saturated and/or polyunsaturated fatty as supplements for growth. Another preferred design enables expression of a dominant selectable marker gene such that transformants of said selectable marker gene are enabled to grow in the presence of an appropriate dominant selectable agent.

More than one copy of a polynucleotide according to the present invention may be inserted into the microbial host cell to mediate production of the product encoded by said polynucleotide. This can be done, preferably by integrating multiple copies of the polynucleotide into the genome of the host cell, or by targeting the integration of the polynucleotide at a highly expressed locus in an operable configuration. Alternatively, integration of multiple copies can be achieved by including an amplifiable selectable marker gene with a polynucleotide according to the present invention, such that cells containing amplified copies of the selectable marker gene (and thereby additional copies of the nucleic acid sequence) can be selected for by cultivating the cells in the presence of the appropriate selectable agent. To increase the number of copies of a polynucleotide according the present invention even more, the technique of gene conversion as described in WO98/46772 may be used.

When a polynucleotide according to the present invention encoding a Cas protein according to the present invention and/or a guide-polynucleotide according to the present invention is integrated into the genome of the host cell, it may be desirable to excise the polynucleotide from the genome, e.g. when the desired genome editing has taken place. The excision of a polynucleotide can be performed by any means known to the person skilled in art; one preferred means is by secondary transformation with a nucleotide which repairs a gene mutation or disruption which induced an auxotrophy such that cells which have been cured of the auxotrophy can instead be selected by growth in a culture medium in which the nutrient required by the auxotrophs has been omitted. Another means for excision would be to the use the CRISPR-Cas system according to the present invention.

A vector according to the present invention may be a single vector or plasmid or a vector system comprising two or more vectors or plasmids, which together contain the polynucleotides according to the present invention to be introduced into the host cell.

A vector according to the present invention may contain one or more selectable markers, which permit easy selection of transformed cells. In an embodiment, in a composition according to the invention, one or more or all vectors comprise a selectable marker, preferably each vector comprising a distinct selectable marker. A selectable marker is a gene the product of which provides for biocide or viral resistance, resistance to heavy metals, prototrophy to auxotrophs, and the like. The selectable marker may be introduced into the cell on the vector as an expression cassette or may be introduced on a separate vector.

A selectable marker for use in a Labyrinthulomycete cell may be selected from the group including, but not limited to, nptII (neomycin phosphotransferase II, conferring paromomycin resistance), ALS (acetolactate synthase, conferring sulfometuronmethyl resistance), bsd (blasticidin-S-deaminase, conferring blasticidin resistance), and Sh ble (phleomycin binding, conferring zeocin resistance).

Alternatively, specific selection markers can be used such as auxotrophic markers which require corresponding mutant host cells harboring inactivating mutations of saturated or polyunsaturated fatty acid synthase genes as previously discussed strains. In a preferred embodiment, the selection marker is deleted from the transformed host cell after introduction of the expression construct so as to obtain transformed host cells capable of producing the polypeptide which are free of selection marker genes.

The procedures used to ligate elements described above to construct a vector according to the present invention are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley Inter-Science, NY, 1995).

A Cas protein in the context of all embodiments of the present invention refers to any Cas protein suitable for the purpose of the invention. A Cas protein may comprise enzymatic activity or may not comprise enzymatic activity. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, Csf3, Csf4, homologs thereof or modified versions thereof. These Cas proteins are known to the person skilled in the art; for example, the amino acid sequence of *S. pyogenes* Cas9 protein may be found in the SwissProt database under accession number Q99ZW2. Preferably, an unmodified Cas protein according to the present invention has DNA cleavage activity, such as e.g. Cas9. Preferably, a Cas protein according is Cas9, and may be Cas9 from *S. pyogenes* or *S. pneumoniae*. Preferably, a Cas protein according to the present invention directs cleavage of one or both polynucleotide strands at the location of the target-polynucleotide, such as within the target-polynucleotide and/or within the reverse complement of the target-polynucleotide. At the location of the target-polynucleotide is herein defined as within about 1, 2, 3, 4, 5, 6, 7, 8, 9, 10, 15, 20, 25, 50, 100, 200, 500, or more nucleotides from the first or last nucleotide of a target-polynucleotide; more preferably, within 1, 2, 3, 4, 5, 6, 7, 8, 9, 10, 15, 20, 25, 50, 100, 200, 500, or more nucleotides from the first or last nucleotide of a target-polynucleotide; even more preferably, within 1, 2, 3, 4, 5, 6, 7, 8, 9, 10, 15, 20, 25, 50 nucleotides from the first or last nucleotide of a target-polynucleotide. Accordingly, a Cas protein according to the present invention preferably directs cleavage of one or both polynucleotide strands within about 1, 2, 3, 4, 5, 6, 7, 8, 9, 10, 15, 20, 25, 50, 100, 200, 500, or more nucleotides from the first or last nucleotide of a target-polynucleotide; more preferably, within 1, 2, 3, 4, 5, 6, 7, 8, 9, 10, 15, 20, 25, 50, 100, 200, 500, or more nucleotides from the first or last nucleotide of a target-polynucleotide; even more preferably, within 1, 2, 3, 4, 5, 6, 7, 8, 9, 10, 15, 20, 25, 50 nucleotides from the first or last nucleotide of a target-polynucleotide. Typically, a target-polynucleotide according to the present invention is associated with a PAM sequence (defined elsewhere herein) and the PAM sequence is preferably immediately downstream (3') of the target-sequence; the formation of the CRISPR-Cas complex typically results in cleavage of one or both polynucleotide strands 3 base pairs upstream (5') of the PAM sequence.

Preferably, a Cas protein in a composition according to the present invention has activity for directing cleavage of both polynucleotide strands at the location of the target-polynucleotide. Cas nuclease activity is typically performed by two separate catalytic domains, namely RuvC and HNH. Each domain cuts one polynucleotide strand each domain can be inactivated by a single point mutation.

A Cas protein according to the present invention may thus conveniently be mutated with respect to a corresponding wild-type Cas protein such that the mutated Cas protein has altered nuclease activity and lacks the ability to cleave one or both strands of a target-polynucleotide. For example, an aspartate-to-alanine substitution (D10A) in the RuvC I catalytic domain of Cas9 from *S. pyogenes* converts Cas9 from a nuclease that cleaves both strands to a nickase, which is herein defined as a Cas protein that cleaves a single strand of a target-polynucleotide. Other examples of mutations that render Cas9 into a nickase include, but are not limited to H840A, N854A, and N863A. In the context of the present invention, a Cas protein having nickase activity may be used for genome editing via homologous recombination, preferably the double nicking technique according to Ran et al., 2013. Accordingly, a preferred Cas protein according to the present invention comprises at least one mutation, such that the protein has altered nuclease activity compared to the corresponding wild-type Cas protein, preferably having activity to direct cleavage of a single polynucleotide strand at the location of the target-sequence. Such so-called nickase mutant can conveniently be used in duplex set-up, i.e. in a composition according to the present invention comprising a Cas protein nickase mutant with RuvC mutated and a Cas protein nickase mutant wherein NHN is mutated, such that the one Cas protein mutant nicks one strand of the polynucleotide target and the other Cas protein mutant nicks the other strand of the polynucleotide target. Depending on the two guide-polynucleotides used, the two different CRISPR-Cas complexes will effectively result in two single-strand nicks in the polynucleotide target; these nicks may be several nucleotides up to 5, 10, 20, 30 or more apart. Such double nicking method greatly enhances specificity of non-homologous end joining (NEJH). Background information on double nicking can be found in e.g. Ran et al., 2013.

A Cas protein according to the present invention may comprise two or more mutated catalytic domains of Cas9, such as RuvC I, RuvC II and/or RuvC III to result in a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. Preferably, a Cas protein is considered to substantially lack all DNA cleavage activity when the DNA cleavage activity of the mutated enzyme is less than about 25%, 10%, 5%, 1%, 0.1%, 0.01%, or lower with respect to its non-mutated form. A Cas protein lacking substantially all enzyme activity can conveniently be used for gene silencing or down regulation of expression since the CRISPR-Cas complex will hamper transcription from the target-polynucleotide. Other mutations may be useful; where the Cas9 or other Cas protein is from a species other than *S. pyogenes*, mutations in corresponding amino acids may be made to achieve similar effects; the person skilled in the art knows how to identify these corresponding amino acids.

A Cas protein according to the present invention may be a fusion protein and comprise at least one heterologous functional domain, such domain preferably is a domain comprising FokI activity such as described by Aggarwal et al. (Aggarwal, A. K.; Wah, D. A.; Hirsch, J. A.; Dorner, L. F.; Schildkraut, I. (1997). "Structure of the multimodular endonuclease FokI bound to DNA". Nature 388 (6637): 97-100). The enzyme FokI is naturally found in *Flavobacterium okeanokoites* and is a bacterial type IIS restriction endonuclease consisting of an N-terminal DNA-binding domain and a non-specific DNA cleavage domain at the C-terminal (Durai et al., 2005). When the FokI protein is bound to double stranded DNA via its DNA-binding domain at the 5'-GGATG-3':3'-CATCC-5' recognition site, the DNA cleavage domain is activated and cleaves, without further sequence specificity, the first strand 9 nucleotides downstream and the second strand 13 nucleotides upstream of the nearest nucleotide of the recognition site (Wah et al., 1998). Cas9-FokI fusions have been described inter alia in Guilinger et al., 2014; and in Tsai et al., 2014.

A Cas fusion protein according to the present invention may comprise 1, 2, 3, 4, 5, 6, 7, 8, 9, 10, or more domains in addition to the Cas protein. Examples of protein domains that may be fused to a Cas protein include, but are not limited to, epitope tags, reporter gene sequences, and protein domains having one or more of the following activities: methylase activity, demethylase activity, transcription activation activity, transcription repression activity, transcription release factor activity, historic modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A Cas protein may be fused to a gene sequence encoding a protein or a fragment of a protein that bind DNA molecules or bind other cellular molecules, including but not limited to, maltose binding protein (MBP), S-tag, Lex A DNA binding domain (DBD) fusions, GAL4 DNA binding domain fusions, and herpes simplex virus (HSV) BP 16 protein fusions. Additional domains that may form part of a fusion protein comprising a CRISPR enzyme are described in US20110059502. A tagged Cas protein may be used to identify the location of a target-polynucleotide. A preferred Cas fusion protein according to the present invention comprises a FokI domain as defined here above.

A preferred Cas protein according to the present invention comprises a nuclear localization sequence, preferably a heterologous nuclear localization sequence. Such nuclear localization sequence is also referred to as a nuclear localization signal. Preferably, such nuclear localization signal confers to the CRISPR-Cas complex sufficient strength to drive accumulation of said CRISPR-Cas complex in a detectable amount in the nucleus of a host cell. Without wishing to be bound by theory, it is believed that a nuclear localization sequence is not necessary for CRISPR-Cas activity in a host cell, but that including such sequences enhances activity of the system, especially as to targeting nucleic acid molecules into the nucleus. Such nuclear localization sequence is preferably present in the Cas protein, but may also be present anywhere else such that targeting of the CRISPR-Cas system to the nucleus is facilitated. A preferred nuclear localization sequence is the SV40 nuclear localization sequence.

In a composition and in any other embodiment according to the present invention, a Cas protein encoding polynucleotide is preferably codon optimized for the host cell it is to be expressed in, more preferably, the Cas protein encoding polynucleotide is codon pair optimized. In general, codon optimization refers to a process of modifying a nucleic acid sequence for enhanced expression in a host cell of interest by replacing at least one codon (e.g. more than 1, 2, 3, 4, 5, 10, 15, 20, 25, 50, or more codons) of a native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See, e.g., Nakamura, Y., et al., 2000. Computer algorithms for codon optimizing a particular sequence for expression in a particular host cell are also available, such as Gene Forge (Aptagen; Jacobus, P A), are also available. Preferably, one or more codons (e.g. 1, 2, 3, 4, 5, 10, 15, 20, 25, 50, or more, or all codons) in a sequence encoding a Cas protein correspond to the most frequently used codon for a particular amino acid. Preferred methods for codon optimization are described in WO2006/077258 and WO2008/000632. WO2008/000632 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence. The amount of Cas protein in a source in a composition according to the present invention may vary and may be optimized for optimal performance. It may be convenient to avoid too high levels of Cas protein in a host cell since high levels of Cas protein may be toxic to the host cell, even without a guide-polynucleotide present (see, e.g., Ryan et al., 2014 and Jacobs et al., 2014). A person skilled in the art knows how to regulate expression levels, such as by choosing a weaker promoter, repressible promoter or inducible promoter for expression of a Cas protein. Examples of promoters suitable for expression of a protein are depicted elsewhere herein.

In a composition according to the present invention wherein a guide-polynucleotide according to the present invention is encoded by a polynucleotide, expression of the guide-polynucleotide may be facilitated by a promoter operably linked to the encoding polynucleotide. Such promoter may be any suitable promoter known to the person skilled in the art. Several types of promoters can be used. It may be convenient to use an RNA polymerase III promoter or an RNA polymerase II promoter. Background information on RNA polymerase III and its promoters can be found e.g. in Marck et al., 2006. Accordingly, it may be convenient to use an RNA polymerase II promoter; these are known to the person skilled in the art and reviewed in, e.g., Kornberg, 1999. However, transcripts from an RNA II polymerase often have complex transcription terminators and transcripts are polyadenylated; this may hamper with the requirements of the guide-polynucleotide which because both its 5' and 3' ends need to be precisely defined in order to achieve the required secondary structure to produce a functional CRISPR-Cas system. These drawbacks can however be circumvented. In case a RNA polymerase II promoter is used, the polynucleotide encoding the guide-polynucleotide may also encode self-processing ribozymes and may be operably linked to an RNA polymerase II promoter; as such the polynucleotide encodes a pre-guide-polynucleotide comprising the guide-polynucleotide and self-processing ribozymes, wherein, when transcribed, the guide-polynucleotide is released by the self-processing ribozymes from the pre-guide-polynucleotide transcript. Preferred constructs comprising a polynucleotide encoding a pre-guide-polynucleotide according to the present invention operably linked to an RNA polymerase II promoter are those depicted in examples 1-4 herein. Background information on such constructs can be found in e.g. Gao et al., 2014.

Preferably, in a composition according to the present invention, the guide-polynucleotide is encoded by a polynucleotide.

Preferably, in a composition according to the present invention wherein the guide-polynucleotide is encoded by a polynucleotide, said polynucleotide is operably linked to an RNA polymerase II promoter and encodes a pre-guide-polynucleotide comprising the guide-polynucleotide and self-processing ribozymes, wherein, when transcribed, the guide-polynucleotide is released by the self-processing ribozymes from the pre-guide-polynucleotide transcript. Preferred constructs comprising a polynucleotide encoding a pre-guide-polynucleotide according to the present invention operably linked to an RNA polymerase II promoter are those depicted in examples 1-4 herein. Conveniently, multiple pre-guide-polynucleotides and multiple self-processing ribozymes may be encoded by a single polynucleotide, operably linked to one or more RNA polymerase II promoters.

The composition according to the first aspect of the present invention can conveniently be used to modulate expression of a polynucleotide in a host cell. Accordingly, in a second aspect, the present invention provides a method of modulating expression of a polynucleotide in a host cell, comprising contacting a host cell with the composition according to the first aspect of the invention, wherein the guide-polynucleotide directs binding of the Cas protein at the target-polynucleotide in the host cell to form a CRISPR-Cas complex.

The term "expression" in the context of the present invention is herein defined as the process by which a polynucleotide is transcribed from a polynucleotide template (e.g. a DNA template polynucleotide is transcribed into an mRNA polynucleotide transcript or other RNA transcript) and/or the process by which an mRNA transcript is subsequently translated into peptides, polypeptides, or proteins. Transcripts and encoded polypeptides may be collectively referred to as "gene product". If the polynucleotide transcript is derived from a genomic template DNA, expression may include splicing of the mRNA transcript in a host cell. The term "modulating expression" refers herein to increased or reduced expression compared to a parent host cell wherein expression is not modulated when assayed using the same conditions. Reduced expression may be a reduced amount of transcript such as mRNA and/or a reduced amount of translation product such as a polypeptide. It follows that increased expression may be an enhanced amount of transcript such as m RNA and/or an enhanced amount of translation product such as a polypeptide.

Preferably, the CRISP R-Cas complex cleaves one or both polynucleotide strands at the location of the target-polynucleotide, resulting in modulated expression of the gene product. The CRISPR-Cas complex may also have altered nuclease activity and substantially lack the ability to cleave one or both strands of a target-polynucleotide; in such case, expression is modulated by the binding of the complex to the target-polynucleotide. A Cas protein lacking substantially all enzyme activity can conveniently be used for gene silencing or down regulation of expression since the CRISPR-Cas complex will hamper transcription from the target-polynucleotide. Alternatively, a Cas protein can be modified into a transcription factor for programmable transcriptional activation or silencing of a gene of interest (Larson, et al., 2013).

A composition according to the first aspect of the present invention can conveniently be used for the deletion of polynucleotide. In an embodiment, when the composition according to the first aspect of the present invention comprises a source of at least one or two guide-polynucleotides and/or a source of at least at least one Cas protein, at least one CRISPR-Cas complex or two different CRISPR-Cas complexes are formed that cleave one or both polynucleotide strands at one location or at different locations of the target-polynucleotide, resulting in deletion of a polynucleotide fragment from the target-polynucleotide. Preferably, such composition according to the present invention comprising at least one or two guide-polynucleotides and/or a source of at least at least one Cas protein additionally comprises an exogenous polynucleotide as defined herein below that is at least partly complementary to the at least one or two target-polynucleotides targeted by the guide-polynucleotide(s). Such polynucleotide fragment to be deleted or deleted fragment may be several nucleotides in length up to a few thousand nucleotides in length, an entire gene may be deleted or a cluster of genes may be deleted. Accordingly, the present invention provides for a method of modulating expression of a polynucleotide in a host cell, wherein a polynucleotide fragment is deleted from a target-polynucleotide.

In an embodiment, the method of modulating expression comprises cleavage of one or both polynucleotide strands in at least one location of the target-polynucleotide followed by modification of the target-polynucleotide by homologous recombination with an exogenous polynucleotide. In such case, the composition according to the first aspect of the present invention preferably further comprises such exogenous polynucleotide. Such modification may result in insertion, deletion or substitution of at least one nucleotide in the target-polynucleotide, wherein the insertion or substitution nucleotide may originate from the exogenous polynucleotide. A modification can also be made when the exogenous polynucleotide is a non-integrating entity such as described in Dong et al. and Beetham et al.; in this case the target-polynucleotide is modified but no nucleotide of the exogenous polynucleotide is introduced into the target-polynucleotide. Consequently, the resulting host is a non-recombinant host cell when the Cas-protein according to the invention is introduced to the host cell as a protein. The exogenous polynucleotide may be any polynucleotide of interest such as a polynucleotide encoding a compound of interest as defined herein below, or a part of such polynucleotide or a variant thereof. Such exogenous polynucleotide is herein referred to as an exogenous polynucleotide according to the present invention and may single-stranded or double-stranded.

Various applications can be considered by the person skilled in the art for the compositions and methods according to the present invention. A polynucleotide (or gene) in a genome may be modified, edited or disrupted using compositions and methods according to the present invention. E.g. when a fully active Cas protein is used that cuts in both strands of the target-polynucleotide and when no exogenous polynucleotide is present as a suitable repair template, the double strand break is repaired by non-homologous end joining repair (NHEJ). During NHEJ insertions and/or deletions (which may be construed as substitution in some cases) of one or several nucleotides may occur, these are randomly inserted or deleted at the repair site; this is characteristic for NHEJ. Such insertions and/or deletions may impact the reading frame of the coding sequence, resulting amino acid changes in the gene product or even a truncated protein in case of genesis of a (premature) stop codon or alteration of a splice site.

A polynucleotide (or gene) in a genome may be modified, edited or disrupted using compositions and methods according to the present invention using homologous end joining repair (HEJ), also known as homology-directed repair (HDR), when an exogenous polynucleotide is present as repair template. E.g. when an exogenous polynucleotide having sequence identity to the target-polynucleotide (i.e. upstream (5') and downstream (3') of the double strand break) is present together with a CRISPR-Cas system according to the present invention, HDR will introduce (or actually reproduce) the corresponding nucleotides of the exogenous polynucleotide at the double strand break in the target-polynucleotide. Preferably, an exogenous polynucleotide according to the present invention does not contain the target sequence itself followed by a functional PAM sequence to avoid the risk of the exogenous polynucleotide itself or the modified target-polynucleotide being (re)cut by the CRISPR-Cas system.

In the embodiments of the present invention, when a CRISPR-Cas system according to the present invention comprises an exogenous polynucleotide (donor polynucleotide, donor DNA, repair template), the CRISPR-Cas system according to the present invention preferably comprises two or more guide-polynucleotides encoded by or present on one or more separate polynucleotides or vectors, and two or more exogenous polynucleotides are provided together with said CRISPR-Cas system enabling the formation of two or more CRISPR-Cas complexes. In a method according to the present invention, such CRISPR-Cas systems according to the present invention can conveniently be used to modulate expression at two or more target-polynucleotides, i.e. a method to target multiple target sites. Such CRISPR-Cas system according to the present invention will by chance form one, two or more CRISPR-Cas complexes at one or more target-polynucleotides. Such method can be used to generate one or more insertions, deletions, substitutions, optionally in combination with the one or more exogenous polynucleotides, in the genome of the host cell, or to modulate expression of genes via the formed CRISPR-Cas complexes.

Host Cells

In a method according to this aspect of the present invention, a preferred host cell comprises a polynucleotide encoding a compound of interest as defined elsewhere herein.

In a method according to this aspect of the present invention, the host cell may be a recombinant host cell or may be a non-recombinant host cell.

In some embodiments, the host cell is a Labyrinthulomycete, preferably a member of the order Thraustochytriales, preferably a member of the family Thraustochytriaceae, more preferably a member of a genus selected from the group consisting of *Aurantiochytrium, Oblongichytrium, Schizochytrium, Thraustochytrium*, and *Ulkenia*, even more preferably *Schizochytrium* sp. ATCC #20888.

A method of modulating expression of a polynucleotide in a host cell according to this aspect of the present invention, results in a modified host cell that preferably comprises components of the composition according to the first aspect of the present invention. Accordingly, in a third aspect, the present invention provides a host cell comprising a composition according to the first aspect of the present invention. Such host cell may be any host cell as defined herein and may further comprise a polynucleotide encoding a compound of interest as defined elsewhere herein.

In a fourth aspect, the present invention provides a method of producing a host cell, comprising contacting a host cell with the composition according to the first aspect of the present invention, wherein the guide-polynucleotide directs binding of the Cas protein at the target-polynucleotide in the host cell to form a CRISPR-Cas complex. In an embodiment, the contacting with the composition according to the first aspect of the invention may be performed in two steps, wherein the host cell is first contacted with a source of a Cas protein according to the invention and subsequently the host cell is contacted with a source of a guide-polynucleotide according to the invention and optionally an exogenous polynucleotide according to the invention. A host cell in this embodiment of the present invention may be any type of host cell as defined herein and may comprise a polynucleotide encoding a compound of interest as defined elsewhere herein. A preferred method of producing a host cell according to the present invention comprises a step to produce an offspring host cell, wherein in said offspring host cell no components of a CRISPR-Cas system according to the present invention are present anymore.

The composition according to the first aspect of the present invention may be any such composition as defined herein. Contacting a host cell with a composition according to the present invention may be performed by any means known to the person skilled in the art. A host cell according to the present invention may simply be brought into a solution comprising a composition according to the present invention. Specific means of delivering a composition according to the present invention into a host cell may be used. The person skilled in the art is aware of such methods (see e.g. Sambrook & Russell; Ausubel, supra)., which include but are not limited to electroporation methods, particle bombardment or microprojectile bombardment, protoplast methods and Agrobacterium mediated transformation (AMT). Labyrinthulomycetes may be transformed using any method known in the art. The general technique for genetic transformation of Thraustochytrids is described in detail in U.S. Pat. Nos. 7,001,772 and 8,637,651, and by Cheng et al. (2012), all of which are incorporated herein by reference in their entirety.

Preferably, the CRISPR-Cas complex cleaves one or both polynucleotide strands at the location of the target-polynucleotide, resulting in modulated expression of the gene product. The CRISPR-Cas complex may also have altered nuclease activity and lack the ability to cleave one or both strands of a target-polynucleotide; in such case, expression is modulated by the binding of the complex to the target-polynucleotide.

In an embodiment, when the composition according to the first aspect of the present invention comprises a source of at least one or two guide-polynucleotides and/or a source of at least one Cas protein, at least one CRISPR-Cas complex or two different CRISPR-Cas complexes are formed that cleave one or both polynucleotide strands at one location or at different locations of the target-polynucleotide, resulting in deletion of a polynucleotide fragment from the target-polynucleotide. Preferably, such composition according to the present invention comprising at least one or two guide-polynucleotides and/or a source of at least at least one Cas protein, additionally comprises an exogenous polynucleotide as defined herein below that is at least partly complementary to the at least one or two target-polynucleotides targeted by the guide-polynucleotide(s). Such polynucleotide fragment to be deleted or deleted fragment may be from several nucleotides in length up to a few thousand nucleotides in length, an entire gene may be deleted or a cluster of genes may be deleted. Accordingly, the present invention provides for a method of modulating expression of a polynucleotide in a host cell, wherein a polynucleotide fragment is deleted from a target-polynucleotide.

In one embodiment, a method of modulating expression of a polynucleotide in a host cell, wherein a polynucleotide fragment is deleted from a target-polynucleotide, comprises contacting a host cell with a composition as described herein, wherein the guide-polynucleotide directs binding of the Cas protein at the target-polynucleotide in the host cell to form a CRISPR-Cas complex. Preferably, a method of modulating expression of a polynucleotide in a host cell, wherein a polynucleotide fragments is deleted from a target-polynucleotide, comprises contacting a host cell with a composition as described herein, wherein the guide-polynucleotide directs binding of the Cas protein at the target-polynucleotide in the host cell to form a CRISPR-Cas complex. In another preferred embodiment, a method of modulating expression of a polynucleotide in a host cell, wherein a polynucleotide fragment is deleted from a target-polynucleotide, comprises contacting a host cell with a composition as described herein, wherein the guide-polynucleotide directs binding of the Cas protein at the target-polynucleotide in the host cell to form a CRISPR-Cas complex, wherein the composition as described herein does not comprise an exogenous or donor polynucleotide. In another embodiment of the method of modulating expression of a polynucleotide in a host cell, the composition is comprised in an autonomously replicating vector.

Therefore, the present invention relates in one embodiment to a method of modulating expression of a polynucleotide in a cell, wherein a polynucleotide fragment is deleted from a target-polynucleotide, comprising contacting a host cell with the composition as described herein but preferably not comprising a donor polynucleotide as defined herein, wherein the guide-polynucleotide directs binding of the Cas protein at the target-polynucleotide in the host cell to form a CRISPR-Cas complex.

In a preferred embodiment, the Cas protein has activity for directing cleavage of both polynucleotide strands at the location of the target-sequence and wherein the cleavage occurs in a region of the genome comprised between two homologous regions which upon cleavage by the Cas protein recombine with each other resulting in the deletion of a polynucleotide comprised between said regions. Preferably, the degree of homology between the two homologous regions is such to allow homologous recombination. Preferably, the two homologous regions have at least 60%, 70%, 80%, 90%, 99% or 100% sequence identity over the whole length of the homologous regions. It has been surprisingly found that the length of homologous region can be very short even in Labyrinthulomycetes, wherein usually a length of at least 1 or several kbp is necessary to allow homologous recombination. Therefore, in a preferred embodiment, the length of the homologous regions is preferably at most 1 kb, at most 0.5 kb, at most 100 bp, at most 50 bp, at most 40 bp, at most 30 bp, at most 20 bp, at most 10 bp.

Preferably the distance between the two homologous regions is at most 10 kb, at most 9, at most 8 kb, at most 7 kb, at most 6 kb, at most 5 kb, at most 4 kb, at most 3 kb, at most 2 kb, at most 1 kb, at most 0.5 kb, at most 100 bp, at most 50 bp, at most 40 bp, at most 30 bp, at most 20 bp, at most 10 bp.

In one aspect, the invention relates to a software algorithms able to identify PAM sites in the genome comprised between homology regions of about 7-20 bp in a neighborhood of the PAM site to design a method to target one or more PAM sites and create deletion of polynucleotides without use of a donor DNA.

The above method can be used for efficient removal of polynucleotide sequences in a designed way. For example, upon introducing a Cas9 expression cassette into the genomic DNA and after several rounds of modifications mediated by the CRISPR/CAS9 system, one can remove the CAS9 expression cassette from the genome by the introduction of a gRNA targeting a site in the Cas9 expression cassette and wherein the Cas9 expression cassette is comprised between two homologous regions as defined above, preferably 100-bp long, more preferably 20-bp, 15-bp long or shorter and cleave out the Cas9 open reading frame or a large part of the expression cassette.

The above method can also be used for transient inactivation of a gene. One could, for example, make a gene (e.g., a carotenoid synthase or saturated fatty acid synthase or polyunsaturated fatty acid synthase) non-functional by inserting a polynucleotide sequence in the ORF of the carotenoid synthase or saturated fatty acid synthase or polyunsaturated fatty acid synthase gene, comprising two homologous regions at the 5'-end and 3'-end respectively, wherein preferably the homologous regions are 100-bp, more preferably 20-bp, 15-bp long or shorter. An aforementioned synthase gene can be made functional again using a CRISPR-Cas9 system without donor DNA as described above.

In an embodiment, the method of modulating expression comprises cleavage of one or both polynucleotide strands in at least one location of the target-polynucleotide followed by modification of the target-polynucleotide by homologous recombination with an exogenous polynucleotide. In such case, the composition according to the first aspect of the present invention preferably further comprises such exogenous polynucleotide. Such modification may result in insertion, deletion or substitution of at least one nucleotide in the target-polynucleotide, wherein the insertion or substitution nucleotide may or may not originate from the exogenous polynucleotide. In one embodiment, the exogenous polynucleotide comprises regions of homology with the target-polynucleotide. Preferably, the degree of homology between these homologous regions is such to allow homologous recombination. Preferably, the homologous regions have at least 60%, 70%, 80%, 90%, 99% or 100% sequence identity over the whole length of the homologous regions. A modification can also be made when the exogenous polynucleotide is a non-integrating entity; in this case the target-polynucleotide is modified but no nucleotide of the exogenous polynucleotide is introduced into the target-polynucleotide. Consequently, the resulting host is a non-recombinant host when the Cas-protein according to the present invention is introduced to the host cell as a protein. In a method according to this aspect of the present invention, the host cell may thus be a recombinant host cell or may be a non-recombinant host cell. The exogenous polynucleotide may be any polynucleotide of interest such as a polynucleotide encoding a compound of interest as defined herein, or a part of such polynucleotide or a variant thereof.

In another aspect, the present invention provides for a method for the production of a compound of interest, comprising culturing under conditions conducive to the compound of interest a host cell according to the third or fourth aspect of the present invention or a host cell obtained by a method according to the second aspect of the present invention, or a host cell obtainable by a method according to the fourth aspect of the present invention and optionally purifying or isolating the compound of interest.

A compound of interest in the context of all embodiments of the present invention may be any biological compound. The biological compound may be biomass or a biopolymer or a metabolite. The biological compound may be encoded by a single polynucleotide or a series of polynucleotides composing a biosynthetic or metabolic pathway or may be the direct result of the product of a single polynucleotide or products of a series of polynucleotides, the polynucleotide may be a gene, the series of polynucleotide may be a gene cluster. In all embodiments of the present invention, the single polynucleotide or series of polynucleotides encoding the biological compound of interest or the biosynthetic or metabolic pathway associated with the biological compound of interest, are preferred targets for the compositions and methods according to the present invention. The biological compound may be native to the host cell or heterologous to the host cell.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. The term polypeptide refers to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics. Polypeptides further include naturally occurring allelic and engineered variations of the above-mentioned polypeptides and hybrid polypeptides. The polypeptide may be native or may be heterologous to the host cell. The polypeptide may be a collagen or gelatine, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may also be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, a maltogenic amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, galactolipase, chlorophyllase, polyphenoloxidase, ribonuclease, transglutaminase, or glucose oxidase, hexose oxidase, monooxygenase.

According to the present invention, a compound of interest can be a polypeptide or enzyme with improved secretion features as described in WO2010/102982. According to the present invention, a compound of interest can be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the host cell. Examples of fusion polypeptides and signal sequence fusions are, for example, as described in WO2010/121933.

The biopolymer may be a polysaccharide. The polysaccharide may be any polysaccharide, including, but not limited to, a mucopolysaccharide (e.g., heparin and hyaluronic acid) and nitrogen-containing polysaccharide (e.g., chitin). In a preferred option, the polysaccharide is hyaluronic acid.

A polynucleotide coding for the compound of interest or coding for a compound involved in the production of the compound of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are unsaturated fats and lipids (including but not limited to the fatty acids docosahexaenoic acid, docosapentaenoic acid, eurcic acid, paullinic acid, vaccenic acid (cis or trans), eicosapentaenoic acid, eicosatetraenoic acid (n-3), arachidonic acid (n-6), octadecapentaenoic acid, stearidonic acid, linolenic acid (n6 or n3), linoleic acid, oleic acid, palm itoleic acid, octacosaoctaenoic acid, and lipids comprised thereof), saturated fats and lipids (including, but not limited to, the fatty acids: caproic acid, caprylic acid, capric acid, lauric acid, myristic acid, palm itic acid, stearic acid, arachidic acid, behenic acid, and lipids comprised thereof), sulfated lipids, sophorolipids, lactones, ceramides, phospholipids, fatty alcohols, fatty acid esters, fatty acid ethers, fatty acid aldehydes, sterols, carotenoids, oxylipins, resolvins, leukotrienes, prostaglandins, organic acids (including, but not limited to, acetic acid, butyric acid, citric acid, gluconic acid, adipic acid, fumaric acid, itaconic acid, malic acid, mevalonic acid, and succinic acid), sugar alcohols, and sugar acids.

A metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

A primary metabolite may be, but is not limited to, an amino acid, fatty acid, nucleoside, nucleotide, sugar, triglyceride, or vitamin.

A secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide.

The biological compound may also be the product of a selectable marker. A selectable marker is a product of a polynucleotide of interest which product provides for biocide or viral resistance, resistance to heavy metals, prototrophy to auxotrophs, and the like. Selectable markers include, but are not limited to, nptII (neomycin phosphotransferase II), ALS (acetolactate synthase), bsd (blasticidin-S-deaminase), and Sh ble (phleomycin binding) as well as equivalents thereof.

According to the invention, a compound of interest is preferably a polypeptide as described in the list of compounds of interest.

According to another embodiment of the invention, a compound of interest is preferably a metabolite.

The host cell according to the present invention may already be capable of producing the compound of interest. The host cell may also be provided with a homologous or heterologous nucleic acid construct that encodes a polypeptide wherein the polypeptide may be the compound of interest or a polypeptide involved in the production of the compound of interest. The person skilled in the art knows how to modify an algal host cell such that it is capable of producing the compound of interest.

General Definitions

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The terms "a" and "an" are used herein to refer to one or to more than one (i.e. to one or at least one) of the grammatical object of the article. By way of example, "an element" may mean one element or more than one element.

The word "about" or "approximately" when used in association with a numerical value (e.g. about 10) preferably means that the value may be the given value (of 10) more or less 1% of the value.

Unless defined otherwise, all technical and scientific terms used herein have the same meaning as commonly understood to one of ordinary skill in the art to which this disclosure belongs.

A preferred nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al. (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

A further preferred nucleotide analogue or equivalent comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O—, S—, or N-alkyl; O—, S—, or N-alkenyl; O—, S— or N-alkynyl; O—, S—, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target.

"Sequence identity" or "identity" in the context of the present invention of an amino acid- or nucleic acid-sequence is herein defined as a relationship between two or more amino acid (peptide, polypeptide, or protein) sequences or two or more nucleic acid (nucleotide, oligonucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole sequence (SEQ ID NO:) as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison is as follows: Algorithm: Needleman and Wunsch, J. Mol. Biol. 48:443-453 (1970); Comparison matrix: BLOSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison is as follows: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide according to the present invention is represented by a nucleotide sequence. A polypeptide according to the present invention is represented by an amino acid sequence. A nucleic acid construct according to the present invention is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct according to the present invention is operably linked to one or more control sequences, which direct the production or expression of the encoded product in a host cell or in a cell-free system.

The sequence information as provided herein should not be so narrowly construed as to require inclusion of erroneously identified bases. The skilled person is capable of identifying such erroneously identified bases and knows how to correct for such errors.

All embodiments of the present invention, i.e. a composition according to the present invention, a method of modulating expression, a host cell comprising a composition according to the present invention, a method of producing a host cell according to the present invention, a host cell according to the present invention and a method for the production of a compound of interest according to the present invention preferably refer to host cell, not to a cell-free in vitro system; in other words, the CRISPR-Cas systems according to the present invention are preferably host cell systems, not cell-free in vitro systems.

In all embodiments of the present invention, e.g. a composition according to the present invention, a method of modulating expression, a host cell comprising a composition according to the present invention, a method of producing a host cell according to the present invention, a host cell according to the present invention and a method for the production of a compound of interest according to the present invention, the host cell may be a haploid, diploid or polyploid host cell.

The host cell according to the present invention is a Labyrinthulomycetes host cell, preferably of the order Thraustochytriales, more preferably of the family Thraustochytriaceae, more preferably a member of a genus selected from the group consisting of *Aurantiochytrium, Oblongichytrium, Schizochytrium, Thraustochytrium*, and *Ulkenia*, even more preferably *Schizochytrium* sp. ATCC #20888

A modification, preferably in the genome, is construed herein as one or more modifications. A modification, preferably in the genome of a host cell according to the present invention, can either be effected by
 a) subjecting a parent host cell to recombinant genetic manipulation techniques; and/or
 b) subjecting a parent host cell to (classical) mutagenesis; and/or
 c) subjecting a parent host cell to an inhibiting compound or composition.

Modification of a genome of a host cell is herein defined as any event resulting in a change in a polynucleotide sequence in the genome of the host cell.

Preferably, a host cell according to the present invention has a modification, preferably in its genome which results in a reduced or no production of an undesired compound as defined herein if compared to the parent host cell that has not been modified, when analysed under the same conditions.

A modification can be introduced by any means known to the person skilled in the art, such as but not limited to classical strain improvement, random mutagenesis followed by selection. Modification can also be introduced by site-directed mutagenesis.

Modification may be accomplished by the introduction (insertion), substitution (replacement) or removal (deletion) of one or more nucleotides in a polynucleotide sequence. A full or partial deletion of a polynucleotide coding for an undesired compound such as a polypeptide may be achieved. An undesired compound may be any undesired compound listed elsewhere herein; it may also be a protein and/or enzyme in a biological pathway of the synthesis of an undesired compound such as a metabolite. Alternatively, a polynucleotide coding for said undesired compound may be partially or fully replaced with a polynucleotide sequence which does not code for said undesired compound or that codes for a partially or fully inactive form of said undesired compound. In another alternative, one or more nucleotides can be inserted into the polynucleotide encoding said undesired compound resulting in the disruption of said polynucleotide and consequent partial or full inactivation of said undesired compound encoded by the disrupted polynucleotide.

In one embodiment, the mutant microbial host cell according to the invention comprises a modification in its genome selected from
 a) a full or partial deletion of a polynucleotide encoding an undesired compound,
 b) a full or partial replacement of a polynucleotide encoding an undesired compound with a polynucleotide sequence which does not code for said undesired compound or that codes for a partially or fully inactive form of said undesired compound, c) a disruption of a polynucleotide encoding an undesired compound by the insertion of one or more nucleotides in the polynucleotide sequence and consequent partial or full inactivation of said undesired compound by the disrupted polynucleotide.

This modification may, for example, be in a coding sequence or a regulatory element required for the transcription or translation of said undesired compound. For example, nucleotides may be inserted or removed so as to result in the introduction of a stop codon, the removal of a start codon or a change or a frame-shift of the open reading frame of a coding sequence. The modification of a coding sequence or a regulatory element thereof may be accomplished by site-directed or random mutagenesis, DNA shuffling methods, DNA reassembly methods, gene synthesis (see, e.g., Young and Dong (2004), Nucleic Acids Research 32(7) electronic access at nar.oupjournals.org/cgi/reprint/32/7/e59 or Gupta et al. (1968), Proc. Natl. Acad. Sci USA, 60: 1338-1344; Scarpulla et al. (1982), Anal. Biochem. 121: 356-365; Stemmer et al. (1995), Gene 164: 49-53), or PCR generated mutagenesis in accordance with methods known in the art. Examples of random mutagenesis procedures are well known in the art, such as, for example, chemical (e.g., NTG), mutagenesis or physical (e.g., UV) mutagenesis. Examples of site-directed mutagenesis procedures are the QuickChange™ site-directed mutagenesis kit (Stratagene Cloning Systems, La Jolla, Calif.), the 'The Altered Sites® II in vitro Mutagenesis Systems (Promega Corporation) or by overlap extension using PCR as described in Ho et al. ("Site-directed mutagenesis by overlap extension using the polymerase chain reaction", Gene, 1989 Apr. 15, 77(1):51-9) or using PCR as described in *Molecular Biology: Current Innovations and Future Trends*. (Eds. A. M. Griffin and H. G. Griffin. ISBN 1-898486-01-8; 1995 Horizon Scientific Press, PO Box 1, Wymondham, Norfolk, U.K.).

Preferred methods of modification are based on recombinant genetic manipulation techniques such as partial or complete gene replacement or partial or complete gene deletion.

For example, in case of replacement of a polynucleotide, nucleic acid construct or expression cassette, an appropriate DNA sequence may be introduced at the target locus to be replaced. The appropriate DNA sequence is preferably present on a cloning vector. Preferred integrative cloning vectors comprise a DNA fragment, which is homologous to the polynucleotide and/or has homology to the polynucleotides flanking the locus to be replaced for targeting the integration of the cloning vector to this pre-determined locus. In order to promote targeted integration, the cloning vector is preferably linearized prior to transformation of the cell. Preferably, linearization is performed such that at least one but preferably either end of the cloning vector is flanked by sequences homologous to the DNA sequence (or flanking sequences) to be replaced. This process is called homologous recombination and this technique may also be used in order to achieve (partial) gene deletion.

For example, a polynucleotide corresponding to the endogenous polynucleotide may be replaced by a defective polynucleotide, that is a polynucleotide that fails to produce a (fully functional) polypeptide. By homologous recombination, the defective polynucleotide replaces the endogenous polynucleotide. It may be desirable that the defective polynucleotide also encodes a marker, which may be used for selection of transformants in which the nucleic acid sequence has been modified.

A modification which results in decreased or no production of an undesired compound can be obtained by different methods, for example by an antibody directed against such undesired compound or a chemical inhibitor or a protein inhibitor or a physical inhibitor (Tour 0. et al., "Genetically targeted chromophore-assisted light inactivation", (2003) Nat. Biotech). Alternatively, or in combination with above-mentioned techniques, decreased or no production of an undesired compound can also be obtained, e.g. by UV or chemical mutagenesis (Lian et al., "Increase of docosahexaenoic acid production by *Schizochytrium* sp. through mutagenesis and enzyme assay" (2010) Appl Biochem Biotechnol 162(4):935-941) or by the use of inhibitors inhibiting enzymatic activity of an undesired polypeptide as described herein (e.g. nojirimycin, which function as inhibitor for β-glucosidases (Ren et al., "Effect of biotin and cerulenin addition on DHA production by *Schizochytrium* sp." (2012-01) Chinese J Bioprocess Engineering).

In an embodiment of the present invention, the modification in the genome of the host cell according to the invention is a modification in at least one position of a polynucleotide encoding an undesired compound.

A deficiency of a cell in the production of a compound, for example of an undesired compound such as an undesired polypeptide and/or enzyme is herein defined as a mutant microbial host cell which has been modified, preferably in its genome, to result in a phenotypic feature wherein the cell:
a) produces less of the undesired compound or produces substantially none of the undesired compound and/or b) produces the undesired compound having a decreased activity or decreased specific activity or the undesired compound having no activity or no specific activity and combinations of one or more of these possibilities as compared to the parent host cell that has not been modified, when analysed under the same conditions.

Preferably, a modified host cell according to the present invention produces 1% less of the un-desired compound if compared with the parent host cell which has not been modified and measured under the same conditions, at least 5% less of the un-desired compound, at least 10% less of the un-desired compound, at least 20% less of the un-desired compound, at least 30% less of the un-desired compound, at least 40% less of the un-desired compound, at least 50% less of the un-desired compound, at least 60% less of the un-desired compound, at least 70% less of the un-desired compound, at least 80% less of the un-desired compound, at least 90% less of the un-desired compound, at least 91')/0 less of the un-desired compound, at least 92% less of the un-desired compound, at least 93% less of the un-desired compound, at least 94% less of the un-desired compound, at least 95% less of the un-desired compound, at least 96% less of the un-desired compound, at least 97% less of the un-desired compound, at least 98% less of the un-desired compound, at least 99% less of the un-desired compound, at least 99.9% less of the un-desired compound, or most preferably 100% less of the un-desired compound.

The sequence information as provided herein should not be so narrowly construed as to require inclusion of erroneously identified bases. The skilled person is capable of identifying such erroneously identified bases and knows how to correct for such errors.

The disclosure of each reference set forth herein is incorporated herein by reference in its entirety.

The present invention is further illustrated by the following examples:

EXAMPLES

Example 1

Design and Building of Cas9 Vectors for Transformations

The *Streptococcus* pyogenes MGAS5005 Cas9 sequence was codon-optimized for expression in *Schizochytrium*. The basic Cas9 peptide sequence used was essentially the same as that used by Jinek et al., 2013, but without the described HA-tag or the GFP fusion (see below). After the Cas9 was synthesized (DNA2.0, Newark, Calif.), it was cloned into pCL122 vector containing a paromomycin selection cassette, resulting in a vector designated pCL122-Cas9 (SEQ ID). OrfA/Pfa1 flanks were synthesized and cloned (Genscript USA, Piscataway, N.J.) into pCL121 (which harbored a zeocin selection cassette) and the final vector was designated pYB31 (SEQ ID NO:2); see, e.g., U.S. Pat. No. 8,940,884. The Cas9 gene was subcloned from pCL122-Cas9 vector into pYB31 vector via digestion and ligation using BamHI and NdeI restriction sites and enzymes (New England Biolabs, Ipswich, Mass.) (FIG. 1), and Rapid DNA Ligation kit (Roche, Risch-Rotkreuz, Switzerland). NEB10β chemically competent cells were transformed (New England Biolabs) and resulting colonies were screened by colony PCR using selected colonies, GoTaq Green Master mix (Promega, Chicago, Ill.) with primers 121 Tub seq F (SEQ ID NO:13) and pYB32/3C R1 (SEQ ID NO:14) (Table 2), and 5% DMSO (v:v), and the following cycling conditions were applied to the reaction: 95° C. for 5 minutes, (95° C. for 30 seconds, 59° C. for 30 seconds, 72° C. for 1 minute)×35 cycles, 72° C. for 5 minutes (FIG. 2). Plasmids were isolated from colonies positive by PCR, sequenced, and one resulting vector was designated pYB32 (SEQ ID NO:3).

TABLE 2

| Primer Name | SEQ ID NO | Primer Sequence, 5'→3' |
|---|---|---|
| 121 Tub seq F | 13 | GGATCTCATGCTGGAGTTCTTC |
| pYB32/3C R1 | 14 | GTACTTCTCGTGGTAGGCAACC |

As previously mentioned, other studies have indicated that the level of Cas9 expression is important for optimizing transformant viability and nuclease activity. In the pYB32 plasmid, the Cas9 gene is under control of the alpha tubulin promoter, a medium strength promoter. A weak promoter from the carotene synthase (CS) gene was selected to be tested as well and was cloned into pYB31 via InFusion PCR Cloning (Clontech/Takara Bio USA, Inc., Mountain View, Calif.). pYB31 plasmid was digested with KpnI and NdeI enzymes (New England Biolabs) in preparation for InFusion cloning. CS promoter was amplified with CS pro KpnI IF F1 (SEQ ID NO:15) and CS pro BamHI IF R1 primers (SEQ ID NO:16) (Table 3), with 5% DMSO (v:v), KOD HotStart Master Mix (EMD Millipore, Billerica, Mass.), and pTH043, plasmid harboring CS promoter, used as a template. Reaction cycling conditions were as follows: 95° C. for 2 minutes, (95° C. for 20 seconds, 66° C. for 10 seconds, 70° C. for 20 seconds)×35 cycles, 70° C. for 2 minutes. Cas9 was amplified with CS pro BamHI IF F2 (SEQ ID NO:17) and CS pro NdeI IF R2 (SEQ ID NO:18) primers (Table 3), with 5% DMSO (v:v), KOD HotStart Master Mix, and pCL122-Cas9 used as a template. Reaction cycling conditions were as follows: 95° C. for 2 minutes, (95° C. for 20 seconds, 65° C. for 10 seconds, 70° C. for 1 minute 45 seconds)×35 cycles, 70° C. for 2 minutes.

TABLE 3

| Primer Name | SEQ ID NO | Primer Sequence, 5'→3' |
|---|---|---|
| CS pro Kpn IF F1 | 15 | GTCTGAATTCCCGGGGTACCGAGCGGGCGATTCCACCGTC |
| CS pro BamH IF R1 | 16 | GTACTTCTTATCCATGGATCCCTCGGTCTCCGAGCGAGCGAG |
| CS pro BamH IF F2 | 17 | TCGCTCGCTCGGAGACCGAGGGATCCATGGATAAGAAGTAC |
| CS pro Nde IF R2 | 18 | GATTCACTAGTTTAGATCATATGTTAGACCTTGCGCTTCTTCTTAGGGTCC |

Figure 2:
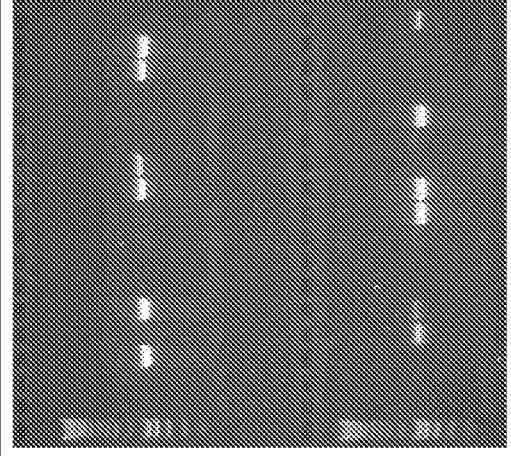
FIG. 2 shows results of colony PCR of transformants resulting from pYB32 and pYB33 bacterial transformations.

PCR products were run on 1% agarose gel (Lonza, Basel, Switzerland), bands of expected sizes were excised and gel purified using QIAquick Gel Extraction kit (Qiagen, Hilden, Germany) (FIG. 1). Following manufacturer's protocol for InFusion cloning, the Cas9 PCR fragment, CS promoter PCR fragment and linearized pYB31 fragment were ligated, NEB10β chemically competent cells were transformed, and resulting colonies were screened by colony PCR as described above (FIG. 2) (with 1 minute 30 seconds extension time at 72° C.). After sequence verification, one of the resulting vectors containing Cas9 operably linked to the CS promoter was designated pYB33 (SEQ ID NO:4).

Cloning of pYB32 and pYB33 was done through a combination of digestions, ligations and InFusion PCR cloning. As shown in FIG. 1, all the fragments were produced and had bands of expected sizes after column purification. Digested plasmids and PCR amplified fragments were run on 1% agarose gel. Expected sizes of fragments were observed in all lanes as follows: pYB31-BamHI+NdeI=838 bp+6555 bp, pYB31-KpnI+NdeI=1289 bp+6104 bp, Cas9-BamHI+NdeI=4157 bp+5773 bp, CS PCR fragment=1046 bp, Cas9 PCR fragment=4189 bp. The molecular weight markers used in this gel and all subsequent gels was DNA Quanti-Ladder (Origene, Rockville, Md.)—fragment sizes are indicated in the panel on the right side of FIG. 1.

Colonies resulting from pYB32 and pYB33 bacterial transformations were analyzed by colony PCR, and colonies with amplicons of the expected size are marked in boldface type in FIG. 2. These colonies are: pYB32-2, -4, -9, -14, -15, -24, -25, -28, and pYB33-16 and pYB33D-1, -14. pYB32-2 and pYB33-16 were among those verified to have correct sequence and were used for subsequent work. For colony PCR results from cloning of pYB32 and pYB33, expected amplicon sizes are as follows: pYB32=1028 bp, pYB33=1584 bp.

Example 2

Transformations and Selection of Cas9 Transformants

The wild-type strain of *Schizochytrium* sp., ATCC 20888, was used for transformation with pYB32 and pYB33 using a particle bombardment method and a biolistics instrument (Bio-Rad, Raleigh, N.C.) as described below. Briefly, 20888 was grown in 25 mL of M50-20 medium (see, e.g., U.S. Pat. No. 8,003,772) in a 250 mL smooth-bottom Erlenmeyer flask at 27° C., shaking at 200 rpm overnight. Following that, the culture was diluted 1/100 into 50 mL of M2B medium (see, e.g., U.S. Pat. No. 8,003,772) in a 250 mL baffled flask and grown under the same conditions overnight. When the Schizochytrium culture was in early log phase (0.6-2 OD units/mL), the culture was harvested by centrifugation at 3,220×g for 10 minutes. Supernatant was decanted, the pellet was resuspended in M2B to final concentration of 20 OD units/mL, and 100 µL of resulting cell suspension was spread in a circular motion on approximately a third of a non-selective M2B agar plate (approximately 4 cm diameter). Plasmids pYB32 and pYB33 were digested with SwaI at 25° C. overnight and purified using QIAquick PCR purification kit (Qiagen, Hilden, Germany). Five µg of each purified plasmid was then mixed with 50 µL of 2.5 M CaCl$_2$, 20 µL of 0.1 M spermidine and 50 µL of prepared M10 Tungsten beads (following the manufacturer's protocol, Bio-Rad), vortexed for 1 minute, then incubated for 10 minutes at room temperature to allow for the beads to settle. DNA-coated beads were washed once with 250 µL of 100% ethanol, and then beads were resuspended in 60 µL of 100% ethanol. Each prepared macrocarrier (following manufacturer's protocol for macrocarrier assembly preparation) had 10 µL of coated beads in ethanol spotted to the center of a macrocarrier disc and ethanol was allowed to dry. Rupture disc holders had 1,100 psi-rated rupture discs placed inside after brief sterilization in 70% isopropanol, and assembled macrocarriers were fitted to the biolistics platform in the top shelf position and M2B agar plates with cell patches of Schizochytrium were placed cell-side-up on the third shelf from the top. When vacuum reached ~27 psi inside the biolistics chamber, helium was fired until rupture disc failure, the flow of helium was closed off, the chamber was vented to atmosphere, and the bombarded plate was removed from the chamber. The bombardment process was repeated for all samples and controls, Schizochytrium sp. 20888 bombarded with pYB32 was designated T188, and Schizochytrium cultures bombarded with pYB33 were designated T189. Bombarded plates were incubated in at 27° C. for 4 hours, after which cells were washed off the plate with ~1 mL of M2B and divided equally between four M2B agar plates containing 0.5 mM DHA (Nu-Chek Prep, Waterville, Minn.) in 0.4% randomly-methylated β-cyclodextrins (CTD Holdings, Inc., High Springs, Fla.) and 50 µg/mL zeocin (Thermo Fisher Scientific, Waltham, Mass.). Cells were spread with 3 mm sterile glass beads, beads removed and plates wrapped and incubated at 27° C. for ~7-10 days. When colonies reached 2-4 millimeters in size, each colony was replica-patched on M2B agar plates containing 100 µg/mL zeocin with or without DHA (complexed with randomly-methylated β-cyclodextrins as described above) to select for auxotrophy induced by disruption of the OrfA/Pfa1 gene.

Figure 3:
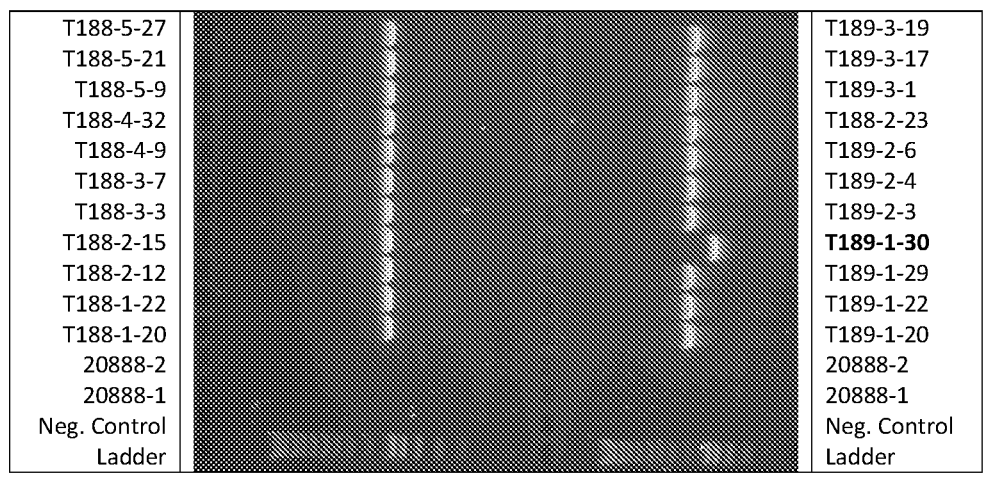
FIG. 3 shows an agarose gel in which amplicons derived from genomic DNA of T188 and T189 transformants were separated, testing for the presence of promoter and partial Cas9.
Figure 4:
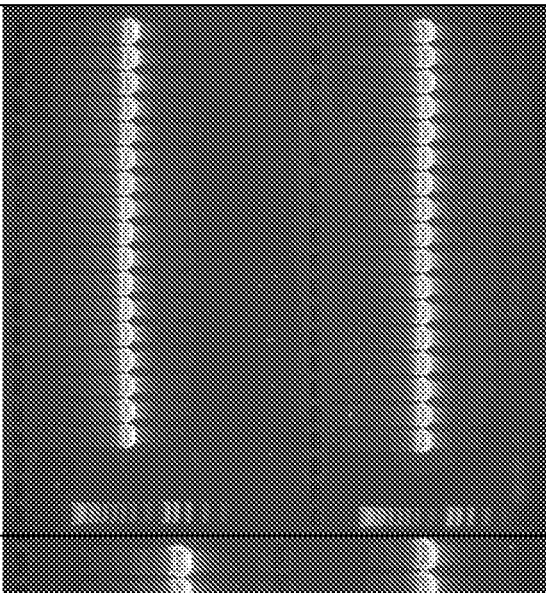
FIG. 4 shows amplicons derived from genomic DNA of T188 and T189 transformants run on an agarose gel verifying integration of Cas9 to the OrfA/Pfa1 locus.

Colonies confirmed to be auxotrophic for DHA were picked and inoculated into 50 mL of M50-20 supplemented with 500 µL of 40% β-cyclodextrins and 50 mM DHA solution in a 250 mL smooth bottom Erlenmeyer flask and placed in a 27° C. shaker at 200 rpm for 48 hrs. After 48 hr incubation time, 2 mL of culture were collected by centrifugation at 5,000×g for 10 minutes, supernatant was decanted, and pellet was used for genomic DNA isolation following a modified phenol-chloroform extraction. Genomic DNA was extracted and used as PCR template with GoTaq Green mastermix (Promega, Durham, N.C.) to verify presence of zeocin cassettes and the Cas9 gene using primers, GoTaq Green master mix and cycling conditions as described for colony PCR screening for pYB32 and pYB33 (FIG. 3). Disruption of the OrfA/Pfa1 gene in T188 and T189 transformants was verified by PCR. Specifically, 5' flanking regions were interrogated by PCR with O A1-KO F (SEQ ID NO:19) and pYB32/3 SV40 R1 (SEQ ID NO:20) primers (Table 4), GoTaq Green mastermix, 5% DMSO (v:v) and T188/T189 gDNA as template, and cycling conditions were as follows: 95° C. for 2 minutes, (95° C. for 30 seconds, 60° C. for 30 second, 72° C. for 2 minutes 15 seconds)×35 cycles, 72° C. for 5 minutes. Furthermore, 3' flanking region were interrogated by PCR with O A1-KO R (SEQ ID NO:21) and pYB32/2 CF 1 (SEQ ID NO:22) primers (Table 4), GoTaq Green mastermix, 5% DMSO (v:v) and T188/T189 gDNA as template, cycling conditions were as follows: 95° C. for 2 minutes, (95° C. for 30 seconds, 59° C. for 30 seconds, 72° C. for 2 minutes)×35 cycles, 72° C. for 5 minutes (FIG. 4).

TABLE 4

| Primer Name | SEQ ID NO | Primer Sequence, 5'→3' |
|---|---|---|
| O A1-KO F | 19 | CCAAGTTCGCCAAGGCTTC |
| pYB32/3 SV40 R1 | 20 | GTGGAATCGAAATCTCGTAGCAC |
| O A1-KO R | 21 | GCTGTTGCAACTTTGCTCCAC |
| pYB32/3C F1 | 22 | GTTAAGAAGACCGAGGTCCAGAC |

Cultures positive by PCR for Cas9 gene integration and a disruption at OrfA/Pfa1 were inoculated into 25 mL of M50-20 supplemented with randomly methylated β-cyclodextrin and DHA, and grown for 24 hours as described previously. The OD600 of the cultures were measured, and 2 OD units of each culture were inoculated into 50 mL of SPFM, pH 6.75, supplemented with randomly methylated β-cyclodextrin and DHA in 250 mL baffled Erlenmeyer flasks, and grown for 48 hrs in a 27° C. shaker at 200 rpm before addition of 5% glycerol (v:v) for cryopreservation. Two clones were selected, one from each transformation group, for further work—T188-1-20 and T189-1-20.

Wild-type Schizochytrium sp. 20888 was transformed with pYB32 and pYB33 plasmids by bombardment resulting in DHA auxotrophy in 20888 due to insertion of Cas9 at OrfA/PFA1 locus of the polyunsaturated fatty acid (PUFA) synthase. Colonies were counted and replica-patched on selective plates with or without DHA. Colonies that were auxotrophic for DHA were picked at random from both transformation groups and were used for further characterization.

As shown below in Table 5, transformation efficiency with pYB33 plasmid was lower than with pYB32 plasmid, and a similar trend was observed with the fraction of auxotrophic colonies found.

TABLE 5

| Transformation | Total Colonies per 5 µg DNA | Auxotrophic Colonies | % Knock-out |
|---|---|---|---|
| T188: pYB32-Tub pro-Cas9 | 160 | 80 | 50% |
| T189: pYB33-CS pro-Cas9 | 96 | 37 | 38.5% |

T188 and T189 transformants were interrogated for the presence of promoters linked to Cas9 and for the upstream region of the Cas9 gene. For T188 clones, the expected amplicon size was 1028 bp, and for T189-1584 bp. As shown in FIG. 3, all but clone T189-1-30 generated the expected amplicon size and were used for further testing.

Integration of Cas9 in the OrfA/Pfa1 locus was verified by PCR, both 5' and 3' flanking regions were amplified with a combination of wild-type-specific external primers and Cas9-specific internal primers, such that amplicons were achievable only if integration occurred (FIG. 4). Expected amplicon sizes for the 5' flank of the Cas9 integration site was 2229 bp, and for the 3' flank was 1973 bp. All of the strains tested were positive for integration of Cas9 at OrfA/Pfa1 locus.

Example 3

Design and Building of gRNA Vectors

Figure 5:
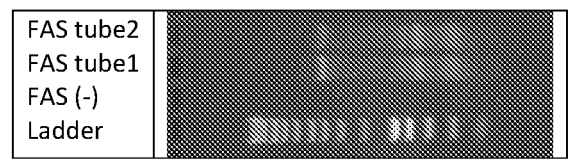
FIG. 5 shows a portion of Schizochytrium fatty acid synthase (FAS) gene amplified from genomic DNA and run on a 1% agarose gel.

All of the guide RNA (gRNA) cassettes were designed to be expressed by the elongation factor 1α (EF-1α) promoter derived from *Schizochytrium*. In each case, the gRNA sequence was flanked by two ribozyme sequences, Hammerhead and HDV (Gao Y and Zhao Y "Self-processing of ribozyme-flanked RNAs into guide RNAs in vitro and in vivo for CRISPR-mediated genome editing" J Integr Plant Biol. 56(4):343-349 (2014)). Four target sequences containing the "NGG" protospacer-adjacent motif were identified within carotene synthase gene and 20 bp immediately upstream of each were chosen as target sequences. One cassette including both ribozymes, target sequence and guide RNA was synthesized and cloned into pCL122 vector using BglII and NdeI sites (DNA2.0) resulting in the vector designated pCL401—a precursor plasmid for additional cloning (SEQ ID NO:7). To prepare the final gRNA cassette vectors, the plasmid pSP73 (Promega) was digested with NdeI and HpaI and the resulting larger fragment was gel purified. A fragment of the *Schizochytrium* Fatty Acid Synthase fragment (FAS) was amplified by PCR off *Schizochytrium* sp. 20888 genomic DNA with 5' FAS PmeNde (SEQ ID NO:23) and 3' FAS PmeHpa (SEQ ID NO:24) primers (Table 6), KOD Hot Start Mastermix, and 5% DMSO, using the following cycling conditions: 95° C. for 2 minutes, (95° C. for 20 seconds, 62° C. for 10 seconds, 70° C. for 51 seconds)×40 cycles, 70° C. for 5 minutes (FIG. 5). The resulting fragment was digested with HpaI and NdeI restriction enzymes and purified.

TABLE 6

| Primer Name | SEQ ID NO | Primer Sequence, 5'→3' |
|---|---|---|
| 5' FAS PmeNde | 23 | TAGCATATGTTTAAACTCGCGGCGTCTTTCGC |
| 3' FAS PmeHpa | 24 | AGTTAACGTTTAAACAGAGGAGGTGGCTGGC |

Figure 6:
FIG. 6 shows the results of PCR cloning of paromomycin and gRNA cassettes into FAS locus in vector pCL400.

The appropriate purified and digested pSP73 and FAS fragments were ligated using Rapid DNA Ligation kit (Roche) and transformed into NEB10β cells (New England Biolabs), resulting in vector pCL399 (SEQ ID NO:5). The pCL399 vector was then digested with NdeI endonuclease alone, the ends were blunted with Mung Bean Nuclease (New England Biolabs), and the vector religated with Rapid DNA Ligation kit, thereby removing NdeI site. The resulting vector was designated pCL400 (SEQ ID NO:6). The paromomycin expression cassette and gRNA cassette were amplified using pCL401 (SEQ ID NO:7) as template to be inserted into pCL400 predigested with XhoI by InFusion PCR cloning to create vector pCL402 (SEQ ID NO:8). Briefly, pCL402 IF F (SEQ ID NO:25) and PCL402 IF R (SEQ ID NO:26) primers (Table 7), 5% DMSO (v:v), KOD Hot Start Mastermix, pCL401 plasmid template were used to amplify the desired fragment from pCL401 using the following cycling conditions: 95° C. for 2 minutes (95° C. for 20 seconds, 60° C. for 10 seconds, 70° C. for 1 minute 25 seconds)×35 cycles, 70° C. for 5 minutes (FIG. 6). The resulting vector was designated pCL402.

TABLE 7

| Primer Name | SEQ ID NO | Primer Sequence, 5'→3' |
|---|---|---|
| pCL402 IF F | 25 | GAGGCGCTGACCGCCGGCCAAGCTTCCAATTTTAGGCC |
| pCL402 IFR | 26 | GCAGGTGCCGAGTTTCTCGAGAAGAATCTGAACTCACGTC |

Four genomic Carotene Synthase target sequences were synthesized (Eurofins, Mebane, N.C.) with BglII and NdeI flank sites. These fragments were designated gRNA3 CS1, CS2, CS3 and CS4. All four fragments and the vector pCL0402 were digested with BglII and NdeI. All appropriate fragments were gel or column purified and then ligated together using Rapid DNA Ligation kit (Roche) and resulting vectors were designated pYB36 (gRNA3 CS1; SEQ ID NO:9), pYB37 (gRNA3 CS2; SEQ ID NO:10), pYB38 (gRNA3 CS3; SEQ ID NO:11), and pYB39 (gRNA3 CS4; SEQ ID NO:12).

In order to remove gene editing components from *Schizochytrium*, both Cas9 and guide RNA cassettes were designed to disrupt ("knock-out") genes thereby inducing auxotrophies. While the auxotrophy with Cas9 selection was for DHA, the induced auxotrophy for gRNA insertion was for palm itic acid due to disruption of the Fatty Acid Synthase locus (FAS). Part of the FAS gene was amplified from *Schizochytrium* sp. 20888 genomic DNA and then run on a 1% agarose gel (FIG. 6). The expected size of the amplicon was 2530 bp. Two samples were prepared and loaded on the gel, the expected size band was the major product of the PCR, however there were other smaller size bands indicating that PCR conditions might have been less ideal and may need to be optimized in the future. The 2.5 kbp band was cut out, gel purified and used for cloning of the vector pCL399.

PCR was set up for cloning of paromomycin and gRNA cassettes into FAS locus in vector pCL400. Expected size of the amplicon was 3376 bp, and it was the major band that appeared on the gel (FIG. 6). This fragment was then cloned into pCL400 to result in pCL402.

Example 4

Transformation and Selection of gRNA Constructs

Figure 7:
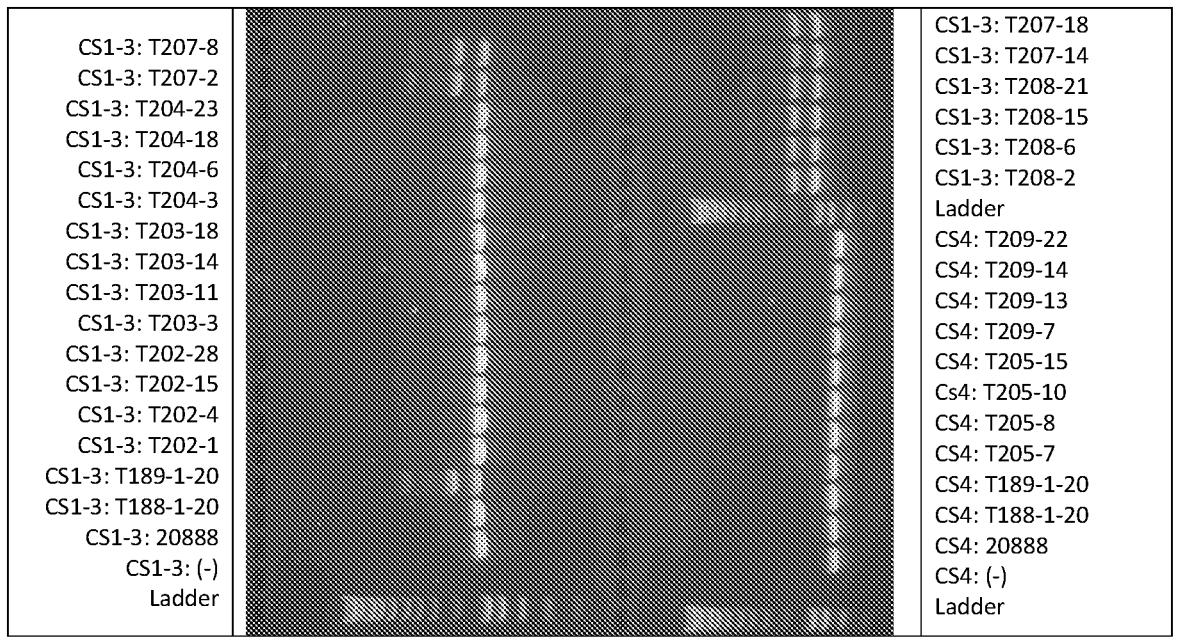
FIG. 7 shows the results of PCR performed to amplify the entire region encompassing the first 3 CS gRNA targets as one amplicon and another PCR to amplify gRNA3 CS4 target separately.

T188-1-20 and T189-1-20 strains, both verified by PCR to contain Cas9 expression cassette under regulation of different promoters, Alpha Tubulin and CS, respectively, and inserted at OrfA/PFA1 locus of PUFA synthase, were inoculated into smooth-bottom Erlenmeyer flasks containing 25 mL of M50-20 supplemented with 0.4% randomly methylated β-cyclodextrins with 0.5 mM DHA and grown overnight at 27° C., 200 rpm. Both strains were diluted 1/50 into baffled flasks containing 50 mL of M2B supplemented with β-cyclodextrin and DHA as described above and grown overnight at 27° C. T188 and T189 cultures were harvested the following day as described above and preparation for bombardment was carried out as described above. pYB36-39 plasmids were digested prior to bombardment with PmeI and column purified, all four digested plasmids were used to transform the two strains resulting in transformations designated T202-209 (T188 with pYB36-39, T189 with pYB36-39, respectively). Resulting transformants were plated on M2B plates containing 0.4% of β-cyclodextrins with 0.5 mM DHA, 0.5 mM C16:0 (palmitic acid, Sigma-Aldrich, St. Louis, Mo.) and 50 µg/mL paromomycin 4 hours after recovery from bombardment. Plates were wrapped and incubated at 27° C. for 7-10 days. Once 2-4 mm in diameter, colonies were replica patched onto M2B+ 0.4% β-cyclodextrins+0.5 mM DHA+50 µg/mL paromomycin with or without 0.5 mM palmitic acid to verify auxotrophy for palmitic acid created as a result of gRNA cassette insertion at FAS locus. Ten colonies from each of the 8 transformations verified to be auxotrophic for both DHA and palmitic acid were picked and inoculated into smooth-bottom Erlenmeyer flasks containing 25 mL of M50-20 supplemented with 0.4% β-cyclodextrins, 0.5 mM DHA and 0.5 mM palmitic acid, cultures were grown for 48 hrs at 27° C., 200 rpm, at which time 2 mL of each culture was collected for genomic DNA preparations. After genomic DNA was extracted with phenol:chloroform, PCR was carried out to amplify carotene synthase locus containing regions where gRNA cassette was targeted. gDNA from selected transformants from T202, 203, 204, 207, 208 was amplified by PCR using pYB36 CS1 F (SEQ ID NO:27) and pYB36 CS3 R (SEQ ID NO:29) primers (Table 8), 5% DMSO (v:v), KOD Hot Start Mastermix, respective gDNA as template using following cycling conditions: 95° C. for 2 minutes, (95° C. for 20 seconds, 61° C. for 10 seconds, 70° C. for 21 seconds)×35 cycles, 70° C. for 5 minutes (FIG. 7). gDNA from T206 was amplified with pYB36 CS1 F and pYB36 CS1 R (SEQ ID NO:28) primers (Table 8), 5% DMSO (v:v), KOD Hot Start Mastermix using following cycling conditions: 95° C. for 2 minutes, (95° C. for 20 seconds, 61° C. for 10 seconds, 70° C. for 11 seconds)×35 cycles, 70° C. for 5 minutes (FIG. 8). gDNA from T205 and T209 was amplified using pYB36 CS4 F (SEQ ID NO:30) and pYB36 CS4 R (SEQ ID NO:31) primers (Table 8), 5% DMSO (v:v), KOD Hot Start Mastermix using following cycling conditions: 95° C. for 2 minutes, (95° C. for 20 seconds, 61° C. for 10 seconds, 70° C. for 21 seconds)×35 cycles, 70° C. for 5 minutes (FIG. 7).

TABLE 8

| Primer Name | SEQ ID NO | Primer Sequence, 5'→3' |
| --- | --- | --- |
| pYB36 CS1 F | 27 | GAGTCGAAGGAGACGTTGTCG |
| pYB36 CS1 R | 28 | GTCATTGCGAATGATGCGATATG |
| pYB36 CS3 R | 29 | GGTCATCATGGAATACAACGCAG |
| pYB36 CS4 F | 30 | CGAGCTCATTTGTGCTACACTCTATG |
| pYB36 CS4 R | 31 | CACAAGATTTGCAGGATTGATGC |

Resulting PCR amplicons were column purified, cloned into pJet1.2 vector (Thermo Fisher, Waltham, Mass.), resulting bacterial transformants were miniprepped, and the inserts sequenced with primers provided in the kit. Sequences were aligned using Geneious software.

Transformations of two Cas9 backgrounds (T188 and T189) with vectors encoding gRNAs were carried out successfully and resulted in a number of doubly auxotrophic strains as shown below in Table 9 (designated T202-209). Select strains were later analyzed on a genetic level to detect any mutations of the carotenoid synthase locus, indicating a non-homologous end joining (NHEJ) event.

TABLE 9

| Transformation | Total colonies (per 3 ug DNA) | Number of 16:0 auxotrophs | Percent KO |
| --- | --- | --- | --- |
| T202 (T188 + gRNA1) | 103 | 17/32 | 53% |
| T203 (T188 + gRNA2) | 93 | 15/32 | 46% |
| T204 (T188 + gRNA3) | 65 | 15/32 | 46% |
| T205 (T188 + gRNA4) | 50 | 15/32 | 46% |
| T206 (T189 + gRNA1) | 53 | 12/32 | 37% |
| T207 (T189 + gRNA2) | 28 | 8/20 | 40% |
| T208 (T189 + gRNA3) | 38 | 9/29 | 31% |
| T209 (T189 + gRNA4) | 28 | 9/22 | 41% |

After gDNA was isolated from gRNA+Cas9 transformants that were shown to be auxotrophic, requiring supplementation with both DHA and palm itic acid, one PCR was used to amplify the entire region encompassing the first 3 CS gRNA targets as one amplicon and another PCR to amplify the gRNA3 CS4 target separately (FIG. 7). The expected size for amplicons from gRNA3 CS1-3 transformant DNA was 1040 bp, and from gRNA 3 CS4 transformants was 715 bp. In the case of amplicons for gRNA CS1-3 targets, samples that came from the T188 lineage had a single band of correct size. However, samples that came from T189 (including gDNA from T189 parental strain itself) had multiple bands with ~1 kbp band being most prominent and ~1.5 kbp band being second most prominent. The 1.5 kbp band was judged to be a product of non-specific amplification. No optimization of the PCR was done in an attempt to reduce the presence of nonspecific bands, and the ~1 kbp band was cut out of the gel for all the transformants and was used for pJet1.2 cloning. All CS4 amplicons were a single band of correct size. Several resulting pJet transformant colonies harboring amplicons from each of the Cas9/gRNA transformants were sent for sequencing to determine whether Cas9/gRNA had any effect on CS sequence.

Figure 8:
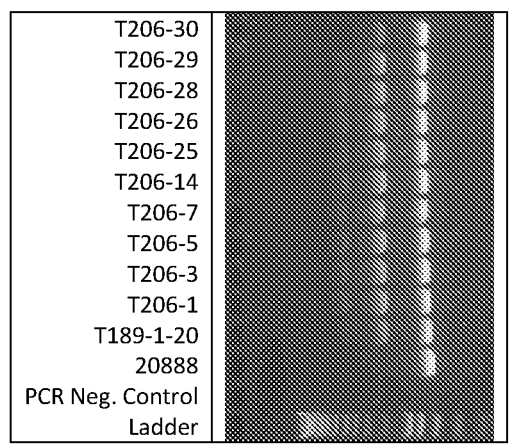
FIG. 8 shows the results of PCR performed to amplify gRNA3 CS1 target separately from genomic DNA of T206 transformants.

Additionally, analyses were performed on the T206 lineage of clones. As described in FIG. 7, T206 transformants had gDNA extracted and used as template for PCR to amplify the gRNA3 CS1 target sequence only and the expected amplicon size was 689 bp. A band of this size was observed on the gel, a major band amidst other, higher molecular weight ones, similar to those observed on the previous figure. The gel fragment of expected ~700 bp size was cut and purified and used for pJet1.2 cloning and sequencing of the fragment to determine whether Cas9-gDNA had induced any sequence changes in CS gene (FIG. 8).

Upon sequencing multiple pJet vectors containing amplicons of CS locus from clones transformed with both Cas9 and gRNA encoding vectors, it was observed that several kinds of changes occurred (Table 10). Previous work has shown that CAS9 cleaves DNA and makes a double stranded break at a position three base pairs upstream of the PAM sequence (Jinek et al. "A programmable dual-RNA-guided DNA endonuclease in adaptive bacterial immunity" Science 337(6096):816-821, 2012). It is known at the site of the double stranded break mutations might arise from imprecise non-homologous end joining (NHEJ)-mediated repair that can produce insertion and/or deletion mutations of variable length (Sander and Joung, "CRISPR-Cas systems for editing, regulating and targeting genomes" Nat Biotechnol. 32(4):347-355, 2014). All of the changes observed occur in the −3 position relative to PAM (AGG in this case), as expected. Exemplary mutations of the carotenoid synthase of *Schizochytrium* sp. 20888 detected in Cas9+gRNA transformants are presented in Table 10, with deletions shown as dashes and insertions shown as underlined text.

TABLE 10

| | Wild-type nucleotide position # | | | | | | |
|---|---|---|---|---|---|---|---|
| | 15 | 16 | 17 | 18 | 19 | 20 | PAM/NGG |
| Wild-type | A | C | G | C | G | C | AGG |
| CS1 target-variant #1 | A | C | G | C | — | — | AGG |
| CS1 target-variant #2 | A | C | — | C | G | C | AGG |
| CS1 target-variant #3 | A | C | G | CC | G | C | AGG |
| CS1 target-variant #4 | A | C | G | TC | G | C | AGG |

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

Example 5

Design and Build of Non-Targeted Cas9 Vector (pYB61)

Figure 9:
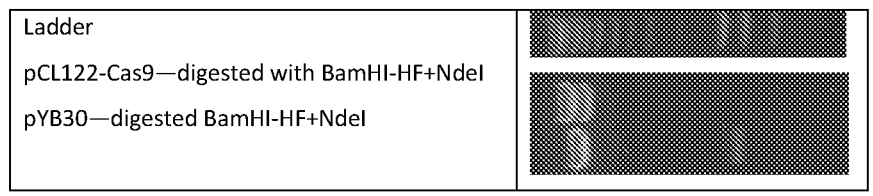
FIG. 9 shows the results of a digest of pLC122-Cas9 and pYB30 plasmids.
Figure 10:
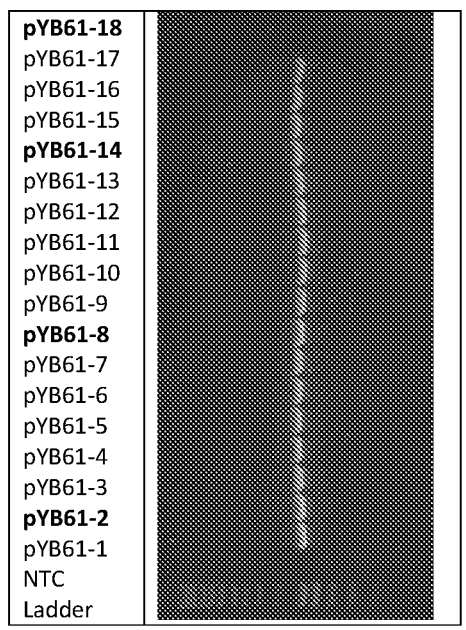
FIG. 10 shows the results of colony PCR of transformants resulting from pYB61 bacterial transformations.

Previously, Cas9 plasmids were designed for targeted integration at a PUFA synthase gene (OrfA subunit; see pYB32 and pYB33). Integration of a Cas9 cassette designed in this way resulted in a knockout of the OrfA gene and DHA auxotrophy. Induction of auxotrophy enables easier screening of transformants for subsequent integration at OrfA locus, but made the differentiation of CRISPR-mediated carotene synthase knockouts more difficult. A plasmid with the expression cassette for Cas9 without targeting to any chromosomal locus was built to test the effect of ectopic, random integration. The plasmid pCL122-Cas9 (SEQ ID NO:1) was digested with BamHI-HF (NEB) and NdeI (NEB) resulting in two fragments, 4140 bp and 5780 bp in size. The 4140 bp fragment was separated on a 1% agarose gel, excised, and purified using QIAquick Gel extraction kit (Qiagen) (FIG. 9). The plasmid pYB30 (SEQ ID NO:32) contains a partial fragment of the Alpha-tubulin promoter that drives expression of GFP and Zeocin resistance. This plasmid was digested with BamHI-HF (NEB) and NdeI (NEB), resulting in two fragments, 838 bp and 4724 bp. The 4724 bp fragment was separated on a 1% agarose gel, excised, and purified using QIAquick Gel extraction kit (Qiagen) (FIG. 9). The two fragments of interest were ligated using the Rapid DNA Ligation kit (Roche). NEB10β chemically competent cells (NEB) were then transformed with some of the ligation reaction. Resulting colonies were used as templates for screening by PCR with: 2×GoTaq Green Master Mix (Promega), primers 121 Tub seq F and pYB32/3C R1, and 5% final DMSO. The following cycling conditions were applied: 95° C. for 5 minutes, [95° C. for 30 seconds, 59° C. for 30 seconds, 72° C. for 1 minute] for 35 cycles, and 72° C. for 5 minutes (described previously) (FIG. 10). Plasmids were extracted from colonies confirmed as positive transformants by PCR, sequenced, and the resulting vector designated pYB61 (SEQ ID NO:33).

TABLE 11

| Primer Name | SEQ ID NO | Primer Sequence, 5'→3' |
|---|---|---|
| 121 Tub seq F | 13 | GGATCTCATGCTGGAGTTCTTC |
| pYB32/3C R1 | 14 | GTACTTCTCGTGGTAGGCAACC |

Example 6

Design and Build of Non-Targeted gRNA Vector (pYB66)

Figure 11:
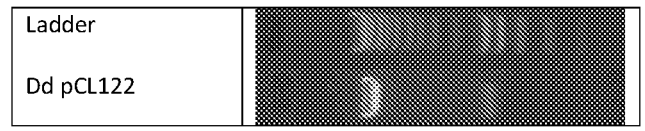
FIG. 11 shows the results of a digest of pCL122 plasmid on a 1% agarose gel.
Figure 12:
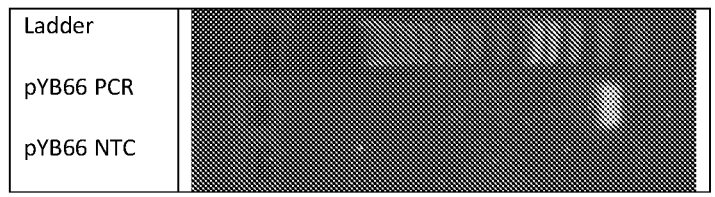
FIG. 12 shows an amplicon of gRNA3 CS1 cassette for pYB66 cloning on a 1% agarose gel.
Figure 13:
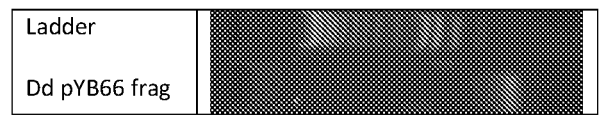
FIG. 13 shows the results of a digestion of gRNA3 CS1 (pYB66 fragment) on a 1% agarose gel.
Figure 14:
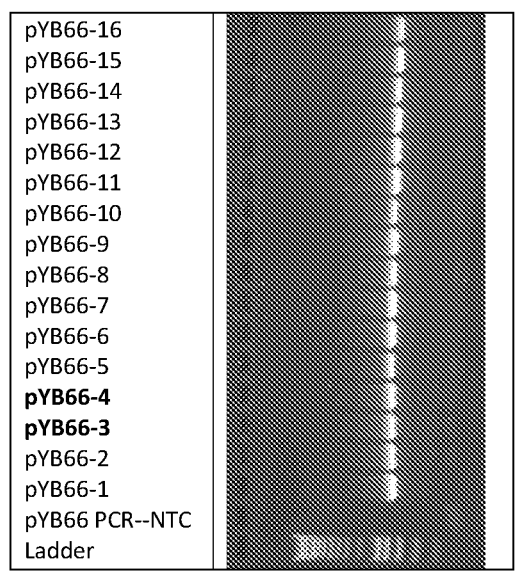
FIG. 14 depicts the results of colony PCR of transformants resulting from pYB66 bacterial transformation.

Previously, gRNA plasmids were targeted to the Fatty Acid Synthase (FAS) gene locus, thereby creating an auxotrophic requirement for palmitic acid. This auxotrophy masked the phenotype that resulted from CRISPR-mediated carotene synthase inactivation. To better discern CRISPR-mediated phenotypic changes at loci involved in carotenoid biosynthesis, a non-targeted gRNA vector was made. The plasmid pCL122 (SEQ ID NO:37) was digested with BamHI-HF (NEB) and NdeI (NEB) to remove the reading frame encoding GFP, resulting in two fragments, sized 838 bp and 5773 bp. The 5773 bp fragment was separated on a 1% agarose gel, excised, and purified using QIAquick Gel extraction kit (Qiagen) (FIG. 11). A cassette encoding gRNA3 CS1 was amplified by PCR using the plasmid pYB36 (SEQ ID NO: 9) as a template with: 2×KOD Hot Start Master Mix (EMD Millipore), primers pYB66 BamBgl F and pYB66 Nde R, and 5% final DMSO. The following cycling conditions were applied: 95° C. for 2 minutes, [95° C. for 20 seconds, 59° C. for 10 seconds, 70° C. for 5 seconds] for 35 cycles, and 72° C. for 2 minutes (FIG. 12). The resulting PCR fragment was column purified using QIAquick PCR purification kit (Qiagen) and digested with BamHI-HF (NEB) and NdeI (NEB). Following digestion, the resulting DNA fragment was again purified using QIAquick PCR purification kit (FIG. 13). The digested pCL122 and gRNA fragments were ligated using Rapid DNA Ligation kit (Roche). NEB10β chemically competent cells were then transformed with a portion of the ligation reaction and resulting bacterial colonies were screened by colony PCR using 2×GoTaq Green MasterMix (Promega), primers pYB66 EF1seq F and pCL122 OrfC R, and 5% final volume of DMSO with following cycling conditions: 95° C. for 10 minutes, [95° C. for 30 seconds, 60° C. for 30 seconds, 72° C. for 45 seconds] for 35 cycles, and 72° C. for 5 minutes (FIG. 14). Plasmids were extracted from colonies positive by PCR, sequenced, and the resulting vector was designated pYB66 (SEQ ID NO:34).

TABLE 12

| Primer Name | SEQ ID NO | Primer Sequence, 5'→3' |
|---|---|---|
| pYB66 BamBgl F | 38 | CAAGGGATCCAGATCTTCCGCACTGATGAGTC |
| pYB66 Nde R | 39 | AACTCATATGGTCCCATTCGCCA |
| pYB66 EF1seq F | 40 | GAGAGGATAGTATCTTGCGTGCTTG |
| pCL122 OrfC R | 41 | GCAAGGTTGGAACATTACGATCAAG |

Example 7

Design and Build of Cas9 and gRNA Vector (pYB73)

Figure 15:
FIG. 15 shows the result of digestion of pYB61 plasmid on a 1% agarose gel.
Figure 16:
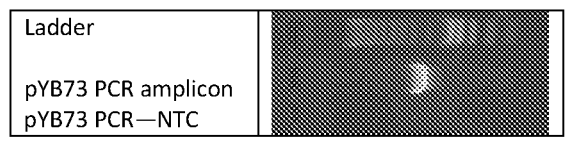
FIG. 16 shows an amplicon of gRNA3 CS1 cassette for pYB73 cloning on a 1% agarose gel.
Figure 17:
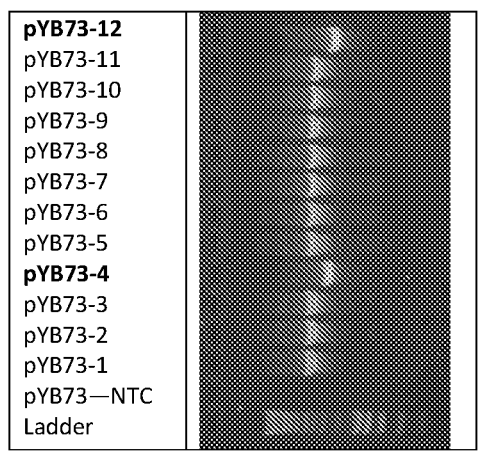
FIG. 17 shows the results of colony PCR of transformants resulting from pYB73 bacterial transformation.

A vector containing both Cas9 and gRNA cassettes on the same vector with a single dominant selectable marker was created to test the efficiency of such configurations on genome editing. Plasmid pYB61 was digested with PstI (NEB) and purified by QIAquick PCR purification kit (Qiagen) (FIG. 15). The gRNA expression cassette was amplified off of pYB36 using PCR with the following: 2×KOD Hot Start Master Mix (Novagen), primers pYB73 gRNA Pst Kpn IF F and pYB73 gRNA Xho Pst IF R, and 5% final DMSO. The cycling conditions were used as follows: 95° C. for 2 minutes, [95° C. for 20 seconds, 58° C. for 10 seconds, 70° C. for 38 seconds] for 35 cycles, and 70° C. for 2 minutes (FIG. 16). A resulting PCR fragment was column purified using QIAquick PCR clean-up kit (Qiagen). Purified, digested pYB61 fragment was ligated to the purified, digested gRNA PCR fragment using InFusion kit (Clontech) following manufacturer's protocol. NEB10β chemically competent cells were transformed with a portion of the InFusion reaction, and resulting bacterial colonies were screened by PCR with the following:2×GoTaq Green Master Mix (Promega), primers pYB73 seq F and pYB73 seq R, and 5% final DMSO. The following cycling conditions were applied: 95° C. for 10 minutes, [95° C. for 30 seconds, 60° C. for 30 seconds, 72° C. for 2 minutes] for 35 cycles, and 72° C. for 5 minutes (FIG. 17). Plasmids were extracted from colonies positive by PCR, sequenced, and the resulting vector was designated pYB73 (SEQ ID NO:35). Plasmid pYB73 is not designed for targeting to any specific gene.

TABLE 13

| Primer Name | SEQ ID NO | Primer Sequence, 5'→3' |
|---|---|---|
| pYB73 gRNA Pst Kpn IF F | 42 | CATACATGGTCGACCTGCAGGGTACCTCTTATCTGCCTCGC |
| pYB73 gRNA Xho Pst IF R | 43 | ATTAATGCAGGTTCCTGCAGCTCGAGAAGAATCTGAACTCACGTC |
| pYB73 seq F | 44 | CACCCCAACTTGTTTATTGCAG |
| pYB73 seq R | 45 | GAGCGAGGAAGCGGAAGAG |

Example 8

Design, Build and Transformation with CarG Strain

To improve the distinction between transformants with CRIPSR-mediated carotene synthase gene inactivation (white colony phenotype) and without CRIPSR-mediated carotene synthase gene inactivation (yellow-orange colony phenotype), the CarG gene (geranylgeranyl pyrophosphate synthase) from *Mucor circinelloides* was codon-optimized for expression in *Schizochytrium*. The CarG gene, which should increase total amount of carotenoids produced and make transformants more orange, was synthesized by DNA2.0 and cloned into a *Schizochytrium* expression vector containing a blasticidin selection cassette. The resulting vector was named pCL310 (SEQ ID NO:36).

Figure 18:
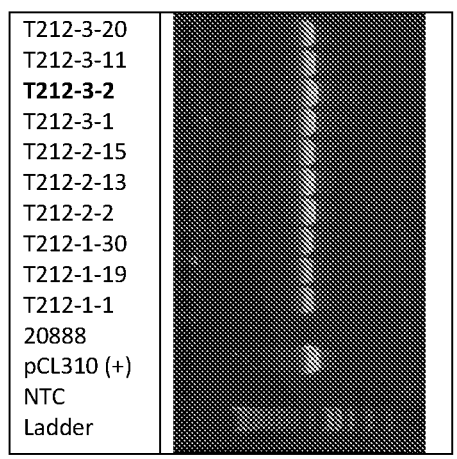
FIG. 18 shows an agarose gel in which amplicons derived from genomic DNA of T212 transformants were separated, testing for the presence of a CarG gene.

Wild-type strain of *Schizochytrium* sp., ATCC 20888, was used for transformation with pCL310 via a particle bombardment method (Bio-Rad). ATCC 20888 was grown in 25 mLs of M50-20 medium in a 250 mL smooth-bottom Erlenmeyer flask at +27° C., shaking at 200 rpm overnight. Following that, the 20888 culture was diluted ¹/₁₀₀ into 50 mLs of M2B medium in a 250 mL baffled flask and grown under the previously used conditions overnight. When the 20888 culture was in early log phase (0.6-2 OD units/mL), it was harvested by centrifugation at 3,220×g for 10 minutes. Supernatant was decanted and the pellet was resuspended in M2B to a final concentration of 20 OD units/mL. One hundred μL of resulting cell suspension was spread on approximately a third of a non-selective M2B agar plate (approximately 2 inches in diameter). Five μg of plasmid DNA and 5 μg of pCL310 was mixed with 50 μL of 2.5M $CaCl_2$, 20 μL of 0.1M spermidine and 50 μL of prepared M10 Tungsten beads (following manufacturer's protocol), vortexed for 1 minute, then incubated for 10 minutes at room temperature to allow for the beads to settle. DNA-coated beads were washed once with 250 μL of 100% ethanol, and then beads were resuspended in 60 μL of 100% ethanol. Each prepared macrocarrier (following manufacturer's protocol for macrocarrier assembly preparation) had 10 μL of coated beads in ethanol spotted to the center under conditions leading to minimal vibrations from the hood and so the ethanol was allowed to dry. Rupture disc holders were affixed with 1,100 psi rupture discs after both were briefly sterilized in 70% isopropanol. Assembled macrocarrier platforms were placed into the top shelf position and M2B agar plates with 20888 cell patch were placed cell-side-up on the third shelf from the top. When vacuum reached approximately 27 inches of mercury inside the chamber of the bombardment machine, helium was fired until rupture disc ruptured. Then, the flow of helium was closed off and the chamber was vented to atmosphere. Bombarded plates were then removed from the chamber. The bombardment process was repeated for all the samples and controls. The 20888 strain bombarded with pCL310 was designated T212. Bombarded plates were incubated in a +27° C. incubator for 4 hours, after which cells were washed off the plate with ~1 mL of M2B and divided equally between four M2B agar plates containing 100 μg/mL blasticidin (ThermoFisher). Cells were spread with 3 mm sterile glass beads. After bead removal, plates were wrapped and incubated at +27° C. for 5 to 8 days. When colonies reached 2-4 millimeters in size, they were patched on M2B agar plates containing 100 μg/mL blasticidin. Colonies confirmed to be resistant to blasticidin were picked and inoculated into 50 mLs of M50-20 in a 250 mL smooth bottom Erlenmeyer flask and placed in a shaker at +27° C. and 200 rpm for 48 hrs. After 48 hr incubation time, two milliliters of culture were collected by centrifugation at 4,000×g for 10 minutes Supernatant was decanted and pellet was used for genomic DNA isolation following a modified phenol-chloroform extraction. Genomic DNA was extracted and used as PCR template with GoTaq Green Master Mix (Promega) to verify presence of Cas9 cassette using primers pYB13 pYB1 seq F and pCL122 OrfC R and DMSO to 5% final concentration. The following cycling conditions were applied: 95° C. for 2 minutes, [95° C. for 30 seconds, 63° C. for 30 seconds, 72° C. for 1 minute 45 seconds] for 35 cycles, and 72° C. for 5 minutes (FIG. 18). Several transformants that were positive for the presence of pCL130 transforming DNA as determined by PCR and which appeared darker orange compared to the wild type control, were analyzed for total carotenoids by UV-Vis method. Out of this analysis two strains were identified to have higher total carotenoids, T212-3-1 and T212-3-2. T212-3-2 was selected for subsequent work with genome editing elements.

TABLE 14

| Primer Name | SEQ ID NO | Primer Sequence, 5'→3' |
|---|---|---|
| pYB1 3 pYB1 seq F | 46 | GAGAGGATAGTATCTTGCGTGCTTGG |
| pCL122 OrfC R | 41 | GCAAGGTTGGAACATTACGATCAAG |

Example 9

Transformation of T212 and 20888 with pYB61, pYB66, and pYB73

Figure 19:
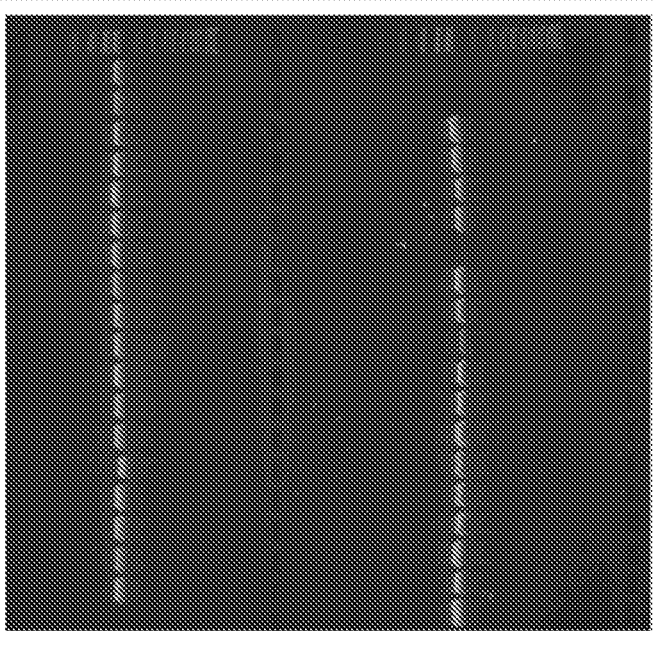
FIG. 19 shows an agarose gel in which amplicons derived from genomic DNA of T280, T281, T285, and T286 transformants were separated, testing for the presence of a partial promoter and Cas9 sequences.
Figure 20:
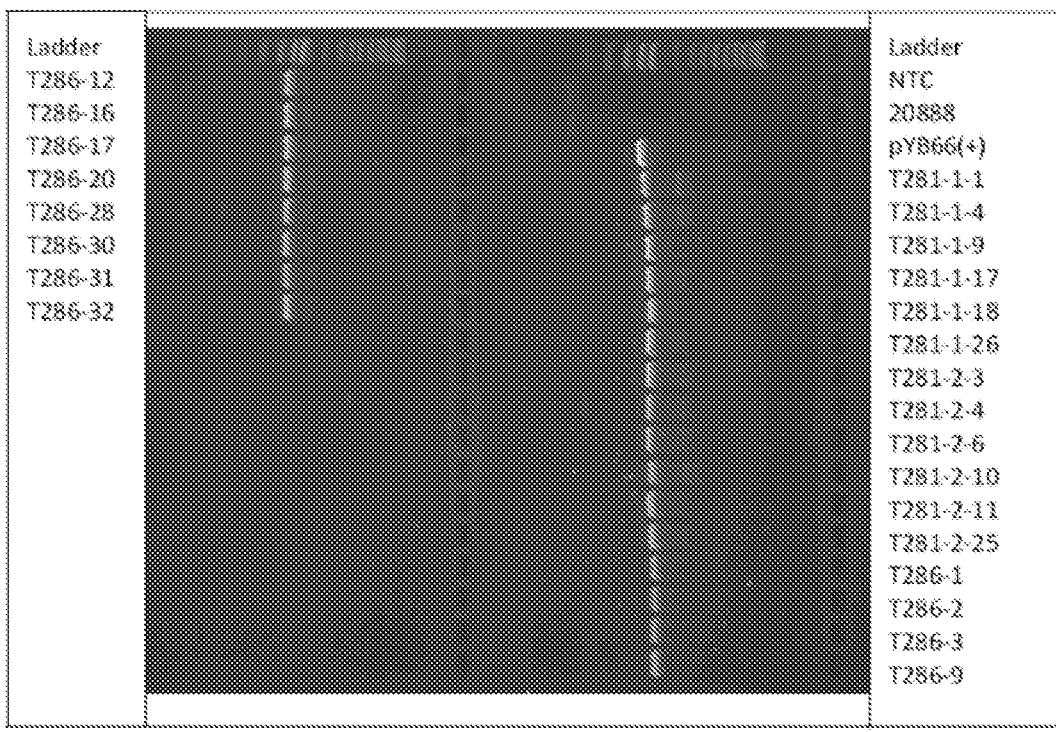
FIG. 20 shows an agarose gel in which amplicons derived from genomic DNA of T281, and T286 transformants were separated, testing for the presence of a gRNA cassette.
Figure 21:
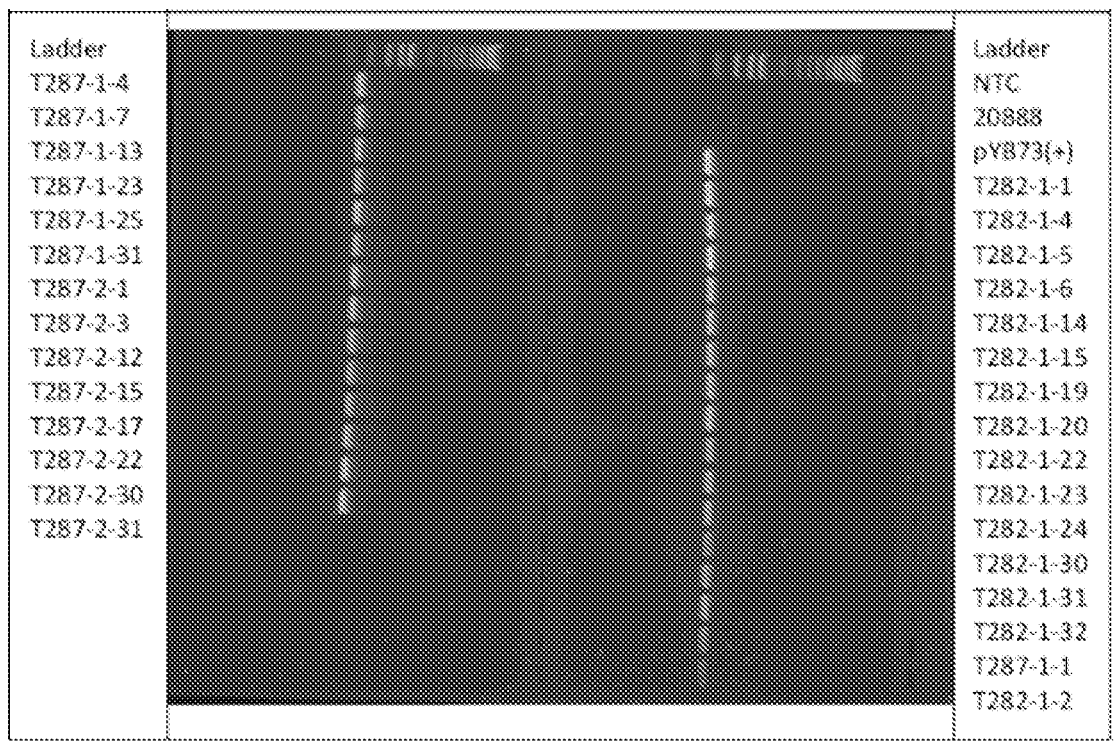
FIG. 21 shows an agarose gel in which amplicons derived from genomic DNA of T282, and T287 transformants were separated, testing for the presence of a partial gRNA cassette.
Figure 22:
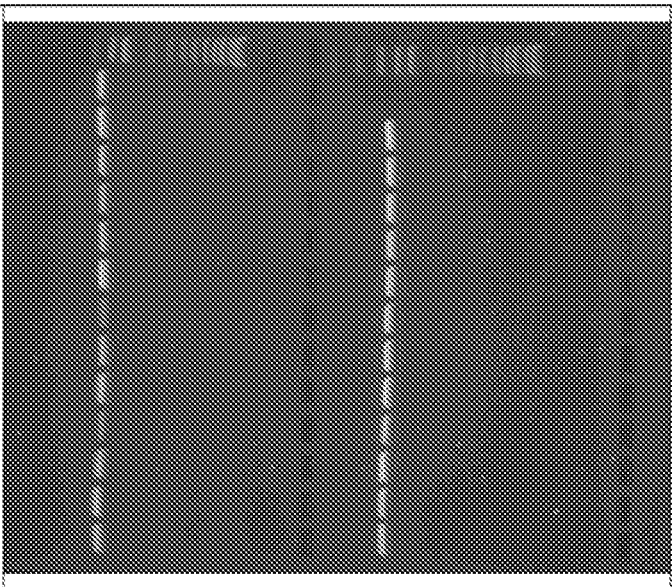
FIG. 22 shows the results of PCR performed to amplify gRNA3 CS1 target separately from genomic DNA of T281, T282, T286, and T287 transformants.

To test the effects of non-targeted vectors on editing efficiency in Schizochytrium several transformations were performed using the particle bombardment method described above. The transformations were set up as follows: T280—T212-3-2 strain transformed with pYB61, and T285—ATCC 20888 wild-type strain transformed with pYB61. Both transformations were conducted to create a recipient strain pre-expressing Cas9 for gRNA testing work. Subsequent transformations were set up as follows: T281—T212-3-2 strain co-transformed with pYB61 and pYB66, and T286—ATCC 20888 wild-type strain co-transformed with pYB61 and pYB66. T281 and T286 transformations were performed to assess editing efficiencies with plasmids not designed for targeting to any particular locus in the genome. T282—T212-3-2 strain transformed with pYB73, and T287—ATCC 20888 wild-type strain transformed with pYB73, were completed to assess editing efficiencies with a single plasmid bearing both elements for genome editing. T280, T282, T285, T287 transformations were selected on M2B plates supplemented with zeocin (ThermoFisher) at 50 μg/mL. T281 and T286 transformations were selected on M2B plates supplemented with zeocin at 50 μg/mL and paromomycin (Sigma) at 100 μg/mL. Colonies resulting from all of these transformations were patched on selective M2B plates containing either 100 μg/mL of zeocin alone or 100 μg/mL zeocin and 100 μg/mL paromomycin together. Patches that grew robustly on the patch plates and that displayed white colony phenotypes when applicable were chosen for further analysis. Those strains were taken off the patch plate and inoculated into 25 mLs of M50-20 medium in 250 mL Erlenmeyer smooth bottom flasks. Flasks were grown at +27° C., 200 rpm for approximately 24 hrs. A 2 mL aliquot of each inoculation was taken and placed in a microcentrifuge tube, spun down at 7,500×g for 10 minutes. Supernatant was decanted and the pellet was used for preparing genomic DNA using a modified phenol-chloroform extraction method. Resulting gDNA was subjected to analysis by PCR for the presence of the selection cassette and gene of interest. For T280, T281, T285, T286, junctions between the terminator of the selection cassette and the beginning of the Cas9 gene were amplified using the following: 2×GoTaq Green Master Mix, primers 121 Tub seq F and pYB32/3 CR1, DMSO to 5% final concentration, and gDNA. The following conditions were applied: 95° C. for 2 minutes, [95° C. for 30 seconds, 58° C. for 30 seconds, 72° C. for 1 minute 2 seconds] for 35 cycles, and 72° C. for 5 minutes (FIG. 19). For T281 and T286. The presence of the gRNA cassette was assessed by PCR amplification of the entire gRNA cassette as follows: 2×GoTaq Green Master Mix, primers pYB66 EF1 seq F and pCL122 OrfC R, DMSO to 5% final concentration, and gDNA. The following cycling conditions were applied: 95° C. for 2 minutes, [95° C. for 30 seconds, 60° C. for 30 seconds, 72° C. for 47 seconds] for 35 cycles, and 72° C. for 5 minutes (FIG. 20). For T282 and T287 the presence of the gRNA cassette was assessed by PCR as follows: 2×GoTaq Green Master Mix, primers pYB66 EF1 seq F and TT pYB73 HDV R, DMSO at 5% final concentration, and gDNA. The following cycling conditions were applied: 95° C. for 2 minutes, [95° C. for 30 seconds, 60.9° C. for 30 seconds, 72° C. for 16 seconds] for 35 cycles, and 72° C. for 5 minutes (FIG. 21). T281, T282, T286 and T287 transformants that tested positive by PCR for Cas9 and gRNA were subjected to PCR to amplify portions of the CS gene where gRNA affected a change in order to sequence the PCR amplicon and observe the types of indels that resulted from the gene editing experiments. The PCR to amplify the relevant portion of the CS gene was prepared with the following: 2×KOD Hot Star Master Mix, primers pYB36 CS1 F and pYB36 CS1 R, DMSO to 5% final concentration, and gDNA. The following cycling conditions were applied: 95° C. for 2 minutes, [95° C. for 20 seconds, 61° C. for 10 seconds, 70° C. for 11 seconds)] for 35 cycles, and 70° C. for 5 minutes (FIG. 22). PCR fragments were column purified using QIAquick PCR purification kit (Qiagen) and were sequence verified with pYB36 CS1 F and pYB36 CS1 R.

TABLE 15

| Primer Name | SEQ ID NO | Primer Sequence, 5'→3' |
|---|---|---|
| pYB66 EF1 seq F | 40 | GAGAGGATAGTATCTTGCGTGCTTG |
| pCL122 OrfC R | 41 | GCAAGGTTGGAACATTACGATCAAG |
| TT pYB73 HDV R | 47 | GAAGCATGTTGCCCAGCC |
| pYB36 CS1 F | 27 | GAGTCGAAGGAGACGTTGTCG |
| pYB36 CS1 R | 28 | GTCATTGCGAATGATGCGATATG |

What is claimed is:

1. A non-naturally occurring or engineered composition comprising a source of a CRISPR-Cas system comprising a guide-polynucleotide and a Cas protein, wherein the guide-polynucleotide comprises a guide-sequence that essentially is the reverse complement of a target-polynucleotide in a host cell and the guide-polynucleotide can direct binding of the Cas protein at the target-polynucleotide in the host cell to form a CRISPR-Cas complex, wherein the guide-sequence is essentially the reverse complement of the (N)y part of a 5'-(N)yPAM-3' polynucleotide sequence target in the genome of the host cell, wherein y is an integer of 8-30, wherein PAM is a protospacer adjacent motif, wherein the host cell is a Schizochytrium, and wherein PAM is a sequence selected from the group consisting of 5'-XGG-3', 5'-XGGXG-3', 5'-XXAGAAW-3',5'-XXXXGATT-3', 5'-XXAGAA-3', 5'-XAAAAC-3', wherein X can be any nucleotide or analog thereof; and W is A or T, and wherein the Cas protein is encoded by a polynucleotide comprised in a vector and the guide-polynucleotide is encoded by or present on another polynucleotide comprised in another vector, wherein the vector encoding the Cas protein is driven by a medium strength Schizochytrium promoter and the vector encoding the guide-polynucleotide is driven by a high strength Schizochytrium promoter.

2. The composition according to claim 1, wherein the guide polynucleotide is encoded by a polynucleotide that is transcribed to provide for the actual guide-polynucleotide.

3. The composition according to claim 2, wherein the vector encoding the Cas protein is driven by a low strength promoter.

4. The composition according to claim 2, wherein one or more or all vectors comprise a selectable marker.

5. The composition according to claim 4, wherein one or more exogenous polynucleotides are operably linked to the guide-polynucleotide.

6. The composition according to claim 5, wherein the Cas protein comprises at least one nuclear localization sequence.

7. The composition according to claim 6, wherein the Cas protein has activity for directing cleavage of both polynucleotide strands at the location of the target-sequence.

8. The composition according to claim 1, wherein the Cas protein encoding polynucleotide is codon optimized for the host cell.

9. The composition according to claim 5, wherein the high strength promoter is any one of the following promoters: Labyrinthulomycete EF-1 promoter, arginase promoter, a pyruvate kinase promoter, heat-shock protein promoter, and glyceraldehyde 3-phosphate dehydrogenase promoter.

10. The composition according to any one of claims 1, 2, and 4-9, wherein the medium strength promoter is any one of the following promoters: alpha tubulin promoter, isocitrate lyase promoter Aconitate hydratase 2 promoter, malate dehydrogenase promoter, and vacuolar ATP synthase subunit D promoter.

11. A method of modulating expression of a polynucleotide in a cell, comprising contacting a host cell with the composition according to any one of claims 1, 2, and 4-9, wherein the guide-polynucleotide directs binding of the Cas protein at the target-polynucleotide in the host cell to form a CRISPR-Cas complex.

12. The method according to claim 11, wherein the host cell comprises a polynucleotide encoding a compound of interest.

13. The method according to claim 11, wherein the host cell is a recombinant host cell.

14. A host cell comprising the composition according to any one of claims 1, 2, and 4-9.

15. A method of producing a host cell, comprising contacting a host cell with the composition according to any one of claims 1, 2, and 4-9, wherein the guide-polynucleotide directs binding of the Cas protein at the target-polynucleotide in the host cell to form a CRISPR-Cas complex.

16. The method according to claim 15, wherein the host cell is first contacted with a source of a Cas protein and subsequently is contacted with a source of a guide-polynucleotide and optionally an exogenous polynucleotide.

17. The method according to claim 16 or the host cell according to claim 14, wherein the host cell comprises a polynucleotide encoding a compound of interest.

18. A method for the production of a compound of interest, comprising culturing under conditions conducive to the production of the compound of interest a host cell obtainable by the method of any one of claims 15-17 or a host cell according to claim 14 or a host cell produced according to the method of any one of claims 15-17 and optionally purifying or isolating the compound of interest.

19. The method according to any one of claims 11-13 and 15-17, wherein the Cas protein is a Cas9 protein.

20. The composition according to claim 1, wherein X can be any nucleotide.

* * * * *